US012618064B2

(12) United States Patent
Dhar et al.

(10) Patent No.: US 12,618,064 B2
(45) Date of Patent: May 5, 2026

(54) ACETYLATED RIBONUCLEIC ACIDS AND USES THEREOF

(71) Applicant: Helix Nanotechnologies Inc, Boston, MA (US)

(72) Inventors: Nikhil Dhar, Boston, MA (US); Kyle Backman, Maynard, MA (US); Dario De Jesus Davila Pasillas, Boston, MA (US); Justin Sean Huang, Jamaica Plain, MA (US); Nikolai Eroshenko, Boston, MA (US)

(73) Assignee: Helix Nanotechnologies Inc, Boston, MA (US)

( * ) Notice: Subject to any disclaimer, the term of this patent is extended or adjusted under 35 U.S.C. 154(b) by 0 days.

(21) Appl. No.: 18/988,105

(22) Filed: Dec. 19, 2024

(65) Prior Publication Data

US 2025/0129364 A1 Apr. 24, 2025

Related U.S. Application Data

(62) Division of application No. 18/143,533, filed on May 4, 2023, now Pat. No. 12,215,317.

(60) Provisional application No. 63/338,429, filed on May 4, 2022.

(51) Int. Cl.

| | |
|---|---|
| ***C07H 19/10*** | (2006.01) |
| ***C07H 13/04*** | (2006.01) |
| ***C07H 19/16*** | (2006.01) |
| ***C07H 19/20*** | (2006.01) |
| ***C12N 15/11*** | (2006.01) |

(52) U.S. Cl.

CPC ............. *C12N 15/11* (2013.01); *C07H 13/04* (2013.01); *C07H 19/10* (2013.01); *C07H 19/16* (2013.01); *C07H 19/20* (2013.01); *C12N 2310/321* (2013.01)

(58) Field of Classification Search

None

See application file for complete search history.

(56) References Cited

U.S. PATENT DOCUMENTS

| | | | |
|---|---|---|---|
| 12,215,317 | B2 | 2/2025 | Dhar et al. |
| 2015/0218202 | A1 | 8/2015 | Koppetsch et al. |
| 2023/0383287 | A1 | 11/2023 | Dhar et al. |

FOREIGN PATENT DOCUMENTS

| | | | |
|---|---|---|---|
| WO | WO-2013/052523 | A1 | 4/2013 |
| WO | WO-2022/031314 | A2 | 2/2022 |
| WO | WO-2023/215516 | A2 | 11/2023 |
| WO | WO-2023/215516 | A3 | 11/2023 |

OTHER PUBLICATIONS

AN 1975:514781 as it relates to Pyaivinen et al., Russian Journal of General Chemistry, 45(5):1170-1176 (1975).

Anand, P and Stahel, P., Review the safety of Covid-19 mRNA vaccines: a review, Patient Saf Surg, 15(1):20 (2021).

Assi, H. et al., 2'-O-Methylation can increase the abundance and lifetime of alternative RNA conformational states, Nuc Acid Res., 48(21):12365-12379 (2020).

Brown, D. and Pasloske, B., Ribonuclease-resistant RNA controls and standards, Methods in Enzymology, 341:648-54 (2001).

Choi, S. and Meyer, K., et al., Acetylation takes aim at mRNA, Nat Struct Mol Biol., 25(12):1067-1068 (2018).

Fernandez-Garcia, C. an Powner, M. W., Selective Acylation of Nucleosides, Nucleotides, and Glycerol-3-phosphocholine in Water, Synlett, 28:78-83 (2017).

Grzeskowiak, K. et al., Chromatography on Sephadex LH20 as an efficient purification step after removal of inter-nucleotide 2,2,2-trichloroethyl protective groups from oligoribonucleotide phosphotriesters, Nucleic Acids Research, 8(5):1097-1105 (1980).

Hudson, G. et al., Thermodynamic contribution and nearest-neighbor parameters of pseudouridine-adenosine base pairs in oligoribonucleotides, RNA, 19(11):1474-82 (2013).

International Search Report for PCT/US23/21060, 6 pages (mailed Feb. 6, 2024).

Mäkinen, J. et al., The mechanism of the nucleo-sugar selection by multi-subunit RNA polymerases, Nature Communications, 12(1):796 (2021).

Marian, M. Acetyl Derivatives of Nucleoside 5'-Triphosphates, Microchemical Journal, 29:219-227 (1984).

Ovodov, S. and Alakhov, Y., mRNA acetylated at 2'-OH-groups of ribose residues is functionally active in the cell-free translation system from wheat embryos, Elsevier Sci Pub., 270(12):111-114 (1990).

PubChem Substance Record for SID 341415430.

Pubchem, SID 405013448, Modify Date: May 4, 2021 [retrieved on Nov. 5, 2023]., Retrieved from the Internet <URL: https://pubchem.ncbi.nlm.nih.gov/ substance/405013448> entire document.

Written Opinion for PCT/US23/21060, 6 pages (mailed Feb. 6, 2024).

*Primary Examiner* — Traviss C McIntosh, III

(74) *Attorney, Agent, or Firm* — Choate, Hall & Stewart LLP; Stephanie L. Schonewald; Mandeep Kaur

(57) ABSTRACT

Disclosed herein is a modified ribonucleotide comprising a nucleoside comprising 2'-O-acetylated ribose, and polyribonucleotides comprising the same. Also provided herein are compositions comprising a polyribonucleotide of the present disclosure and methods of making and using the same.

27 Claims, 63 Drawing Sheets

Specification includes a Sequence Listing.

2-O-Acetyl ATP

2-O-Acetyl GTP

2-O-Acetyl CTP

2-O-Acetyl UTP

Chemical Formula: $C_{22}H_{40}N_5O_5Si_2^+$ $[M+H]^+$, Exact Mass: 510.2563

ACETYLATED RIBONUCLEIC ACIDS AND USES THEREOF

CROSS-REFERENCE TO RELATED APPLICATIONS

This application is a Divisional of U.S. application Ser. No. 18/143,533 filed on May 4, 2023, which claims priority to U.S. Provisional Patent Application 63/338,429 filed on May 4, 2022, the entire contents of each of which is hereby incorporated by reference.

SEQUENCE LISTING

The instant application contains a Sequence Listing which has been submitted electronically in XML format and is hereby incorporated by reference in its entirety. Said XML copy, created on Jul. 5, 2023 is named 2012611-0057_SL.xml and is 4,908 bytes in size.

BACKGROUND

RNA therapeutics is a new and emerging field.

SUMMARY

The present disclosure identifies certain challenges with the production of RNA for use in applications such as therapeutic applications, and challenges with the use of RNAs as therapeutics. For example, in some embodiments, the present disclosure identifies certain problems that can be encountered with using currently available RNAs for therapeutics due to, e.g., the short-lived activity and/or instability of RNAs. In some embodiments, instability of an RNA can be traced, e.g., to the reactivity of the hydroxyl group on carbon 2 of the ribose of a ribonucleotide.

Among other things, the present disclosure provides technologies related to 2'-O-acetylated nucleotides in which a hydroxyl group on carbon 2 of a ribose is acetylated (2'-O-acetylated ribose). Without wishing to be bound by theory, in some embodiments, a ribonucleotide having a 2'-O-acetylated ribose can maintain crucial hydrogen bonding interactions necessary for transcription, translation, and duplex formation, while simultaneously having reduced reactivity that would otherwise promote RNA autohydrolysis and nuclease degradation. In some embodiments, a ribonucleotide having a 2'-O-acetylated ribose is more stable than a comparable RNA having fewer 2'-O-acetyl groups on a ribose.

Among the technologies provided by this disclosure are technologies for using 2'-O-acetylated nucleotide triphosphates as a reagent for in vitro transcription of polyribonucleotides with RNA polymerase. In some embodiments, RNA polymerase can use 2'-O-acetylated nucleotide triphosphates to produce 2'-O-acetylated polyribonucleotides which can be translated by the intracellular machinery of a cell. In some embodiments, 2'-O-acetylated polyribonucleotides can be used for a variety of applications, including therapeutic applications, research applications, diagnostic applications, agricultural applications, and any other suitable applications.

The present disclosure also provides technologies for reducing immunogenicity of RNA therapeutics by providing a polyribonucleotide comprising a modified ribonucleotide, e.g., a 2'-O-acetylated ribose. Without wishing to be bound by theory, the present disclosure proposes that a polyribonucleotide comprising a 2'-O-acetylated ribose can achieve reduced immunogenicity when administered in a cell, tissue or subject by reduced activation of an innate immune response. In some embodiments, reduced activation of an innate immune response, e.g., reduced activation of NF-kb or an NF-kb pathway, IRF or an IRF pathway, and/or other inflammatory cytokines; or reduced detection of uncapped RNA by a molecular sensor (e.g., RIG-I), with a polyribonucleotide comprising a 2'-O-acetylated ribose or a composition comprising the same allows for repeated dosing of, e.g., at least two doses of, said polyribonucleotide or a composition comprising the same. In some embodiments, a polyribonucleotide comprising a 2'-O-acetylated ribose, or a composition comprising the same can be administered at a higher dose compared to a reference polyribonucleotide that includes fewer 2'-O-acetyl groups on a ribose.

Also provided herein are technologies for increasing expression from RNA therapeutics by providing a polyribonucleotide comprising a modified ribonucleotide, e.g., a ribonucleotide comprising a 2'-O-acetylated ribose. Without wishing to be bound by theory, the present disclosure proposes that a polyribonucleotide comprising 2'-O-acetylated ribose can achieve increased levels of protein or polypeptide expression when administered in a cell, tissue or subject, as compared to administration of a comparable polyribonucleotide having fewer 2'-O-acetyl groups on a ribose.

Further provided herein are technologies for increasing persistence of RNA therapeutics by providing a polyribonucleotide comprising a modified ribonucleotide, e.g., a ribonucleotide comprising a 2'-O-acetylated ribose. Without wishing to be bound by theory, the present disclosure proposes that a polyribonucleotide comprising 2'-O-acetylated ribose can achieve increased persistence when administered in a cell, tissue or subject, as compared to administration of a comparable polyribonucleotide having fewer 2'-O-acetyl groups on a ribose. In some embodiments, increased persistence is a result of increased resistance to one or more nucleases. In some embodiments, increased persistence may also allow for reduced dosing frequency and/or reduced doses of a polyribonucleotide comprising a modified ribonucleotide, e.g., a ribonucleotide comprising a 2'-O-acetylated ribose.

Also provided herein are compositions comprising a polyribonucleotide comprising 2'-O-acetylated ribose and methods of making and using the same.

This disclosure provides a modified ribonucleotide comprising a nucleoside, wherein a nucleoside comprises a ribose moiety comprising an acetyl group, wherein a ribose is 2'-O-acetylated. In some embodiments, a modified ribonucleotide has a structure of:

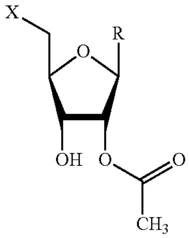

(a) wherein X is a 5' monophosphate, a 5' diphosphate, or a 5' triphosphate; and (b) wherein R is a nucleobase chosen from: adenine or a modified version thereof, a guanine or a modified version thereof, a cytosine or a modified version thereof, or a uracil or a modified version thereof.

In some embodiments, a modified ribonucleotide has a 5' triphosphate and a structure of:

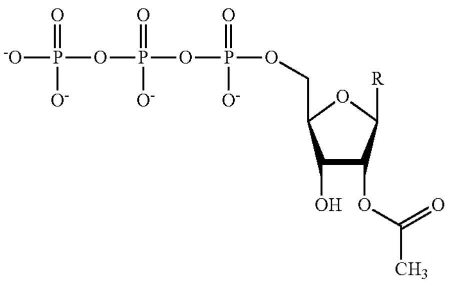

wherein R is a nucleobase chosen from: adenine or a modified version thereof, a guanine or a modified version thereof, a cytosine or a modified version thereof, or a uracil or a modified version thereof.

In some embodiments, a nucleobase is adenine. In some embodiments, a polyribonucleotide comprising adenine has a 5' triphosphate and a structure of:

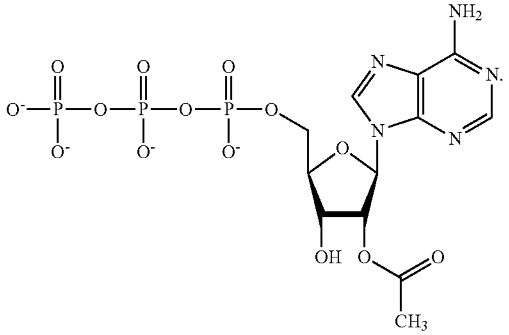

In some embodiments, a nucleobase is guanine. In some embodiments, a polyribonucleotide comprising guanine has a 5' triphosphate and a structure of:

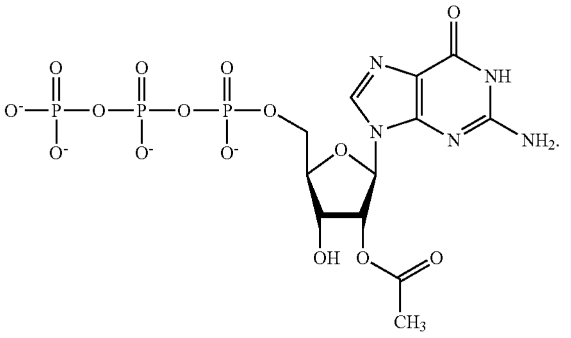

In some embodiments, a nucleobase is cytosine. In some embodiments, a polyribonucleotide comprising cytosine has a 5' triphosphate and a structure of:

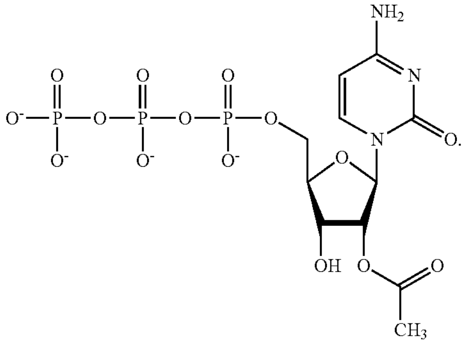

In some embodiments, a nucleobase is uracil. In some embodiments, a polyribonucleotide comprising has a 5' triphosphate and a structure of and has a structure of:

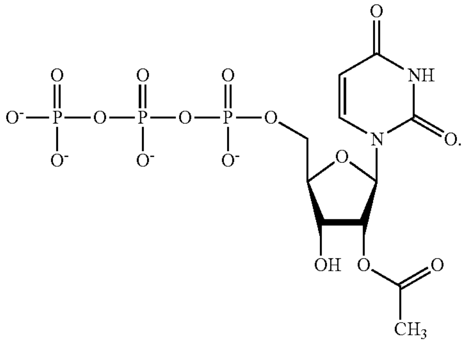

Also provided herein is a polyribonucleotide comprising one or more modified ribonucleotides, e.g., a ribonucleotide comprising a 2'-O-acetylated ribose. In some embodiments, a polyribonucleotide comprises a plurality of ribonucleotides chosen from: adenine, guanine, cytosine, or uracil, or any combination thereof.

In some embodiments, at least 5%, at least 10%, at least 15%, at least 20%, at least 25%, at least 30%, at least 35%, at least about 40%, at least 45%, at least 50%, at least 55%, at least 60%, at least 65%, at least 70%, at least 75%, at least 80%, at least 85%, at least 90%, at least 95%, or at least 99% ribose moieties in a polyribonucleotide are acetylated (2'-O-acetylated).

In some embodiments, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% of ribose moieties in a polyribonucleotide are acetylated (2'-O-acetylated).

In some embodiments, at least about 95% of ribose moieties are 2'-O-acetylated.

In some embodiments, 100% ribose moieties in a polyribonucleotide are acetylated (2'-O-acetylated).

In some embodiments, polyribonucleotide comprises a cap structure. In some embodiments, a cap structure does not comprise a 2'-O-acetylated ribose. In some embodiments, a cap structure comprises a 2'-O-acetylated ribose.

In some embodiments, a polyribonucleotide comprising a 2'-O-acetylated ribose (e.g., comprising an adenine comprising a 2'-O-acetylated ribose, a guanine comprising a 2'-O-acetylated ribose, a cytosine comprising a 2'-O-acetylated ribose, and/or a uracil comprising a 2'-O-acetylated ribose) further comprises a modification comprising: a modified backbone, a modified nucleobase, or any combination thereof.

In some embodiments, a polyribonucleotide comprising a 2'-O-acetylated ribose (e.g., comprising an adenine comprising a 2'-O-acetylated ribose, a guanine comprising a 2'-O-acetylated ribose, a cytosine comprising a 2'-O-acetylated ribose, and/or a uracil comprising a 2'-O-acetylated ribose) further comprises a modified backbone.

In some embodiments, a polyribonucleotide comprising a 2'-O-acetylated ribose (e.g., comprising an adenine comprising a 2'-O-acetylated ribose, a guanine comprising a 2'-O-acetylated ribose, a cytosine comprising a 2'-O-acetylated ribose, and/or a uracil comprising a 2'-O-acetylated ribose) further comprises a modified nucleobase. In some embodiments, a nucleobase comprising a modification is chosen from adenine, guanine, cytosine, or uracil. In some embodiments, a nucleobase comprising a modification is an adenine. In some embodiments, a nucleobase comprising a modification is a cytosine. In some embodiments, a nucleobase comprising a modification is a guanine. In some embodiments, a nucleobase comprising a modification is a uracil.

In some embodiments, a nucleobase modification comprises a modification known in the art or as disclosed herein. In some embodiments, a nucleobase modification comprises: N4-acetyl-cytidine (ac4C), 5-hydroxymethyluridine (5-hmU), N1-methylpseudouridine, pseudouridine, pyridin-4-one ribonucleoside, 5-aza-uridine, 6-aza-uridine, 2-thio-5-aza-uridine, 2-thio-uridine (s2U), 5-methyl cytidine (m5C), 5-aza-cytidine, 6-aza-cytidine, pseudoisocytidine, 3-methyl-cytidine (m3C), 5-formyl-cytidine (f5C), N4-methyl-cytidine (m4C), 2-amino-purine, 2, 6-diaminopurine, 2-amino-6-halo-purine, 6-halo-purine, inosine (I), 1-methyl-inosine (m1 I), wyosine (imG), methylwyosine (mimG), or any combination thereof.

In some embodiments, a polyribonucleotide comprising a 2'-O-acetylated ribose (e.g., comprising an adenine comprising a 2'-O-acetylated ribose, a guanine comprising a 2'-O-acetylated ribose, a cytosine comprising a 2'-O-acetylated ribose, and/or a uracil comprising a 2'-O-acetylated ribose) further comprises a nucleoside comprising an acetyl group, wherein the nucleoside is N4-acetylcytidine and the modified ribonucleotide has a structure of:

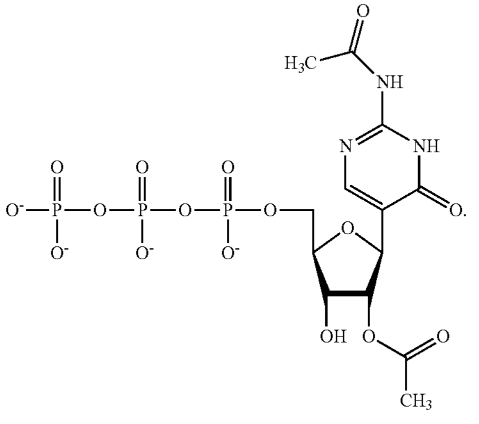

In some embodiments, a polyribonucleotide comprises cytidine residues and about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of cytidine residues in the polyribonucleotide comprise N4-acetylcytidine.

In some embodiments, a polyribonucleotide comprises cytidine residues and at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% of cytidine residues in the polyribonucleotide comprise N4-acetylcytidine.

In some embodiments, a polyribonucleotide comprising a 2'-O-acetylated ribose (e.g., an adenine comprising a 2'-O-acetylated ribose, a guanine comprising a 2'-O-acetylated ribose, a cytosine comprising a 2'-O-acetylated ribose, and/or a uracil comprising a 2'-O-acetylated ribose) further comprises one or more modified ribonucleotides comprising a hydroxymethyl group. In some embodiments, one or more modified ribonucleotides comprises a nucleoside chosen from: an adenosine, a guanosine, a cytidine or a uridine, or any combination thereof. In some embodiments, a nucleoside of a one or more modified ribonucleotides is 5-hydroxymethyluridine, and the modified ribonucleotide has the structure of:

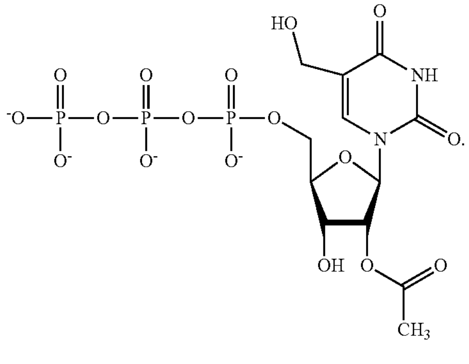

In some embodiments, a polyribonucleotide comprises uridine residues and about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of uridine residues in the polyribonucleotide comprise 5-hydroxymethyluridine.

In some embodiments, a polyribonucleotide comprises uridine residues and at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% of uridine residues in the polyribonucleotide comprise 5-hydroxymethyluridine.

This disclosure also provides methods of making a polyribonucleotide comprising a 2-O-acetylated ribose. In some embodiments, disclosed herein is method of producing a polyribonucleotide comprising a step of incubating an in vitro transcription mixture, wherein the in vitro transcription mixture comprises: (i) a DNA template; (ii) at least one RNA polymerase or a variant or a fragment thereof; and (iii) a plurality of ribonucleotides comprising at least one modified ribonucleotide comprising a 2'-O-acetylated ribose; thereby producing a polyribonucleotide comprising a 2'-O-acetylated ribose.

Also disclosed herein are in vitro transcription mixtures useful in producing a polyribonucleotide comprising a 2'-O-acetylated ribose. In some embodiments, disclosed herein is an in vitro transcription mixture comprising: (i) a DNA template; (ii) at least one RNA polymerase or a variant or a fragment thereof; and (iii) a plurality of ribonucleotides comprising at least one modified ribonucleotide comprising a 2'-O-acetylated ribose.

In some embodiments, a method or an in vitro transcription mixture produces a plurality of polyribonucleotides. In some embodiments, each polyribonucleotide in a plurality of polyribonucleotides comprises a 2'-O-acetylated ribose.

In some embodiments, a polyribonucleotide produced using a method or an in vitro transcription mixture disclosed herein further comprises one or more modifications, e.g., one or more base modifications.

In some embodiments, an RNA polymerase is chosen from: a bacteriophage RNA polymerase, a mitochondrial RNA polymerase, a eukaryotic RNA polymerase, a bacterial RNA polymerase, or any combination thereof. In some embodiments, an RNA polymerase comprises a T7 RNA polymerase, a T3 RNA polymerase, a SP6 RNA polymerase, a viral RNA polymerase, a N4 virion RNA polymerase, or a variant of any of the foregoing.

In some embodiments, a polyribonucleotide produced by a method disclosed herein or for using in an in vitro transcription mixture comprises a polyribonucleotide comprises a coding region.

In some embodiments, a polyribonucleotide produced by a method disclosed herein or for using in an in vitro transcription mixture comprises a polyribonucleotide does not comprise a coding region.

In some embodiments, a polyribonucleotide produced by a method disclosed herein, or using an in vitro transcription mixture comprises a guide RNA, a short hairpin RNA, an siRNA, a microRNA, a long non-coding RNA, or a messenger RNA (mRNA), a circular RNA, or any combination thereof.

In some embodiments, a polyribonucleotide produced by a method disclosed herein or using an in vitro transcription mixture encodes a payload. In some embodiments, a payload comprises one or more target polypeptides.

In some embodiments of a method of producing a ribonucleotide disclosed herein, an incubating step occurs at a temperature of at least 37° C.

In some embodiments of a method of producing a ribonucleotide disclosed herein, an incubating step occurs at a temperature of about 45° C., 46° C., 47° C., 48° C., 49° C., 50° C., 51° C., 52° C., 53° C., 54° C., 55° C., or higher.

In some embodiments of a method of producing a ribonucleotide disclosed herein, an incubating step is performed for at least 1 hour, at least 2 hours, at least 3 hours, at least 4 hours or longer.

Further provided herein are compositions comprising a polyribonucleotide disclosed herein, e.g., a polyribonucleotide made according to a method disclosed herein. In some embodiments, a composition is or comprises a pharmaceutical composition. In some embodiments, a composition is a pharmaceutical composition. In some embodiments, a pharmaceutical composition is or comprises an immunogenic composition. In some embodiments, a pharmaceutical composition is or comprises an antibody therapy. In some embodiments, a pharmaceutical composition is or comprises an immune-modulation therapy. In some embodiments, a pharmaceutical composition is or comprises a vaccine. In some embodiments, a pharmaceutical composition is or comprises a gene therapy. In some embodiments, a pharmaceutical composition is or comprises a chemotherapy. In some embodiments, a pharmaceutical composition is or comprises a protein replacement therapy. In some embodiments, a pharmaceutical composition is or comprises an immunotherapy. In some embodiments, a pharmaceutical composition is or comprises a cell engineering therapy.

In some embodiments, a composition comprises double stranded RNA.

Also provided herein is a method comprising administering a polyribonucleotide disclosed herein, or a composition comprising the same to a cell, tissue, or subject. In some embodiments, a method further comprises determining cell viability of the cell, tissue or subject.

In some embodiments, a cell viability is a measure of the length of time one or more cells of a cell, tissue or subject live. In some embodiments, a cell viability is a measure of a number of cells of a cell, tissue or subject alive at one or more time points. In some embodiments, a cell, tissue or subject to which a polyribonucleotide or a composition comprising the same has been administered exhibits improved cell viability as compared to a reference cell viability. In some embodiments, a reference cell viability is a cell viability of a cell, tissue or subject that has been administered a comparable polyribonucleotide or a composition comprising the same that includes fewer 2'-O-acetylated ribose (e.g., does not include any 2'-O-acetylated ribose).

In some embodiments, a method further comprises comprising determining an immune system response of the cell, tissue or subject to which a polyribonucleotide or a composition comprising the same has been administered. In some embodiments, an immune response comprises an innate immune system response comprising innate immune system induced toxicity. In some embodiments, determining an innate immune system response comprises determining a level of NF-κB, IRF, and/or other inflammatory cytokines in the cell, tissue or subject. In some embodiments, a cell, tissue or subject to which a polyribonucleotide or a composition comprising the same has been administered exhibits a reduced innate immune system response as compared to a reference. In some embodiments, a reference is an innate immune system response of a cell, tissue or subject that has been administered a comparable polyribonucleotide or a composition comprising the same that includes fewer 2'-O-acetylated ribose (e.g., does not include any 2'-O-acetylated ribose).

In some embodiments, a method of administration disclosed herein further comprises determining efficacy of a polyribonucleotide or a composition comprising the same in the cell, tissue or subject to which the polyribonucleotide or a composition comprising the same has been administered. In some embodiments, determining efficacy comprises determining an antibody response or cellular response in the cell, tissue or subject. In some embodiments, a cell, tissue or subject to which a polyribonucleotide or a composition comprising the same has been administered exhibits an increased antibody response or cellular response as compared to a reference. In some embodiments, a reference is an antibody response or cellular response of a cell, tissue or subject that has been administered a comparable polyribonucleotide or a composition comprising the same that includes fewer 2'-O-acetylated ribose (e.g., does not include any 2'-O-acetylated ribose).

In some embodiments, a method comprises administering the polyribonucleotide or a composition comprising the same to the cell, tissue or subject at least two times. In some embodiments, a method comprises administering a polyribonucleotide or a composition comprising the same to the cell, tissue or subject at least 2 times, at least 3 times, at least 4 times, at least 5 times, at least 6 times, at least 7 times, at least 8 times, at least 9 times or at least 10 times. In some embodiments, at least two administrations of a polyribonucleotide or a composition comprising the same to a cell, tissue or subject does not result in reduced efficacy of a polyribonucleotide or a composition comprising the same compared to administration of one dose of a polyribonucleotide or a composition comprising the same.

In some embodiments, a method comprises administering a polyribonucleotide or a composition comprising the same to a cell, tissue or subject at a higher dose compared to an appropriate reference comparator. In some embodiments, a reference comparator comprises a comparable polyribonucleotide that includes fewer 2'-O-acetylated ribose (e.g., does not include any 2'-O-acetylated ribose). In some embodiments, a cell is a mammalian cell, the tissue is a mammalian tissue, or the subject is a mammal.

In some embodiments, a polyribonucleotide disclosed herein is or comprises an RNA oligo.

In some embodiments, a polyribonucleotide disclosed herein comprises a coding region. In some embodiments, a coding region encodes a gene product. In some embodiments, a gene product is or comprises a polypeptide. In some embodiments, a gene product is or comprises a transcript.

In some embodiments, a polyribonucleotide disclosed herein does not comprise a coding region.

In some embodiments, a polyribonucleotide disclosed herein is or comprises a messenger RNA (mRNA).

In some embodiments, a polyribonucleotide disclosed herein is or comprises a gRNA.

In some embodiments, a polyribonucleotide disclosed herein is or comprises an inhibitory RNA.

In some embodiments, a polyribonucleotide disclosed herein is or comprises an miRNA or siRNA.

In some embodiments, a polyribonucleotide disclosed herein is or comprises a long non-coding RNA.

In some embodiments, a polyribonucleotide disclosed herein is or comprises an antisense oligonucleotide.

In some embodiments, a method is a method to stimulate an immune response.

In some embodiments, a method is a vaccination method.

In some embodiments, a method is an antibody therapy method.

In some embodiments, a method is an immune-modulation therapy method.

In some embodiments, a method is a gene therapy method.

In some embodiments, a method comprises delivery of one or more components of a gene therapy such as a gRNA.

In some embodiments, a method is a cell therapy engineering method.

In some embodiments, a method is an immunotherapy method. In some embodiments, an immunotherapy method comprises delivery of an immune-modulation therapy and/or an immune checkpoint therapy.

In some embodiments, a method is a protein replacement therapy method. In some embodiments, a protein replacement therapy method comprises delivery of an enzyme replacement therapy.

In some embodiments, a method is a chemotherapeutic method.

Also provided herein is a method of vaccination comprising administering one or more polyribonucleotides disclosed herein or a composition comprising the same to a cell, tissue or subject.

Disclosed herein is a method of immunotherapy comprising administering one or more polyribonucleotides disclosed herein or a composition comprising the same to a cell, tissue or subject.

Provided herein is a method of providing an antibody therapy comprising administering one or more polyribonucleotides disclosed herein or a composition comprising the same to a cell, tissue or subject. In some embodiments, an antibody therapy comprises an antibody, a fragment, a variant, or a fusion thereof. In some embodiments, an antibody therapy comprises a fragment comprising an antigen-recognition domain (e.g., an scFv, a Fab or other fragments), or an intact antibody, or a polypeptide comprising antigen binding specificity fused to an Fc. In some embodiments, an antibody therapy comprises a bispecific, a multispecific, a heterodimer, a Crossmab, a DVD-Ig, a 2 in 1 IgG, an IgG-sc-FV, an scFv-scFv, a BiTE, a DART, a diabody, a Fab-scFv fusion, a Fab-Fab fusion, a tandem antibody, or any other art recognized antibody formats.

Provided herein is a method of providing an immune-modulation therapy comprising administering one or more polyribonucleotides disclosed herein or a composition comprising the same to a cell, tissue or subject. In some embodiments, an immune-modulation therapy comprises: a cytokine or a variant or fragment thereof, a chemokine or a variant or fragment thereof, a T-cell modulator, an NK cell modulator, a B cell modulator, a myeloid cell modulator, a modulator of any other immune cell, or any combination thereof. In some embodiments, an immune-modulation therapy comprises a chimeric antigen receptor (CAR) therapy. In some embodiments, an immune-modulation therapy, comprises an engineered T cell receptor (TCR) therapy.

Provided herein is a method of gene therapy comprising administering one or more polyribonucleotides disclosed herein or a composition comprising the same to a cell, tissue or subject.

This disclosed provides, a method of protein replacement therapy, comprising administering one or more polyribonucleotides disclosed herein or a composition comprising the same to a cell, tissue or subject.

Also disclosed herein is a method of cell engineering therapy, comprising administering one or more polyribonucleotides disclosed herein or a composition comprising the same to a cell, tissue or subject.

This disclosed provides, a method of obtaining a lower level of immunogenicity in a subject who has received a polyribonucleotide comprising a modified ribonucleotide, or a composition comprising the same, as compared with a subject who has received a comparable unmodified polyribonucleotide. In some embodiments, a method comprises administering a polyribonucleotide comprising a modified ribonucleotide or a composition comprising the same to a subject.

In some embodiments of any of the methods, uses or compositions disclosed herein, a polyribonucleotide comprising a modified ribonucleotide does not comprise a 5' cap, e.g., a 5'-5' triphosphate linked guanosine. In some embodiments, a polyribonucleotide comprising a modified ribonucleotide comprises a 5' phosphate and/or a hydroxyl group at the 5' terminus of the polyribonucleotide.

In some embodiments of any of the methods, uses or compositions disclosed herein, a polyribonucleotide comprising a modified ribonucleotide comprises a 5' cap, e.g., a 5'-5' triphosphate linked guanosine.

In some embodiments, a subject who has received a polyribonucleotide comprising a modified ribonucleotide or a composition comprising the same, and a subject who has received a comparable unmodified polyribonucleotide are the same subject.

In some embodiments, a subject who has received a polyribonucleotide comprising a modified ribonucleotide or a composition comprising the same, and a subject who has received a comparable unmodified polyribonucleotide are different subjects.

Provided herein is a method of manufacturing an RNA composition comprising introducing at least one modified ribonucleotide disclosed herein into a polyribonucleotide. In some embodiments, a method does not comprise removing double-stranded RNA from the RNA composition.

Disclosed herein is a cell comprising a polyribonucleotide disclosed herein or a composition comprising the same.

Also disclosed herein is use of a modified ribonucleotide disclosed herein in the production of a polyribonucleotide.

This disclosure provides use of a polyribonucleotide disclosed herein or a composition comprising the same in the preparation of a medicament for stimulating an immune response.

Provided herein is use of a polyribonucleotide disclosed herein or a composition comprising the same in the preparation of a medicament for use as a vaccine.

This disclosure provides use of a polyribonucleotide disclosed herein or a composition comprising the same in the preparation of a medicament for use as an immunotherapy.

Provided herein is use of a polyribonucleotide disclosed herein or a composition comprising the same in the preparation of a medicament for use as an antibody therapy.

Provided herein is use of a polyribonucleotide disclosed herein or a composition comprising the same in the preparation of a medicament for use as an immune-modulation therapy.

Provided herein is use of a polyribonucleotide disclosed herein or a composition comprising the same in the preparation of a medicament for use as a gene therapy.

This disclosure provides use of a polyribonucleotide disclosed herein or a composition comprising the same in the preparation of a medicament for use as a protein replacement therapy.

Provided herein is use of a polyribonucleotide disclosed herein or a composition comprising the same in the preparation of a medicament for use as a cell engineering therapy.

This disclosure provides use of a polyribonucleotide disclosed herein or a composition comprising the same in the preparation of a medicament for use as a chemotherapy.

This disclosure provides use of a polyribonucleotide disclosed herein or a composition comprising the same in the preparation of a medicament for stimulating an immune response.

Provided herein is a composition comprising a polyribonucleotide disclosed herein for use as a vaccine.

This disclosure provides a composition comprising a polyribonucleotide disclosed herein for use as an immunotherapy.

Provided herein is a composition comprising a polyribonucleotide disclosed herein for use as an antibody therapy.

Provided herein is a composition comprising a polyribonucleotide disclosed herein for use as an immune-modulation therapy.

Provided herein is a composition comprising a polyribonucleotide disclosed herein for use as a gene therapy.

This disclosure a composition comprising a polyribonucleotide disclosed herein for use as a protein replacement therapy.

Provided herein is a composition comprising a polyribonucleotide disclosed herein for use as a cell engineering therapy.

This disclosure provides a composition comprising a polyribonucleotide disclosed herein for use as a chemotherapy.

In some embodiments of any of the uses or methods provided herein, a polyribonucleotide or a composition comprising the same is administered to a cell, tissue or subject.

In some embodiments of any of the uses or methods provided herein a cell is a mammalian cell, a tissue is a mammalian tissue, or a subject is a mammal. In some embodiments, a mammal is a human.

CERTAIN DEFINITIONS

Figure 1A:
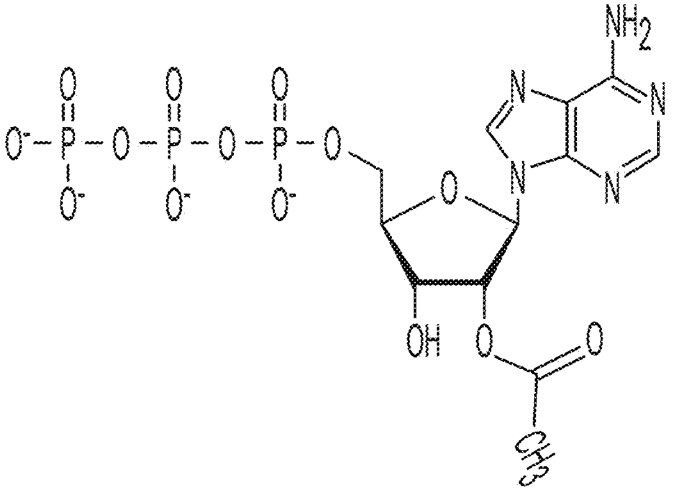
FIGS. 1A-1D provide structures of natural base 2'-O-acetyl ribonucleotide analogs.
Figure 1B:
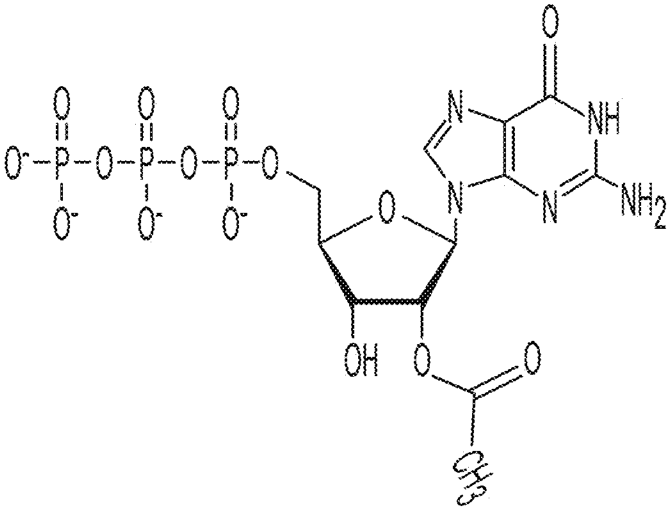
Figure 1C:
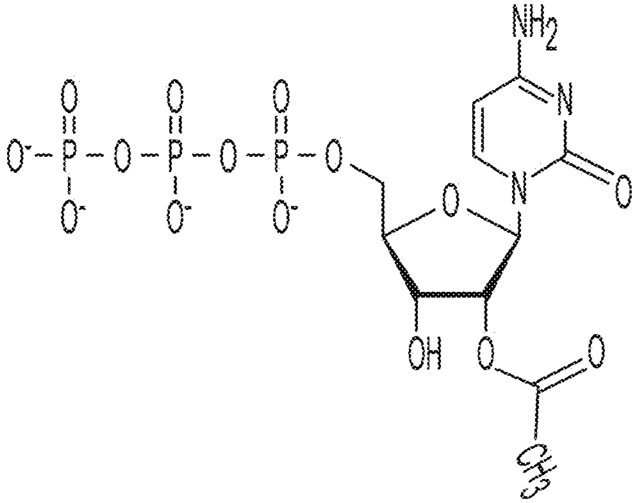
Figure 1D:
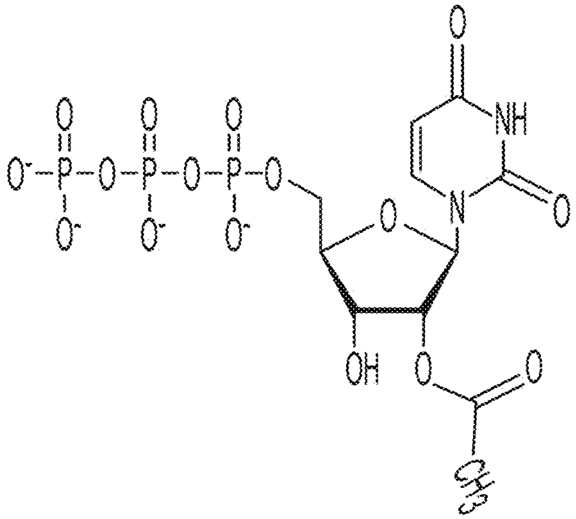

About or approximately: As used herein, the terms “about” and “approximately,” when used herein in reference to a value, refers to a value that is similar, in context to the referenced value. In general, those skilled in the art, familiar with the context, will appreciate the relevant degree of variance encompassed by “about” or “approximately” in that context. For example, in some embodiments, the term "about" or "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administering: As used herein, the term "administering" or "administration" typically refers to administration of a composition to a subject to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Antigen: The term "antigen", as used herein, refers to an agent that elicits an immune response; and/or (ii) an agent that binds to a T cell receptor (e.g., when presented by an MHC molecule) or to an antibody. In some embodiments, an antigen elicits a humoral response (e.g., including production of antigen-specific antibodies); in some embodiments, an antigen elicits a cellular response (e.g., involving T-cells whose receptors specifically interact with the antigen). In some embodiments, an antigen comprises at least one epitope of a target protein. In some embodiments, an epitope may be a linear epitope. In some embodiments, an epitope may be a conformational epitope. In some embodiments, an antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments other than a biologic polymer [e.g., other than a nucleic acid or amino acid polymer) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is a recombinant antigen.

Delivery contacting: As used interchangeably herein, the term "delivery," "delivering," or "contacting" refers to introduction of a fusion polynucleotide (e.g., as described herein) or a fusion polypeptide (e.g., as described herein) into a target cell. A target cell can be cultured in vitro or ex vivo or be present in a subject (in vivo). Methods of introducing a fusion polynucleotide (e.g., as described herein) or a fusion polypeptide (e.g., as described herein) into a target cell can vary with in vitro, ex vivo, or in vivo applications. In some embodiments, a fusion polynucleotide (e.g., as described herein) or a fusion polypeptide (e.g., as described herein) can be introduced into a target cell in a cell culture by in vitro transfection. In some embodiments, a fusion polynucleotide (e.g., as described herein) or a fusion polypeptide (e.g., as described herein) can be introduced into a target cell via delivery vehicles (e.g., nanoparticles, liposomes, and/or complexation with a cell-penetrating agent). In some embodiments, a fusion polynucleotide (e.g., as described herein) or a fusion polypeptide (e.g., as described herein) can be introduced into a target cell in a subject by administering a fusion polynucleotide (e.g., as described herein) or a fusion polypeptide (e.g., as described herein) to a subject.

Expression: As used herein, the term "expression" of a nucleic acid sequence refers to the generation of any gene product from the nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, etc); (3) translation of an RNA into a polypeptide or protein; and/or (4) post-translational modification of a polypeptide or protein.

Functional: As used herein, the term "functional" is used to refer to a form or fragment of an entity that exhibits a particular property and/or activity.

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a fragment comprises a polynucleotide fragment. In some embodiments, a fragment comprises a polypeptide fragment. In some embodiments, a polynucleotide fragment or a polypeptide fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polynucleotide or whole polypeptide. In some embodiments, a polynucleotide fragment or a polypeptide fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polynucleotide or whole polypeptide. The whole polypeptide or whole polynucleotide may in some embodiments be referred to as the "parent" of the polynucleotide fragment or polypeptide fragment.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Nucleic acid Oligonucleotide Polynucleotide: As used herein, the terms "nucleic acid" and "polynucleotide" and "oligonucleotide" are used interchangeably, and refer to a polymer of 3 nucleotides or more. In some embodiments, a nucleic acid comprises DNA. In some embodiments, a nucleic acid comprises RNA. In some embodiments, a nucleic acid comprises messenger RNA (mRNA). In some embodiments, a nucleic acid is single stranded. In some embodiments, a nucleic acid is double stranded. In some embodiments, a nucleic acid comprises both single and double stranded portions. In some embodiments, a nucleic acid comprises a backbone that comprises one or more phosphodiester linkages. In some embodiments, a nucleic acid comprises a backbone that comprises both phosphodiester and non-phosphodiester linkages. For example, in some embodiments, a nucleic acid may comprise a backbone that comprises one or more phosphorothioate or 5'-N-phosphoramidite linkages and/or one or more peptide bonds, e.g., as in a "peptide nucleic acid". In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises on or more, or all, non-natural residues. In some embodiments, a non-natural residue comprises a nucleoside analog (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 6-O-methylguanine, 2-thiocytidine, methylated bases, intercalated bases, and combinations thereof). In some embodiments, a non-natural residue comprises one or more modified sugars (e.g., 2'-fluororibose, ribose, 2'-deoxyribose, arabinose, and hexose) as compared to those in natural residues. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, or 20,000 or more residues or nucleotides long. When a number of nucleotides is used as an indication of size, e.g., of a fusion polynucleotide, a certain number of nucleotides refers to the number of nucleotides on a single strand, e.g., of a fusion polynucleotide.

Polypeptide: The term "polypeptide", as used herein, generally has its art-recognized meaning of a polymer of at least three amino acids or more. Those of ordinary skill in the art will appreciate that the term "polypeptide" is intended to be sufficiently general as to encompass not only polypeptides having a complete sequence recited herein, but also to encompass polypeptides that represent functional, biologically active, or characteristic fragments, portions or domains (e.g., fragments, portions, or domains retaining at least one activity) of such complete polypeptides. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, polypeptides may comprise natural amino acids, non-natural amino acids, synthetic amino acids, and combinations thereof.

Polyribonucleotide: As used herein, the term "polyribonucleotide" refers to a polymer of 3 ribonucleotides or more. In some embodiments, a polyribonucleotide is single stranded. In some embodiments, a polyribonucleotide is double stranded. In some embodiments, a polyribonucleotide comprises both single and double stranded portions. In some embodiments, a polyribonucleotide can comprise a backbone structure as described in the definition of "Nucleic acid Oligonucleotide" above. A polyribonucleotide can include a coding region which encodes a gene product, or a polyribonucleotide may not include a coding region. Additionally, a polyribonucleotide can be a regulatory RNA (e.g., siRNA, microRNA, etc.), or a messenger RNA (mRNA) oligonucleotide. In some embodiments where a polyribonucleotide is a polyribonucleotide comprising a coding region, e.g., an mRNA oligonucleotide, a polyribonucleotide typically comprises at its 3' end a poly(A) region. In some embodiments where a polyribonucleotide is a polyribonucleotide comprising a coding region, e.g., an mRNA oligonucleotide, a polyribonucleotide typically comprises at its 5' end an art-recognized cap structure, e.g., for recognizing and attachment of a polyribonucleotide, e.g., an mRNA, to a ribosome to initiate translation. In some embodiments, where a polyribonucleotide does not comprise a coding region, said polyribonucleotide may comprise long non-coding RNAS (lncRNA), microRNAs, siRNAs, piRNAs, snoRNAs, snRNAs, exRNAs, scaRNAs rRNA, tRNAs, or combinations thereof. In some embodiments, a polyribonucleotide comprises an RNA oligonucleotide. When a number of ribonucleotides is used as an indication of size, e.g., for a polyribonucleotide, a certain number of nucleotides refers to the number of ribonucleotides on a single strand.

Subject: As used herein, the term "subject" refers an organism, typically a mammal (e.g., a human). In some embodiments, a subject is suffering from a disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide.

Standard techniques may be used for recombinant DNA, oligonucleotide synthesis, e.g., RNA synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2nd ed., Cold Spring Harbor Laboratory Press, Cold Spring Harbor, N.Y. (1989)), which is incorporated herein by reference for any purpose.

DETAILED DESCRIPTION OF CERTAIN EMBODIMENTS

RNA, e.g., messenger RNA (mRNA), has enormous potential to provide life changing therapies for diseases that were previously determined to be untreatable. However, in the broader picture of therapeutic modalities, RNA technology is still in its early development. Much progress has been made in the field to get the technology to its present form, but to truly unlock its full capabilities further improvements to the platform still have to be made.

One of the unsolved issues is that RNA is an inherently unstable molecule. The use of pseudouridine derivatives instead of uridine has provided some improvement on this front as a result of proposed mechanisms of increased base stacking and hydrogen bonding (Hudson, Bloomingdale, & Znosko, RNA 2013). However, in its current commercial form, its stability and activity is still very short lived (Anand & Stahel, Patient Saf Surg 2021). Indeed, the transient nature of RNA is largely seen as a benefit of the platform, which contributes to its safety as a therapeutic modality. However, a separate perspective that is contrary to this perceived benefit, is that in order for RNA to be used for indications beyond vaccination, it's critical that the half-life of therapeutic RNA is extended at least somewhat beyond what it is currently. This is because indications like cancer therapy and enzyme replacement require expression, e.g., for a certain period of time, of the therapeutic protein of interest for optimal benefit to the patient. A therapeutic that loses activity, and therefore its benefit to the patient, in a matter of hours, requires frequent dosing and compounding cost. This is likely to become intolerable and unsustainable for the average patient and potentially limits the use of the therapy. In some embodiments, extending RNA half-life does not mean making it perpetually active. Rather, it is a matter of increasing the half-life of an RNA such that the dosing frequency required can be more tenable. It is also important to note that the optimal RNA half-life for a given indication may be different from another one, but the underlying theme is that some extension is required.

Without wishing to be bound by theory, in some embodiments, the instability of RNA, even base modified RNA, can be traced, e.g., to the reactivity of the hydroxyl group on carbon 2 of the ribose of a ribonucleotide. When RNA is exposed to conditions of elevated pH, high temperature, divalent cations, or some combination thereof, the oxygen atom is able to initiate nucleophilic attack on the phosphate backbone of the RNA strand. It is the same hydroxyl group that is targeted by ubiquitous RNase enzymes that quickly degrade any RNA (Brown & Pasloske, Methods in Enzymology 2001). The lack of this hydroxyl group is what provides DNA its exceptional stability in comparison to RNA. Accordingly, reducing the reactivity of this hydroxyl group should improve the stability of RNA. This exact phenomenon is observed when 2-O-methyl nucleoside triphosphates (NTPs) are used in RNA, which provide increased thermal stability to RNA duplexes and resistance to nuclease (Assi, et al., NAR 2020). However, the issue with using 2-O-methyl and other currently available 2-O modified NTPs is that they can only be incorporated into short RNA oligonucleotides by chemical synthesis since only error-prone RNA polymerases are able to use 2-O-methyl NTPs as a substrate due to abolishment of key hydrogen bonding interactions (Meyer, et al., NAR 2015). The size limit of RNAs made by chemical synthesis using 2-O-methyl NTPs also means that gene-length RNA is not currently possible by this method. When considering RNA therapeutics, these issues are all superseded by the fact that 2-O-methyl modification throughout an RNA transcript inhibits its translation due to steric hindrance of critical ribosomal RNA residues and codon-anticodon interactions (Choi, et al., Nat Struct Mol Biol 2018).

Given the knowledge in the field, it was hypothesized that an ideal 2-O-modification for RNA applications would be a functional group that can maintain crucial hydrogen bonding interactions necessary for transcription, translation, and duplex formation, while simultaneously having reduced reactivity that would otherwise promote RNA autohydrolysis and nuclease degradation. Based on principles of biochemistry, it was further hypothesized that 2'-O-acetylated NTPs (FIGS. 1A-1D), could provide such a profile. Accordingly, the present disclosure provides technologies related to 2'-O-acetylated nucleotides in which a hydroxyl group on carbon 2 of a ribose is acetylated (2'-O-acetylated ribose). Technologies provided in the present disclosure include: modified ribonucleotides comprising a 2'-O-acetylated ribose, polyribonucleotides comprising modified ribonucleotides comprising a 2'-O-acetylated ribose, compositions comprising such modified ribonucleotides and/or polyribonucleotides, as well as methods of making such polyribonucleotides, and methods of using such polyribonucleotides for a variety of applications.

Tyrosine (Tyr) 639 Of T7 RNA polymerase appears to be a major discriminating amino acid residue that governs whether T7 RNA polymerase can use a nucleotide as substrate (Mäkinen, et al., Nature Communications 2021). It was hypothesized that the carbonyl oxygen of the acetyl group could act as a hydrogen bond acceptor to maintain that critical interaction with Tyr639 and allow use of 2'-O-acetyl nucleotides with wild-type bacteriophage RNA polymerases like T7 RNA polymerase. This would be in contrast to 2-O-methyl NTPs, where the methyl group prevents hydrogen bonding between the 2' oxygen and Tyr639 and therefore prevents use of 2-O-methyl NTPs for in vitro transcription.

An earlier study found that RNA that has been chemically acetylated with acetic anhydride after transcription is translationally active in a wheat embryo cell-free translational system (Ovodov & Alakhov, FEBS 1990). The authors in that study were unable to confirm specific acetylation of the 2-OH and only claimed that up to 75% of the 2-OH groups in the RNA was acetylated. Ovodov and Alakhov also used a cell free translation system; there was no report in their study on whether the chemically acetylated RNA can be introduced into living cells and/or translated by the intracellular ribosomal machinery. Thus, the utility of the chemically acetylated RNA of Ovodov and Alakhov was limited to an artificial cell-free translation system.

Among other things disclosed herein is the novel discovery that 2'-O-acetylated nucleotide triphosphates can be accepted by RNA polymerase as a substrate for in vitro transcription of RNA. This disclosure also provides the insight that RNA polymerase can use 2'-O-acetylated nucleotide triphosphates to produce fully acetylated RNA. In some embodiments, RNA produced by a method disclosed herein is 100% 2'-O-acetylated except for a cap structure, which does not comprise a 2'-O-acetylated ribose, e.g., due to co-transcriptional capping. In some embodiments, RNA produced by a method disclosed herein is 100% 2'-O-acetylated including a cap structure that comprises 2'-O-acetylation. This discovery of a novel modified nucleotide that can be used to generate RNA using in vitro transcription reactions, allows for the use of 2'-O-acetylated ribose in the manufacturing of RNAs for a variety of applications, including therapeutic applications, research applications, diagnostic applications, agricultural applications, and any other suitable applications.

Furthermore, the present disclosure is also the first to demonstrate the surprising finding that RNA comprising 2'-O-acetylated ribose can be translated by the intracellular ribosomal machinery of a cell. FIGS. 2-5 herein provide exemplary polypeptide expression from 2-O-acetylated RNAs. Also provided herein is the insight that the yield of 2'-O-acetylated RNAs is comparable to RNAs without this modification. Table 1 provides exemplary yields that can be obtained with 2'-O-acetylated RNAs.

Figure 4:
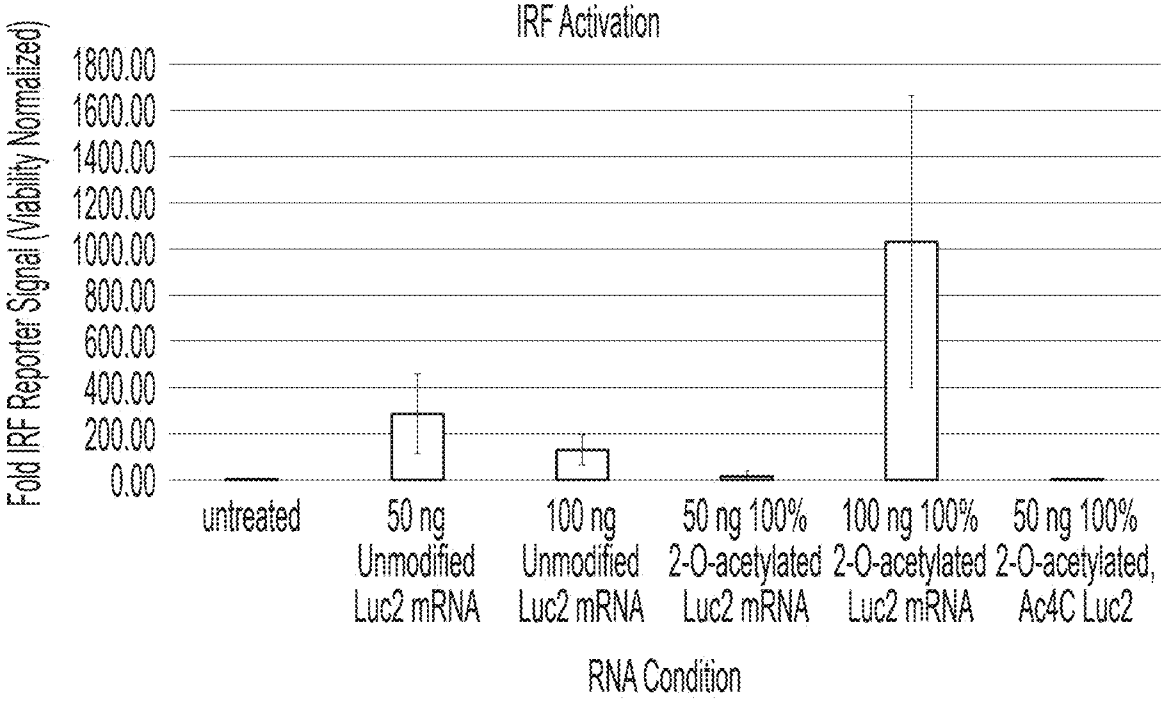
FIG. 4 is a graph depicting IRF reporter activation by dose of RNA synthesized with indicated nucleotide composition.
Figure 5:
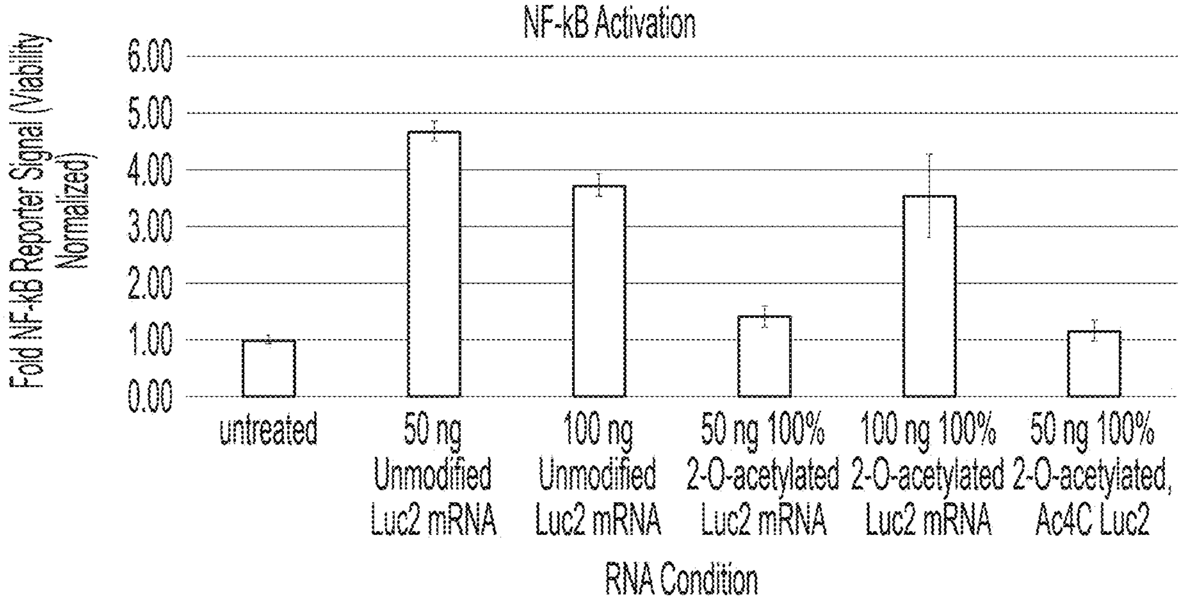
FIG. 5 is a graph depicting NF-κB reporter activation by dose of RNA synthesized with indicated nucleotide composition.

Furthermore, this disclosure provides the insight that polyribonucleotides comprising 2'-O-acetylated ribose, such as those produced with an in vitro transcription reaction, are functional and have desired properties such as reduced immunogenicity, evasion of an innate immune system activation, improved viability of cells into which said polyribonucleotide is introduced, increased expression of a payload in cells into which said polyribonucleotide is introduced, and/or increase persistence of polyribonucleotides. In some embodiments, evasion of an innate immune system comprises a reduction in activation of NFkb or an NFkb pathway, IRF or an IRF pathway, and/or other inflammatory cytokines in a cell, tissue or organism into which said polyribonucleotide is introduced. In some embodiments, evasion of an innate immune system comprises a reduction in detection of uncapped RNA in a cell, tissue or organism into which said polyribonucleotide is introduced. In some embodiments, in vitro transcribed RNAs containing 2'-O-acetylated ribose can improve the efficacy of RNA therapeutics due to a reduction in undesired innate immune response. In some embodiments, reduction of an undesired innate immune response with RNAs containing 2'-O-acetylated ribose can be further enhanced (e.g., undesired innate immune response can be further reduced) by including one or more base modifications in the RNA. For example, FIGS. 4 and 5 show reduced innate immune activation with polyribonucleotides comprising 2'-O-acetylated ribose in combination with an exemplary modified cytosine base (N4-acetyl-cytidine; Ac4C). This data supports the use of including one or more base modifications to polyribonucleotides comprising 2'-O-acetylated ribose to reduce innate immune activation while increasing payload expression and/or persistence.

Also provided herein is the insight that the expression level of an RNA can be modulated by including 2'-O-acetylated ribose in the RNA. For example, FIG. 2 herein provides an exemplary increase in expression of a payload with a polyribonucleotide comprising a 2'-O-acetylated ribose as compared to a polyribonucleotide that does not have 2'-O-acetylated ribose.

Further provided herein is the insight that polyribonucleotides having 2'-O-acetylated ribose can increase persistence of a polyribonucleotide. For example, FIGS. 62A-62B herein provide exemplary data showing comparable gene expression from LNP delivered 2-O acetylated as compared with LNP delivered N1-methylpseudouridine modified polyribonucleotide. This observation when considered with the increased immunogenicity seen with 2-O ribose acetylated polyribonucleotides without any additional modifications (Example 1, FIGS. 4 and 5), suggests that polyribonucleotides having 2'-O-acetylated ribose have increased persistence likely due to increased resistance to nuclease degradation.

Accordingly, provided herein is the insight that using polyribonucleotides comprising 2'-O-acetylated ribose alone or in combination with one or more base modifications can be useful in applications (e.g., therapeutic applications) in which increased persistence (e.g., increased nuclease resistance) of a polyribonucleotide is desired. Without wishing to be bound by any particular theory, polyribonucleotides having increased persistence can be achieved by combining reduced immunogenicity from a base modification (e.g., Ac4C, 5hmU, N1-methylpseudouridine, etc.) and nuclease resistance from a ribosome compatible backbone modification (e.g., 2-O ribose acetylation as described herein).

In some embodiments, provided methods can be useful for enhancing persistence or uptake of a polyribonucleotide comprising 2'-O-acetylated ribose, in a target cell. In some embodiments, persistence or uptake of a polyribonucleotide comprising 2'-O-acetylated ribose in a target cell is enhanced by at least 30% or more, as compared to the persistence or uptake of an otherwise similar polyribonucleotide without 2'-O-acetylated ribose or with lesser 2'-O-acetylated ribose. In some embodiments, persistence or uptake of a polyribonucleotide comprising 2'-O-acetylated ribose in a target cell is enhanced by at least 30% or more, as compared to the persistence or uptake of an otherwise similar polyribonucleotide without 2'-O-acetylated ribose or with lesser 2'-O-acetylated ribose.

Figure 62A:
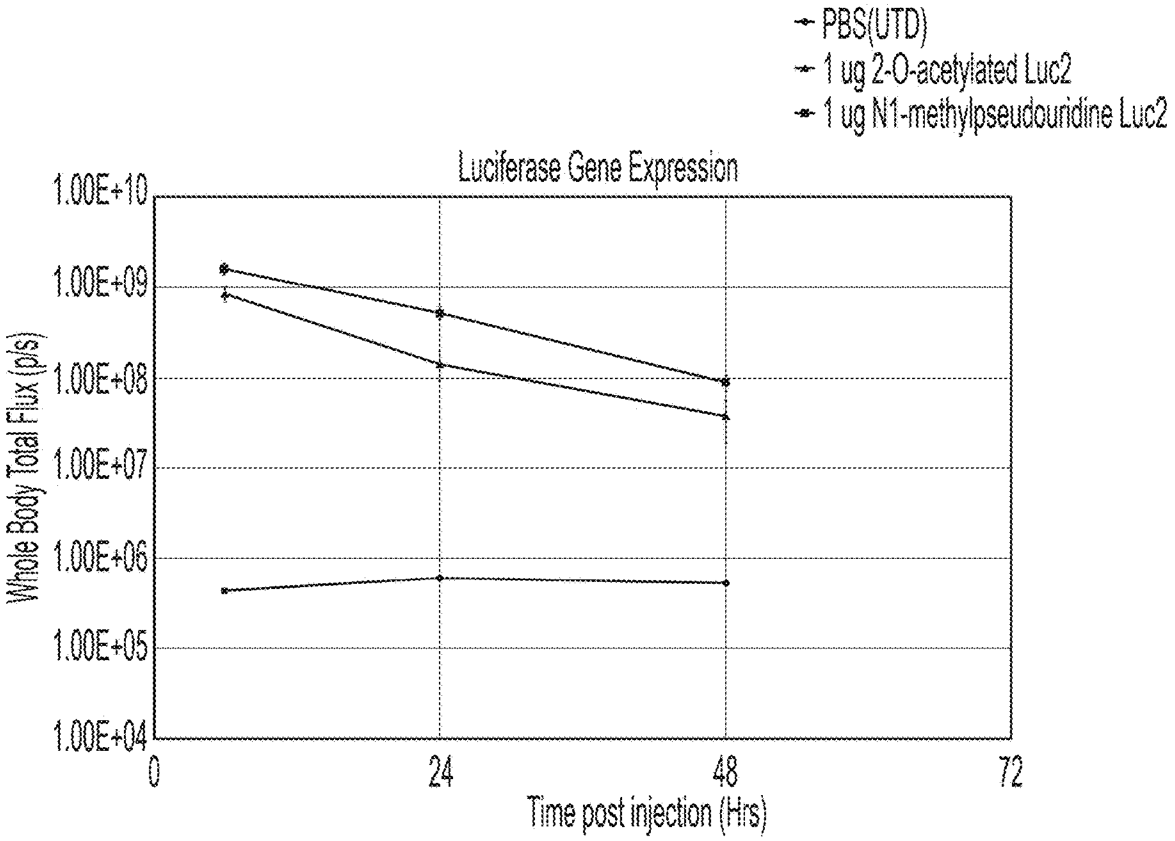
FIGS. 62A-62B are graphs showing in vivo luciferase gene expression from LNP delivered 2-O acetylated RNA or LNP delivered N1-methylpseudouridine modified RNA. Luciferase gene expression was measured in all animals at 6 hours, 24 hours, and 48 hours after administration of LNPs.
Figure 62B:
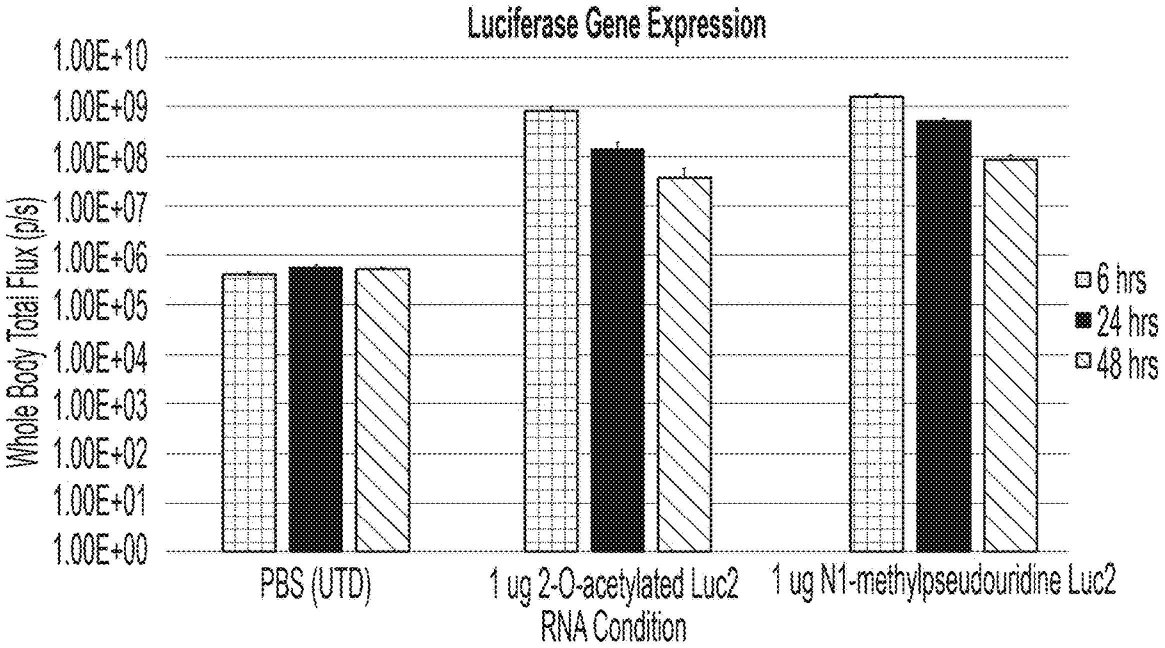

As shown in FIGS. 62A-62B, this disclosure further provides that 2'-O-acetylated polyribonucleotides can be delivered in vivo and by LNPs. Accordingly, provided herein is the insight that 2'-O-acetylated polyribonucleotides can be delivered with delivery vehicles such as LNPs for delivering a polyribonucleotide to a cell, tissue or subject, for treating a disease or disorder, and/or for ameliorating a symptom of a disease or disorder.

In some embodiments, a payload is or comprises a polypeptide encoded by a polyribonucleotide comprising a modified ribonucleotide.

In some embodiments, a payload is or comprises an RNA situated in a polyribonucleotide comprising a modified ribonucleotide.

In some embodiments, use of a polyribonucleotide comprising 2'-O-acetylated ribose allows for improved efficacy of RNA therapeutics comprising the same and/or better tolerability in a subject administered the same.

2'-O-Acetylated Nucleotides

Among other things, provided herein are polyribonucleotides comprising one or more modified ribonucleotides comprising a ribose moiety comprising an acetyl group instead of a hydroxyl group. In some embodiments, a modified ribonucleotide comprises a 2'-O-acetylated ribose. In some embodiments, a modified ribonucleotide comprising a 2'-O-acetylated ribose comprises a 5' monophosphate, a 5' diphosphate or a 5' triphosphate. In some embodiments, a modified ribonucleotide comprising a 2'-O-acetylated ribose comprises a nucleobase chosen from: adenine or a modified version thereof, a guanine or a modified version thereof, a cytosine or a modified version thereof, or a uracil or a modified version thereof.

In some embodiments, a modified ribonucleotide has a structure of:

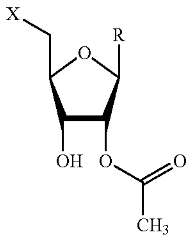

(a) wherein X is a 5' monophosphate, a 5' diphosphate, or a 5' triphosphate; and (b) wherein R is a nucleobase chosen from: adenine or a modified version thereof, a guanine or a modified version thereof, a cytosine or a modified version thereof, or a uracil or a modified version thereof.

In some embodiments, a modified ribonucleotide comprising a 2'-O-acetylated ribose has a 5' triphosphate and a structure of:

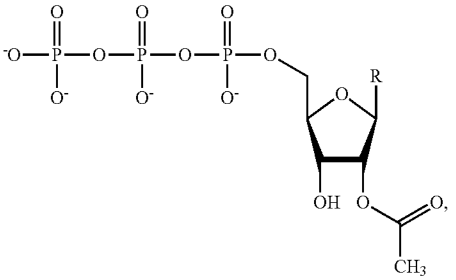

wherein R is a nucleobase chosen from: adenine (e.g., an unmodified or modified adenine), guanine (e.g., an unmodified or modified guanine), cytosine (e.g., an unmodified or modified cytosine), or uracil (e.g., an unmodified or modified uracil).

In some embodiments, a modified ribonucleotide comprising a 2'-O-acetylated ribose comprise an adenine and a 5' monophosphate, a 5' diphosphate or a 5' triphosphate. In some embodiments, a modified ribonucleotide has a structure of:

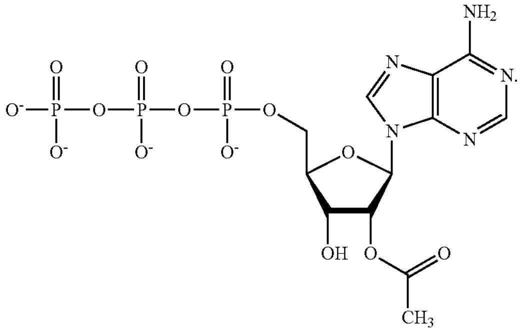

In some embodiments, a modified ribonucleotide comprising a 2'-O-acetylated ribose comprises a guanine and a 5' monophosphate, a 5' diphosphate or a 5' triphosphate. In some embodiments, a modified ribonucleotide has a structure of:

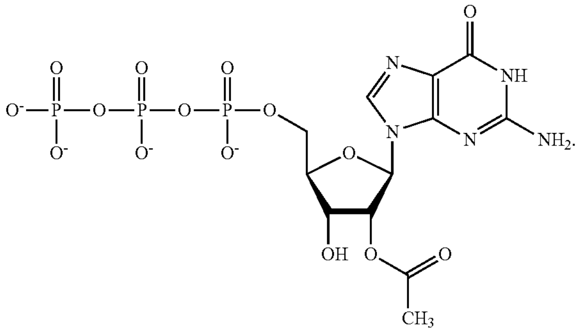

In some embodiments, a modified ribonucleotide comprising a 2'-O-acetylated ribose comprises a cytosine and a 5' monophosphate, a 5' diphosphate or a 5' triphosphate. In some embodiments, a modified ribonucleotide has a structure of:

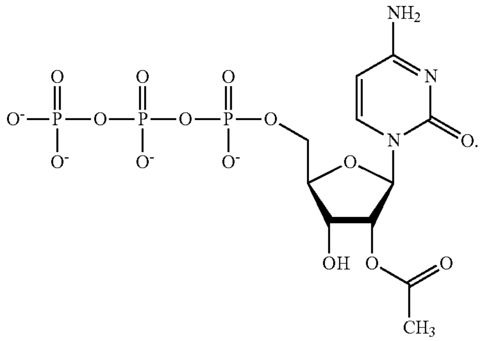

In some embodiments, a modified ribonucleotide comprising a 2'-O-acetylated ribose comprises a uracil, and a 5' monophosphate, a 5' diphosphate or a 5' triphosphate. In some embodiments, a modified ribonucleotide has a structure of:

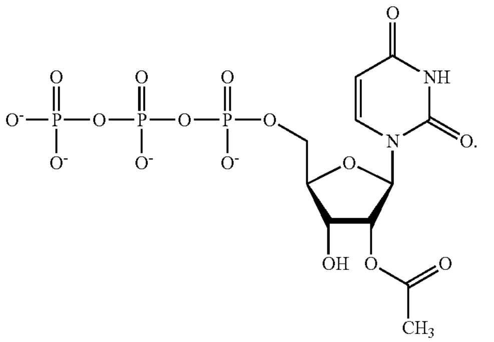

In some embodiments, a modified ribonucleotide comprising a 2'-O-acetylated ribose comprises an N4-acetylcytidine and a 5' monophosphate, a 5' diphosphate or a 5' triphosphate. In some embodiments, a modified ribonucleotide has a structure of:

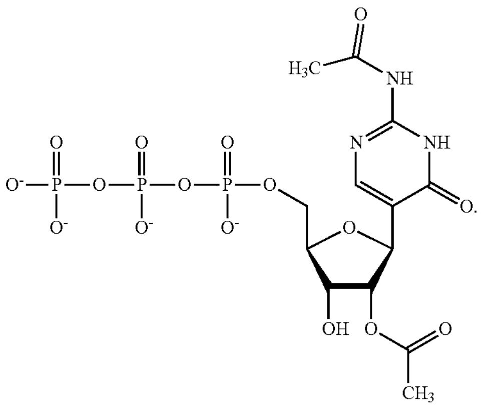

In some embodiments, a modified ribonucleotide comprising a 2'-O-acetylated ribose comprises a 5-hydroxymethyluridine and a 5' monophosphate, a 5' diphosphate or a 5' triphosphate. In some embodiments, a modified ribonucleotide has a structure of:

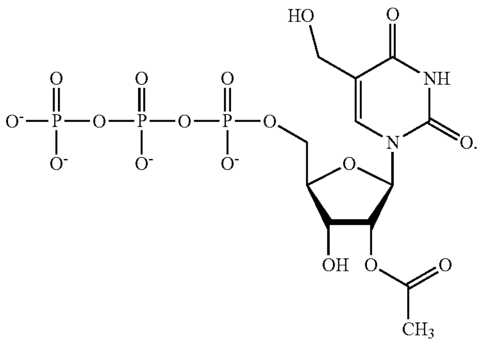

In some embodiments, a modified ribonucleotide comprising a 2'-O-acetylated ribose comprises an N1-methylpseudouridine and a 5' monophosphate, a 5' diphosphate or a 5' triphosphate. In some embodiments, a modified ribonucleotide has a structure of:

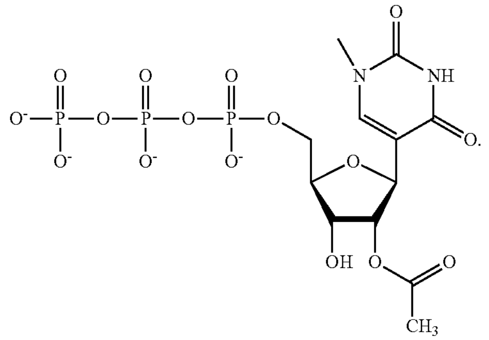

Also provided herein are polyribonucleotides comprising one or more modified ribonucleotides, e.g., a nucleotide comprising a 2'-O-acetylated ribose. In some embodiments, a nucleotide comprises a modified nucleotide or an unmodified nucleotide, e.g., as described herein.

In some embodiments, at least 5%, at least 10%, at least 15%, at least 20%, at least 25%, at least 30%, at least 35%, at least about 40%, at least 45%, at least 50%, at least 55%, at least 60%, at least 65%, at least 70%, at least 75%, at least 80%, at least 85%, at least 90%, at least 95%, or at least 99% ribose moieties in a polyribonucleotide are acetylated (2'-O-acetylated).

In some embodiments, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of ribose moieties in a polyribonucleotide are acetylated (2'-O-acetylated).

In some embodiments, 100% ribose moieties in a polyribonucleotide are acetylated (2'-O-acetylated).

In some embodiments, about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of ribose moieties in a polyribonucleotide are acetylated (2'-O-acetylated).

In some embodiments, about 76% to about 100%, about 77% to about 100%, about 78% to about 100%, about 79% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, about 99% to about 100%, of ribose moieties in a polyribonucleotide are acetylated (2'-O-acetylated).

In some embodiments, about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of ribose moieties in a polyribonucleotide are acetylated (2'-O-acetylated).

In some embodiments, about 76% to about 99%, about 76% to about 98%, about 76% to about 97%, about 76% to about 96%, about 76% to about 95%, about 76% to about 94%, about 76% to about 93%, about 76% to about 92%, about 76% to about 91%, about 76% to about 90%, about 76% to about 89%, about 76% to about 88%, about 76% to about 87%, about 76% to about 86%, about 76% to about 85%, about 76% to about 84%, about 76% to about 83%, about 76% to about 82%, about 76% to about 81%, about 76% to about 80%, about 76% to about 79%, about 76% to about 78%, about 76% to about 77%, of ribose moieties in a polyribonucleotide are acetylated (2'-O-acetylated).

In some embodiments, a polyribonucleotide comprises a cap structure and the cap structure does not comprise a 2'-O-acetylated ribose.

In some embodiments, a polyribonucleotide is fully 2'-O-acetylated (100% ribose moieties are 2'-O-acetylated) except for a cap structure. In some embodiments, a cap structure of a polyribonucleotide comprises a hydroxyl group on carbon 2 of a ribose.

In some embodiments, a polyribonucleotide is less than 100% 2'-O-acetylated (less than 100% ribose moieties are 2'-O-acetylated) and includes a cap structure that does not comprise a 2'-O-acetylated ribose. In some embodiments, a cap structure of a polyribonucleotide comprises a hydroxyl group on carbon 2 of a ribose.

In some embodiments, a polyribonucleotide is at least 5% 2'-O-acetylated (at least 5% ribose moieties are 2'-O-acetylated) and includes a cap structure that does not comprise a 2'-O-acetylated ribose. In some embodiments, a cap structure of a polyribonucleotide comprises a hydroxyl group on carbon 2 of a ribose.

In some embodiments, a polyribonucleotide comprises a cap structure and a cap structure comprises a 2'-O-acetylated ribose.

In some embodiments, a polyribonucleotide is fully 2'-O-acetylated (100% ribose moieties are 2'-O-acetylated) and includes a 2'-O-acetylated cap structure.

In some embodiments, a polyribonucleotide is less than 100% 2'-O-acetylated (less than 100% ribose moieties are 2'-O-acetylated) and includes a 2'-O-acetylated cap structure.

In some embodiments, a polyribonucleotide is at least 5% 2'-O-acetylated (at least 5% ribose moieties are 2'-O-acetylated) and includes a 2'-O-acetylated cap structure.

In some embodiments, a polyribonucleotide can have a length of at least 5 nucleotides or longer. In some embodiments, a polyribonucleotide can have a length of at least 5 nucleotides, at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides, at least 75 nucleotides, at least 80 nucleotides, at least 85 nucleotides, at least 90 nucleotides, at least 95 nucleotides, at least 100 nucleotides, at least 200 nucleotides, at least 300 nucleotides, at least 400 nucleotides, at least 500 nucleotides, at least 1000 nucleotides, at least 2000 nucleotides, at least 5000 nucleotides or longer.

In some embodiments, a polyribonucleotide can have a length of about 5 nucleotides to about 200,000 nucleotides, about 5 nucleotides to about 150,000 nucleotides, about 5 nucleotides to about 100,000 nucleotides, about 5 nucleotides to about 50,000 nucleotides, about 5 nucleotides to about 10,000 nucleotides, about 5 nucleotides to about 5000 nucleotides, about 5 nucleotides to about 1000 nucleotides, about 5 nucleotides to about 500 nucleotides, about 5 nucleotides to about 400 nucleotides, about 5 nucleotides to about 300 nucleotides, about 5 nucleotides to about 200 nucleotides, about 5 nucleotides to about 100 nucleotides, about 5 nucleotides to about 90 nucleotides, about 5 nucleotides to about 85 nucleotides, about 5 nucleotides to about 80 nucleotides, about 5 nucleotides to about 75 nucleotides, about 5 nucleotides to about 70 nucleotides, about 5 nucleotides to about 65 nucleotides, about 5 nucleotides to about 60 nucleotides, about 5 nucleotides to about 55 nucleotides, about 5 nucleotides to about 50 nucleotides, about 5 nucleotides to about 45 nucleotides, about 5 nucleotides to about 40 nucleotides, about 5 nucleotides to about 35 nucleotides, about 5 nucleotides to about 30 nucleotides, about 5 nucleotides to about 25 nucleotides, about 5 nucleotides to about 20 nucleotides, about 5 nucleotides to about 15 nucleotides, about 5 nucleotides to about 10 nucleotides.

In some embodiments, a polyribonucleotide can have a length of about 5 nucleotides to about 200,000 nucleotides, about 10 nucleotides to about 200,000 nucleotides, 15 nucleotides to about 200,000 nucleotides, about 20 nucleotides to about 200,000 nucleotides, about 30 nucleotides to about 200,000 nucleotides, about 40 nucleotides to about 200,000 nucleotides, about 50 nucleotides to about 200,000 nucleotides, about 100 nucleotides to about 200,000 nucleotides, about 200 nucleotides to about 200,000 nucleotides, about 300 nucleotides to about 200,000 nucleotides, about 400 nucleotides to about 200,000 nucleotides, about 500 nucleotides to about 200,000 nucleotides, about 1000 nucleotides to about 200,000 nucleotides, about 2000 nucleotides to about 200,000 nucleotides, about 3000 nucleotides to about 200,000 nucleotides, about 4000 nucleotides to about 200,000 nucleotides, about 5000 nucleotides to about 200,000 nucleotides, about 10,000 nucleotides to about 200,000 nucleotides, about 20, 000 nucleotides to about 200,000 nucleotides, about 30,000 nucleotides to about 200,000 nucleotides, about 40,000 nucleotides to about 200,000 nucleotides, about 50,000 nucleotides to about 200,000 nucleotides, about 100,000 nucleotides to about 200,000 nucleotides, about 150,000 nucleotides to about 200,000 nucleotides.

In some embodiments, a polyribonucleotide can have a length of no more than 200,000 nucleotides, no more than 150,000 nucleotides, no more than 100,000 nucleotides, or no more than 50,000 nucleotides.

Additional Nucleotide Modifications

In some embodiments, a polyribonucleotide comprising a 2'-O-acetylated ribose further comprises a modification comprising a modified backbone, a modified nucleobase, or any combination thereof.

In some embodiments, a polyribonucleotide comprising a 2'-O-acetylated ribose further comprises a modified backbone.

In some embodiments, a polyribonucleotide comprising a 2'-O-acetylated ribose further comprises a modified nucleobase. A modification on a nucleobase includes a modification on one or more of: adenine, cytosine, uracil, or guanine.

In some embodiments, a polyribonucleotide comprising a 2'-O-acetylated ribose further comprises a modified adenine. In some embodiments, a modified adenine comprises: 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2, 6-diaminopurine, 7-deaza-8-aza-2,6-diaminopurine, 1-methyl-adenosine (m1A), 2-methyl-adenine (m2A), N6-methyl-adenosine (m6A), 2-methylthio-N6-methyl-adenosine (ms2m6A), N6-isopentenyl-adenosine (i6A), 2-methylthio-N6-isopentenyl-adenosine (ms2i6 A), N6-(cis-hydroxyisopentenyl) adenosine (io6A), 2-methylthio-N6-(cis-hydroxyisopentenyl) adenosine (ms2io6A), N6-glycinylcarbamoyl-adenosine (g6A), N6-threonylcarbamoyl-adenosine (t6A), N6-methyl-N6-threonylcarbamoyl-adenosine (m6t6A), 2-methylthio-N6-threonylcarbamoyl-adenosine (ms2g6A), N6,N6-dimethyl-adenosine (m\A), N6-hydroxynorvalylcarbamoyl-adenosine (hn6A), 2-methylthio-N6-hydroxynorvalylcarbamoyladenosine (ms2hn6A), N6-acetyl-adenosine (ac6A), 7-methyl-adenine, 2-methylthio-adenine, 2-methoxy-adenine, a-thio-adenosine, 2'-O-methyl-adenosine (Am), N6,2'-O-dimethyl-adenosine (m6Am), N6,N6,2'-O-trimethyl-adenosine (m62Am), 1,2'-O-dimethyl-adenosine (m1Am), 2'-O-ribosyladenosine (phosphate) (Ar(p)), 2-amino-N6-methyl-purine, 1-thio-adenosine, 8-azidoadenosine, 2'-F-ara-adenosine, 2'-F-adenosine, 2'-OH-ara-adenosine, N6-(1 9-amino-pentaoxanonadecyl)-adenosine, or any combination thereof.

In some embodiments, a polyribonucleotide comprising a 2'-O-acetylated ribose and a modified adenine, further comprises one or more modified nucleobases other than a modified adenine, e.g., as described herein.

In some embodiments, a polyribonucleotide comprising a 2'-O-acetylated ribose further comprises a modified cytosine. In some embodiments, a modified cytosine comprises: 5-aza-cytidine, 6-aza-cytidine, pseudoisocytidine, 3-methyl-cytidine (m3C), N4-acetyl-cytidine (ac4C), 5-formyl-cytidine (f5C), N4-methyl-cytidine (m4C), 5-methyl-cytidine (m5C), 5-halo-cytidine (e.g., 5-iodo-cytidine), 5-hydroxymethyl-cytidine (hm5C), 1-methyl-pseudoisocytidine, pyrrolo-cytidine, pyrrolopseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deazapseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), a-thio-cytidine, 2'-O-methyl-cytidine (Cm), 5,2'-O-dimethyl-cytidine (m5Cm), N4-acetyl-2'-O-methyl-cytidine (ac4Cm), N4,2'-O-dimethylcytidine (m4Cm), 5-formyl-2'-O-methyl-cytidine (f5Cm), N4,N4,2'-O-trimethyl-cytidine (m\Cm), 1-thio-cytidine, 2'-F-ara-cytidine, 2'-F-cytidine, 2'-OH-ara-cytidine, or any combination thereof.

In some embodiments, a polyribonucleotide comprising a 2'-O-acetylated ribose comprises a modified cytosine comprising N4-acetyl-cytidine (ac4C).

In some embodiments, a polyribonucleotide comprising a 2'-O-acetylated ribose and a modified cytosine, further comprises one or more modified nucleobases other than a modified cytosine, e.g., as described herein.

In some embodiments, a polyribonucleotide comprising a 2'-O-acetylated ribose and a modified cytosine comprising Ac4C, further comprises one or more modified nucleobases other than a modified cytosine comprising Ac4C, e.g., as described herein.

In some embodiments, a polyribonucleotide comprising a 2'-O-acetylated ribose further comprises a modified uracil. In some embodiments, a modified uracil comprises: 5-hydroxymethyluridine, pseudouridine, pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyluridine, 5-halo-uridine (e.g., 5-iodo-uridine or 5-bromo-uridine), 3-methyl-uridine (m3U), 5-methoxy-uridine (mo5U), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonyhnethyl-uridine (mcm5U), 5-methoxycarbonylmethyl-2-thio-uridine (mcm5s2U), 5-aminomethyl-2-thio-uridine (nm5s2U), 5-methylaminomethyl-uridine (nmm5U), 5-methylaminomethyl-2-thio-uridine (nmm5s2U), 5-methylaminomethyl-2-seleno-uridine (nmm5se2U), 5-carbamoylmethyl-uridine (ncm5U), 5-carboxymethylaminomethyl-uridine (cmnm5U), 5-carboxymethylaminomethyl-2-thio-uridine (cnmm5s2U), 5-propynyl-uridine, 1-propynylpseudouridine, 5-taurinomethyl-uridine (TITI5U), 1-taurinomethyl-pseudouridine, 5-taurinomethyl-2-thio-uridine (TITI5s2U), 1-taurinomethyl-4-thio-pseudouridine, 5-methyl-uridine (m5U, i.e., having the nucleobase deoxythymine), 5-methyl-2-thio-uridine (m5s2U), Imethyl-4-thio-pseudouridine, 4-thio-1-methyl-pseudouridine, 3-methyl-pseudouridine, 2-thio-1-methyl-pseudouridine, 1-methyl-1-deaza-pseudouridine, 2-thio-1-methyl-1-deazapseudouridine, dihydrouridine (D), dihydropseudouridine, 5,6-dihydrouridine, 5-methyldihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methylpseudouridine, 3-(3-amino-3-carboxypropyl) uridine (acp3U), 1-methyl-3-(3-amino-3-carboxypropyl) pseudouridine, 5-(isopentenylaminomethyl) uridine (inm5U), 5-(isopentenylaminomethyl)-2-thio-uridine (inm5s2U), a-thio-uridine, 2'-O-methyl-uridine (Um), 5,2'-O-dimethyl-uridine (m5Um), 2'-O-methyl-pseudouridine, 2-thio-2'-O-methyl-uridine (s2Um), 5-methoxycarbonyhnethyl-2'-O-methyl-uridine (mcm5Um), 5-carbamoylmethyl-2'-O-methyl-uridine (ncm5Um), 5-carboxymethylaminomethyl-2'-O-methyl-uridine (cnmm5Um), 3,2'-O-dimethyluridine (m3Um), and 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino) uridine, or any combination thereof.

In some embodiments, a polyribonucleotide comprising a 2'-O-acetylated ribose further comprises a modified uracil comprising 5-hydroxymethyluridine.

In some embodiments, a polyribonucleotide comprising a 2'-O-acetylated ribose further comprises a modified uracil comprising N1-methylpseudouridine.

In some embodiments, a polyribonucleotide comprising a 2'-O-acetylated ribose and a modified uracil, further comprises one or more modified nucleobases other than a modified uracil, e.g., as described herein.

In some embodiments, a polyribonucleotide comprising a 2'-O-acetylated ribose and a modified uracil comprising 5-hydroxymethyluridine, further comprises one or more modified nucleobases other than a modified uracil comprising 5-hydroxymethyluridine, e.g., as described herein.

In some embodiments, a polyribonucleotide comprising a 2'-O-acetylated ribose and a modified uracil comprising N1-methylpseudouridine, further comprises one or more modified nucleobases other than a modified uracil comprising N1-methylpseudouridine, e.g., as described herein.

In some embodiments, a polyribonucleotide comprising a 2'-O-acetylated ribose further comprises a modified guanine. In some embodiments, a modified guanine comprises: inosine (I), 1-methyl-inosine (m1 I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanosine, queuosine (Q), epoxyqueuosine (oQ), galactosylqueuosine, mannosyl-queuosine (manQ), 7-cyano-7-deaza-guanosine (preQ0), 7-aminomethyl-7-deaza-guanosine (preQ1), archaeosine (G+), 7-deaza-8-aza-guanosine, 6-thioguanosine, 6-thio-7-deaza-guanosine, 6-thio-7-deaza-8-aza-guanosine, 7-methyl-guanosine (m7 G), 6-thio-7-methyl-guanosine, 7-methyl-inosine, 6-methoxy-guanosine, 1-methyl-guanosine (m1G), N2-methyl-guanosine (m2G), N2,N2-dimethyl-guanosine (m\G), N2,7-dimethyl-guanosine (m27G), N2, N2,7-dimethyl-guanosine (m2'2'7G), 8-oxo-guanosine, 7-methyl-8-oxo-guanosine, 1-methyl-6-thio-guanosine, N2-methyl-6-thio-guanosine, N2,N2-dimethyl-6-thio-guanosine, a-thio-guanosine, 2'-O-methyl-guanosine (Gm), N2-methyl-2'-O-methyl-guanosine (m2Gm), N2,N2-dimethyl-2'-Omethyl-guanosine (m22Gm), 1-methyl-2'-O-methyl-guanosine (m1Gm), N2,7-dimethyl-2'-O-methylguanosine (m2'7Gm), 2'-O-methyl-inosine (Im), 1,2'-O-dimethyl-inosine (m1Im), 2'-Oribosylguanosine (phosphate) (Gr(p)), 1-thio-guanosine, 06-methyl-guanosine, 2'-F-ara-guanosine, 2'-F-guanosine, or any combination thereof.

In some embodiments, a polyribonucleotide comprising a 2'-O-acetylated ribose and a modified guanine, further comprises one or more modified nucleobases other than a modified guanine, e.g., as described herein.

In some embodiments, a polyribonucleotide comprising a 2'-O-acetylated ribose further comprises purine analog and/or a pyrimidine analog. In some embodiments, a polyribonucleotide comprising a 2'-O-acetylated ribose comprises a nucleobase comprising naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo [3,4-d]pyrimidine, imidazo [1,5-a] 1, 3, 5 triazinones, 9-deazapurines, imidazo[4,5-d]pyrazines, thiazolo[4, 5-d]pyrimidines, pyrazin-2-ones, 1,2,4-triazine, pyridazine; 1,3,5 triazine; or any combination thereof.

Exemplary nucleotide modifications, including nucleobase modifications, include those provided in International Patent Application WO 2013/052523 filed on 3 Oct. 2012, the entire contents of which are herein incorporated by reference.

N4-Acetylcytidine Modified Nucleotides

In some embodiments, a polyribonucleotide comprising a 2'-O-acetylated ribose further comprises a base comprising an acetyl group, wherein the nucleoside is N4-acetylcytidine and the modified ribonucleotide has a structure of:

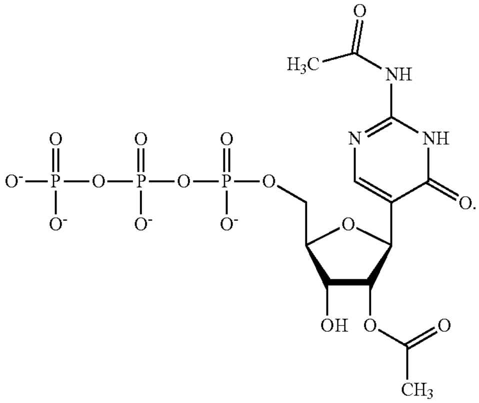

In some embodiments, a polyribonucleotide disclosed herein comprises cytidine residues. In some embodiments, at least 1% cytidine residues comprise a 2'-O-acetylated ribose. In some embodiments, no more than 90% cytidine residues comprise a 2'-O-acetylated ribose.

In some embodiments, a polyribonucleotide disclosed herein comprises cytidine residues and at least 5% of cytidine residues comprise N4-acetylcytidine. In some embodiments, at least 1% of N4-acetylcytidine residues comprise a 2'-O-acetylated ribose. In some embodiments, no more than 90% of N4-acetylcytidine residues comprise a 2'-O-acetylated ribose.

In some embodiments, a polyribonucleotide disclosed herein comprises cytidine residues and less than 100% of cytidine residues comprise N4-acetylcytidine. In some embodiments, at least 1% of N4-acetylcytidine residues comprise a 2'-O-acetylated ribose. In some embodiments, no more than 90% of N4-acetylcytidine residues comprise a 2'-O-acetylated ribose.

In some embodiments, a polyribonucleotide disclosed herein comprises cytidine residues and at least 5% of cytidine residues in a polyribonucleotide comprises N4-acetylcytidine. In some embodiments, a polyribonucleotide disclosed herein comprises cytidine residues and at least 10% of cytidine residues in a polyribonucleotide comprises N4-acetylcytidine. In some embodiments, a polyribonucleotide disclosed herein comprises cytidine residues and at least 15% of cytidine residues in a polyribonucleotide comprises N4-acetylcytidine. In some embodiments, a polyribonucleotide disclosed herein comprises cytidine residues and at least 20% of cytidine residues in a polyribonucleotide comprises N4-acetylcytidine. In some embodiments, a polyribonucleotide disclosed herein comprises cytidine residues and at least 25% of cytidine residues in a polyribonucleotide comprises N4-acetylcytidine. In some embodiments, a polyribonucleotide disclosed herein comprises cytidine residues and at least 30% of cytidine residues in a polyribonucleotide comprises N4-acetylcytidine. In some embodiments, a polyribonucleotide disclosed herein comprises cytidine residues and at least 35% of cytidine residues in a polyribonucleotide comprises N4-acetylcytidine. In some embodiments, a polyribonucleotide disclosed herein comprises cytidine residues and at least 40% of cytidine residues in a polyribonucleotide comprises N4-acetylcytidine. In some embodiments, a polyribonucleotide disclosed herein comprises cytidine residues and at least 45% of cytidine residues in a polyribonucleotide comprises N4-acetylcytidine. In some embodiments, a polyribonucleotide disclosed herein comprises cytidine residues and at least 50% of cytidine residues in a polyribonucleotide comprises N4-acetylcytidine. In some embodiments, a polyribonucleotide disclosed herein comprises cytidine residues and at least 55% of cytidine residues in a polyribonucleotide comprises N4-acetylcytidine. In some embodiments, a polyribonucleotide disclosed herein comprises cytidine residues and at least 60% of cytidine residues in a polyribonucleotide comprises N4-acetylcytidine. In some embodiments, a polyribonucleotide disclosed herein comprises cytidine residues and at least 65% of cytidine residues in a polyribonucleotide comprises N4-acetylcytidine. In some embodiments, a polyribonucleotide disclosed herein comprises cytidine residues and at least 70% of cytidine residues in a polyribonucleotide comprises N4-acetylcytidine. In some embodiments, a polyribonucleotide disclosed herein comprises cytidine residues and at least 75% of cytidine residues in a polyribonucleotide comprises N4-acetylcytidine. In some embodiments, a polyribonucleotide disclosed herein comprises cytidine residues and at least 80% of cytidine residues in a polyribonucleotide comprises N4-acetylcytidine. In some embodiments, a polyribonucleotide disclosed herein comprises cytidine residues and at least 85% of cytidine residues in a polyribonucleotide comprises N4-acetylcytidine. In some embodiments, a polyribonucleotide disclosed herein comprises cytidine residues and at least 90% of cytidine residues in a polyribonucleotide comprises N4-acetylcytidine. In some embodiments, a polyribonucleotide disclosed herein comprises cytidine residues and at least 95% of cytidine residues in a polyribonucleotide comprises N4-acetylcytidine. In some embodiments, at least 1% of N4-acetylcytidine residues comprise a 2'-O-acetylated ribose. In some embodiments, no more than 90% of N4-acetylcytidine residues comprise a 2'-O-acetylated ribose.

In some embodiments, a polyribonucleotide disclosed herein comprises cytidine residues. In some embodiments, about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of cytidine residues in a polyribonucleotide comprises N4-acetylcytidine. In some embodiments, at least 1% of N4-acetylcytidine residues comprise a 2'-O-acetylated ribose. In some embodiments, no more than 90% of N4-acetylcytidine residues comprise a 2'-O-acetylated ribose.

In some embodiments, a polyribonucleotide disclosed herein comprises cytidine residues and more than about 60% of cytidine residues in a polyribonucleotide comprises N4-acetylcytidine. In some embodiments, a polyribonucleotide disclosed herein comprises cytidine residues and more than about 65% of cytidine residues in a polyribonucleotide comprises N4-acetylcytidine. In some embodiments, a polyribonucleotide disclosed herein comprises cytidine residues and more than about 70% of cytidine residues in a polyribonucleotide comprises N4-acetylcytidine. In some embodiments, a polyribonucleotide disclosed herein comprises cytidine residues and more than about 75% of cytidine residues in a polyribonucleotide comprises N4-acetylcytidine. In some embodiments, a polyribonucleotide disclosed herein comprises cytidine residues and more than about 80% of cytidine residues in a polyribonucleotide comprises N4-acetylcytidine. In some embodiments, a polyribonucleotide disclosed herein comprises cytidine residues and more than about 85% of cytidine residues in a polyribonucleotide comprises N4-acetylcytidine. In some embodiments, a polyribonucleotide disclosed herein comprises cytidine residues and more than about 90% of cytidine residues in a polyribonucleotide comprises N4-acetylcytidine. In some embodiments, a polyribonucleotide disclosed herein comprises cytidine residues and more than about 95% of cytidine residues in a polyribonucleotide comprises N4-acetylcytidine. In some embodiments, a polyribonucleotide disclosed herein comprises cytidine residues and more than about 99% of cytidine residues in a polyribonucleotide comprises N4-acetylcytidine. In some embodiments, a polyribonucleotide disclosed herein comprises cytidine residues and about 5% of cytidine residues in a polyribonucleotide comprises N4-acetylcytidine. In some embodiments, at least 1% of N4-acetylcytidine residues comprise a 2'-O-acetylated ribose. In some embodiments, no more than 90% of N4-acetylcytidine residues comprise a 2'-O-acetylated ribose.

In some embodiments, a polyribonucleotide disclosed herein comprises cytidine residues and about 10% of cytidine residues in a polyribonucleotide comprises N4-acetylcytidine. In some embodiments, a polyribonucleotide disclosed herein comprises cytidine residues and about 15% of cytidine residues in a polyribonucleotide comprises N4-acetylcytidine. In some embodiments, a polyribonucleotide disclosed herein comprises cytidine residues and about 20% of cytidine residues in a polyribonucleotide comprises N4-acetylcytidine. In some embodiments, a polyribonucleotide disclosed herein comprises cytidine residues and about 25% of cytidine residues in a polyribonucleotide comprises N4-acetylcytidine. In some embodiments, a polyribonucleotide disclosed herein comprises cytidine residues and about 30% of cytidine residues in a polyribonucleotide comprises N4-acetylcytidine. In some embodiments, a polyribonucleotide disclosed herein comprises cytidine residues and about 35% of cytidine residues in a polyribonucleotide comprises N4-acetylcytidine. In some embodiments, a polyribonucleotide disclosed herein comprises cytidine residues and about 40% of cytidine residues in a polyribonucleotide comprises N4-acetylcytidine. In some embodiments, a polyribonucleotide disclosed herein comprises cytidine residues and about 45% of cytidine residues in a polyribonucleotide comprises N4-acetylcytidine. In some embodiments, a polyribonucleotide disclosed herein comprises cytidine residues and about 50% of cytidine residues in a polyribonucleotide comprises N4-acetylcytidine. In some embodiments, a polyribonucleotide disclosed herein comprises cytidine residues and about 55% of cytidine residues in a polyribonucleotide comprises N4-acetylcytidine. In some embodiments, a polyribonucleotide disclosed herein comprises cytidine residues and about 60% of cytidine residues in a polyribonucleotide comprises N4-acetylcytidine. In some embodiments, a polyribonucleotide disclosed herein comprises cytidine residues and about 65% of cytidine residues in a polyribonucleotide comprises N4-acetylcytidine. In some embodiments, a polyribonucleotide disclosed herein comprises cytidine residues and about 75% of cytidine residues in a polyribonucleotide comprises N4-acetylcytidine. In some embodiments, a polyribonucleotide disclosed herein comprises cytidine residues and about 80% of cytidine residues in a polyribonucleotide comprises N4-acetylcytidine. In some embodiments, a polyribonucleotide disclosed herein comprises cytidine residues and about 85% of cytidine residues in a polyribonucleotide comprises N4-acetylcytidine. In some embodiments, a polyribonucleotide disclosed herein comprises cytidine residues and about 90% of cytidine residues in a polyribonucleotide comprises N4-acetylcytidine. In some embodiments, a polyribonucleotide disclosed herein comprises cytidine residues and about 95% of cytidine residues in a polyribonucleotide comprises N4-acetylcytidine. In some embodiments, a polyribonucleotide disclosed herein comprises cytidine residues and about 99% of cytidine residues in a polyribonucleotide comprises N4-acetylcytidine. In some embodiments, a polyribonucleotide disclosed herein comprises cytidine residues and 100% of cytidine residues in a polyribonucleotide comprise N4-acetylcytidine. In some embodiments, at least 1% of N4-acetylcytidine residues comprise a 2'-O-acetylated ribose. In some embodiments, no more than 90% of N4-acetylcytidine residues comprise a 2'-O-acetylated ribose.

In some embodiments, a polyribonucleotide in which at least 5% cytidine residues are N4-acetylcytidine comprises at least 5%, at least 10%, at least 15%, at least 20%, at least 25%, at least 30%, at least 35%, at least about 40%, at least 45%, at least 50%, at least 55%, at least 60%, at least 65%, at least 70%, at least 75%, at least 80%, at least 85%, at least 90%, at least 95%, or at least 99% 2'-O-acetylated ribose. In some embodiments, at least 1% of N4-acetylcytidine residues comprise a 2'-O-acetylated ribose. In some embodiments, no more than 90% of N4-acetylcytidine residues comprise a 2'-O-acetylated ribose.

In some embodiments, a polyribonucleotide in which at least 5% cytidine residues are N4-acetylcytidine, comprises at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% 2'-O-acetylated ribose. In some embodiments, at least 1% of N4-acetylcytidine residues comprise a 2'-O-acetylated ribose. In some embodiments, no more than 90% of N4-acetylcytidine residues comprise a 2'-O-acetylated ribose.

In some embodiments, a polyribonucleotide in which at least 5% cytidine residues are N4-acetylcytidine, comprises 100% 2'-O-acetylated ribose.

In some embodiments, a polyribonucleotide in which at least 5% cytidine residues are N4-acetylcytidine, comprises about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% 2'-O-acetylated ribose. In some embodiments, at least 1% of N4-acetylcytidine residues comprise a 2'-O-acetylated ribose. In some embodiments, no more than 90% of N4-acetylcytidine residues comprise a 2'-O-acetylated ribose.

In some embodiments, a polyribonucleotide in which at least 5% cytidine residues are N4-acetylcytidine, comprises about 76% to about 100%, about 77% to about 100%, about 78% to about 100%, about 79% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, about 99% to about 100%, 2'-O-acetylated ribose. In some embodiments, at least 1% of N4-acetylcytidine residues comprise a 2'-O-acetylated ribose. In some embodiments, no more than 90% of N4-acetylcytidine residues comprise a 2'-O-acetylated ribose.

In some embodiments, a polyribonucleotide comprising 2'-O-acetylated ribose and cytidine residues comprising N4-acetylcytidine (e.g., a portion of N4-acetylcytidine having 2-O ribose acetylation), further comprises one or more modified nucleotides.

5-Hydroxymethyl Modified Nucleotides

In some embodiments, a polyribonucleotide comprising a 2'-O-acetylated ribose further comprises a base comprising a hydroxymethyl group, wherein the nucleoside is 5-hydroxymethyluridine and the modified ribonucleotide has a structure of:

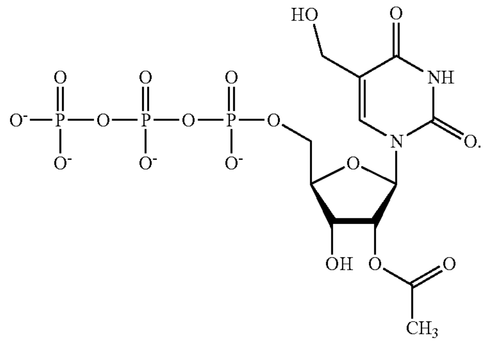

In some embodiments, a polyribonucleotide disclosed herein comprises uridine residues. In some embodiments, at least 1% of uridine residues comprise a 2'-O-acetylated ribose. In some embodiments, no more than 90% of uridine residues comprise a 2'-O-acetylated ribose.

In some embodiments, a polyribonucleotide disclosed herein comprises uridine and at least 5% of uridine residues comprise 5-hydroxymethyluridine. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide disclosed herein comprises uridine and less than 100% of uridine residues comprise 5-hydroxymethyluridine. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide disclosed herein comprises uridine residues and at least 5% of uridine residues in a polyribonucleotide comprises 5-hydroxymethyluridine. In some embodiments, a polyribonucleotide disclosed herein comprises uridine residues and at least 10% of uridine residues in a polyribonucleotide comprises 5-hydroxymethyluridine. In some embodiments, a polyribonucleotide disclosed herein comprises uridine residues and at least 15% of uridine residues in a polyribonucleotide comprises 5-hydroxymethyluridine. In some embodiments, a polyribonucleotide disclosed herein comprises uridine residues and at least 20% of uridine residues in a polyribonucleotide comprises 5-hydroxymethyluridine. In some embodiments, a polyribonucleotide disclosed herein comprises uridine residues and at least 25% of uridine residues in a polyribonucleotide comprises 5-hydroxymethyluridine. In some embodiments, a polyribonucleotide disclosed herein comprises uridine residues and at least 30% of uridine residues in a polyribonucleotide comprises 5-hydroxymethyluridine. In some embodiments, a polyribonucleotide disclosed herein comprises uridine residues and at least 35% of uridine residues in a polyribonucleotide comprises 5-hydroxymethyluridine. In some embodiments, a polyribonucleotide disclosed herein comprises uridine residues and at least 40% of uridine residues in a polyribonucleotide comprises 5-hydroxymethyluridine. In some embodiments, a polyribonucleotide disclosed herein comprises uridine residues and at least 45% of uridine residues in a polyribonucleotide comprises 5-hydroxymethyluridine. In some embodiments, a polyribonucleotide disclosed herein comprises uridine residues and at least 50% of uridine residues in a polyribonucleotide comprises 5-hydroxymethyluridine. In some embodiments, a polyribonucleotide disclosed herein comprises uridine residues and at least 55% of uridine residues in a polyribonucleotide comprises 5-hydroxymethyluridine. In some embodiments, a polyribonucleotide disclosed herein comprises uridine residues and at least 60% of uridine residues in a polyribonucleotide comprises 5-hydroxymethyluridine. In some embodiments, a polyribonucleotide disclosed herein comprises uridine residues and at least 65% of uridine residues in a polyribonucleotide comprises 5-hydroxymethyluridine. In some embodiments, a polyribonucleotide disclosed herein comprises uridine residues and at least 70% of uridine residues in a polyribonucleotide comprises 5-hydroxymethyluridine. In some embodiments, a polyribonucleotide disclosed herein comprises uridine residues and at least 75% of uridine residues in a polyribonucleotide comprises 5-hydroxymethyluridine. In some embodiments, a polyribonucleotide disclosed herein comprises uridine residues and at least 80% of uridine residues in a polyribonucleotide comprises 5-hydroxymethyluridine. In some embodiments, a polyribonucleotide disclosed herein comprises uridine residues and at least 85% of uridine residues in a polyribonucleotide comprises 5-hydroxymethyluridine. In some embodiments, a polyribonucleotide disclosed herein comprises uridine residues and at least 90% of uridine residues in a polyribonucleotide comprises 5-hydroxymethyluridine. In some embodiments, a polyribonucleotide disclosed herein comprises uridine residues and at least 95% of uridine residues in a polyribonucleotide comprises 5-hydroxymethyluridine. In some embodiments, a polyribonucleotide disclosed herein comprises uridine residues and at least 99% of uridine residues in a polyribonucleotide comprises 5-hydroxymethyluridine. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide disclosed herein comprises uridine residues. In some embodiments, about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of uridine residues in a polyribonucleotide comprises 5-hydroxymethyluridine. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide disclosed herein comprises uridine residues and more than 60% of uridine residues in a polyribonucleotide comprises 5-hydroxymethyluridine. In some embodiments, a polyribonucleotide disclosed herein comprises uridine residues and more than 65% of uridine residues in a polyribonucleotide comprises 5-hydroxymethyluridine. In some embodiments, a polyribonucleotide disclosed herein comprises uridine residues and more than 70% of uridine residues in a polyribonucleotide comprises 5-hydroxymethyluridine. In some embodiments, a polyribonucleotide disclosed herein comprises uridine residues and more than 75% of uridine residues in a polyribonucleotide comprises 5-hydroxymethyluridine. In some embodiments, a polyribonucleotide disclosed herein comprises uridine residues and more than 80% of uridine residues in a polyribonucleotide comprises 5-hydroxymethyluridine. In some embodiments, a polyribonucleotide disclosed herein comprises uridine residues and more than 85% of uridine residues in a polyribonucleotide comprises 5-hydroxymethyluridine. In some embodiments, a polyribonucleotide disclosed herein comprises uridine residues and more than 90% of uridine residues in a polyribonucleotide comprises 5-hydroxymethyluridine. In some embodiments, a polyribonucleotide disclosed herein comprises uridine residues and more than 95% of uridine residues in a polyribonucleotide comprises 5-hydroxymethyluridine. In some embodiments, a polyribonucleotide disclosed herein comprises uridine residues and more than 99% of uridine residues in a polyribonucleotide comprises 5-hydroxymethyluridine. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide disclosed herein comprises uridine residues and about 5% of uridine residues in a polyribonucleotide comprises 5-hydroxymethyluridine. In some embodiments, a polyribonucleotide disclosed herein comprises uridine residues and about 10% of uridine residues in a polyribonucleotide comprises 5-hydroxymethyluridine. In some embodiments, a polyribonucleotide disclosed herein comprises uridine residues and about 15% of uridine residues in a polyribonucleotide comprises 5-hydroxymethyluridine. In some embodiments, a polyribonucleotide disclosed herein comprises uridine residues and about 20% of uridine residues in a polyribonucleotide comprises 5-hydroxymethyluridine. In some embodiments, a polyribonucleotide disclosed herein comprises uridine residues and about 25% of uridine residues in a polyribonucleotide comprises 5-hydroxymethyluridine. In some embodiments, a polyribonucleotide disclosed herein comprises uridine residues and about 30% of uridine residues in a polyribonucleotide comprises 5-hydroxymethyluridine. In some embodiments, a polyribonucleotide disclosed herein comprises uridine residues and about 35% of uridine residues in a polyribonucleotide comprises 5-hydroxymethyluridine. In some embodiments, a polyribonucleotide disclosed herein comprises uridine residues and about 40% of uridine residues in a polyribonucleotide comprises 5-hydroxymethyluridine. In some embodiments, a polyribonucleotide disclosed herein comprises uridine residues and about 45% of uridine residues in a polyribonucleotide comprises 5-hydroxymethyluridine. In some embodiments, a polyribonucleotide disclosed herein comprises uridine residues and about 50% of uridine residues in a polyribonucleotide comprises 5-hydroxymethyluridine. In some embodiments, a polyribonucleotide disclosed herein comprises uridine residues and about 55% of uridine residues in a polyribonucleotide comprises 5-hydroxymethyluridine. In some embodiments, a polyribonucleotide disclosed herein comprises uridine residues and about 60% of uridine residues in a polyribonucleotide comprises 5-hydroxymethyluridine. In some embodiments, a polyribonucleotide disclosed herein comprises uridine residues and about 65% of uridine residues in a polyribonucleotide comprises 5-hydroxymethyluridine. In some embodiments, a polyribonucleotide disclosed herein comprises uridine residues and about 75% of uridine residues in a polyribonucleotide comprises 5-hydroxymethyluridine. In some embodiments, a polyribonucleotide disclosed herein comprises uridine residues and about 80% of uridine residues in a polyribonucleotide comprises 5-hydroxymethyluridine. In some embodiments, a polyribonucleotide disclosed herein comprises uridine residues and about 85% of uridine residues in a polyribonucleotide comprises 5-hydroxymethyluridine. In some embodiments, a polyribonucleotide disclosed herein comprises uridine residues and about 90% of uridine residues in a polyribonucleotide comprises 5-hydroxymethyluridine. In some embodiments, a polyribonucleotide disclosed herein comprises uridine residues and about 95% of uridine residues in a polyribonucleotide comprises 5-hydroxymethyluridine. In some embodiments, a polyribonucleotide disclosed herein comprises uridine residues and about 99% of uridine residues in a polyribonucleotide comprises 5-hydroxymethyluridine. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide disclosed herein comprises uridine residues and 100% of uridine residues in a polyribonucleotide comprises 5-hydroxymethyluridine. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide in which at least 5% uridine residues are 5-hydroxymethyluridine, comprises at least 5%, at least 10%, at least 15%, at least 20%, at least 25%, at least 30%, at least 35%, at least about 40%, at least 45%, at least 50%, at least 55%, at least 60%, at least 65%, at least 70%, at least 75%, at least 80%, at least 85%, at least 90%, at least 95%, or at least 99% 2-O acetylated ribose. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide in which at least 5% uridine residues are 5-hydroxymethyluridine, comprises at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% 2'-O-acetylated ribose. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide in which at least 5% uridine residues are 5-hydroxymethyluridine, comprises 100% 2'-O-acetylated ribose.

In some embodiments, a polyribonucleotide in which at least 5% uridine residues are 5-hydroxymethyluridine, comprises about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% 2'-O-acetylated ribose. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide in which at least 5% uridine residues are 5-hydroxymethyluridine, comprises about 76% to about 100%, about 77% to about 100%, about 78% to about 100%, about 79% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, about 99% to about 100%, 2'-O-acetylated ribose. In some embodiments, at least 1% of 5-hydroxymethyluridine residues comprise a 2'-O-acetylated ribose. In some embodiments, no more than 90% of 5-hydroxymethyluridine residues comprise a 2'-O-acetylated ribose.

In some embodiments, a polyribonucleotide comprising 2'-O-acetylated ribose and uridine residues comprising 5-hydroxymethyluridine (e.g., a portion of 5-hydroxymethyluridine having 2-O ribose acetylation), further comprises one or more modified nucleotides.

N1-Methylpseudouridine Modified Nucleotides

In some embodiments, a polyribonucleotide comprising a 2'-O-acetylated ribose further comprises a base comprising a methyl group, wherein the nucleoside is N1-methylpseudouridine (m1Ψ) and the modified ribonucleotide has a structure of:

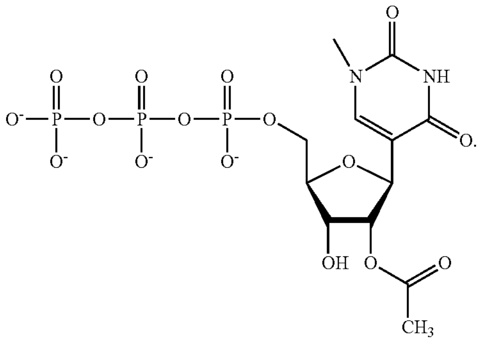

In some embodiments, a polyribonucleotide comprising 2'-O-acetylated ribose comprises uridine residues and at least 5% of uridine residues comprise N1-methylpseudouridine. In some embodiments, at least 1% of N1-methylpseudouridine residues comprise a 2'-O-acetylated ribose. In some embodiments, no more than 90% of N1-methylpseudouridine residues comprise a 2'-O-acetylated ribose.

In some embodiments, a polyribonucleotide comprising 2'-O-acetylated ribose comprises uridine residues less than 100% of uridine residues in a polyribonucleotide comprise N1-methylpseudouridine. In some embodiments, at least 1% of N1-methylpseudouridine residues comprise a 2'-O-acetylated ribose. In some embodiments, no more than 90% of N1-methylpseudouridine residues comprise a 2'-O-acetylated ribose.

In some embodiments, a polyribonucleotide comprising 2'-O-acetylated ribose comprises uridine residues and at least 5%, at least 10%, at least 20%, at least 30%, at least 40%, at least 50%, at least 60%, at least 70%, at least 80%, at least 90%, at least 95%, at least 99% of uridine residues in a polyribonucleotide comprises N1-methylpseudouridine. In some embodiments, a polyribonucleotide comprising 2'-O-acetylated ribose comprises uridine residues and at least 10% of uridine residues in a polyribonucleotide comprises N1-methylpseudouridine.

In some embodiments, a polyribonucleotide comprising 2'-O-acetylated ribose comprises uridine residues and about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of uridine residues comprise N1-methylpseudouridine. In some embodiments, a polyribonucleotide comprising 2'-O-acetylated ribose comprises uridine residues and at least 10% of uridine residues in a polyribonucleotide comprises N1-methylpseudouridine.

In some embodiments, a polyribonucleotide comprising 2'-O-acetylated ribose comprises uridine residues and more than 60%, no more than 70%, no more than 80%, no more than 90%, no more than 95%, or no more than 99%, of uridine residues comprise N1-methylpseudouridine. In some embodiments, a polyribonucleotide comprising 2'-O-acetylated ribose comprises uridine residues and at least 10% of uridine residues in a polyribonucleotide comprises N1-methylpseudouridine.

In some embodiments a polyribonucleotide comprising 2'-O-acetylated ribose comprises uridine residues and about 5%, about 10%, about 20%, about 30%, about 40%, about 50%, about 60%, about 70%, about 80%, about 90%, about 95%, or about 99% of uridine residues in a polyribonucleotide comprises N1-methylpseudouridine. In some embodiments, a polyribonucleotide comprising 2'-O-acetylated ribose comprises uridine residues and at least 10% of uridine residues in a polyribonucleotide comprises N1-methylpseudouridine.

In some embodiments, a polyribonucleotide comprising 2'-O-acetylated ribose comprises uridine residues and 100% of uridine residues in a polyribonucleotide comprises N1-methylpseudouridine. In some embodiments, a polyribonucleotide comprising 2'-O-acetylated ribose comprises uridine residues and at least 10% of uridine residues in a polyribonucleotide comprises N1-methylpseudouridine.

In some embodiments, a polyribonucleotide in which at least 5% uridine residues are N1-methylpseudouridine, comprises at least 5%, at least 10%, at least 15%, at least 20%, at least 25%, at least 30%, at least 35%, at least about 40%, at least 45%, at least 50%, at least 55%, at least 60%, at least 65%, at least 70%, at least 75%, at least 80%, at least 85%, at least 90%, at least 95%, or at least 99% 2'-O-acetylated ribose. In some embodiments, a polyribonucleotide comprising 2'-O-acetylated ribose comprises uridine residues and at least 10% of uridine residues in a polyribonucleotide comprises N1-methylpseudouridine.

In some embodiments, a polyribonucleotide in which at least 5% uridine residues are N1-methylpseudouridine, comprises at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% 2'-O-acetylated ribose. In some embodiments, a polyribonucleotide comprising 2'-O-acetylated ribose comprises uridine residues and at least 10% of uridine residues in a polyribonucleotide comprises N1-methylpseudouridine.

In some embodiments, a polyribonucleotide in which at least 5% uridine residues are N1-methylpseudouridine, comprises 100% 2'-O-acetylated ribose. In some embodiments, a polyribonucleotide comprising 2'-O-acetylated ribose comprises uridine residues and at least 10% of uridine residues in a polyribonucleotide comprises N1-methylpseudouridine.

In some embodiments, a polyribonucleotide in which at least 5% uridine residues are N1-methylpseudouridine, comprises about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% 2'-O-acetylated ribose. In some embodiments, a polyribonucleotide comprising 2'-O-acetylated ribose comprises uridine residues and at least 10% of uridine residues in a polyribonucleotide comprises N1-methylpseudouridine.

In some embodiments, a polyribonucleotide in which at least 5% uridine residues are N1-methylpseudouridine, comprises about 76% to about 100%, about 77% to about 100%, about 78% to about 100%, about 79% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, about 99% to about 100%, 2'-O-acetylated ribose. In some embodiments, a polyribonucleotide comprising 2'-O-acetylated ribose comprises uridine residues and at least 10% of uridine residues in a polyribonucleotide comprises N1-methylpseudouridine.

In some embodiments, a polyribonucleotide comprising 2'-O-acetylated ribose and uridine residues comprising N1-methylpseudouridine (e.g., a portion of N1-methylpseudouridine having 2-O ribose acetylation), further comprises one or more modified nucleotides.

Compositions

Among other things, the present disclosure provides compositions. Compositions disclosed herein comprise one or more polyribonucleotides comprising one or more modified ribonucleotides comprising a 2'-O-acetylated ribose.

In some embodiments, a composition comprising one or more polyribonucleotides comprising a 2'-O-acetylated ribose is or comprises a pharmaceutical composition.

In some embodiments, a composition comprising one or more polyribonucleotides comprising a 2'-O-acetylated ribose is or comprises an immunogenic composition. An immunogenic composition is a composition that induces an immune response. In some embodiments, an immunogenic composition comprising one or more polyribonucleotides does not itself induce an immune response, but rather the one or more polyribonucleotides encode, e.g., one or more polypeptides that induce an immune response.

In some embodiments, a composition comprising one or more polyribonucleotides comprising a 2'-O-acetylated ribose is or comprises a vaccine.

In some embodiments, a composition comprising one or more polyribonucleotides comprising a 2'-O-acetylated ribose is or comprises a gene therapy.

In some embodiments, a composition comprising one or more polyribonucleotides comprising a 2'-O-acetylated ribose is or comprises a chemotherapy.

In some embodiments, a composition comprising one or more polyribonucleotides comprising a 2'-O-acetylated ribose is or comprises a protein replacement therapy.

In some embodiments, a composition comprising one or more polyribonucleotides comprising a 2'-O-acetylated ribose is or comprises an immunotherapy.

In some embodiments, a composition comprising one or more polyribonucleotides comprising a 2'-O-acetylated ribose is or comprises a cell engineering therapy.

In some embodiments, a composition comprising one or more polyribonucleotides comprising a 2'-O-acetylated ribose comprises double stranded RNA.

In some embodiments, a composition comprising one or more polyribonucleotides comprising a 2'-O-acetylated ribose does not comprise double stranded RNA.

In some embodiments, a composition comprising a polyribonucleotide disclosed herein is characterized in that when assessed in a cell, tissue or an organism that has been administered the polyribonucleotide, reduces immunogenicity is observed relative to an appropriate reference comparator. In some embodiments, a reference comparator comprises an otherwise similar cell, tissue or organism that has been administered a composition comprising a comparable polyribonucleotide that includes fewer 2'-O-acetylated ribose (e.g., does not include any 2'-O-acetylated ribose) than a polyribonucleotide in a composition. In some embodiments, reduced immunogenicity comprises reduced activation of an innate immune response induced toxicity. In some embodiments, reduced activation of an immune response comprises reduced activation of NFkb or an NFkb pathway, IRF or an IRF pathway, and/or other inflammatory cytokines in the cell, tissue or organism. In some embodiments, reduced activation of an immune response comprises reduced detection of uncapped RNA by a molecular sensor, e.g., RIG-I.

In some embodiments, reduced immunogenicity allows for repeated dosing, e.g., administration of at least two doses, of a composition comprising a polyribonucleotide disclosed herein to a cell, tissue or subject. In some embodiments, repeated dosing comprises administration of at least two, at least three, at least four, at least five, at least six, at least seven, at least eight, at least nine or at least ten doses of composition comprising a polyribonucleotide disclosed herein. In some embodiments, repeated dosing comprises administration of a same dose of a composition as compared to a dose of a previous administration of a composition. In some embodiments, repeated dosing comprises administration of a different dose of a composition as compared to a dose of a previous administration of a composition.

In some embodiments, repeated dosing of a composition disclosed herein comprises administering a first dose at a first time point followed by administration of a subsequent dose at a second time point. In some embodiments, a first time point is about 1 day, about 2 days, about 3 days, about 4 days, about 5 days, about 6 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, or about 12 months prior to a second time point.

In some embodiments, a second or subsequent dose of a composition comprising a polyribonucleotide disclosed herein has a substantially similar efficacy in a cell, tissue or subject compared to a first dose of a composition comprising a polyribonucleotide disclosed herein.

In some embodiments, reduced immunogenicity allows for administration of a higher dose of a composition comprising a polyribonucleotide disclosed herein related to an appropriate reference comparator. In some embodiments, a reference comparator comprises a comparable polyribonucleotide includes fewer 2'-O-acetylated ribose (e.g., does not include any 2'-O-acetylated ribose) compared to a polyribonucleotide disclosed herein.

In some embodiments, a composition comprising a polyribonucleotide disclosed herein is characterized in that when assessed in a cell, tissue or an organism that has been administered a polyribonucleotide, increased cell viability is observed relative to an appropriate reference comparator. In some embodiments, a reference comparator is a cell viability of a cell, tissue or organism that has been administered a comparable polyribonucleotide that includes fewer 2'-O-acetylated ribose (e.g., does not include any 2'-O-acetylated ribose) compared to a polyribonucleotide disclosed herein.

In some embodiments, cell viability is a measure of the length of time one or more cells of a cell, tissue or subject live.

In some embodiments, cell viability is a measure of a number of cells of a cell, tissue or subject alive at one or more time points.

In some embodiments, a composition disclosed herein is or comprises an in vitro transcribed polyribonucleotide comprising a modified ribonucleotide disclosed herein.

In some embodiments, a composition disclosed herein is or comprises an expression vector comprising one or more polynucleotides disclosed herein.

In some embodiments, a composition disclosed herein comprises a polyribonucleotide comprising one or more modified ribonucleotides disclosed herein.

In some embodiments, a composition disclosed herein comprises a plurality of polyribonucleotides each comprising one or more modified ribonucleotides disclosed herein. In some embodiments, a composition comprises a plurality of ribonucleotides wherein a first polyribonucleotide comprises a first modified ribonucleotide, and a second polyribonucleotide comprises a second modified ribonucleotide. In some embodiments, a first modified ribonucleotide and a second modified ribonucleotide are the same modified ribonucleotide. In some embodiments, a first modified ribonucleotide and a second modified ribonucleotide are different modified ribonucleotides. In some embodiments, a first polyribonucleotide and/or a second polyribonucleotide further comprises one or more modified nucleotides.

In some embodiments, a composition disclosed herein is administered at a dose of about 5 ng to about 1000 ng, about 5 ng to about 900 ng, about 5 ng to about 800 ng, about 5 ng to about 700 ng, about 5 ng to about 600 ng, about 5 ng to about 500 ng, about 5 ng to about 400 ng, about 5 ng to about 300 ng, about 5 ng to about 200 ng, about 5 ng to about 100 ng, about 5 ng to about 90 ng, about 5 ng to about 80 ng, about 5 ng to about 70 ng, about 5 ng to about 60 ng, about 5 ng to about 50 ng, about 5 ng to about 40 ng, about 5 ng to about 30 ng, about 5 ng to about 20 ng, or about 5 ng to about 10 ng. In some embodiments, a composition disclosed herein is administered at a dose of about 10 ng to about 1000 ng, about 20 ng to about 1000 ng, about 30 ng to about 1000 ng, about 40 ng to about 1000 ng, about 50 ng to about 1000 ng, about 60 ng to about 1000 ng, about 70 ng to about 1000 ng, about 80 ng to about 1000 ng, about 90 ng to about 1000 ng, about 100 ng to about 1000 ng, about 200 ng to about 1000 ng, about 300 ng to about 1000 ng, about 40 ng to about 1000 ng, about 50 ng to about 1000 ng, about 60 ng to about 1000 ng, about 700 ng to about 1000 ng, about 800 ng to about 1000 ng, or about 900 ng to about 1000 ng.

In some embodiments, a composition disclosed herein is administered at a dose of about 5 ng, about 10 ng, about 20 ng, about 30 ng, about 40 ng, about 50 ng, about 60 ng, about 70 ng, about 80 ng, about 90 ng, about 100 ng, 150 ng, about 200 ng, about 250 ng, about 300 ng, about 350 ng, about 400 ng, about 450 ng, about 500 ng, about 550 ng, about 600 ng, about 650 ng, about 700 ng, about 750 ng, about 800 ng, about 850 ng, about 900 ng, about 950 ng, or about 1000 ng.

In some embodiments, a composition disclosed herein is administered at a dose of at least 5 ng, at least 10 ng, at least 20 ng, at least 30 ng, at least 40 ng, at least 50 ng, at least 60 ng, at least 70 ng, at least 80 ng, at least 90 ng, at least 100 ng, at least 150 ng, at least 200 ng, at least 250 ng, at least 300 ng, at least 350 ng, at least 400 ng, at least 450 ng, at least 500 ng, at least 550 ng, at least 600 ng, at least 650 ng, at least 700 ng, at least 750 ng, at least 800 ng, at least 850 ng, at least 900 ng, at least 950 ng, or at least 1000 ng.

Pharmaceutical Compositions

In some embodiments, a composition comprising one or more polyribonucleotides comprising a 2'-O-acetylated ribose is a pharmaceutical composition. In some embodiments, a pharmaceutical composition further comprises a pharmaceutically acceptable excipient. Pharmaceutical compositions of the present disclosure may comprise a polypeptide disclosed herein, a polynucleotide disclosed herein, or an expression vector comprising a polynucleotide disclosed herein.

In some embodiments, a pharmaceutical composition can include a pharmaceutically acceptable carrier or excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, MD, 2006; incorporated herein by reference) discloses various excipients used in formulating pharmaceutical compositions and known techniques for the preparation thereof. Suitable pharmaceutically acceptable carriers include but are not limited to water, salt solutions (e.g., NaCl), saline, buffered saline, glycerol, sugars such as mannitol, sucrose, or others, dextrose, fatty acid esters, etc., as well as combinations thereof.

A pharmaceutical composition can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like), which do not deleteriously react with the active compounds or interfere with their activity. In certain embodiments, a water-soluble carrier suitable for intravenous administration is used. In some embodiments, a pharmaceutical composition can be sterile.

A suitable pharmaceutical composition, if desired, can also contain minor amounts of wetting or emulsifying agents, or pH buffering agents. A pharmaceutical composition can be a liquid solution, suspension, or emulsion.

A pharmaceutical composition can be formulated in accordance with the routine procedures as a pharmaceutical composition adapted for administration to human beings. The formulation of a pharmaceutical composition should suit the mode of administration. For example, in some embodiments, a composition for intravenous administration is typically a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where a pharmaceutical composition is to be administered by infusion, it can be dispensed with an infusion bottle containing sterile pharmaceutical grade water, saline or dextrose/water. Where a pharmaceutical composition is administered by injection, an ampule of sterile water for injection or saline can be provided so that the ingredients may be mixed prior to administration.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts or cells in vitro or ex vivo. Modification of pharmaceutical compositions suitable for administration to humans in order to render the compositions suitable for administration to various animals or cells in vitro or ex vivo is well understood, and the ordinarily skilled practitioner, e.g., a veterinary pharmacologist, can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of a pharmaceutical composition described herein.

Method of Making Polyribonucleotides Comprising a 2'-O-Acetylated Ribose

This disclosure provides, among other things, methods of making a polyribonucleotide comprising a 2-O-acetylated ribose. In some embodiments, disclosed herein is method of producing a polyribonucleotide comprising a step of incubating an in vitro transcription mixture, wherein the in vitro transcription mixture comprises: (i) a DNA template; (ii) at least one RNA polymerase or a variant or a fragment thereof; and (iii) a plurality of ribonucleotides comprising at least one modified ribonucleotide comprising a 2'-O-acetylated ribose; thereby producing a polyribonucleotide comprising a 2'-O-acetylated ribose.

Also disclosed herein are in vitro transcription mixtures useful in producing a polyribonucleotide comprising a 2'-O-acetylated ribose. In some embodiments, disclosed herein is in vitro transcription mixture comprising: (i) a DNA template; (ii) at least one RNA polymerase or a variant or a fragment thereof; and (iii) a plurality of ribonucleotides comprising at least one modified ribonucleotide comprising a 2'-O-acetylated ribose.

In some embodiments, a method or an in vitro transcription mixture produces a plurality of polyribonucleotides. In some embodiments, each polyribonucleotide in a plurality of polyribonucleotides comprises a 2'-O-acetylated ribose.

In some embodiments, an RNA polymerase is chosen from: a bacteriophage RNA polymerase, a mitochondrial RNA polymerase, a eukaryotic RNA polymerase, a bacterial RNA polymerase, or any combination thereof. In some embodiments, an RNA polymerase comprises a T7 RNA polymerase, a T3 RNA polymerase, a SP6 RNA polymerase, a viral RNA polymerase, a N4 virion RNA polymerase, or a variant of any of the foregoing.

In some embodiments, a polyribonucleotide produced by a method disclosed herein or using an in vitro transcription mixture comprises a coding region. In some embodiments, a coding region encodes a gene product, e.g., as described herein.

In some embodiments, a polyribonucleotide produced by a method disclosed herein or using an in vitro transcription mixture does not comprise a coding region. In some embodiments, a polyribonucleotide which does not comprises a coding region can also be referred to as a non-coding RNA. Exemplary non-coding RNA include, but are not limited to, long non-coding RNAS (lncRNA), microRNAs, siRNAs, piRNAs, snoRNAs, snRNAs, exRNAs, scaRNAs IRNA, and tRNA, In some embodiments, a polyribonucleotide produced by a method disclosed herein or using an in vitro transcription mixture comprises a guide RNA, a short hairpin RNA, an siRNA, a microRNA, a long non-coding RNA, a circular RNA, or a messenger RNA (mRNA), or any combination thereof.

In some embodiments, a polyribonucleotide produced by a method disclosed herein or using an in vitro transcription mixture encodes a payload. In some embodiments, a payload comprises one or more target polypeptides.

In some embodiments of a method of producing a ribonucleotide disclosed herein, an incubating step occurs at a temperature of at least 37 C.

In some embodiments of a method of producing a ribonucleotide disclosed herein, an incubating step occurs at a temperature of about 45 C, 46 C, 47 C, 48 C, 49 C, 50 C, 51 C, 52 C, 53 C, 54 C, 55 C, or higher.

In some embodiments of a method of producing a ribonucleotide disclosed herein, an incubating step is performed for at least 1 hour, at least 2 hours, at least 3 hours, at least 4 hours or longer.

RNA Formulations

Among other things, provided herein are compositions comprising polyribonucleotides comprising 2'-O-acetylated ribose, and formulations thereof. In some embodiments, a composition comprising a polyribonucleotide disclosed herein is formulated in a lipid nanoparticle (LNP) formulation.

In some embodiments, a polyribonucleotide disclosed herein encodes for a polypeptide. In some embodiments, a polyribonucleotide disclosed herein is or comprises a messenger RNA. In some embodiments, a composition comprising a polyribonucleotide comprising a messenger RNA is formulated in a lipid nanoparticle (LNP) formulation.

In some embodiments, a polyribonucleotide disclosed herein is or comprises a gRNA. In some embodiments, a composition comprising a polyribonucleotide comprising a gRNA is formulated in a lipid nanoparticle (LNP) formulation.

In some embodiments, a polyribonucleotide disclosed herein is or comprises an inhibitory RNA. In some embodiments, a composition comprising a polyribonucleotide comprising an inhibitory RNA is formulated in a lipid nanoparticle (LNP) formulation.

In some embodiments, a polyribonucleotide disclosed herein is or comprises an miRNA or siRNA. In some embodiments, a composition comprising a polyribonucleotide comprising a miRNA or siRNA is formulated in a lipid nanoparticle (LNP) formulation.

In some embodiments, a polyribonucleotide disclosed herein is or comprises an antisense oligonucleotide. In some embodiments, a composition comprising a polyribonucleotide comprising an antisense oligonucleotide is formulated in a lipid nanoparticle (LNP) formulation In some embodiments, the disclosure provides an LNP formulation comprising a polyribonucleotide disclosed herein for use in a pharmaceutical composition, e.g., an immunogenic composition.

Methods of Using Compositions Disclosed Herein

The disclosure provides, among other things, methods for using a polyribonucleotide disclosed herein, or a composition comprising the same.

In some embodiments, provided herein is a method of administering a polyribonucleotide disclosed herein or a composition comprising a polyribonucleotide disclosed herein to a cell, tissue or subject.

In some embodiments, provided herein is a vaccination method comprising administering a polyribonucleotide disclosed herein or a composition comprising a polyribonucleotide disclosed herein to a cell, tissue or subject.

In some embodiments, disclosed herein is a gene therapy method comprising administering a polyribonucleotide disclosed herein or a composition comprising a polyribonucleotide disclosed herein to a cell, tissue or subject. In some embodiments, a gene therapy method comprises delivery of one or more components of a gene therapy, e.g., a guide RNA and/or a Cas polypeptide.

In some embodiments, provided herein is a method for stimulating an immune response comprising administering a polyribonucleotide disclosed herein or a composition comprising a polyribonucleotide disclosed herein to a cell, tissue or subject.

In some embodiments, also provided herein is a cell therapy engineering method comprising administering a polyribonucleotide disclosed herein or a composition comprising a polyribonucleotide disclosed herein to a cell, tissue or subject.

In some embodiments, provided herein is an immunotherapy method comprising administering a polyribonucleotide disclosed herein or a composition comprising a polyribonucleotide disclosed herein to a cell, tissue or subject. In some embodiments, an immunotherapy method comprises delivery of an antibody therapy and/or an immune checkpoint therapy.

In some embodiments, disclosed herein is a protein replacement therapy method comprising administering a polyribonucleotide disclosed herein or a composition comprising a polyribonucleotide disclosed herein to a cell, tissue or subject. In some embodiments, a protein replacement therapy comprises delivery of an enzyme replacement therapy.

In some embodiments, provided herein is a chemotherapeutic method comprising administering a polyribonucleotide disclosed herein or a composition comprising a polyribonucleotide disclosed herein to a cell, tissue or subject.

In some embodiments, a method or use disclosed herein comprises determining cell viability of a cell, tissue or subject. In some embodiments, cell viability is a measure of a length of time one or more cells of a cell, tissue or subject live. In some embodiments, cell viability is a measure of a number of cells of a cell, tissue or subject alive at one or more time points.

In some embodiments, a cell, tissue or subject to which a polyribonucleotide or a composition comprising the same has been administered exhibits improved cell viability as compared to a reference cell viability. In some embodiments, a reference cell viability is a cell viability of a cell, tissue or subject that has been administered a comparable polyribonucleotide or a composition comprising the same that includes fewer 2'-O-acetylated ribose (e.g., does not include any 2'-O-acetylated ribose) compared to a polyribonucleotide disclosed herein.

In some embodiments, a method or use disclosed herein further comprises determining an immune system response of a cell, tissue or subject to which a polyribonucleotide or a composition comprising the same has been administered. In some embodiments, an immune response comprises an innate immune system response comprising innate immune system induced toxicity. In some embodiments, determining an innate immune system response comprises determining a level and/or activation of NF-κB or an NF-κB pathway; IRF or an IRF pathway; or inflammatory cytokines, or any combination thereof in a cell, tissue or subject. In some embodiments, determining an innate immune system response comprises determining a level of uncapped RNA detection in a cell, tissue or subject.

In some embodiments, a cell, tissue or subject to which a polyribonucleotide or a composition comprising the same has been administered exhibits a reduced innate immune system response as compared to a reference. In some embodiments, a reference is an innate immune system response of a cell, tissue or subject that has been administered a comparable polyribonucleotide or a composition comprising the same that includes fewer 2'-O-acetylated ribose (e.g., does not include any 2'-O-acetylated ribose) compared to a polyribonucleotide disclosed herein.

In some embodiments, a method or use disclosed herein further comprises determining efficacy of a polyribonucleotide or a composition comprising the same in a cell, tissue or subject to which a polyribonucleotide or a composition comprising the same has been administered.

In some embodiments, determining efficacy comprises determining an antibody response or cellular response in a cell, tissue or subject. In some embodiments, a cell, tissue or subject to which a polyribonucleotide or a composition comprising the same has been administered exhibits an increased antibody response or cellular response as compared to a reference. In some embodiments, a reference is an antibody response or cellular response of a cell, tissue or subject that has been administered a comparable polyribonucleotide or a composition comprising the same that includes: fewer 2'-O-acetylated ribose (e.g., does not include any 2'-O-acetylated ribose) compared to a polyribonucleotide disclosed herein.

In some embodiments, a method or use disclosed herein comprises administering a polyribonucleotide or a composition comprising the same to a cell, tissue or subject at least two times. In some embodiments, a method disclosed herein comprises administering a polyribonucleotide or a composition comprising the same to a cell, tissue or subject at least 2 times, at least 3 times, at least 4 times, at least 5 times, at least 6 times, at least 7 times, at least 8 times, at least 9 times or at least 10 times.

In some embodiments, a method or use disclosed herein comprises administering a plurality of doses of a polyribonucleotide or a composition comprising the same to a cell, tissue or subject. In some embodiments, a second or subsequent dose of a polyribonucleotide or a composition comprising the same has a substantially similar efficacy in a cell, tissue, or subject compared to administration of a first dose of a composition comprising a polyribonucleotide.

In some embodiments of any of the methods or uses disclosed herein, a polyribonucleotide or a composition comprising the same is administered to a cell, tissue or subject at a higher dose compared to an appropriate reference comparator. In some embodiments, a reference comparator comprise a comparable polyribonucleotide that includes fewer 2'-O-acetylated ribose (e.g., does not include any 2'-O-acetylated ribose) compared to a polyribonucleotide disclosed herein.

In some embodiments of any of the methods or uses disclosed herein, the composition is administered via any one of the following routes of administration: intramuscular, intravenous, subcutaneous, intrathecal, intradermal, ocular, intranasal, sublingual, or oral.

In some embodiments of any of the methods or uses disclosed herein a cell is a mammalian cell.

In some embodiments of any of the methods or uses disclosed herein a tissue is a mammalian tissue.

In some embodiments of any of the methods or uses disclosed herein, a subject is a mammal. In some embodiments, a mammal is a human.

Kits

Another aspect of the present disclosure further provides a pharmaceutical pack or kit. In some embodiments, a kit can comprise a polyribonucleotide or a composition described herein. In some embodiment, kits may be used in any applicable method, e.g., methods as described herein.

EXEMPLIFICATION

Example 1: Use of 2'-O-Acetylated NTPs by T7 RNA Polymerase as a Substrate for In Vitro Transcription This Example shows that wild type T7 RNA polymerase can use 2'-O-acetylated nucleotide triphosphates as a substrate for in vitro transcription of RNA and that the resulting RNAs are translationally active.

Methods:

Example 3 discloses methods used to make 2'-O-acetylated nucleotide triphosphates used in this Example and disclosed herein.

In vitro transcription (IVT) of Luc2 RNA for A549 Assays

Luc2 RNA was synthesized in 20 μL IVT reactions consisting of 200 ng Luc2 T7 template, 20 mM MgCl2, 7.5 mM each of either natural NTPs or 2'-O-acetyl NTPs, 7.5 mM CleanCap AG (TriLink), 1× HiScribe Transcription Buffer, and 2 uL HiScribe polymerase mix (NEB) and incubated at 37° C. for 4 hours.

All IVT products were cleaned up using Monarch 500 μg RNA Clean Up kit (NEB) and eluted into 88 μL nuclease-free water. Eluted products were then digested in 100 μL reactions consisting of 1× DNase I buffer and 10U of DNase I (RNase-free) (New England Biolabs) at 37° C. for 5 minutes to degrade DNA template. DNase I treated samples were cleaned up using Monarch 500 ug RNA Clean Up kit (New England Biolabs) and eluted into 88 μL nuclease-free water.

The DNAse I treated products, which have a co-transcriptionally added Cap 1 structure, were treated with 1× DNase I buffer (NEB) and 100U Calf Intestinal Alkaline Phosphotase (CIAP) (Promega) at 37° C. for 5 min as a polishing step to remove rare immunogenic 5' triphosphates from RNA transcripts that did not incorporate CleanCap AG. DNase I buffer was used for this enzymatic step as we have found that this CIAP enzyme performs better in DNAse I buffer for this RNA polishing step (unpublished data).

CIAP treated RNAs were cleaned up using Monarch 500 ug RNA Clean Up kit (NEB) and eluted into 100 uL nuclease free water.

RNA Quantification: RNA concentration was determined using a NanoDrop OneC spectrophotometer (Thermo Scientific).

A549 Cell Culture Methods: A549-Dual (InvivoGen) were cultured in high glucose GlutaMAX Dulbecco's Modified Eagle Medium supplemented with 10% heat-inactivated fetal bovine serum, 100 units/mL penicillin, 100 μg/mL streptomycin, 10 μg/mL blasticidin, and 100 μg/mL zeocin and maintained at 37° C. and 5% $CO_2$.

Cells were plated to a 96-well at 2,000 cells/well 1 day prior to transfection. 50 or 100 ng of each RNA were transfected using Lipofectamine MessengerMAX Transfection Reagent (ThermoFisher) using a 1:1.5 μg:uL ratio of RNA:MessengerMAX. Transfections were performed in triplicate.

Viability and luciferase expression were determined using the ONE-Glo+Tox Luciferase Reporter and Cell Viability Assay (Promega). NF-κB activation was measured via the SEAP reporter gene using the QUANTI-Blue detection reagent (InvivoGen) as described by the manufacturer. The IRF pathway activation was measured via the activity of Lucia luciferase gene using QUANTI-Luc detection reagent (InvivoGen) as described by the manufacturer.

Results:

Reduced immunogenicity and improved cell viability with 2'-O-acetylated RNA. As shown in Table 1, T7 RNA polymerase used 2'-O-acetyl analogs to produce appreciable amounts of fully 2'-O-acetylated full length RNA, albeit at a reduced yield compared to natural nucleotides.

TABLE 1

| In vitro transcribed RNA | Yield |
|---|---|
| Natural Luc2 RNA | 1142.4 ng/uL in 100 uL H2O |
| 100% 2'-O-acetylated Luc2 RNA | 202.1 ng/uL in 75 uL H2O |
| 100% 2'-O-acetylated, Ac4C Luc2 RNA | 90.4 ng/uL in 75 uL H2O |

Figure 2:
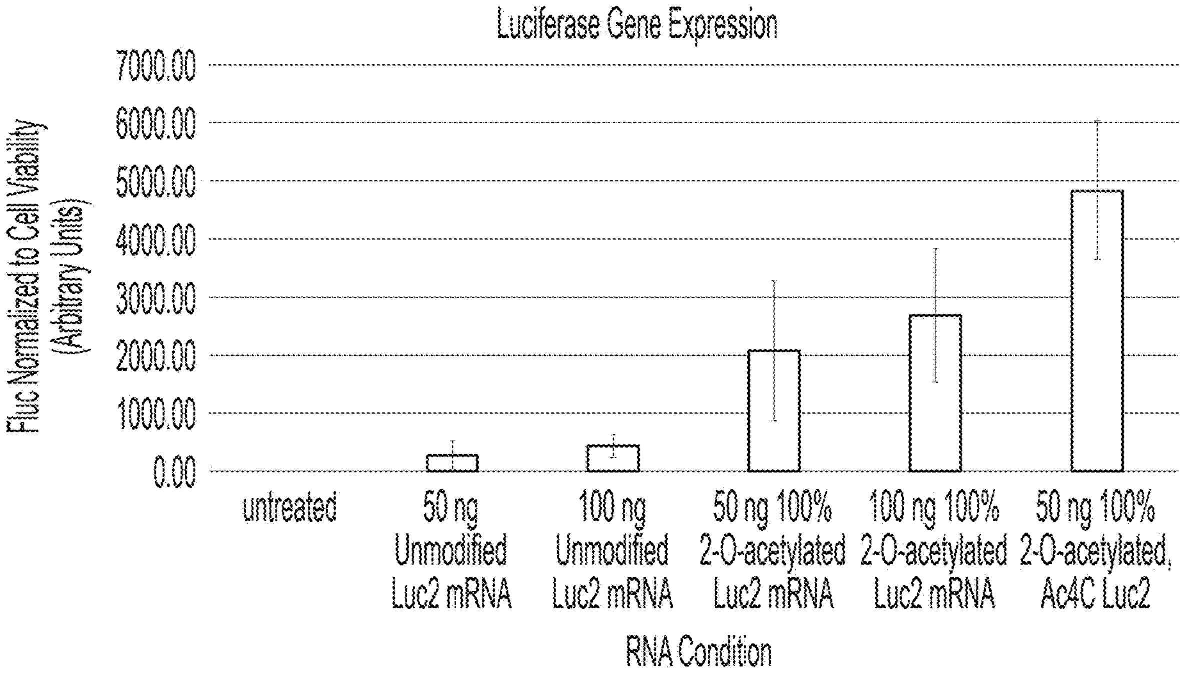
FIG. 2 is a graph depicting luciferase gene expression normalized to cell viability by dose of RNA synthesized with indicated nucleotide composition.

Not only were the fully 2'-O-acetylated full length RNAs translationally active, but they also outperformed unmodified RNA in terms of reporter gene expression, cell viability, and immunogenicity. FIG. 2 shows that fully 2'-O-acetylated RNA can be introduced into eukaryotic cells and translated by the eukaryotic ribosomal machinery and expressed better than unmodified RNA. Without wishing to be bound by any particular theory, this observation is expected to be due to improved stability and/or half-life of the 2'-O-acetylated RNA.

Figure 3:
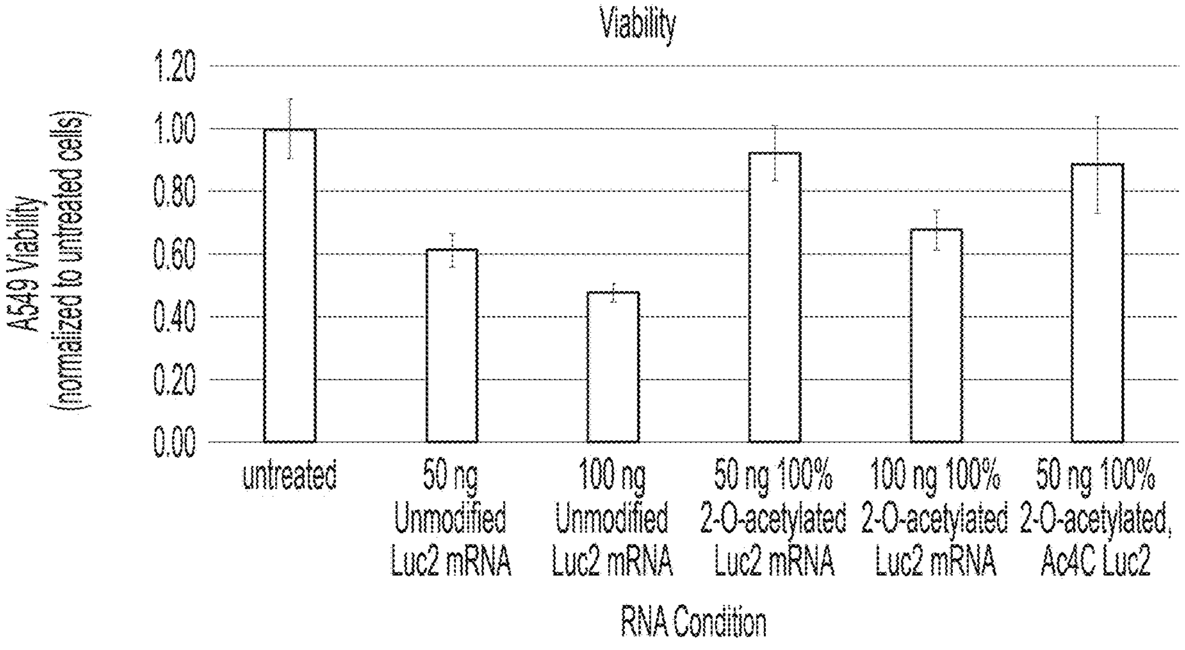
FIG. 3 is a graph depicting viability of A549 cells following transfection with respective doses of RNA synthesized with indicated nucleotide composition.

The results from the experiments further showed that 2'-O-acetylated RNA was less immunogenic than its unmodified counterpart. FIG. 3 shows the improvement in cell viability with 2'-O-acetylated RNA compared to unmodified RNA. This trend in viability improvement followed a similar trend in the reduction of both immunogenicity markers, NF-Kb (FIG. 5) and IRF (FIG. 4).

In the assays testing for immunogenicity of the 2'-O-acetylated RNAs (see FIGS. 4-5), increased immunogenicity was seen with 100 ng of 2'-O-acetylated RNA. Without wishing to be bound by any particular theory, this increased immunogenicity at the higher doses of 2'-O-acetylated RNA was hypothesized to be likely due to novel RNA structures that are detected by cytoplasmic RNA sensors, increased protein burden to cells due to longer RNA half-life, or a combination of said factors. To test this hypothesis, a 2'-O-acetyl analog of the base modified nucleotide N4-Acetylcytidine, which was previously shown to reduce innate immunogenicity, was tested in the 2'-O-acetylated RNA (see FIGS. 4 and 5, last bars on the right labeled "50 ng 100% 2-O-acetylated, Ac4C Luc2"). In some embodiments, this data provides support for the use of 2'-O-acetyl nucleotide triphosphates that are also base modified to further improve RNA performance when using higher doses of 2'-O-acetyl RNA.

Characterization of 2'-O acetylation of nucleotides: To confirm full 2'-O-acetylation of the nucleotides being used, NMR data was obtained for the purified ribose acetylated NTPs. The data shows that the purified ribose acetylated NTPs only consist of a mix of 2'-O-acetyl and 3-O-acetyl NTP (see Example 3 and FIGS. 6-61. This mix was apparently due to a spontaneous switch of the position of the acetyl group when in solution as a triphosphate. However, this spontaneous switch and resulting mix of structures, does not indicate that the RNAs used in this Example were not fully 2'-O-acetylated. This is because RNA transcription requires 3' OH of the ribose to be available for chain elongation. Accordingly, any RNA product that is produced when using 2'-O-acetylated NTPs for transcription must only have the 2'-O-acetyl modification since 3'-O-acetyl group would act as a transcription terminator.

Conclusion: Taken together, this Example and the data herein demonstrate for the first time that 2'-O-acetylated RNAs can be transcribed by wild type T7 RNA polymerase, and that the resulting RNA perform better than unmodified RNA. These findings have uncovered the discovery of a novel class of nucleotide triphosphates that can readily be used for in vitro transcription of RNAs for use in a variety of applications including as therapeutics in medical applications.

Example 2: In Vivo Gene Expression from LNP Delivered 2'O-Acetylated Ribose RNA is Comparable to LNP Delivered N1-Methylpseudouridine Modified RNA This Example describes in vivo gene expression from animals administered LNP formulations comprising 2'-O-acetylated ribose RNA or N1-methylpseudouridine modified RNA.

Methods: Luc2 IVT Template production: The luc2 gene encoding an optimized version of firefly luciferase was amplified from pGL4.10 [luc2] (Promega). Amplification was carried out at an annealing temperature of 70° C. in a 20 μL reaction consisting of 0.25 μM each primer Luc2_fwd and Luc2_rev, 1× Herculase II buffer, 25 mM each dNTP, 15 ng pGL4.10 [luc2] plasmid (Promega), 0.25M Betaine and 0.4 μL Herculase II enzyme. PCR product was purified using the DNA Clean & Concentrator-25 Kit (Zymo Research) according to the manufacturer's protocol and eluted into 45 μL Nuclease free water. 42.5 uL of the eluted product was subjected to treatment with 125U of Dpn1 enzyme (New England Biolabs) in a 50 μL reaction to digest template plasmid. The digested product was purified again using the DNA Clean & Concentrator-25 Kit (Zymo Research) according to the manufacturer's protocol and eluted into 40 μL nuclease free water. This digested, primary PCR product was then amplified at 50C in a 20 μL reaction consisting of 0.25 M each primer T7-AGG_fwd and 120 pA_rev, 1× Herculase II buffer, 25 mM each dNTP, 15 ng Luc2 primary amplification product, and 0.4 μL Herculase II enzyme. This secondary PCR product was cleaned up using the DNA Clean & Concentrator-25 Kit (Zymo Research) according to the manufacturer's protocol and eluted into nuclease free water.

The sequences of primers used were as follows:

```
Luc2_fwd:
                                    (SEQ ID NO: 1)
CTTGTTCTTT TTGCAGAAGC TCAGAATAAA CGCTCAACTT

TGGCCACCat ggaagatgcc aaaaacatta agaagggc

Luc2_rev
                                    (SEQ ID NO: 2)
AGAATGTGAA GAAACTTTCT TTTTATTAGG AGCAGATACG

AATGGCTACA TTTTGGGGGA CAACATTTTG TAAAGTGTAA

GTTGGTATTA TGTAGCTTAG AGACTCCATT CGGGTGTTCT

TGAGGCTGGT CTATCATTAc acggcgatct tgccgcc
```

-continued

```
T7-AGG_fwd:
                                    (SEQ ID NO: 3)
gaattTAATA CGACTCACTA TAAGGcttgt tctttttgca

gaagc

120pA_rev
                                    (SEQ ID NO: 4)
TTTTTTTTTT TTTTTTTTTT TTTTTTTTTT TTTTTTTTTT

TTTTTTTTTT TTTTTTTTTT TTTTTTTTTT TTTTTTTTTT

TTTTTTTTTT TTTTTTTTTT TTTTTTTTTT TTTTTTTTTT

agaatgtgaa gaaactttct ttttattag
```

In vitro transcription (IVT) of Luc2 RNA for A549 Assays: Luc2 RNA was synthesized in 20 μL IVT reactions consisting of 200 ng Luc2 T7 template, 20 mM MgCl2, 7.5 mM each of either natural NTPs or 2'-O-acetyl NTPs, 7.5 mM CleanCap AG (TriLink), 1× HiScribe Transcription Buffer, and 2 uL HiScribe polymerase mix (NEB) and incubated at 37° C. for 4 hours.

All IVT products were cleaned up using Monarch 500 μg RNA Clean Up kit (NEB) and eluted into 88 μL nuclease-free water. Eluted products were then digested in 100 μL reactions consisting of 1× DNase I buffer and 10U of DNase I (RNase-free) (New England Biolabs) at 37° C. for 5 minutes to degrade DNA template. DNase I treated samples were cleaned up using Monarch 500 ug RNA Clean Up kit (New England Biolabs) and eluted into 88 μL nuclease-free water.

The DNAse I treated products, which have a co-transcriptionally added Cap 1 structure, were treated with 1× DNase I buffer (NEB) and 100U Calf Intestinal Alkaline Phosphotase (CIAP) (Promega) at 37° C. for 5 min as a polishing step to remove rare immunogenic 5' triphosphates from RNA transcripts that did not incorporate CleanCap AG. DNase I buffer was used for this enzymatic step as we have found that this CIAP enzyme performs better in DNAse I buffer for this RNA polishing step (unpublished data).

CIAP treated RNAs were cleaned up using Monarch 500 ug RNA Clean Up kit (NEB) and eluted into 100 uL nuclease free water.

RNA Quantification: RNA concentration was determined using a NanoDrop OneC spectrophotometer (Thermo Scientific).

A549 Cell Culture Methods: A549-Dual (InvivoGen) were cultured in high glucose GlutaMAX Dulbecco's Modified Eagle Medium supplemented with 10% heat-inactivated fetal bovine serum, 100 units/mL penicillin, 100 μg/mL streptomycin, 10 μg/mL blasticidin, and 100 μg/mL zeocin and maintained at 37° C. and 5% $CO_2$.

Cells were plated to a 96-well at 2,000 cells/well 1 day prior to transfection. 50 or 100 ng of each RNA were transfected using Lipofectamine MessengerMAX Transfection Reagent (ThermoFisher) using a 1:1.5 μg:uL ratio of RNA:MessengerMAX. Transfections were performed in triplicate.

Viability and luciferase expression were determined using the ONE-Glo+Tox Luciferase Reporter and Cell Viability Assay (Promega). NF-κB activation was measured via the SEAP reporter gene using the QUANTI-Blue detection reagent (InvivoGen) as described by the manufacturer. The IRF pathway activation was measured via the activity of Lucia luciferase gene using QUANTI-Luc detection reagent (InvivoGen) as described by the manufacturer.

In vitro transcription (IVT) of Luc2 RNA for In Vivo Studies: For 2'-O-acetylated Luc2 mRNA, mRNA was synthesized in 20 μL IVT reactions consisting of 200 ng Luc2 T7 template, 20 mM MgCl2, 7.5 mM each 2'-O-acetyl NTP, 7.5 mM CleanCap AG (TriLink), 1× HiScribe Transcription Buffer, and 2 uL HiScribe polymerase mix (NEB) and incubated at 37° C. for 4 hours.

For N1-Methylpseudouridine modified Luc2 mRNA, mRNA was synthesized in 20 μL IVT reactions consisting of 200 ng Luc2 T7 template, 20 mM MgCl2, 7.5 mM each NTP with N1-methylpseudouridine triphosphate fully replacing uridine triphosphate, 7.5 mM CleanCap AG (TriLink), 1× HiScribe Transcription Buffer, and 2 uL HiScribe polymerase mix (NEB) and incubated at 37° C. for 4 hours.

All IVT products were cleaned up using Monarch 500 μg RNA Clean Up kit (NEB) and eluted into 88 μL nuclease-free water. Eluted products were then digested in 100 μL reactions consisting of 1× DNase I buffer and 10U of DNase I (RNase-free) (New England Biolabs) at 37° C. for 5 minutes to degrade DNA template. DNase I treated samples were cleaned up using Monarch 500 ug RNA Clean Up kit (New England Biolabs) and eluted into 88 μL nuclease-free water.

The DNAse I treated products, which have a co-transcriptionally added Cap 1 structure, were treated with 1× DNase I buffer (NEB) and 100U Calf Intestinal Alkaline Phosphotase (CIAP) (Promega) at 37° C. for 5 min as a polishing step to remove rare immunogenic 5' triphosphates from RNA transcripts that did not incorporate CleanCap AG. DNase I buffer was used for this enzymatic step as we have found that this CIAP enzyme performs better in DNAse I buffer for this RNA polishing step (unpublished data).

IVT products were cleaned up using Monarch 500 μg RNA Clean Up kit (NEB) and eluted into 100 μL 1 mM sodium citrate, pH 6.5 (ThermoFisher). IVT products were cleaned up using Monarch 500 μg RNA Clean Up kit (NEB) and eluted into 100 μL 1 mM sodium citrate, pH 6.5 (ThermoFisher).

RNA Quantification: RNA concentration was determined using a NanoDrop OneC spectrophotometer (Thermo Scientific).

mRNA-LNP Formulations. Formulations of mRNA in lipid nanoparticles (mRNA-LNPs) were prepared using an Ignite microfluidic mixer (Precision Nanosystems, Vancouver, BC). Briefly, Gen Voy-ILM lipid mixture (Precision-Nanosystems NWW0042) was diluted to 12.5 mM in anhydrous ethanol and combined with an aqueous solution of mRNA (0.14 mg/mL) in PNI buffer (Precision Nanosystems NWW0043), using the manufacturer-recommended formulation parameters. Formulations were immediately diluted 30:1 in phosphate-buffered saline (Gibco 10010023), concentrated using Amicon centrifugation filters (MilliporeSigma UFC901008), and adjusted to an estimated final volume with PBS. Next, formulations were characterized on a Stunner UV-VIS/DLS instrument (Unchained Labs) then further diluted with PBS as necessary to a precise payload concentration (ug/mL). Formulations were stored at 4° C. until in vivo administration.

mRNA administration studies in mice. Animal experiments were carried out in accordance with the guidelines set forth by Charles River Accelerator Development Lab (CRADL, Cambridge, MA, USA) and were approved by the CRADL Institutional Animal Care and Use (IACUC) committee. Female BALB/C mice (7-9 weeks old) were purchased from Charles River Laboratories (Wilmington, MA, USA) and housed at CRADL. Mice (n=5 per condition) were acclimated for at least 2 days before the initiation of the study. For the single administration study (FIG. 6), animals received one IM mRNA-LNP administration. Mice were imaged via whole body bioluminescence imaging at three time points following mRNA injection (~6 hours, ~24 hours and ~48 hours post administration). All mRNA injections consisted of 50 uL mRNA-LNP formulation (1 ug Luc2 mRNA dose per animal) delivered via IM injection in the left lateral. For whole body bioluminescence imaging, animals were injected with 200 μL of D-luciferin K+ salt (PerkinElmer122799) diluted to 15 mg/mL in PBS, via intraperitoneal (IP) injection, 10 minutes prior to the imaging time point. Three minutes prior to imaging, mice were placed under 3% isoflurane anesthesia in an induction chamber, then moved to isoflurane-delivering nosecones in the imaging chamber (IVIS-Spectrum Model 124262; Perkin Elmer, Waltham, MA) immediately prior to imaging. Mice were positioned with left lateral side up in the imaging chamber and were maintained on 3% isoflurane throughout imaging. Images were acquired using field of view D and continued to be exposed until 30,000 photons were collected or 1 min has passed, whichever occurred first. After imaging, animals were returned to their home cage for recovery.

Results: FIGS. 62A and 62B, show that reporter gene expression from LNP delivered fully 2'-O-acetylated RNA is comparable to reporter gene expression from LNP delivered N1-methylpseudouridine modified RNA, which is a modification that is commonly used in RNA therapeutics. The reporter gene expression levels were comparable from both RNAs at 6 hours, 24 hours and 48 hours post-administration. This data suggest that 2'-O-acetylated RNA has a similar persistence in vivo compared to the in vivo persistence of N1-methylpseudouridine modified RNA.

This result is unexpected for several reasons, one being the in vitro data showing residual IRF and NK-kB signaling from 2'-O-acetylated RNA having no base modification (Example 1 and FIGS. 4-5). Since IRF and NF-kB activity can lead to upregulation of nucleases from anti-viral response, and the level of reporter expression seen with 2-O acetylated RNA is similar to that of N1-methylpseudouridine modified RNA, without wishing to be bound by any particular theory, this data suggests that use of 2'-O-acetylated NTPs for in vitro transcription can provide RNAs with increased persistence, e.g., with increased resistance to nuclease degradation.

In some embodiments, using 2'-O-acetylated derivatives of known base modified NTPs for in vitro transcription can provide RNA with increased persistence compared to the commonly used N1-methylpseudouridine modified mRNA. Without wishing to be bound by any particular theory, polyribonucleotides having increased persistence can be achieved by combining reduced immunogenicity from a base modification (e.g., Ac4C, 5hmU, N1-methylpseudouridine, etc.) and nuclease resistance from a ribosome compatible backbone modification (e.g., 2'-O-acetylated ribose as described herein).

Example 3: Synthesis of 2'-O-Acetylated NTPs

Figure 6:
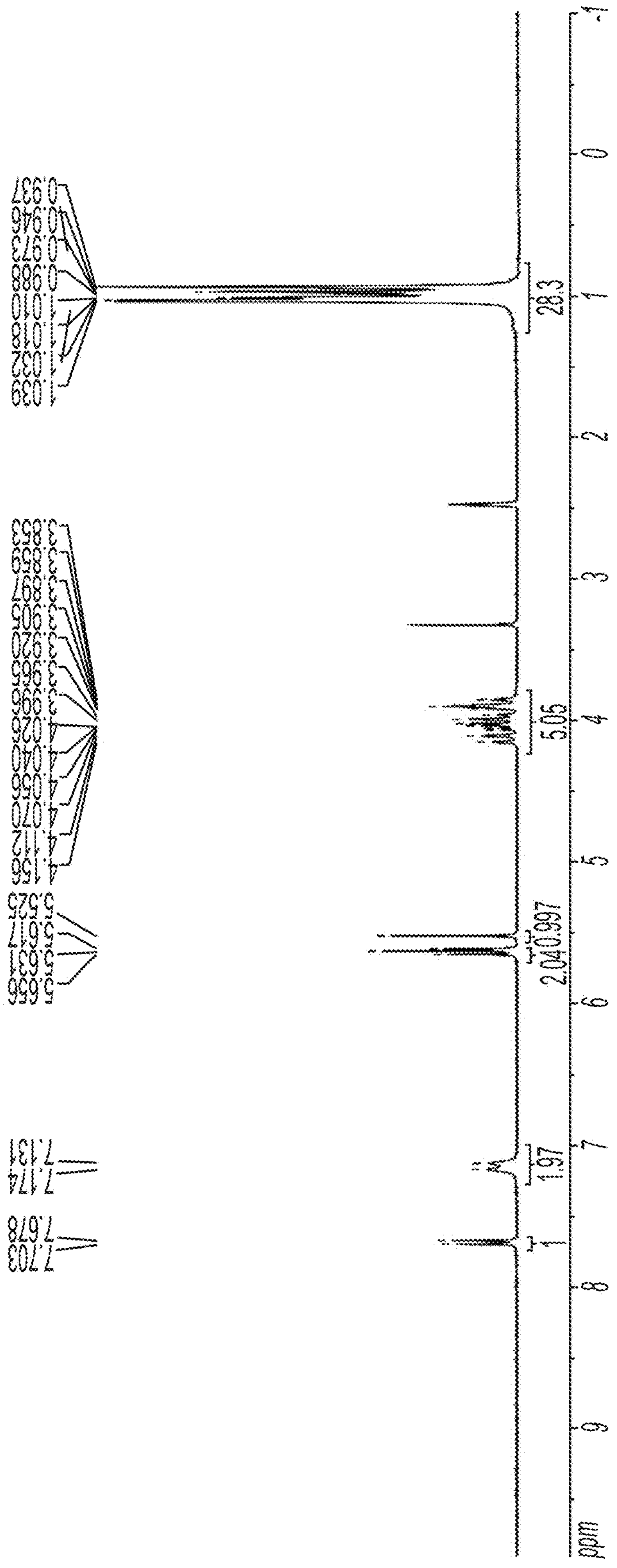
FIG. 6 is a graph depicting 1H NMR (300 MHz; DMSO-d6) of Silyl-Protected cytidine 2.
Figure 7:
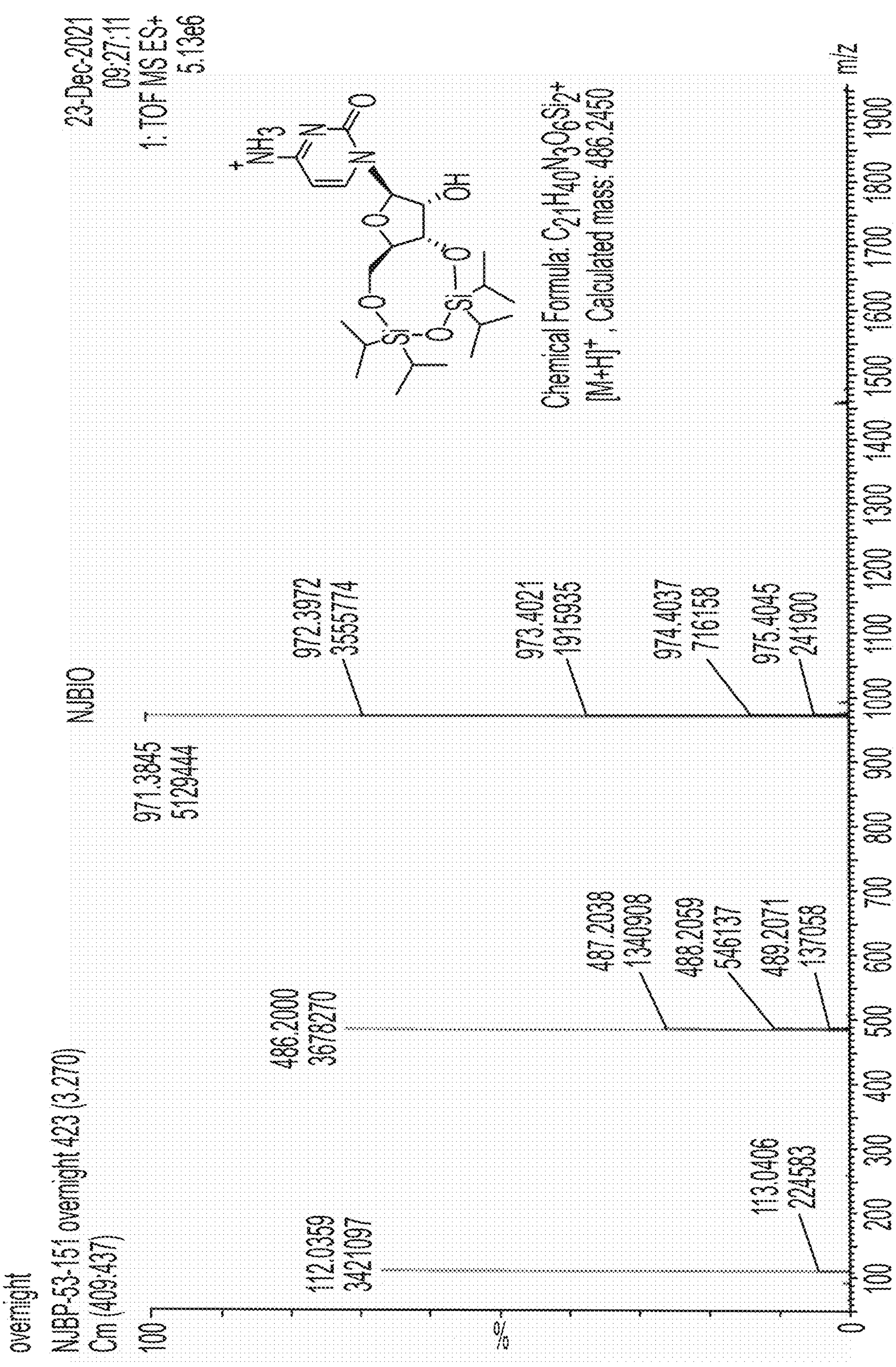
FIG. 7 is a mass spectrum (ESI+, 100% CH3OH, TOF) of Silyl-Protected cytidine 2.
Figure 8:
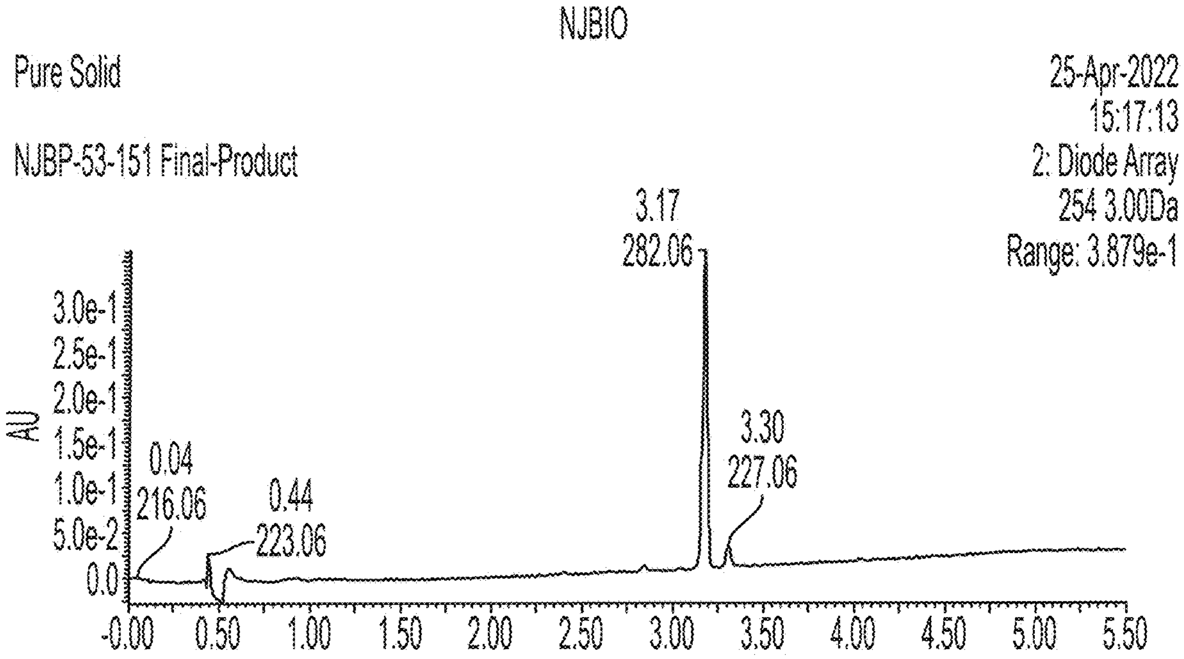
FIG. 8 is a HPLC chromatogram (CH3OH) of Silyl-Protected cytidine 2.
Figure 9:
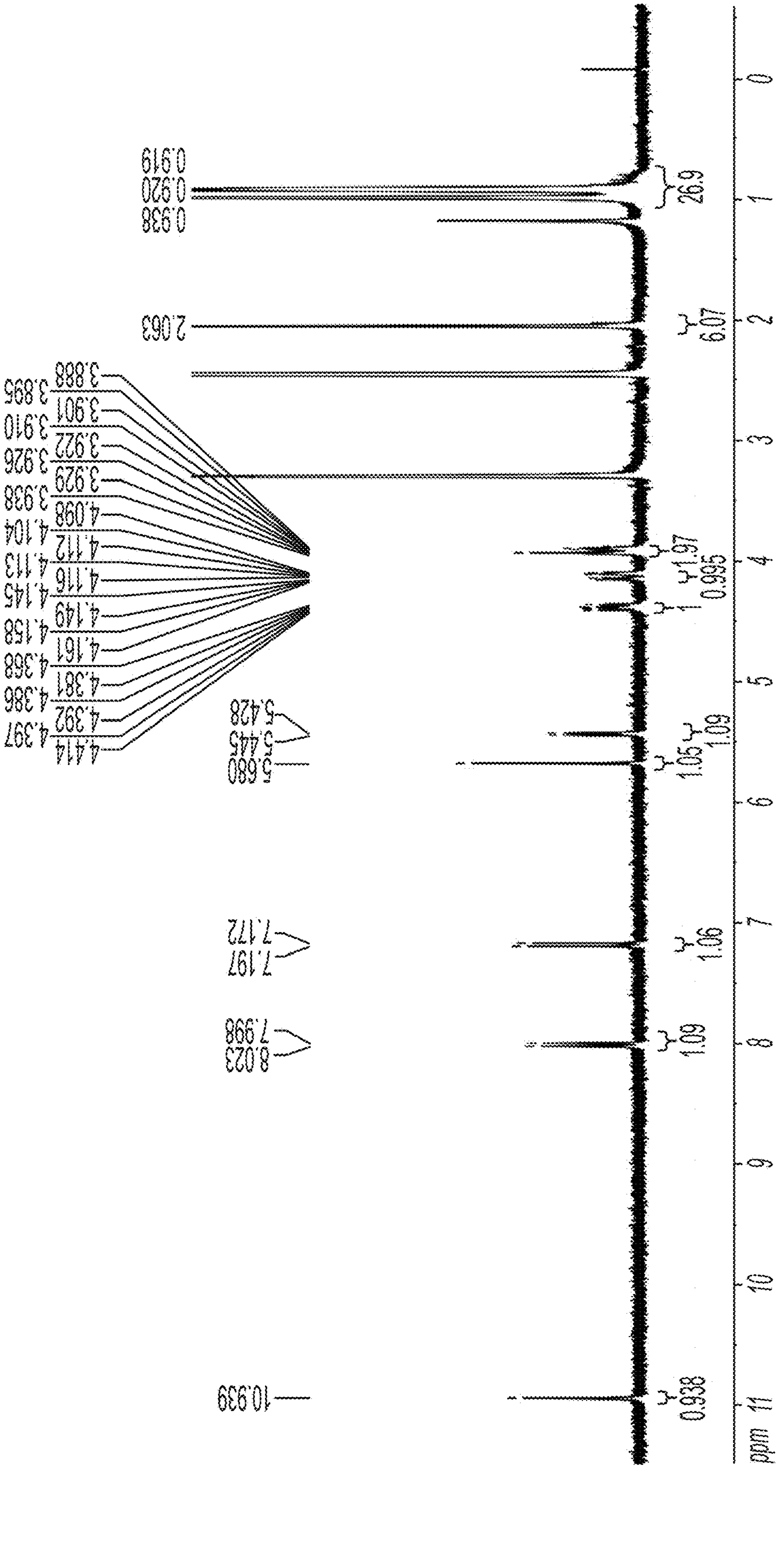
FIG. 9 is a graph depicting 1H NMR (300 MHz, DMSO-d6) of diacetylated cytidine 3.
Figure 10:
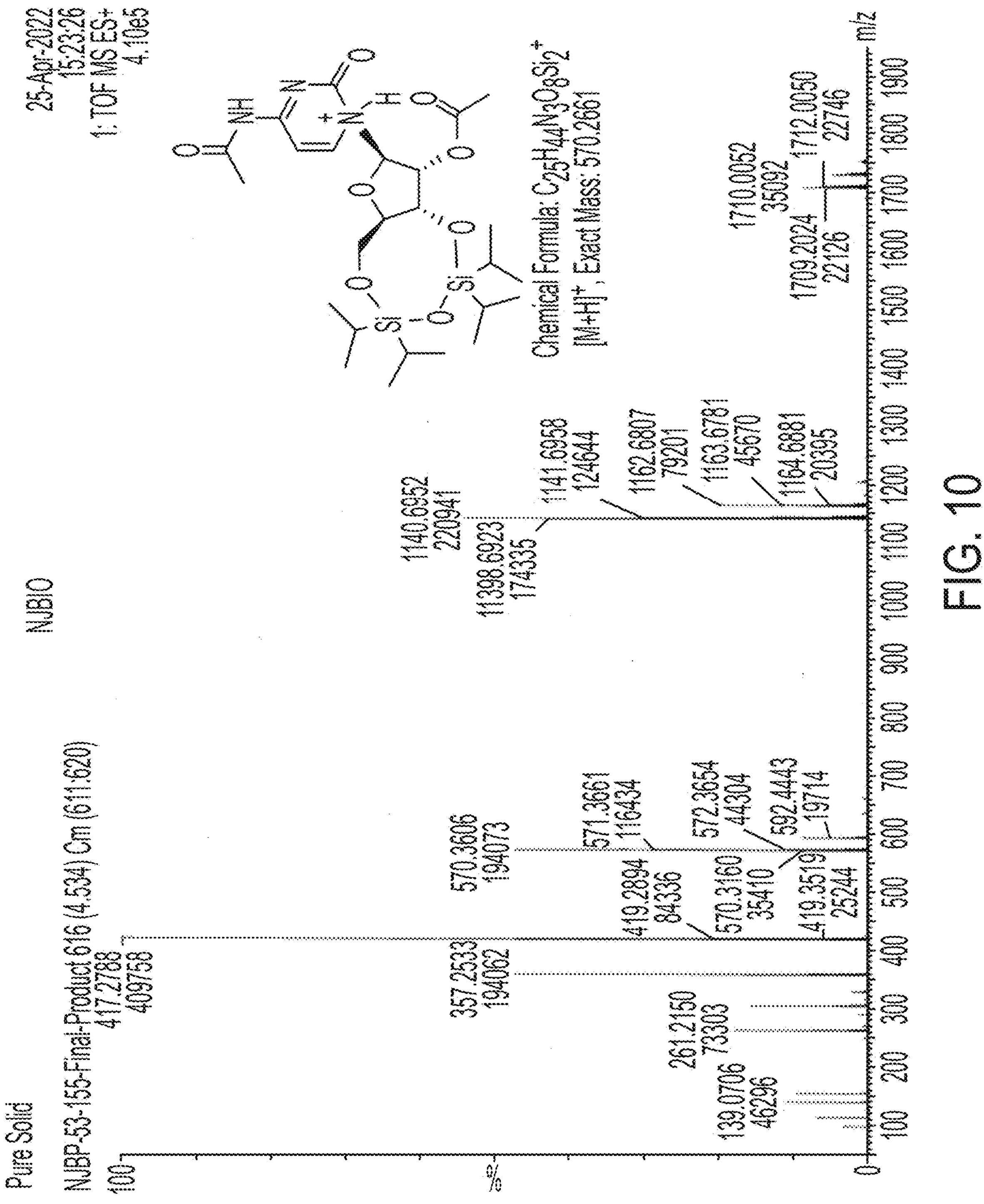
FIG. 10 is a mass spectrum ($ESI^+$, 100% $CH_3OH$, TOF), retention time (4.534) of diacetylated cytidine 3.
Figure 11:
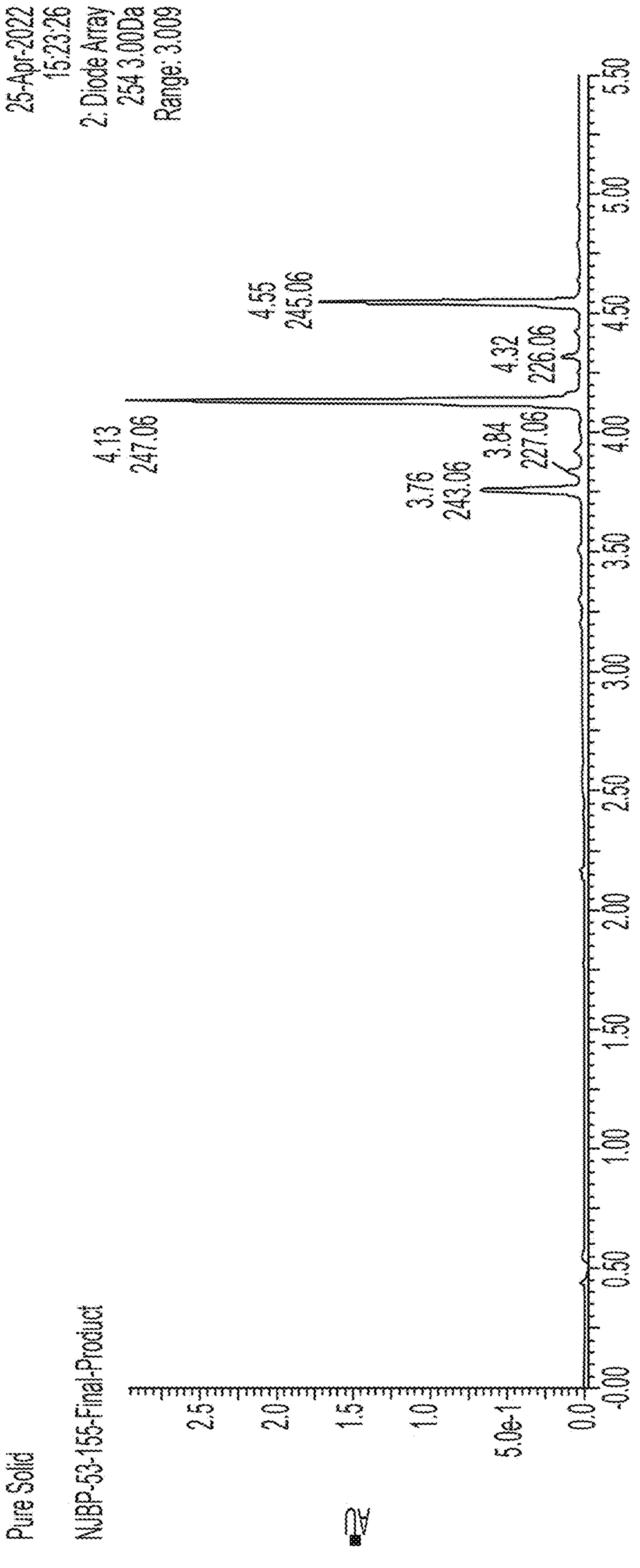
FIG. 11 is a HPLC chromatogram ($CH_3OH$) of diacetylated cytidine 3 (Compound unstable on LC-MS)
Figure 12:
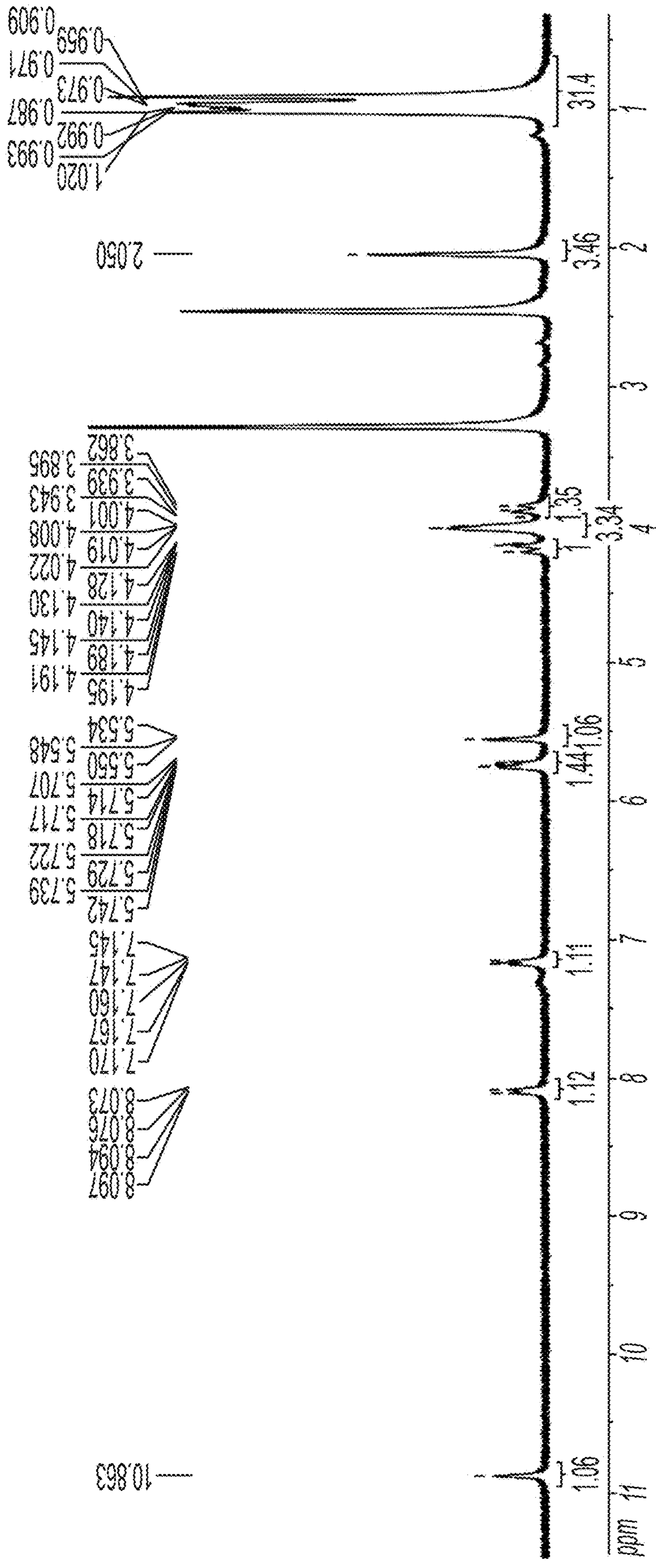
FIG. 12 is a graph depicting $^1H$ NMR (300 MHz, DMSO-$d_6$) of 2'-O-acetylated silyl protected cytidine 4.
Figure 13:
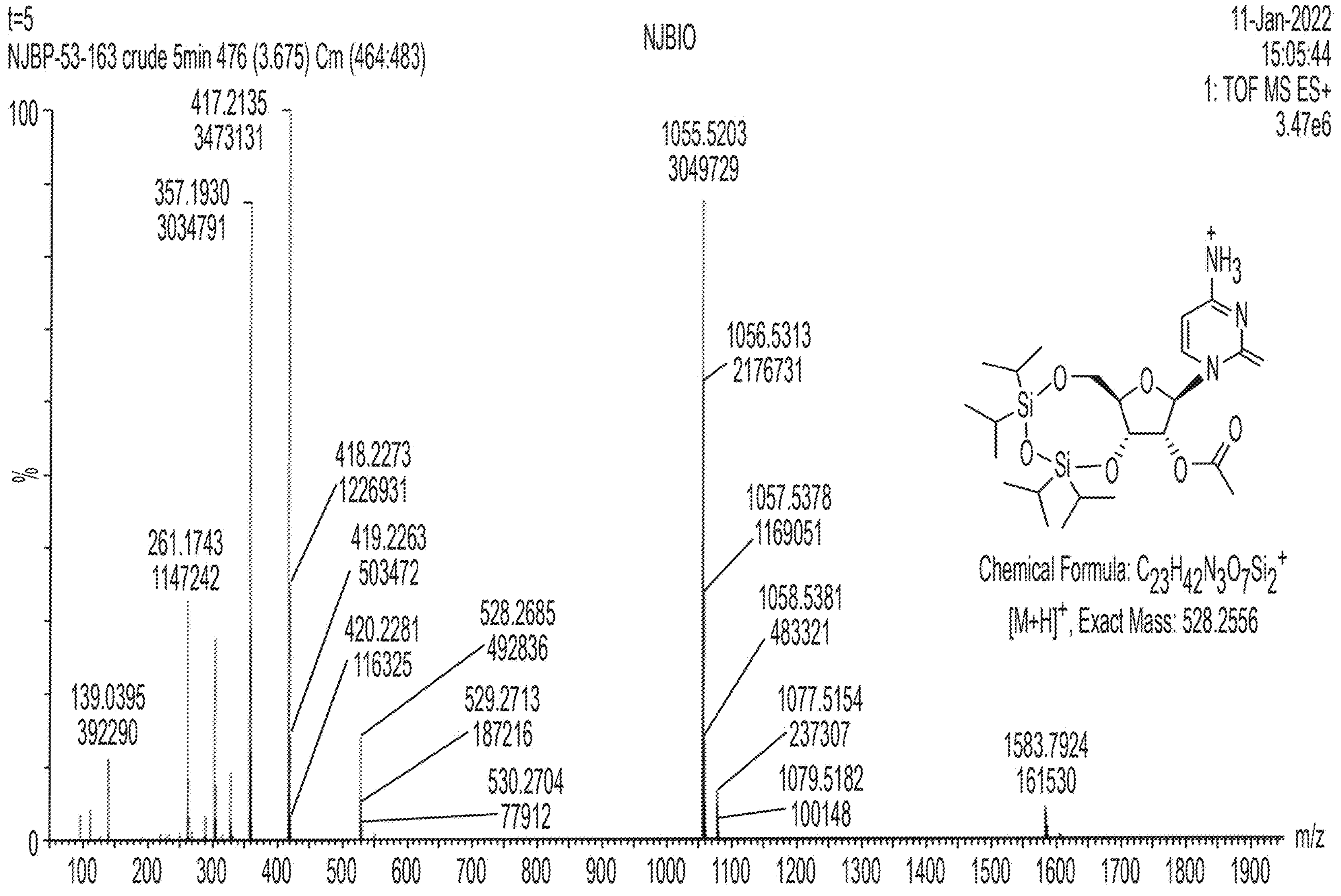
FIG. 13 is a mass spectrum ($ESI^+$, 100% $CH_3OH$, TOF) of 2'-O-acetylated silyl protected cytidine 4.
Figure 14:
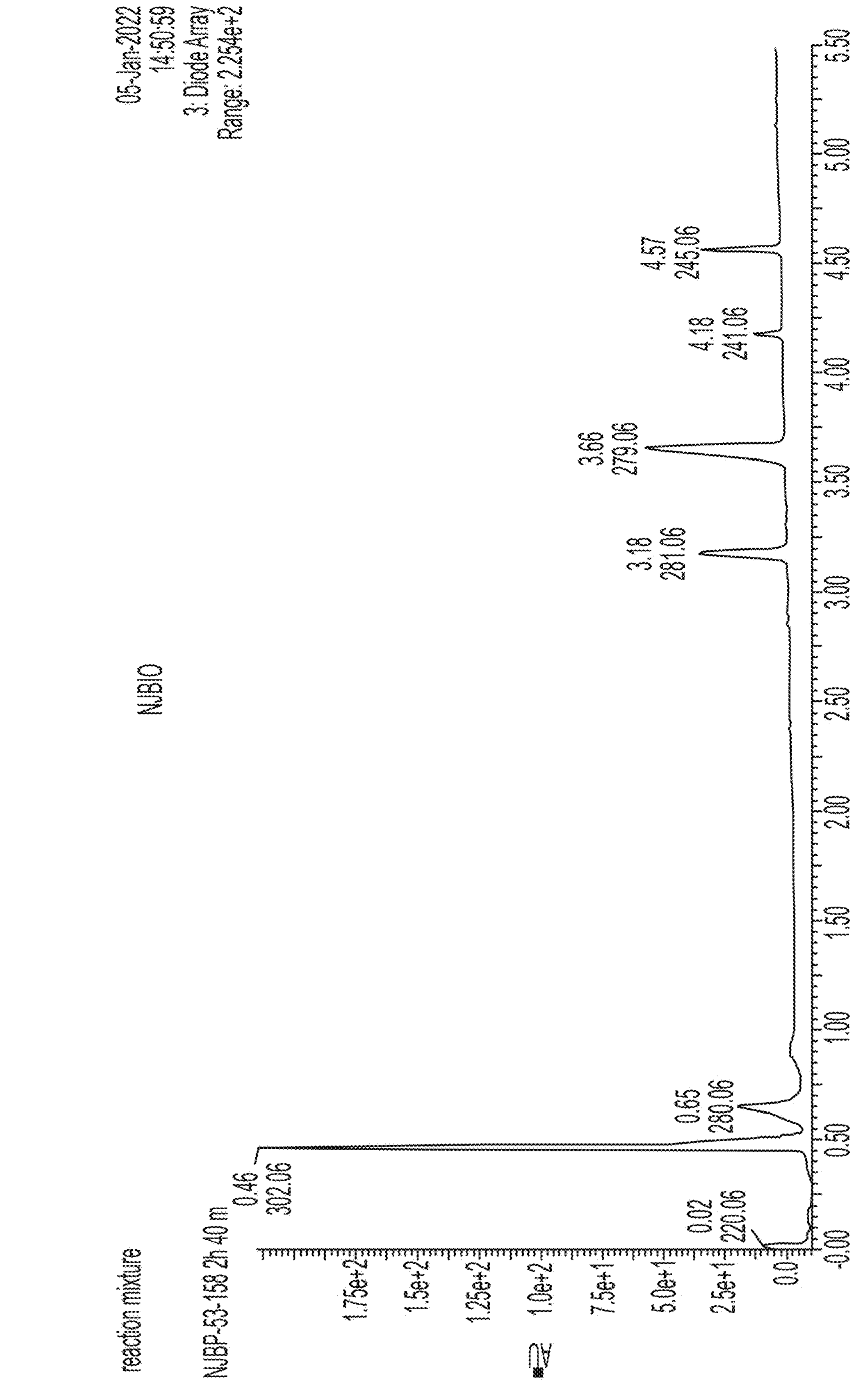
FIG. 14 is a HPLC chromatogram ($CH_3OH$) of 2'-O-acetylated silyl protected cytidine 4 (Compound unstable on LC-MS).
Figure 15:
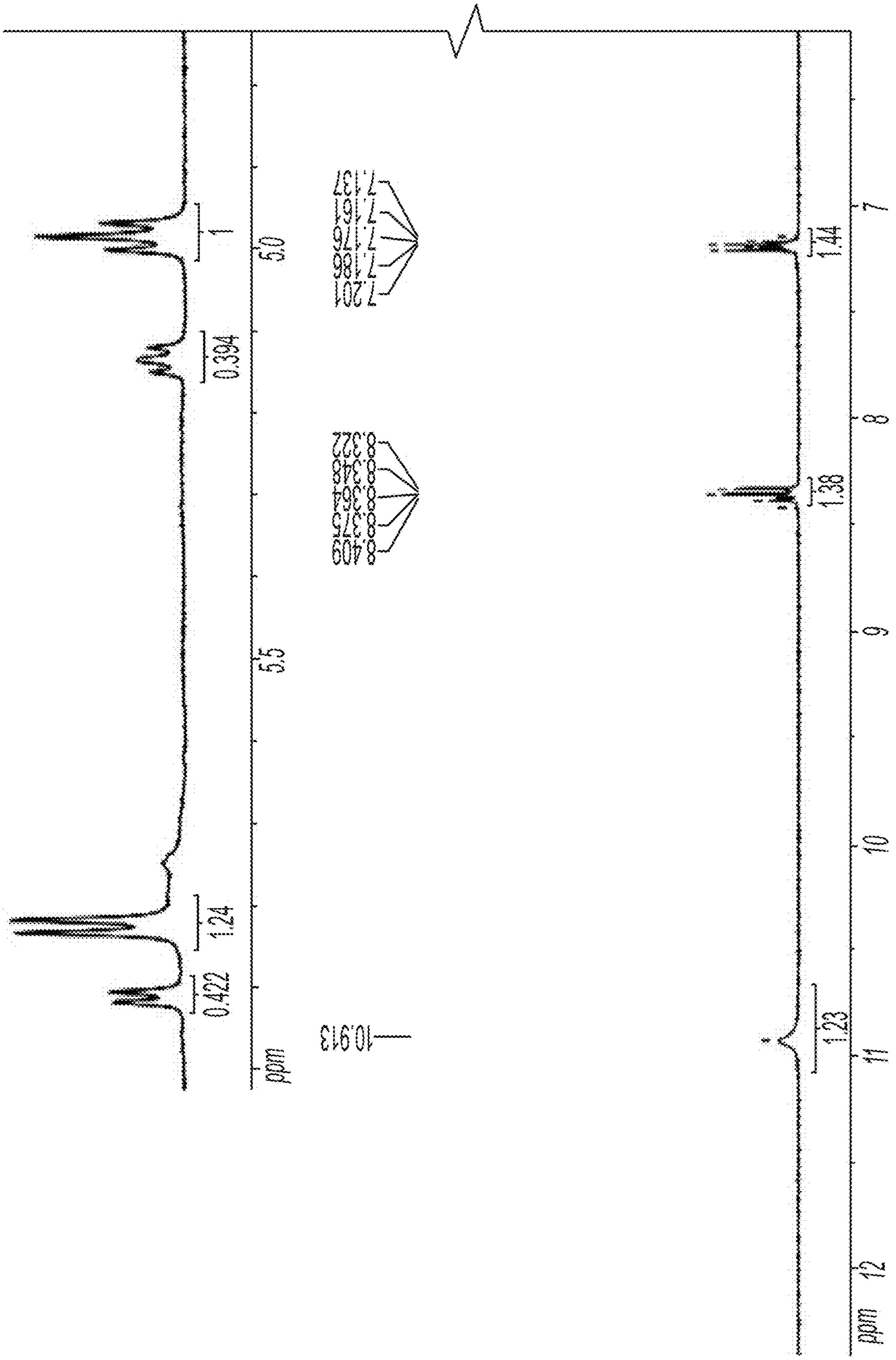
FIG. 15 is a graph depicting 1H NMR (300 MHz, DMSO-$d_6$) of N, O-Diacetyl-Cytidine 6 (Mixture of 2'-OAc and 3'-OAc Regioisomers).
Figure 15:
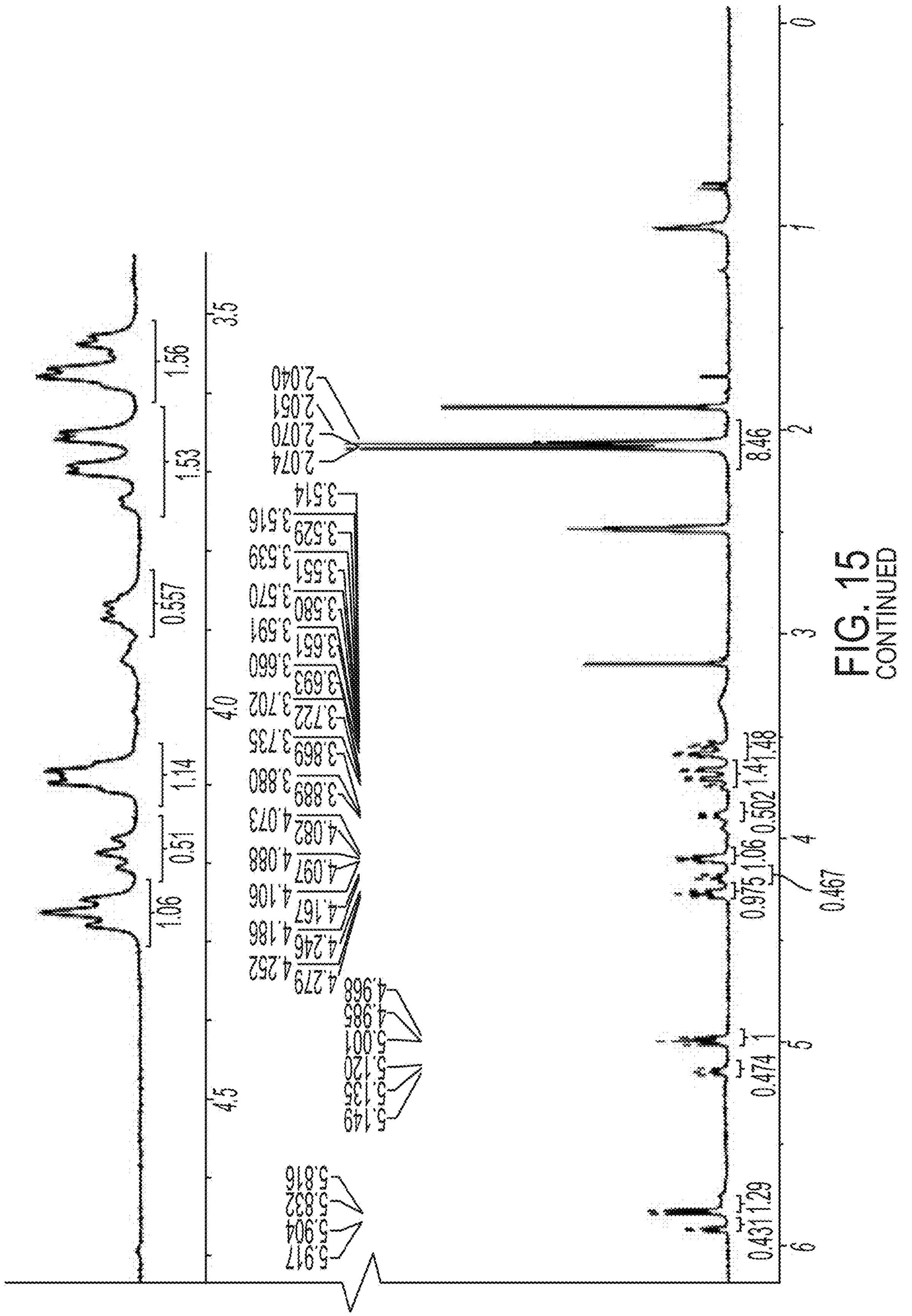
Figure 16:
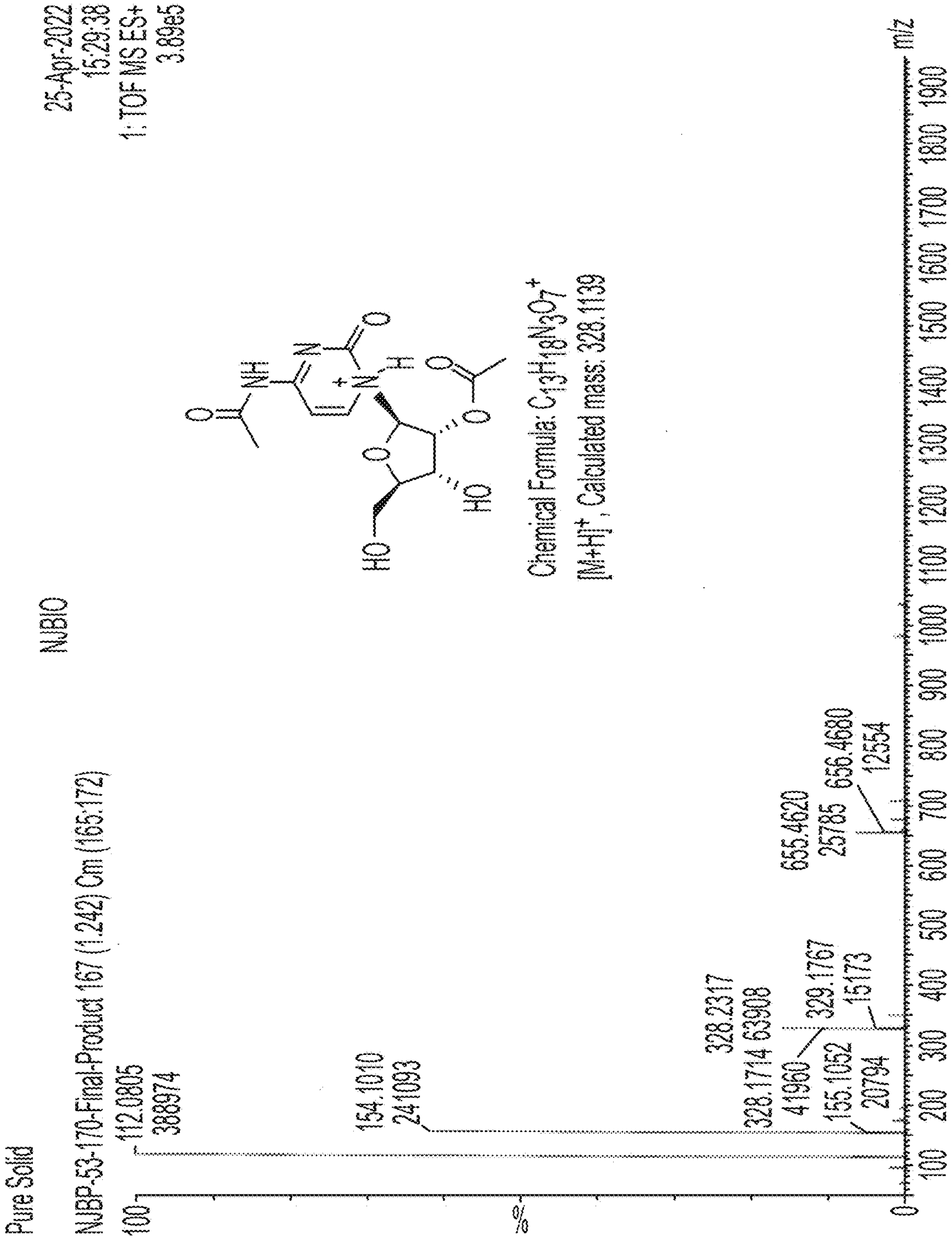
FIG. 16 is a mass spectrum ($ESI^+$, 100% $CH_3OH$, TOF) of N, O-Diacetyl-Cytidine 6 (Mixture of 2'-OAc and 3'-OAc Regioisomers).
Figure 17:
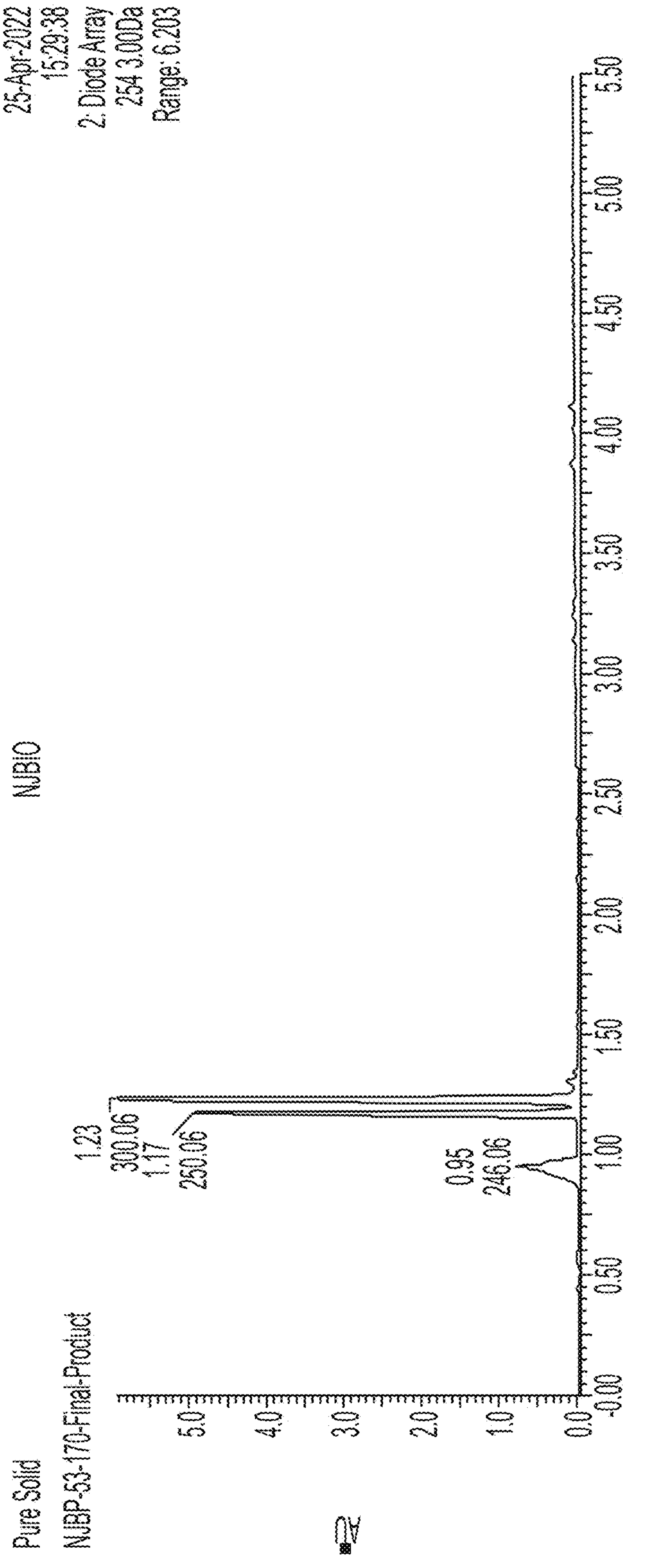
FIG. 17 is a HPLC chromatogram ($CH_3OH$) of N, O-Diacetyl-Cytidine 6 (Mixture of 2'-OAc and 3'-OAc Regioisomers).
Figure 18:
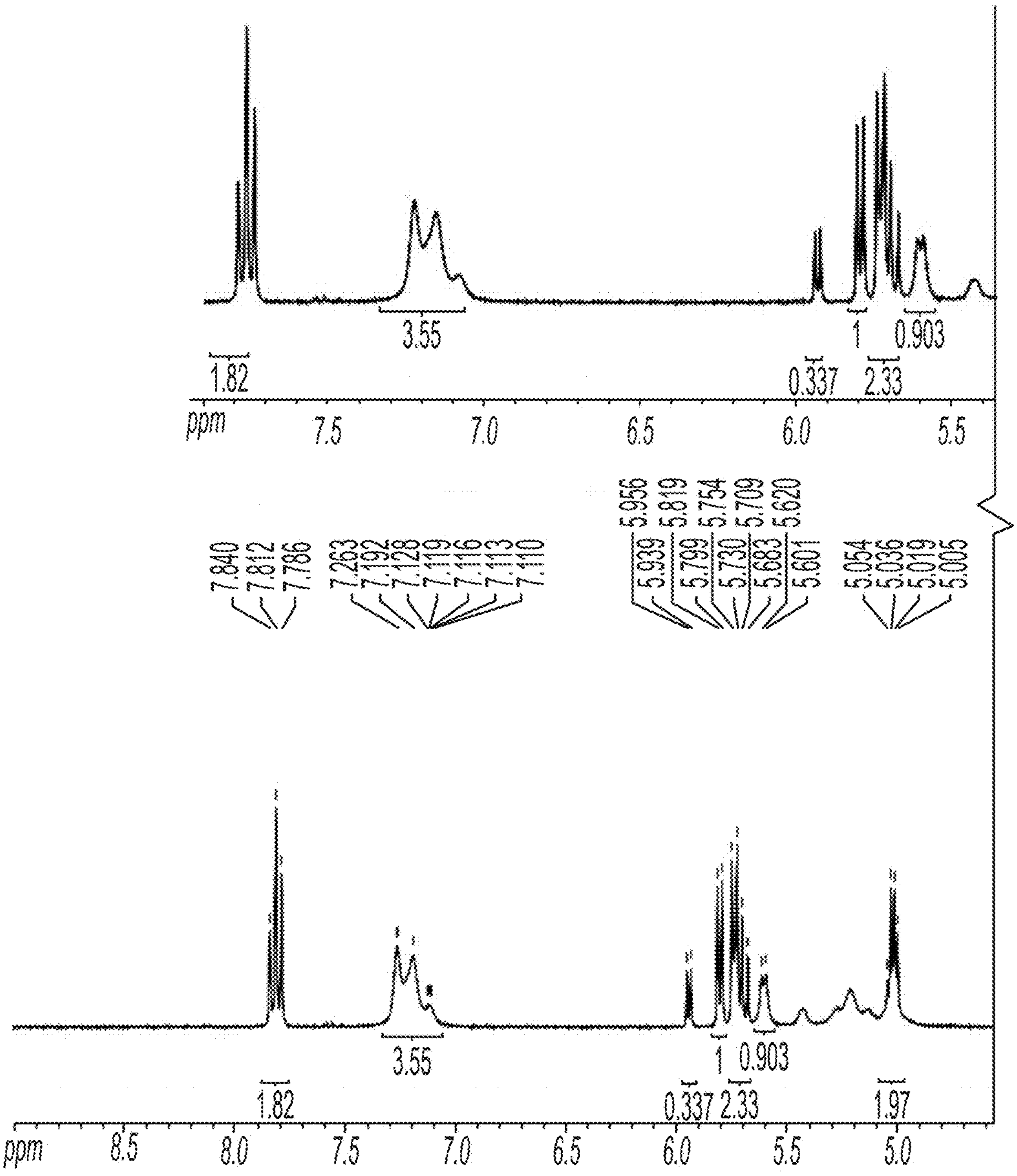
FIG. 18 is a graph depicting 1H NMR (300 MHz, DMSO-$d_6$) of 2'-O-Monoacetyl-Cytidine 7 (Mixture of 2'-OAc and 3' OAc).
Figure 18:
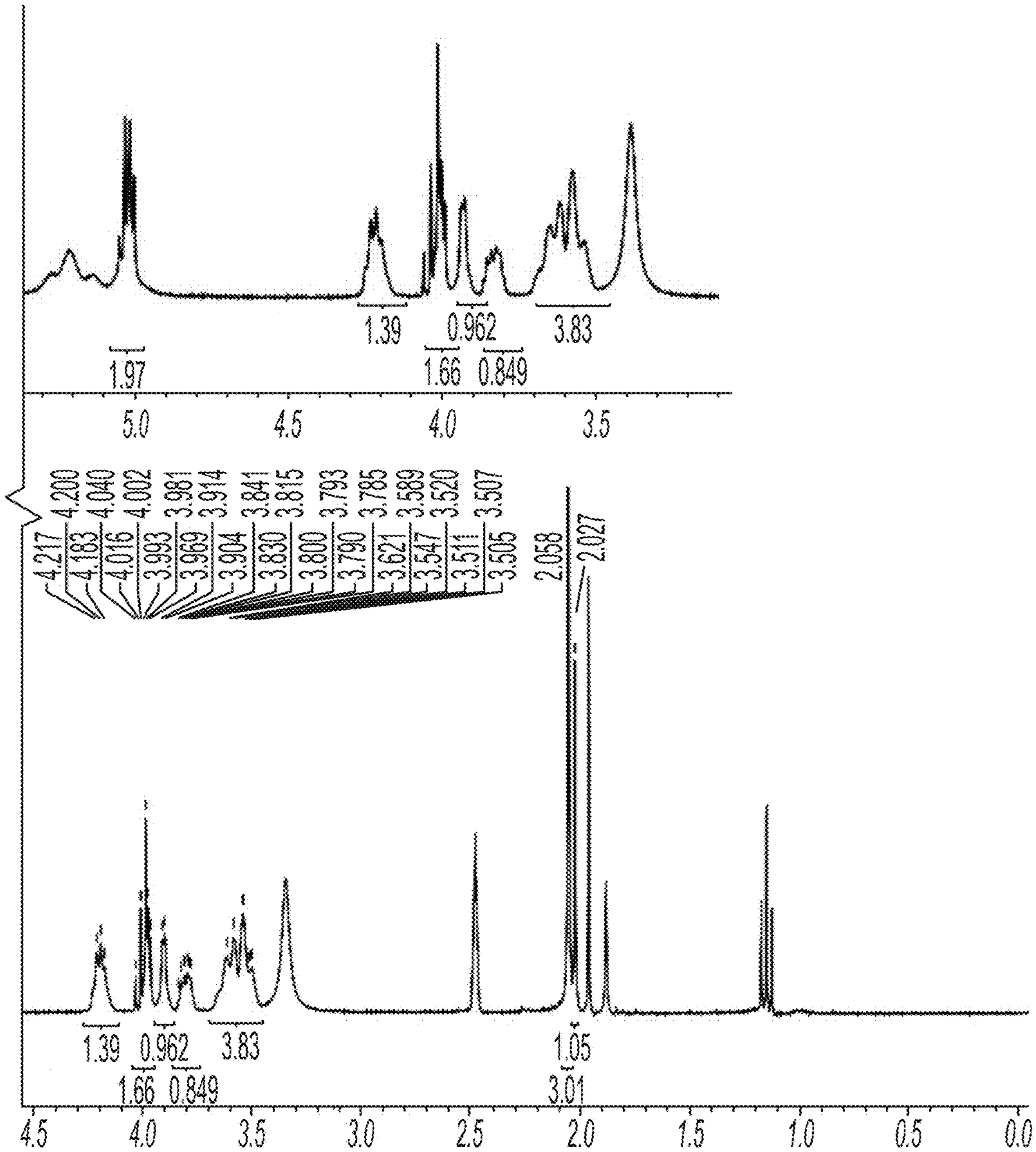
Figure 19:
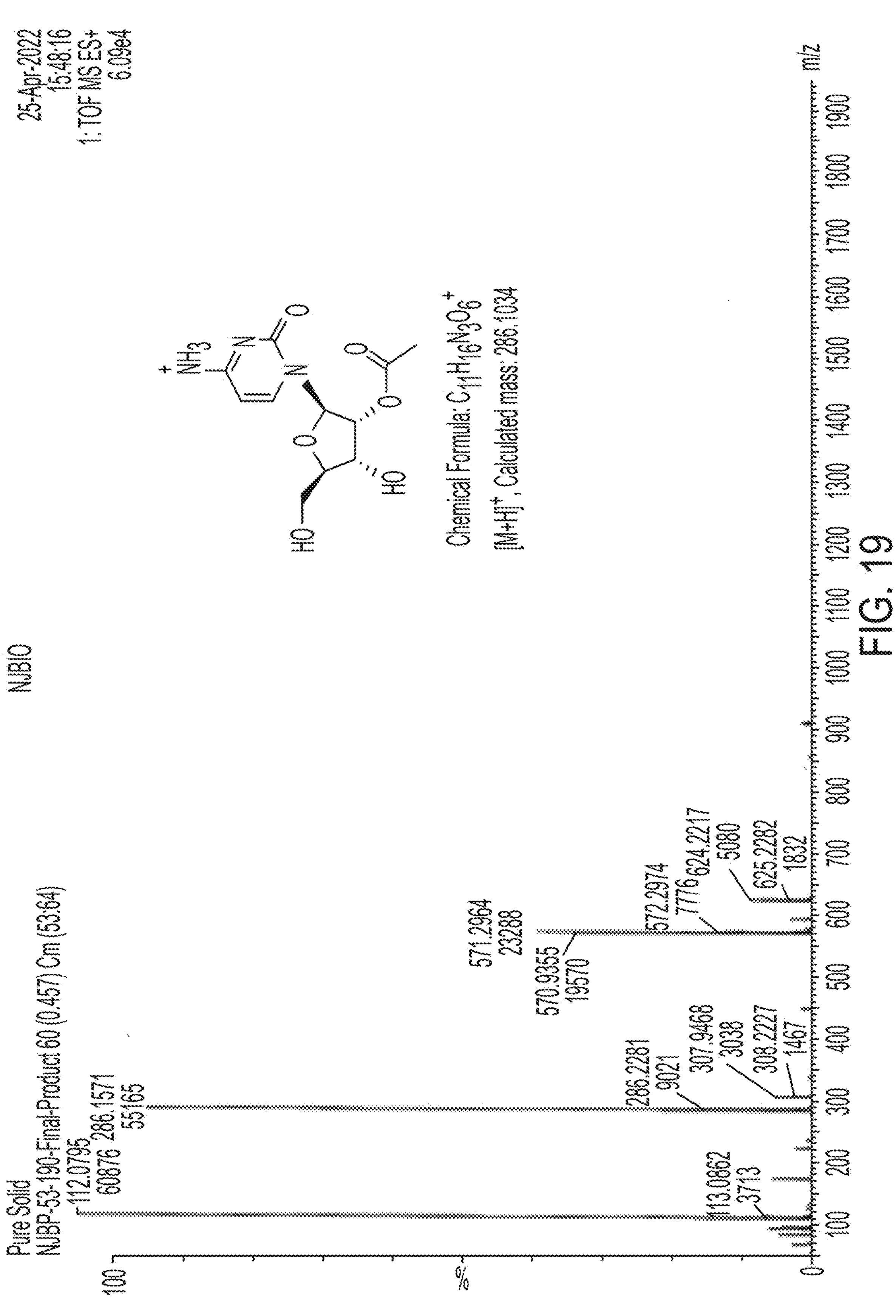
FIG. 19 is a mass spectrum ($ESI^+$, 100% $CH_3OH$, TOF) of 2'-O-acetyl-Cytidine 7.
Figure 20:
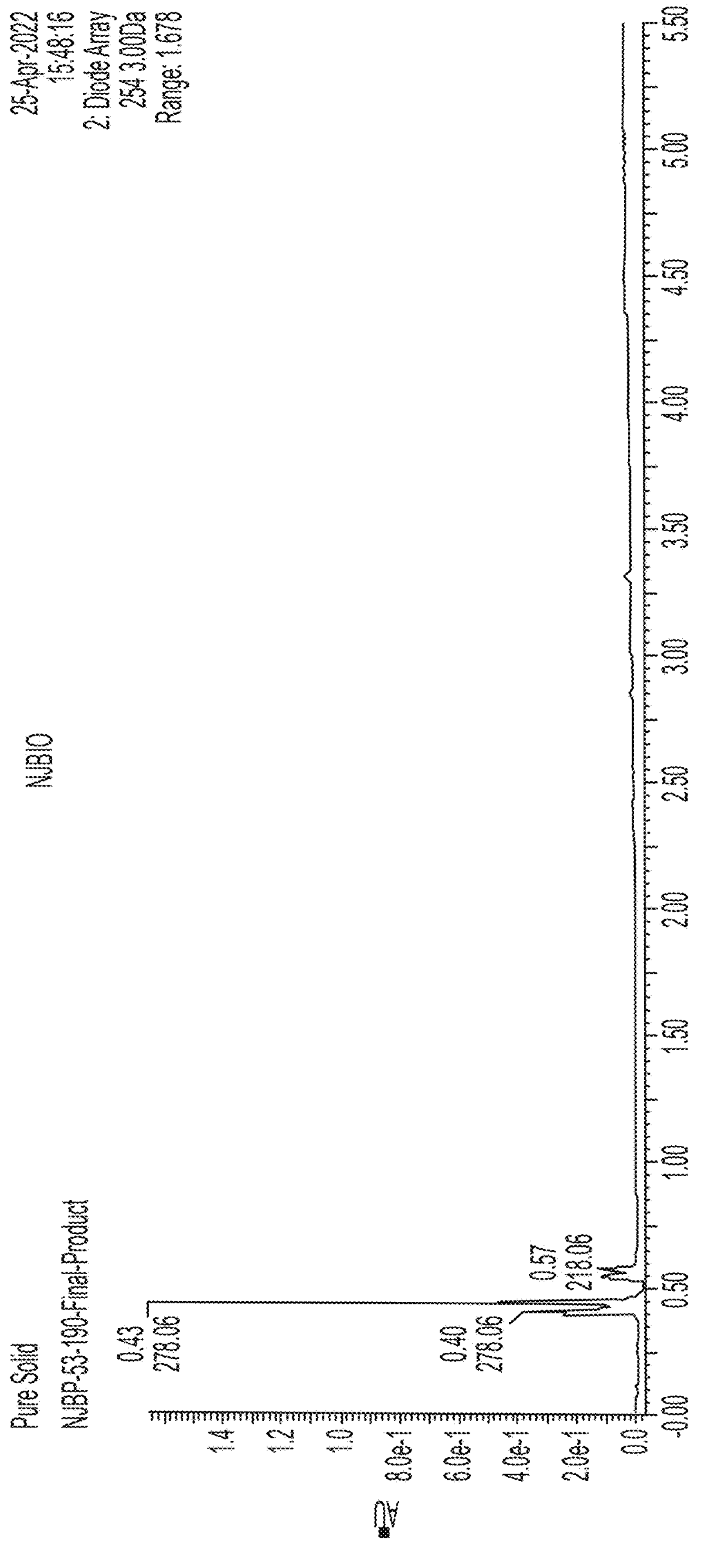
FIG. 20 is a graph depicting HPLC chromatogram ($CH_3OH$) of 2'-O-acetyl-Cytidine 7.
Figure 21:
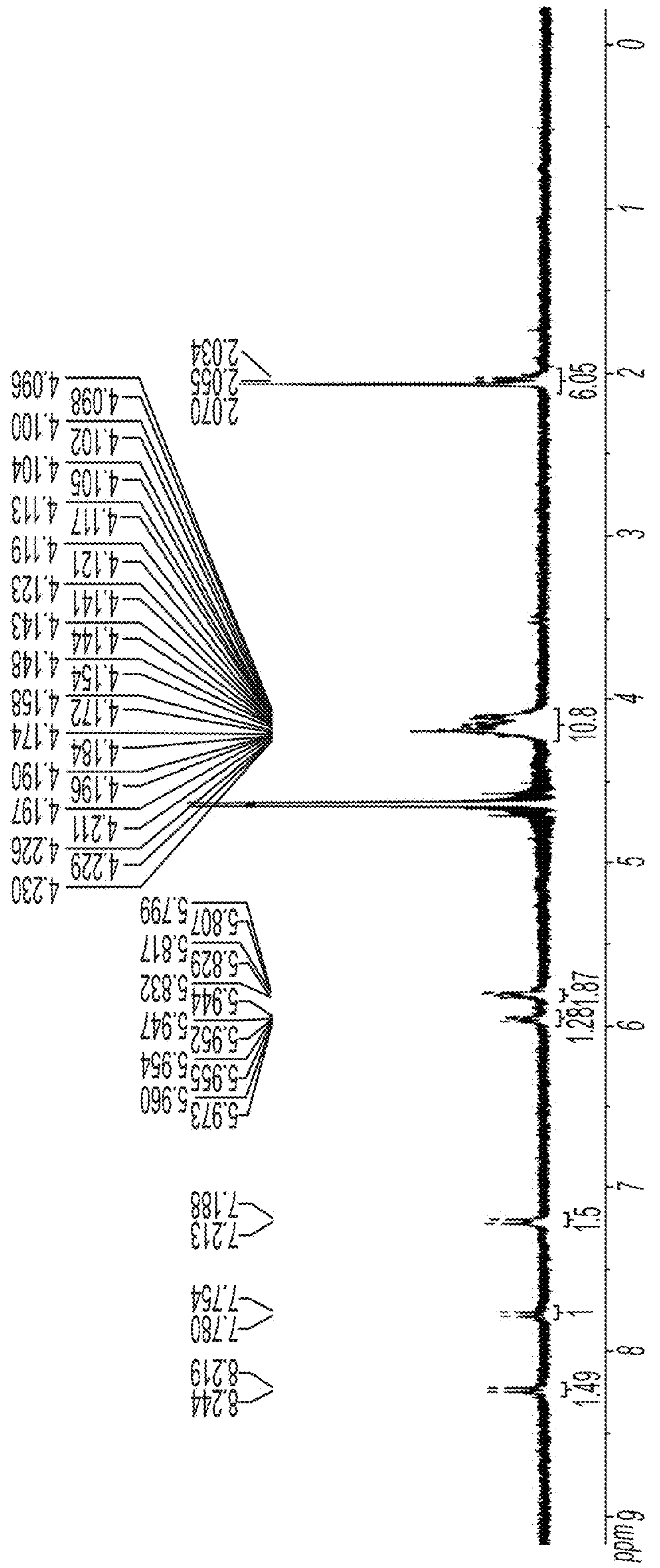
FIG. 21 is a graph depicting $^1H$ NMR (300 MHZ, $D_2O$) of N, O-Diacetyl-Cytidine triphosphate sodium salt 9 (Mixture of 2'-OAc and 3'-OAc).
Figure 22:
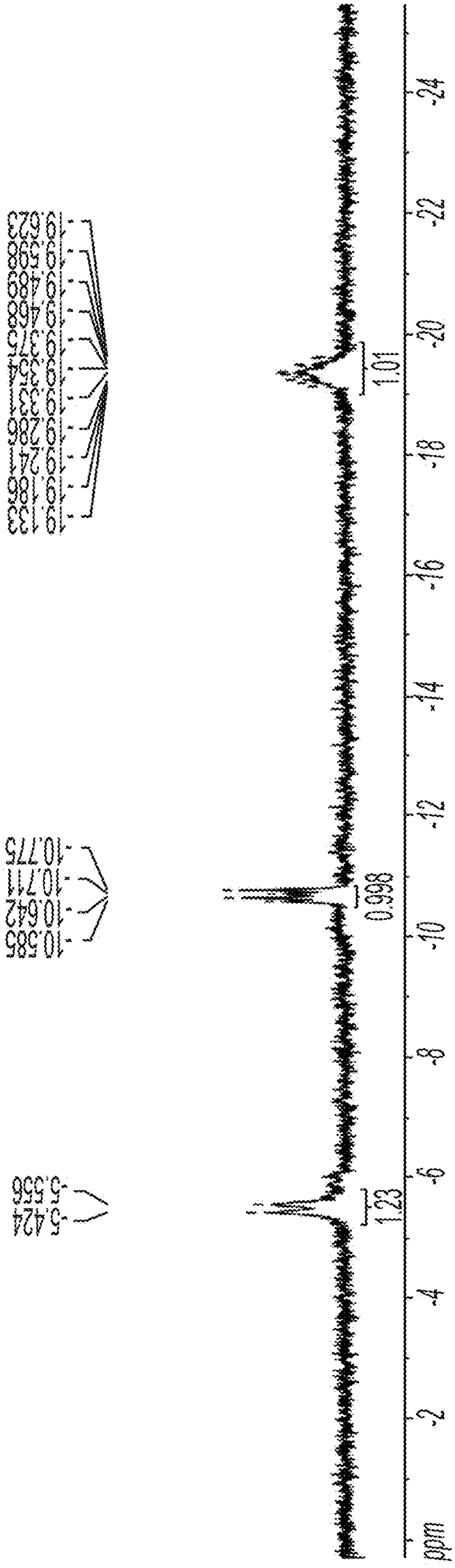
FIG. 22 is a graph depicting $^{31}P$ NMR (121 MHZ, $D_2O$) of N, O-Diacetyl-Cytidine triphosphate sodium salt 9 (Mixture of 2'-OAc and 3'-OAc Regioisomers).
Figure 23:
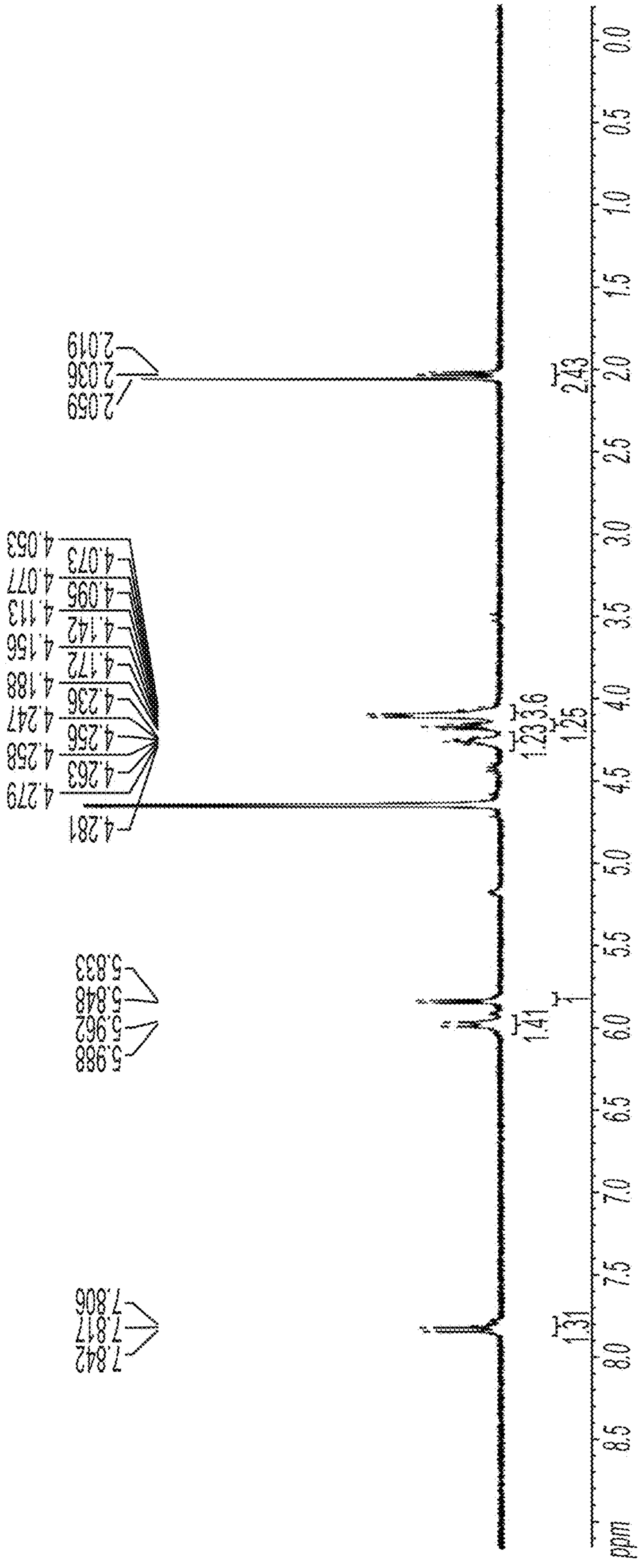
FIG. 23 is a graph depicting 1H NMR (300 MHZ, $D_2O$) of 2'-O-acetyl-Cytidine Triphosphate sodium salt 11 (Mixture of 2'-OAc and 3'-OAc Regioisomers).
Figure 24:
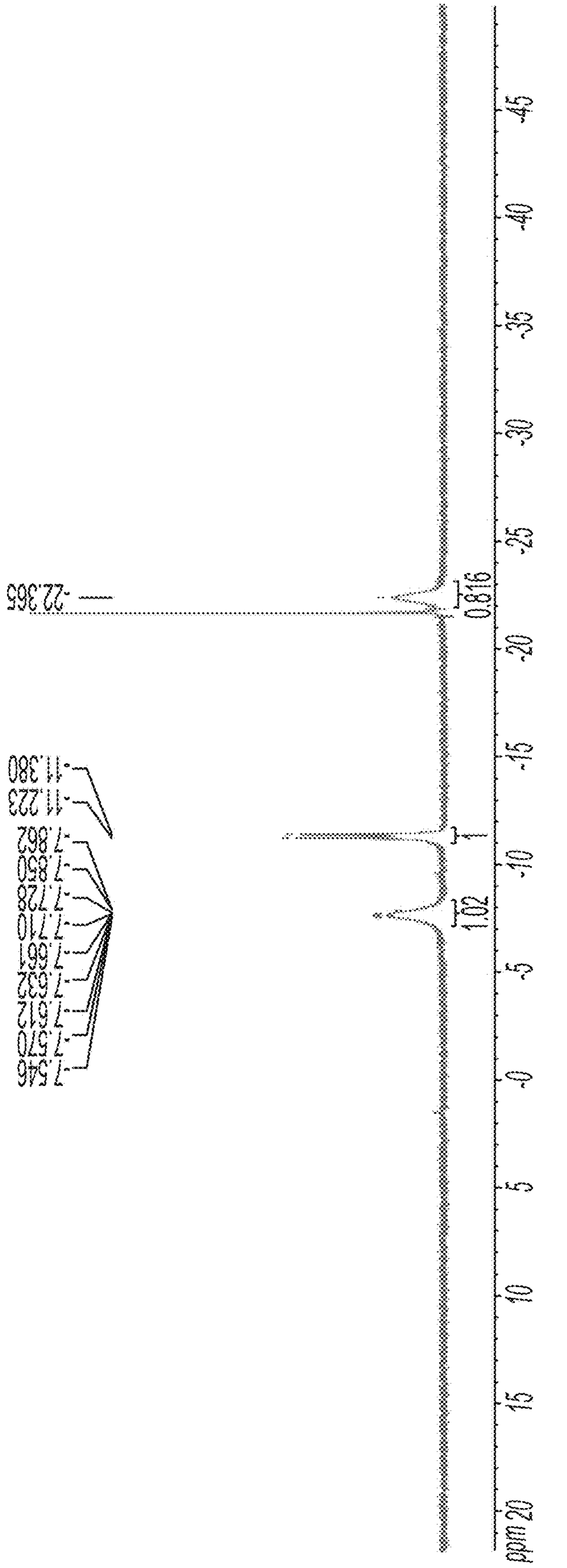
FIG. 24 is a graph depicting $^{31}P$ NMR (121 MHZ, $D_2O$) of 2'-O-acetyl Cytidine Triphosphate sodium salt 11 (Mixture of 2'-OAc and 3'-OAc Regioisomers).
Figure 25:
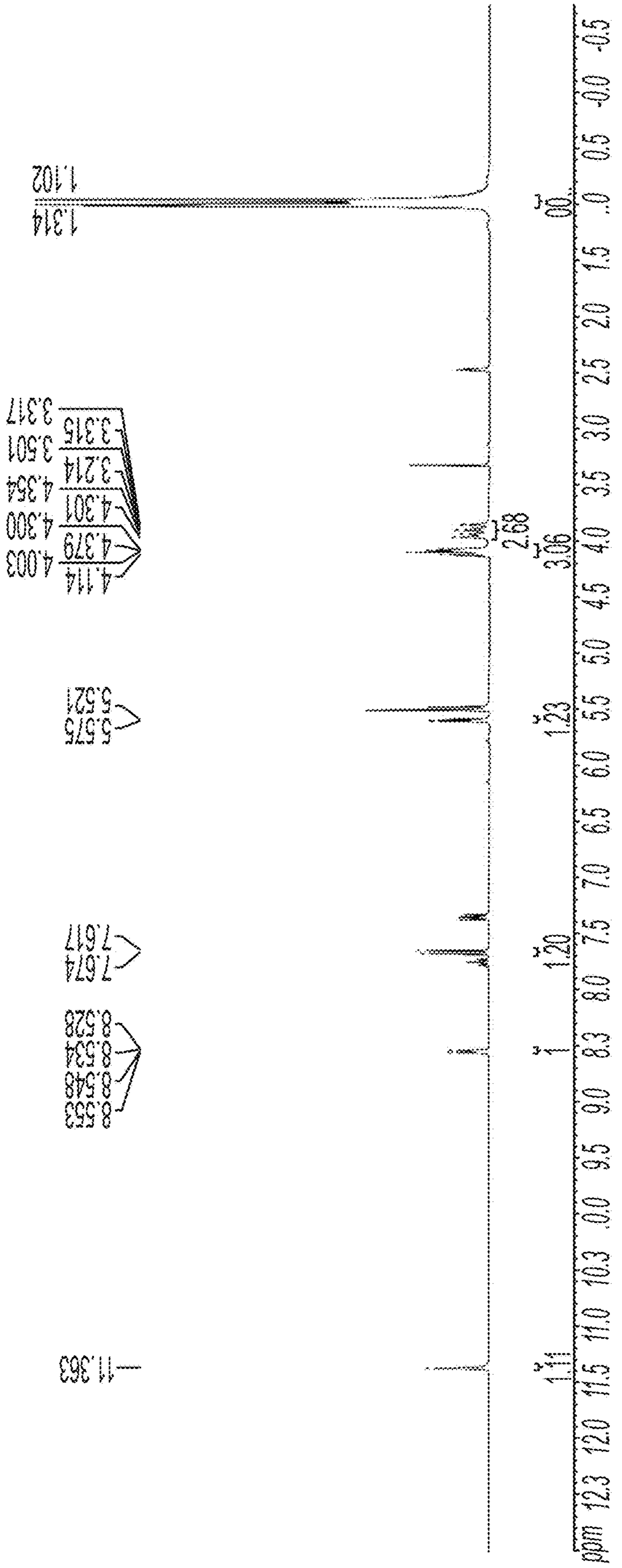
FIG. 25 is a graph depicting $^1H$ NMR (300 MHZ, DMSO-$d_6$) of Silyl-protected Uridine 13.
Figure 26:
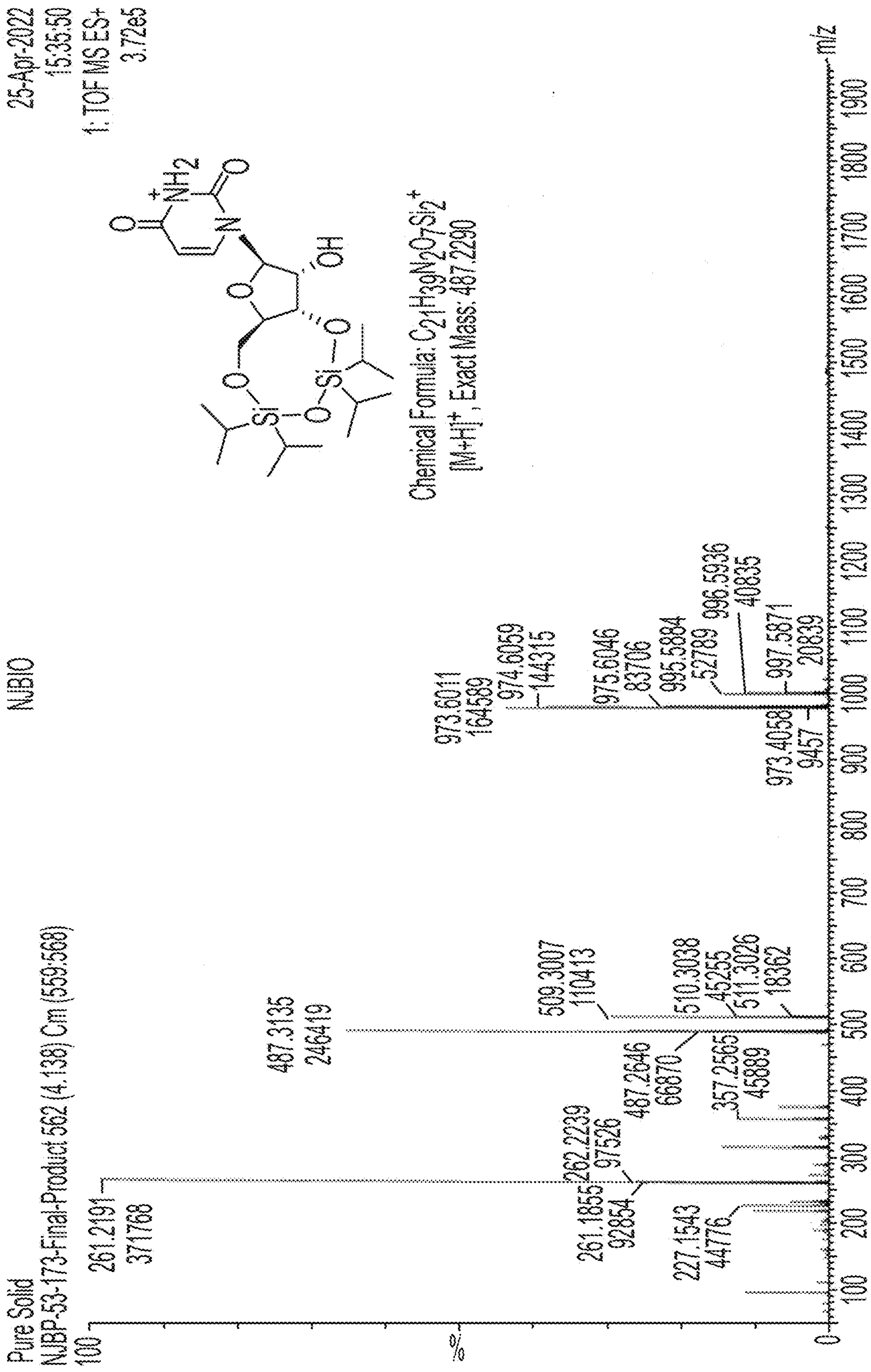
FIG. 26 is a mass spectrum (ESI+, 100% CH3OH, TOF) of Silyl-protected Uridine 13.
Figure 27:
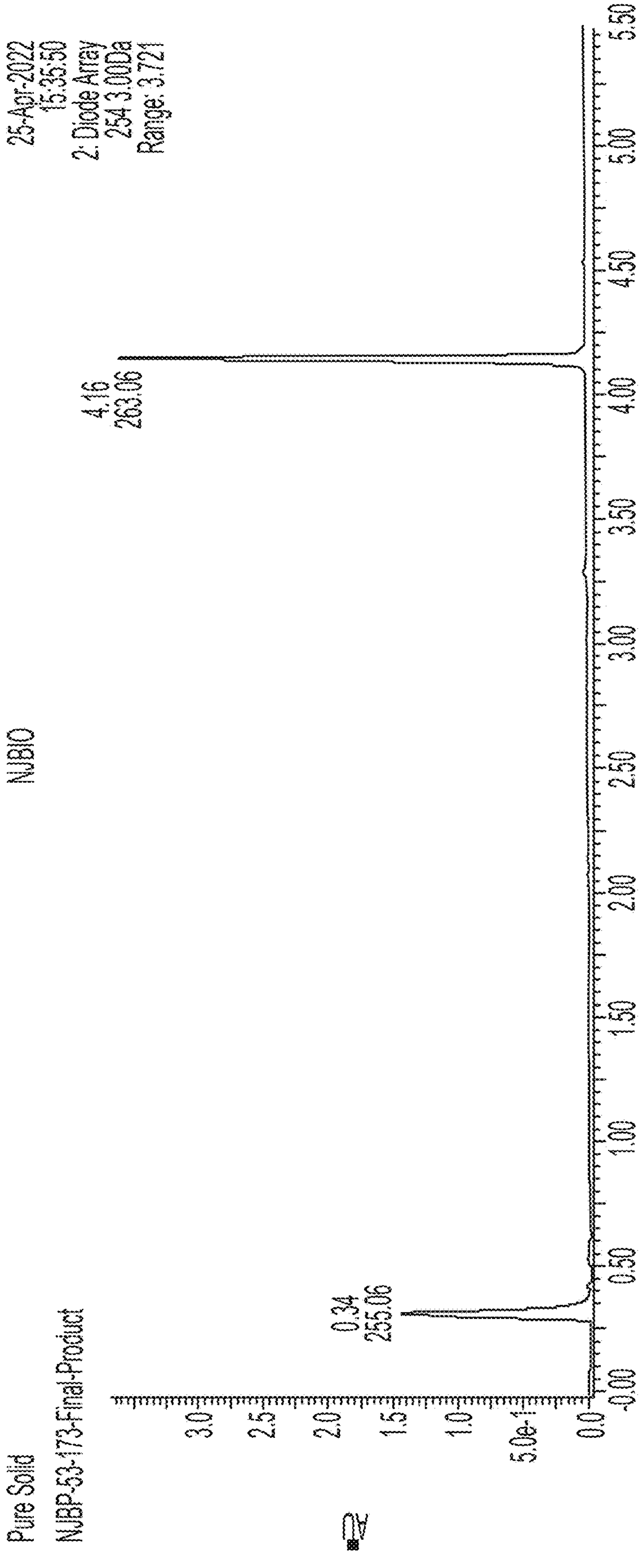
FIG. 27 is a HPLC chromatogram ($CH_3OH$) of Silyl-protected Uridine 13.
Figure 28:
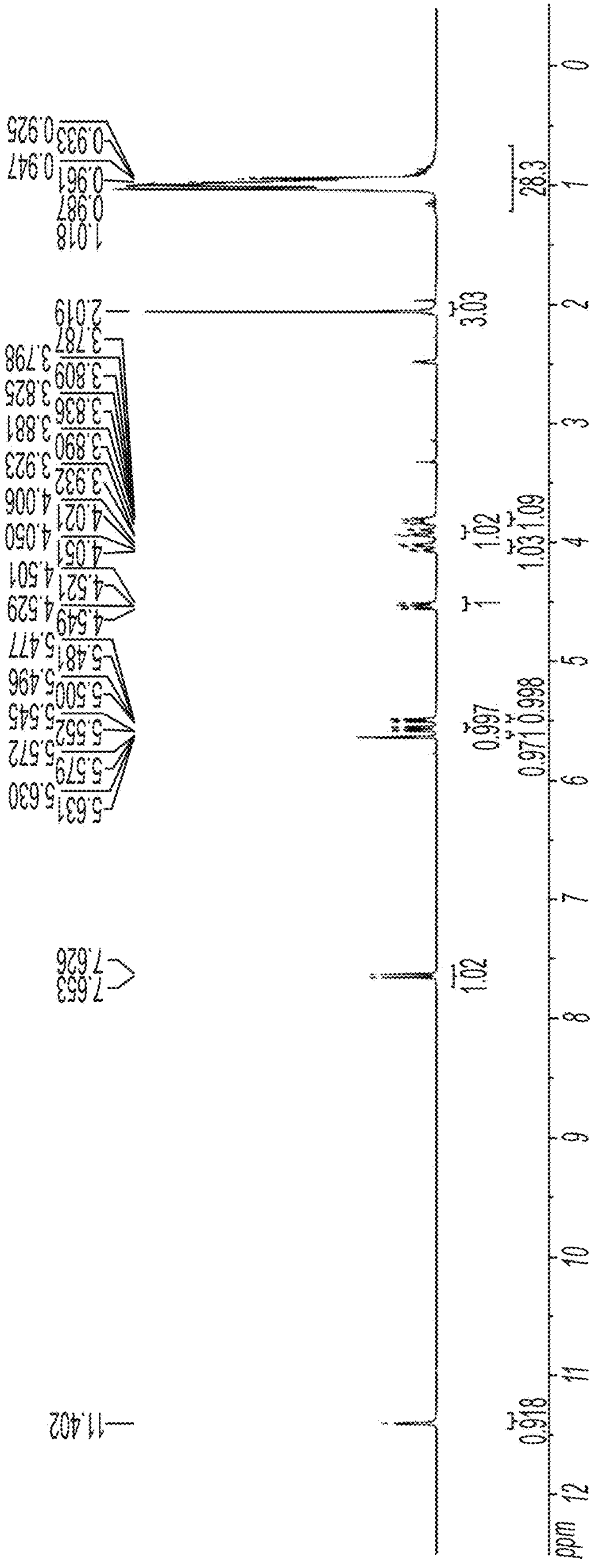
FIG. 28 is a graph depicting $^1H$ NMR (300 MHZ, $D_2O$) of 2'-O-acetyl-Silyl Protected Uridine 14.
Figure 29:
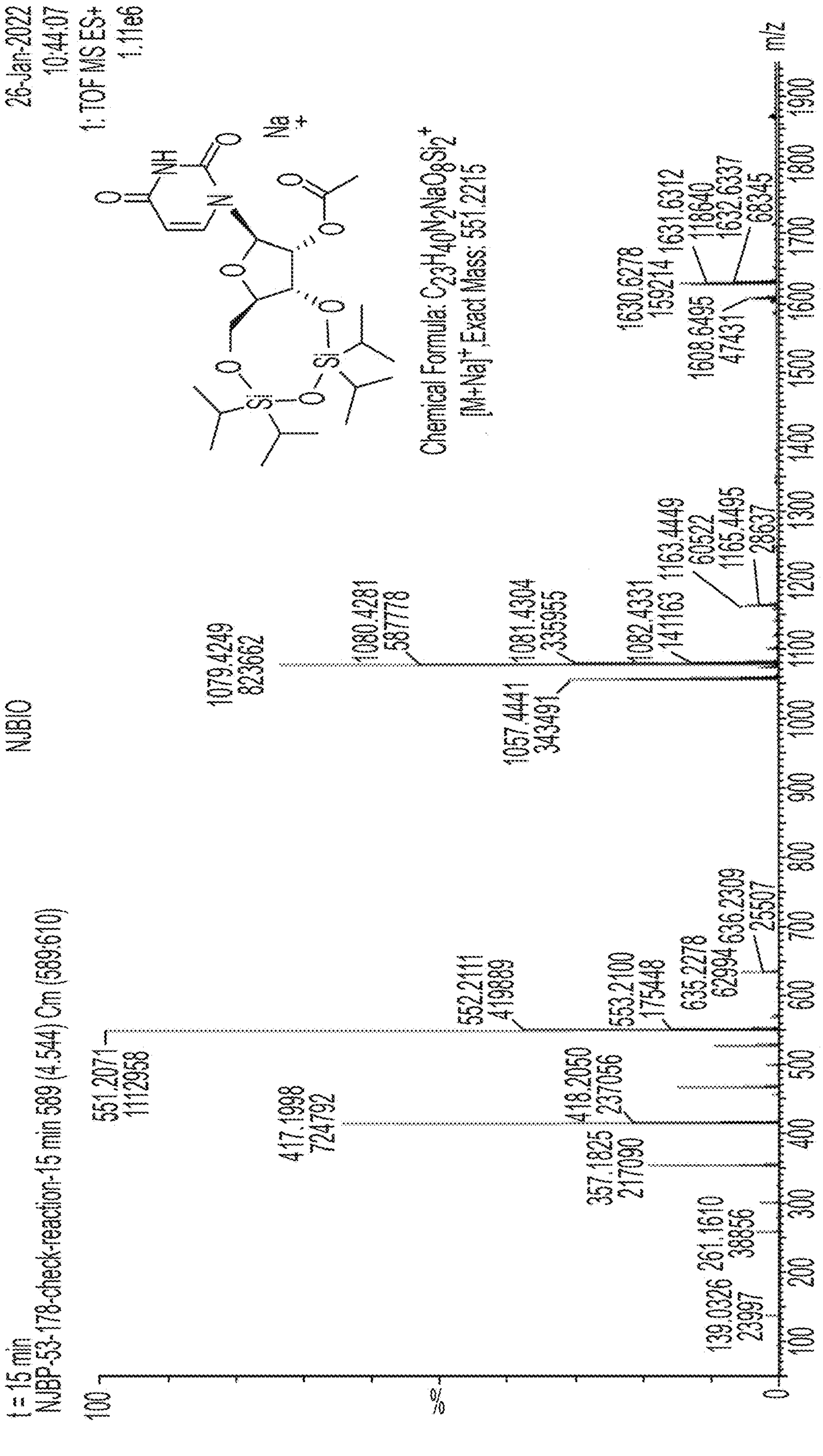
FIG. 29 is a Mass spectrum (ESI+, 100% CH3OH, TOF) of 2'-O-acetyl-Silyl Protected Uridine 14.
Figure 30:
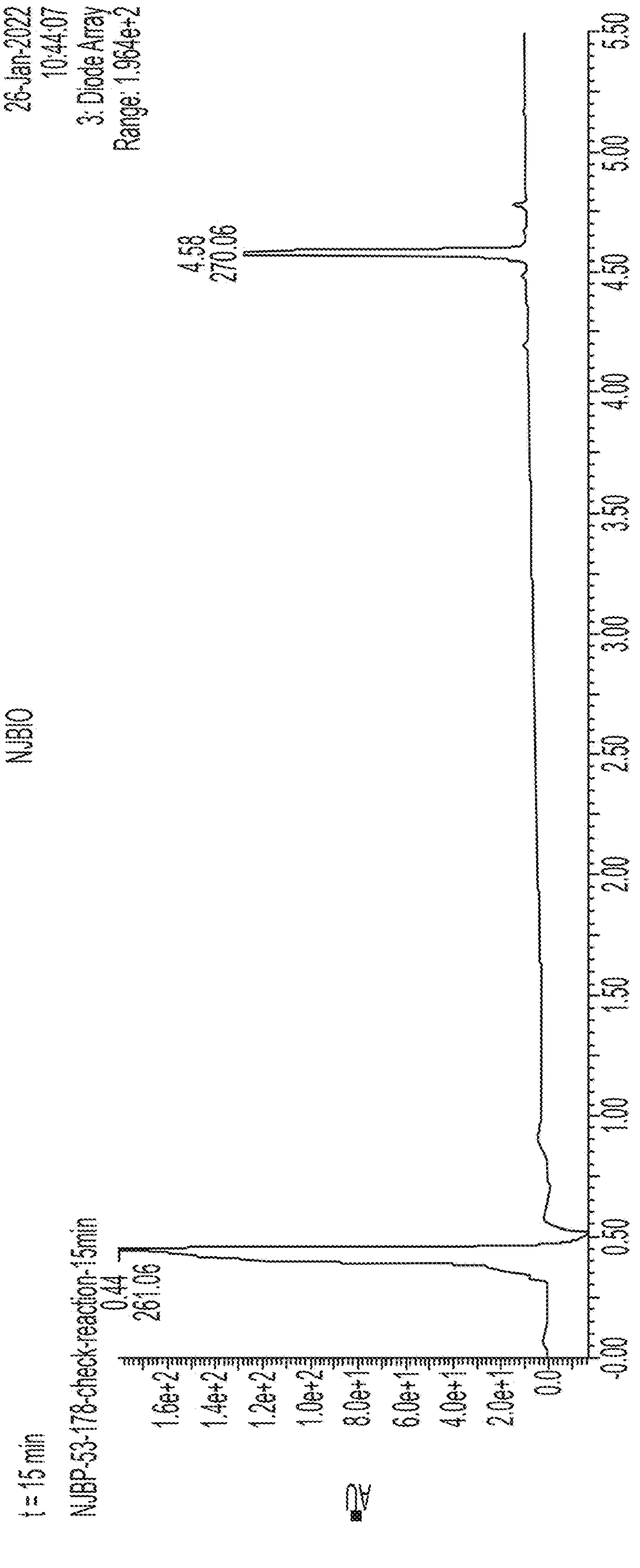
FIG. 30 is a HPLC chromatogram of 2'-O-acetyl-Silyl Protected Uridine 14.
Figure 31:
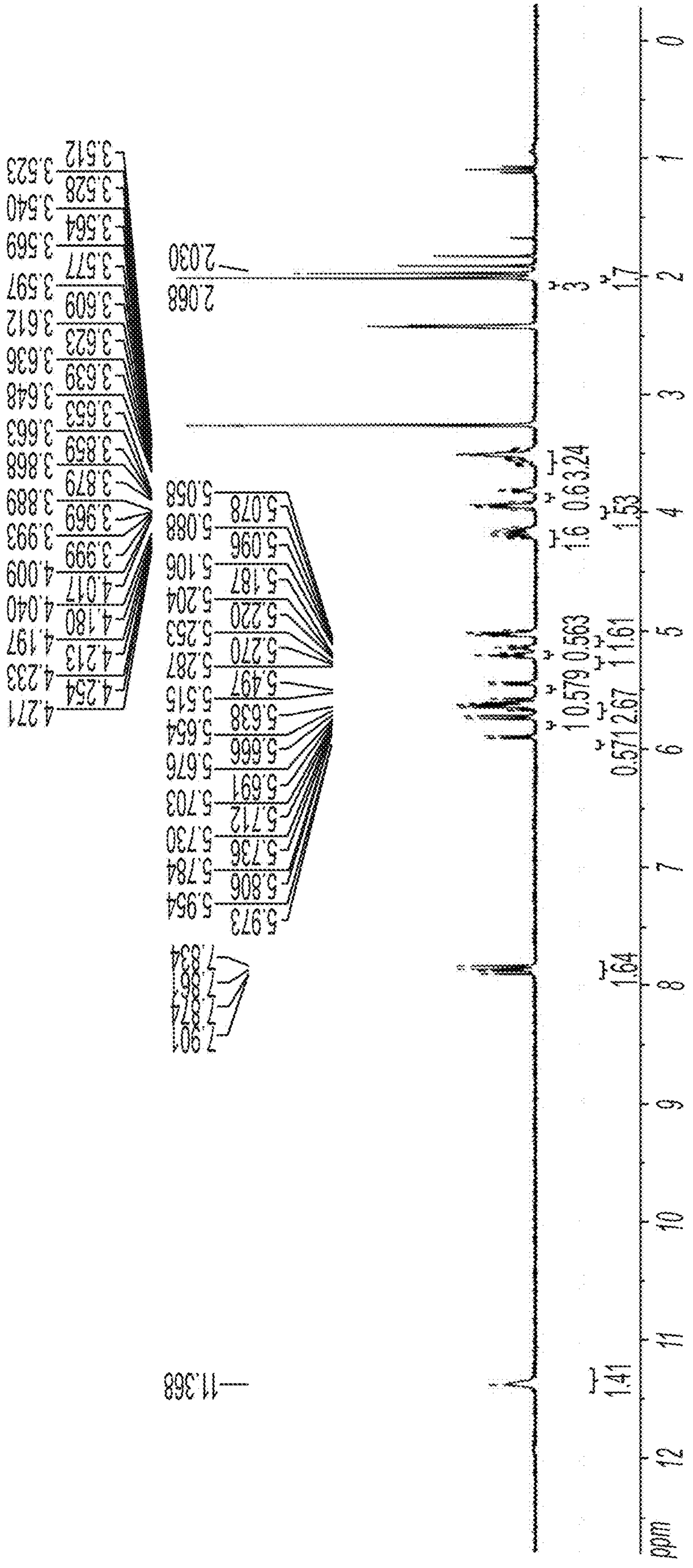
FIG. 31 is a graph depicting $^1H$ NMR (300 MHz, DMSO-$d_6$) of 2'-O-acetyl-Uridine 15 (mixture of 2'-OAc and 3'-OAc regioisomers).
Figure 32:
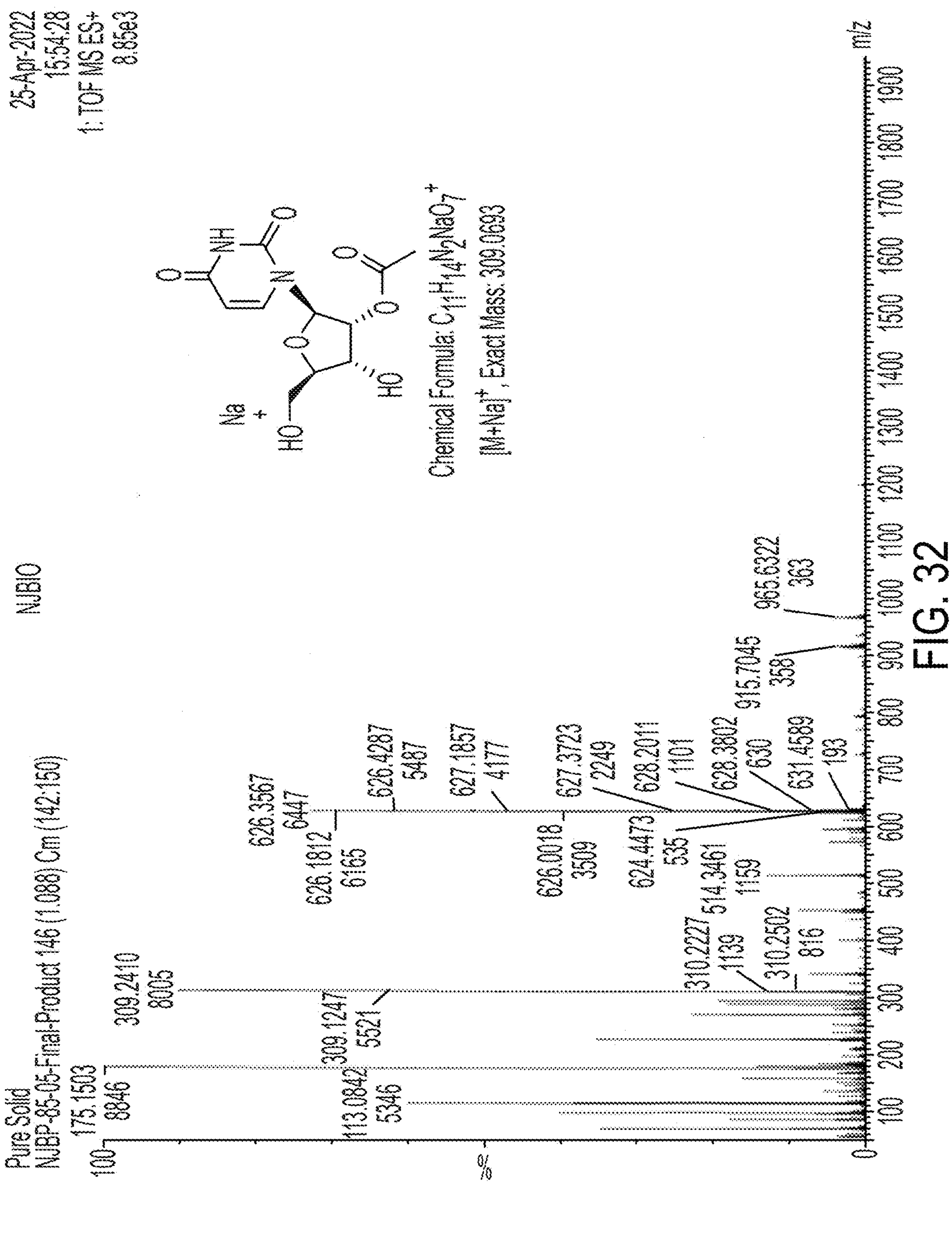
FIG. 32 is a mass spectrum ($ESI^+$, 100% $CH_3OH$, TOF) of 2'-O-acetyl-Uridine 15 (mixture of 2'-OAc and 3'-OAc Regioisomers).
Figure 33:
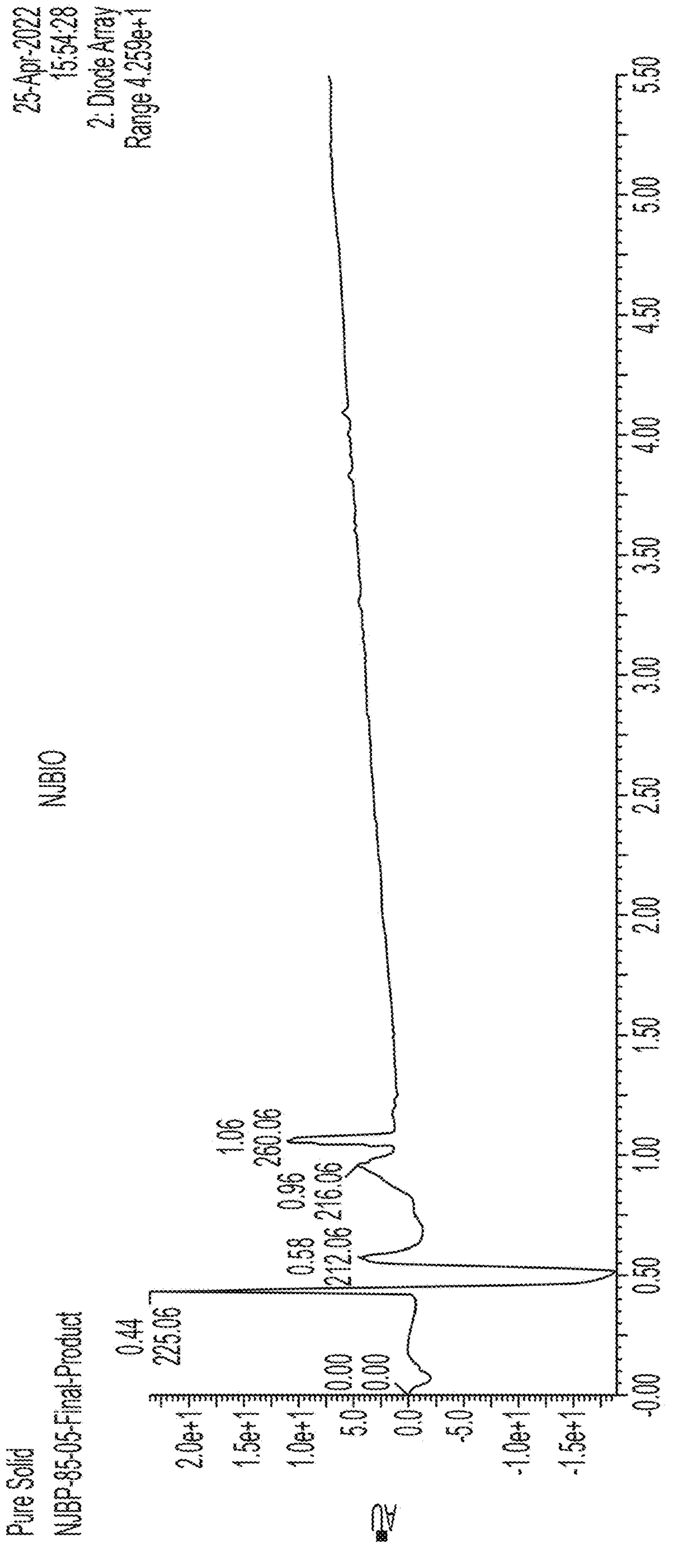
FIG. 33 is a HPLC chromatogram ($CH_3OH$) of 2'-O-acetyl-Uridine 15 (mixture of 2'-OAc and 3'-OAc regioisomers).
Figure 34:
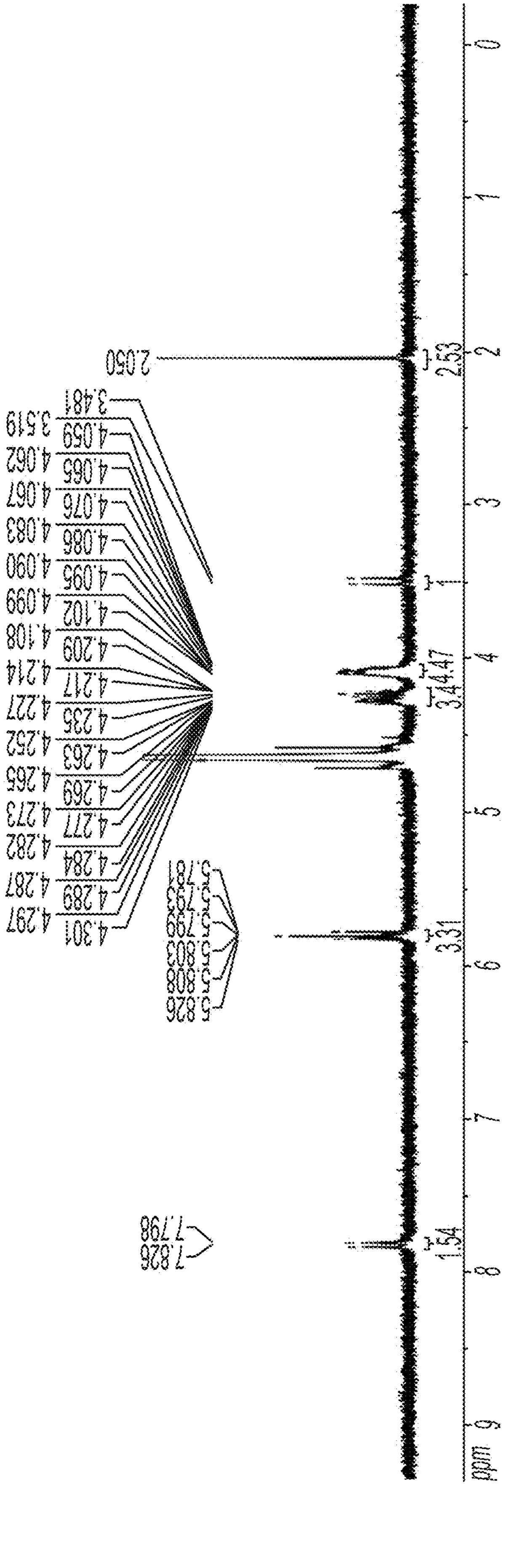
FIG. 34 is a graph depicting $^1H$ NMR (300 MHZ, $D_2O$) of 2'-O-acetyl-Uridine Triphosphate 17 (mixture of 2'OAc and 3'-OAc Regioisomers).
Figure 35:
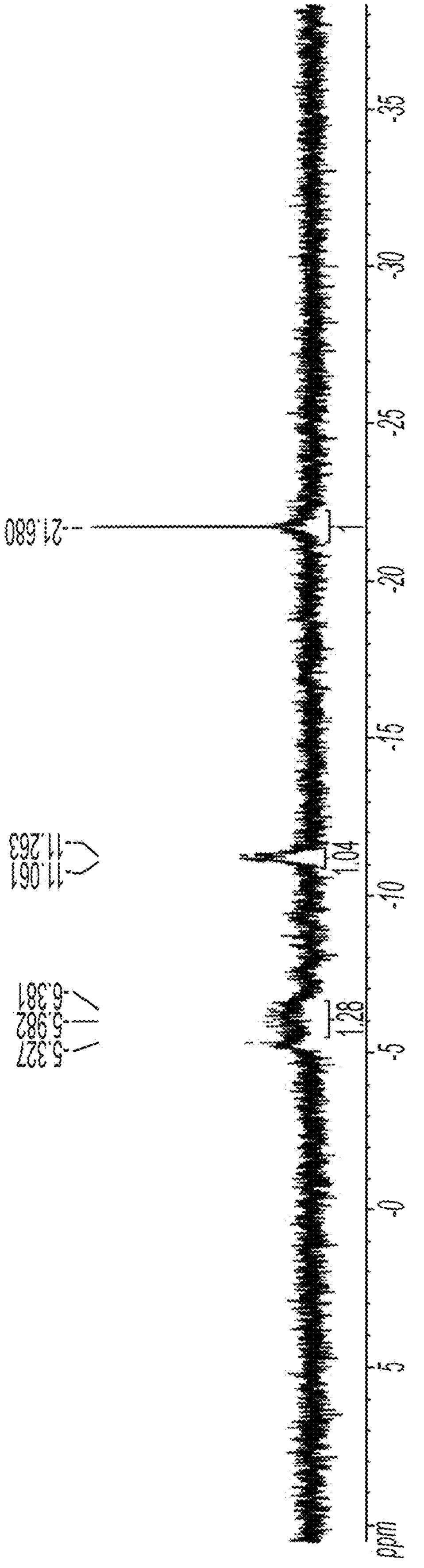
FIG. 35 is a graph depicting $^{31}P$ NMR (121 MHZ, $D_2O$) of 2'-O-acetyl-Uridine Triphosphate 17 (mixture of 2'OAc and 3'-OAc Regioisomers).
Figure 36:
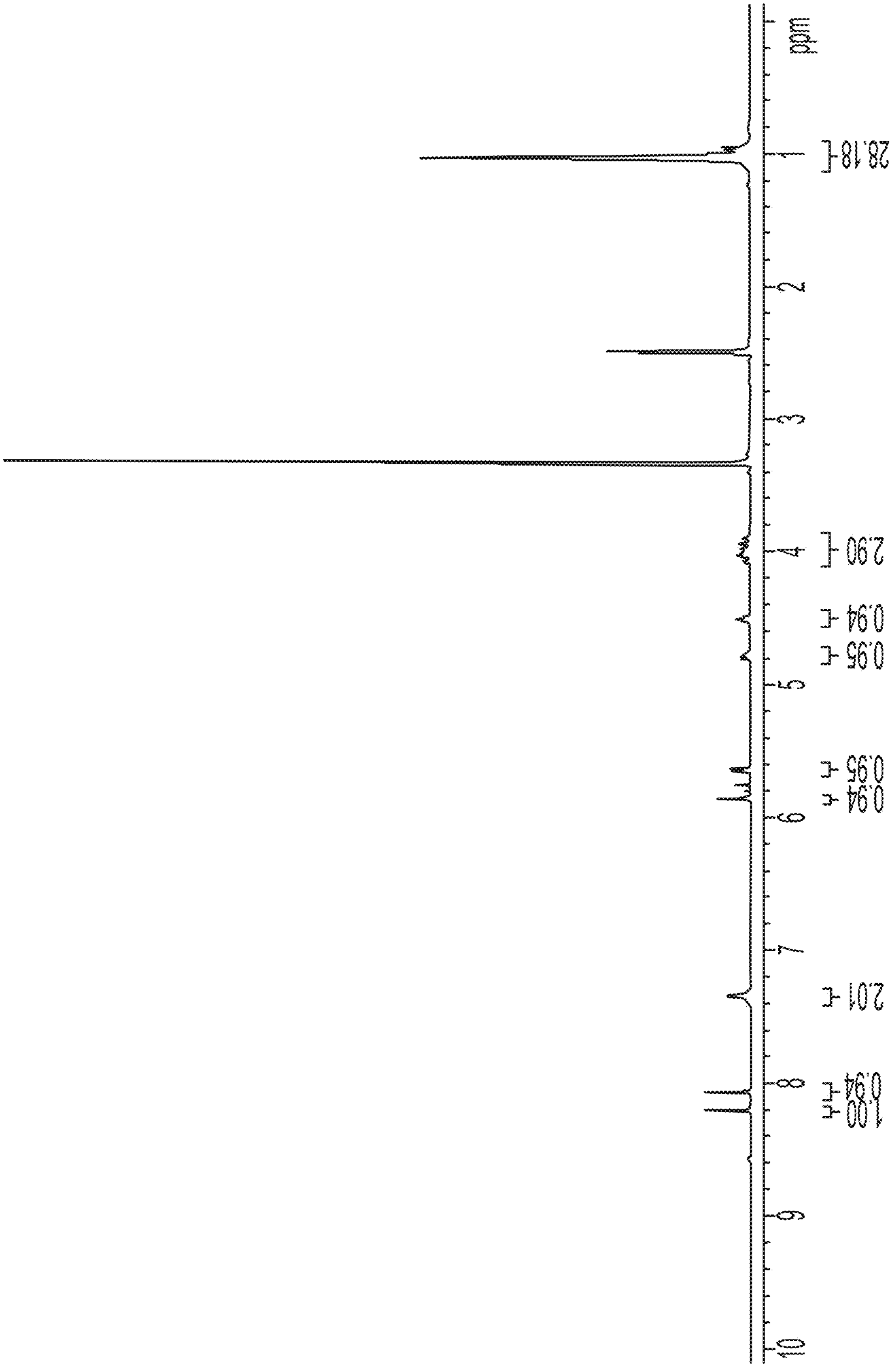
FIG. 36 is a graph depicting $^1H$ NMR (300 MHZ, DMSO-$d_6$) of Silyl-protected Adenosine 19.
Figure 37:
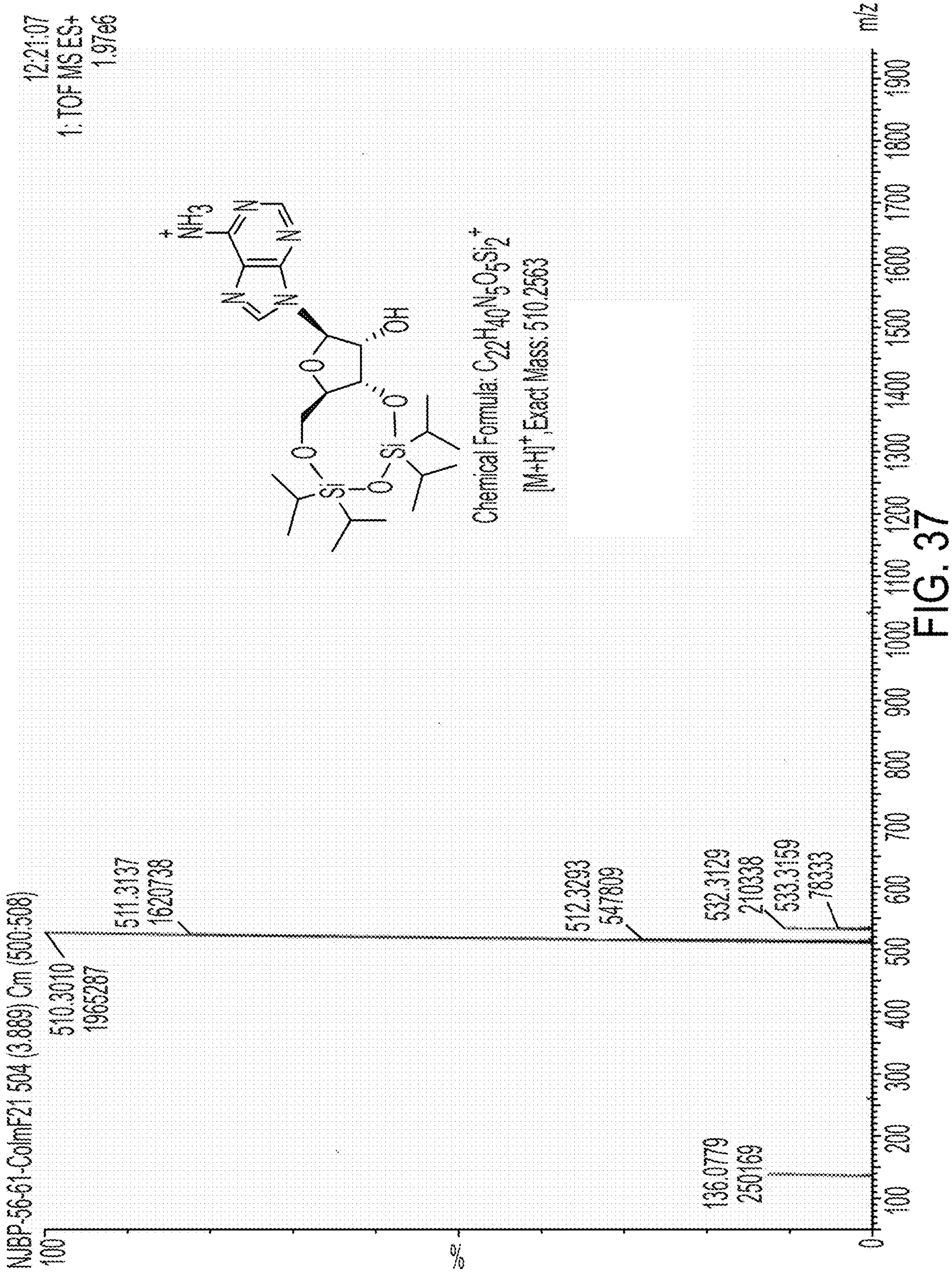
FIG. 37 is a mass spectrum ($ESI^+$, 100% $CH_3OH$, TOF) of Silyl-protected Adenosine 19.
Figure 38:
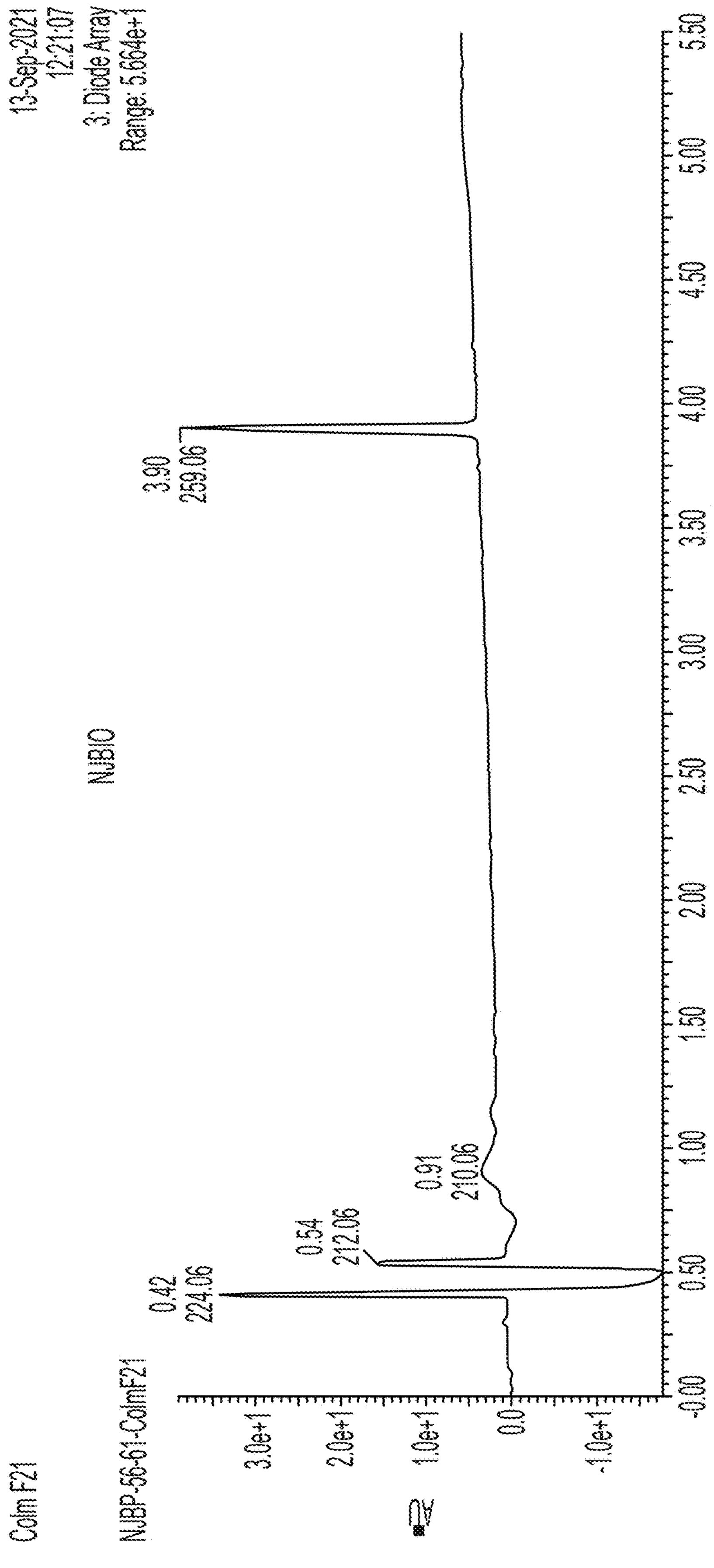
FIG. 38 is a HPLC chromatogram ($CH_3OH$) of Silyl-protected Adenosine 19.
Figure 39:
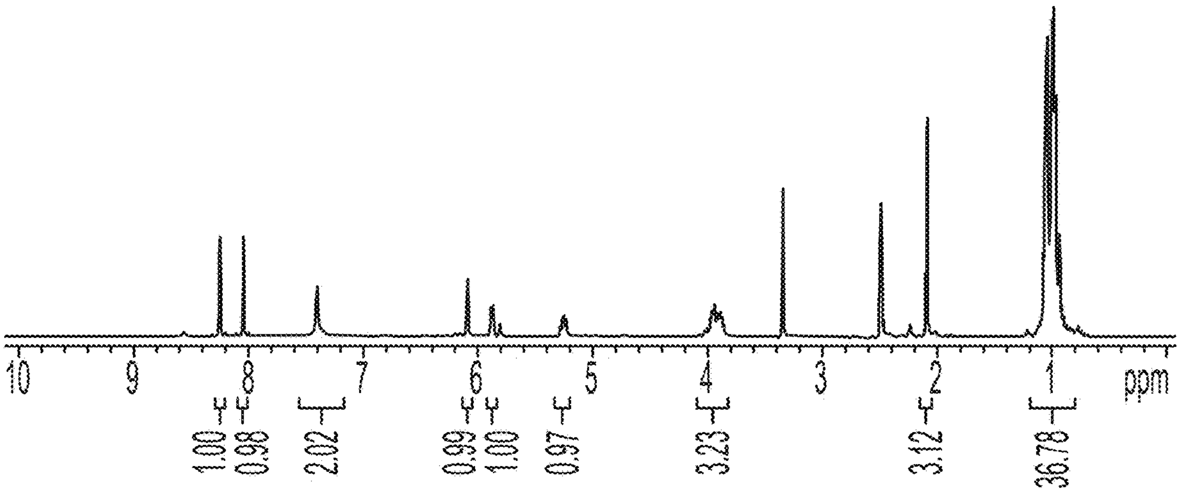
FIG. 39 is a graph depicting $^1H$ NMR (300 MHz, DMSO-$d_6$) of 2'-O-Acetylated Silyl-protected Adenosine 20.
Figure 40:
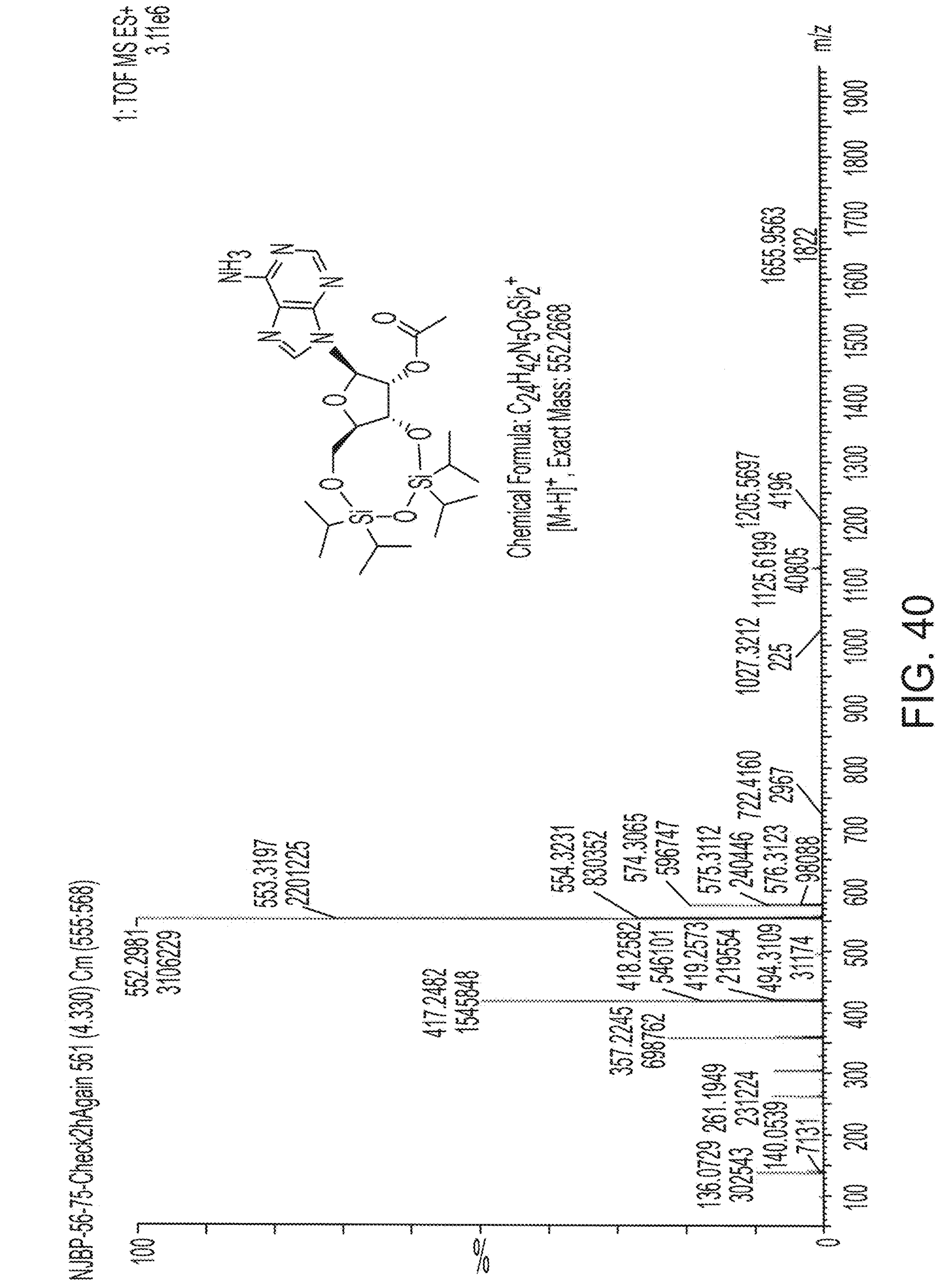
FIG. 40 is a mass spectrum ($ESI^+$, 100% $CH_3OH$, TOF) of 2'-O-Acetylated Silyl-protected Adenosine 20.
Figure 41:
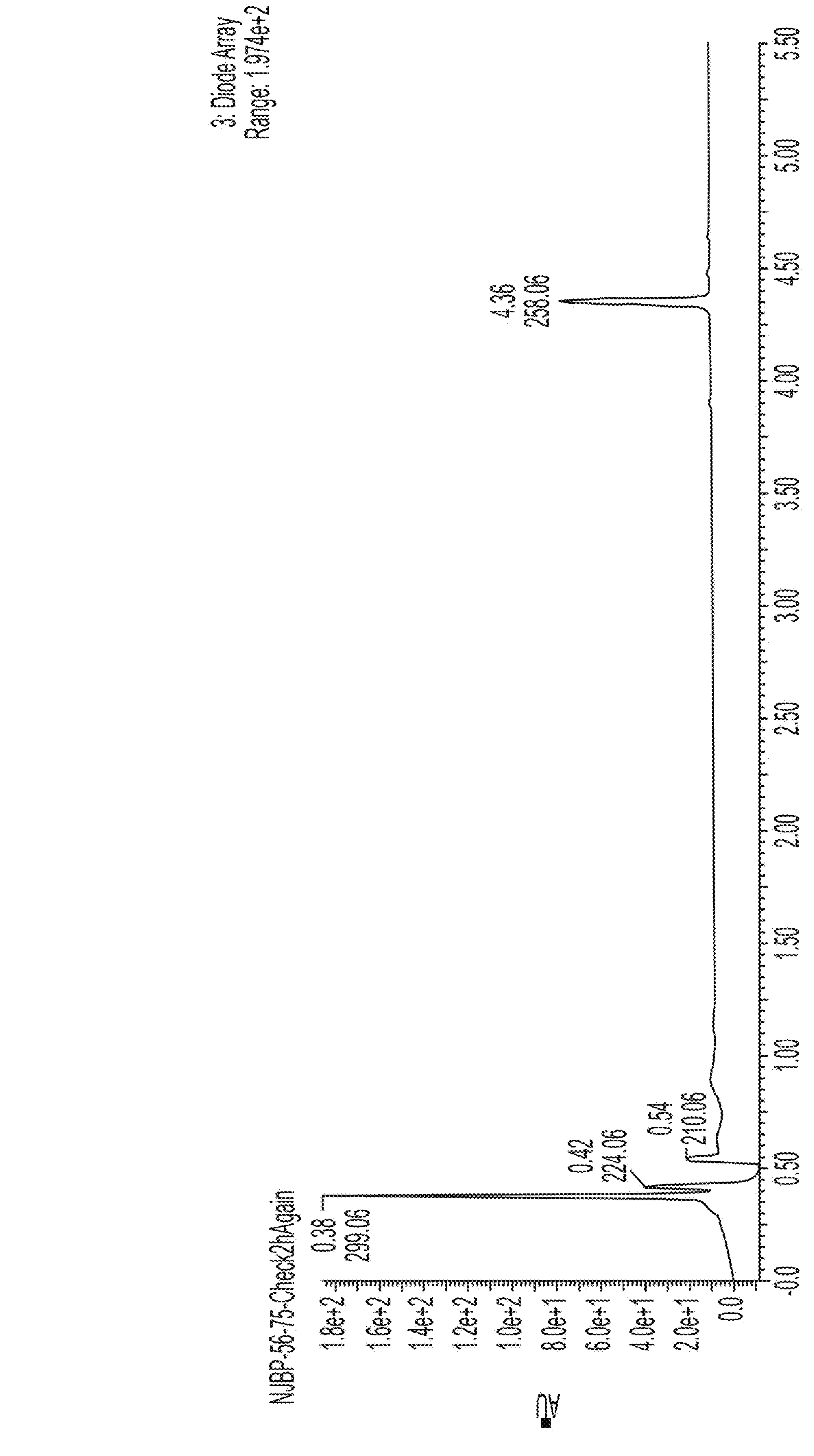
FIG. 41 is a HPLC chromatogram ($CH_3OH$) of 2'-O-Acetylated Silyl-protected Adenosine 20.
Figure 42:
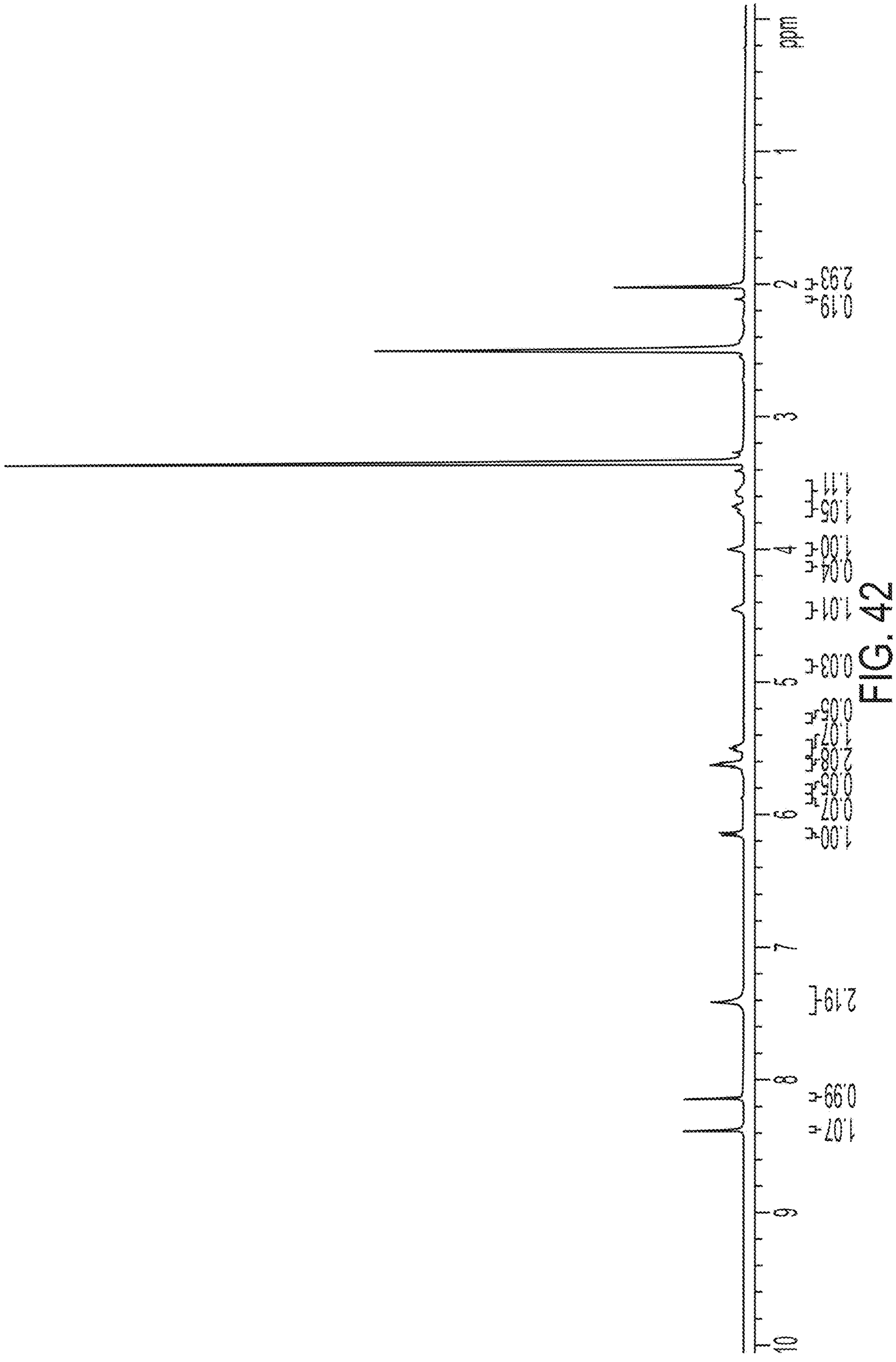
FIG. 42 is a graph depicting $^1H$ NMR (300 MHz, DMSO-$d_6$) of 2'-OAc Adenosine 21 (minor).
Figure 43:
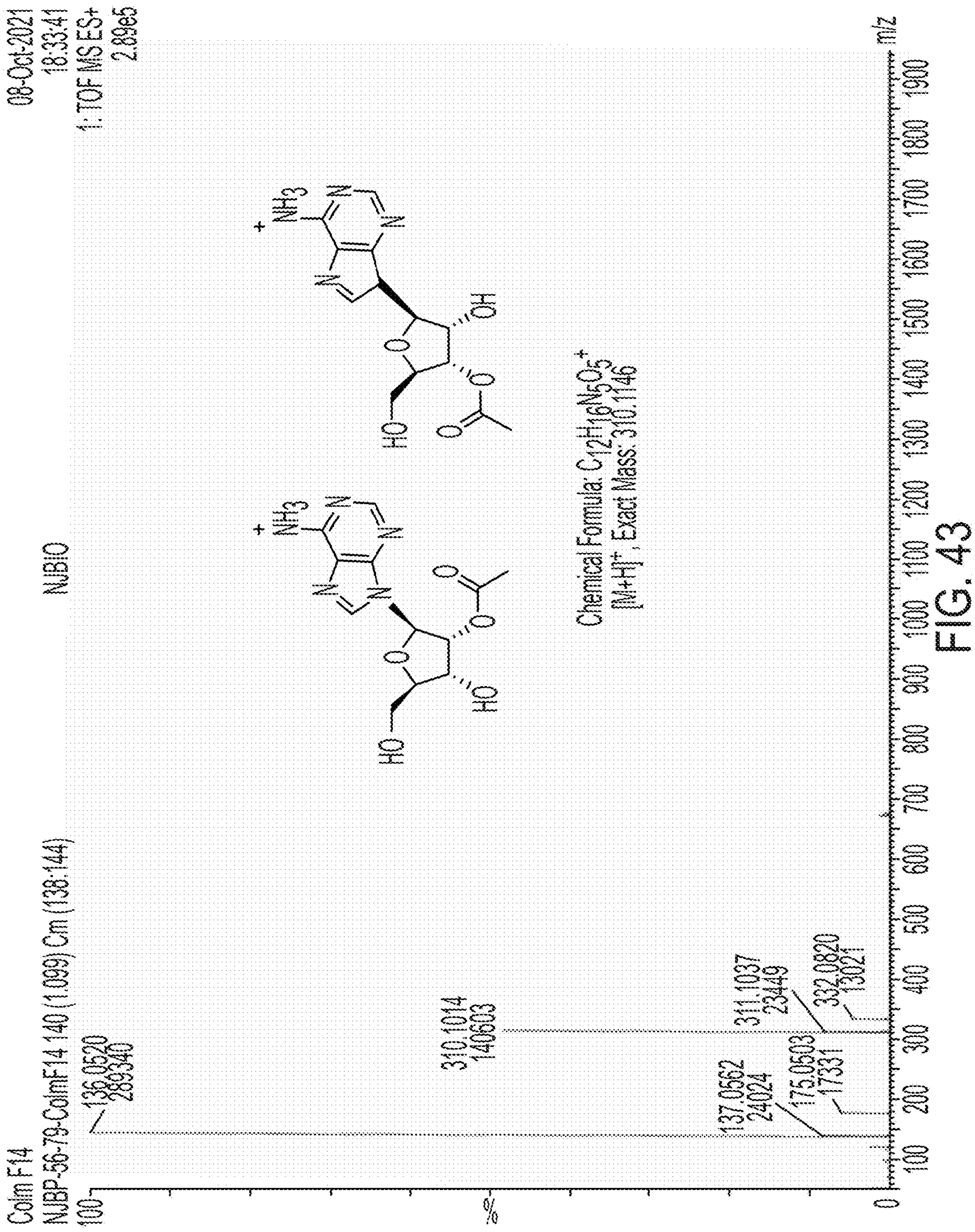
FIG. 43 is a mass spectrum ($ESI^+$, 100% $CH_3OH$, TOF) of 2'-OAc Adenosine 21 (minor).
Figure 44:
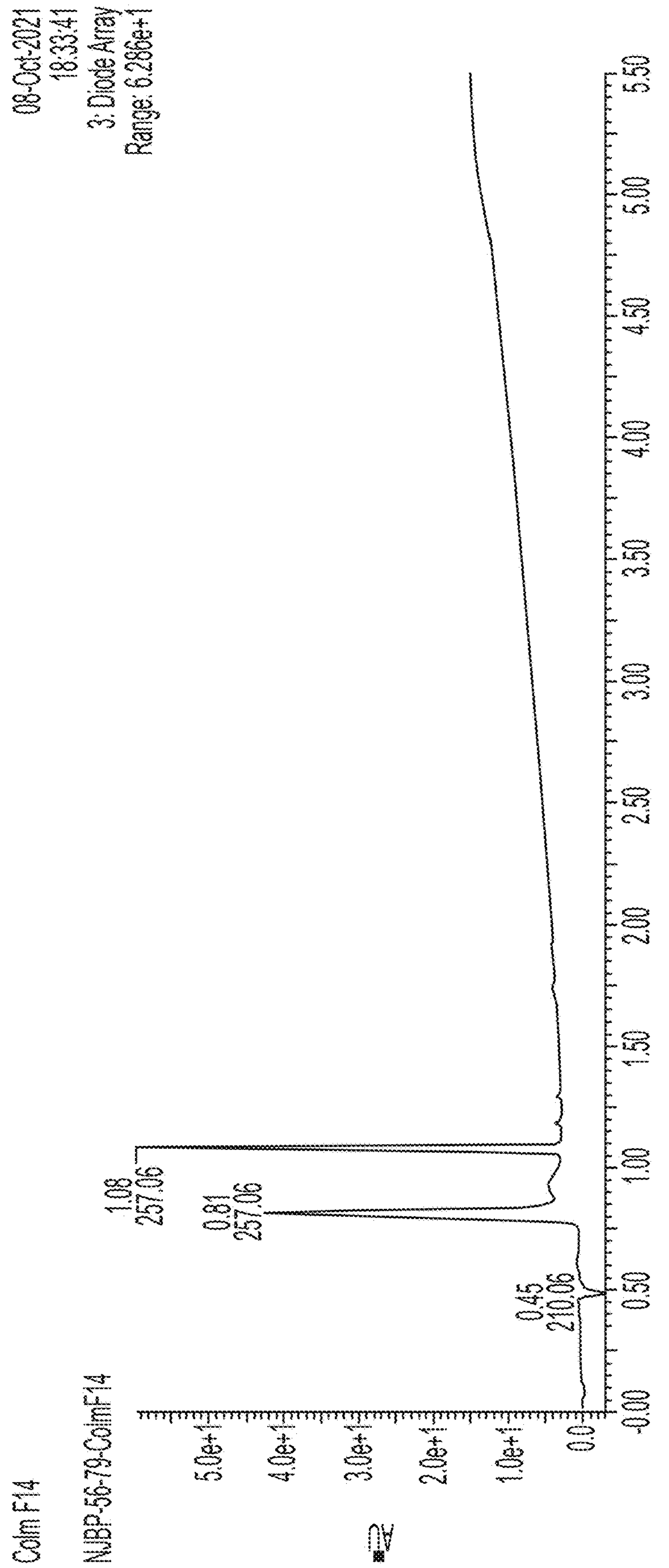
FIG. 44 is a HPLC chromatogram ($CH_3OH$) of 2'-OAc Adenosine 21 (minor).
Figure 45:
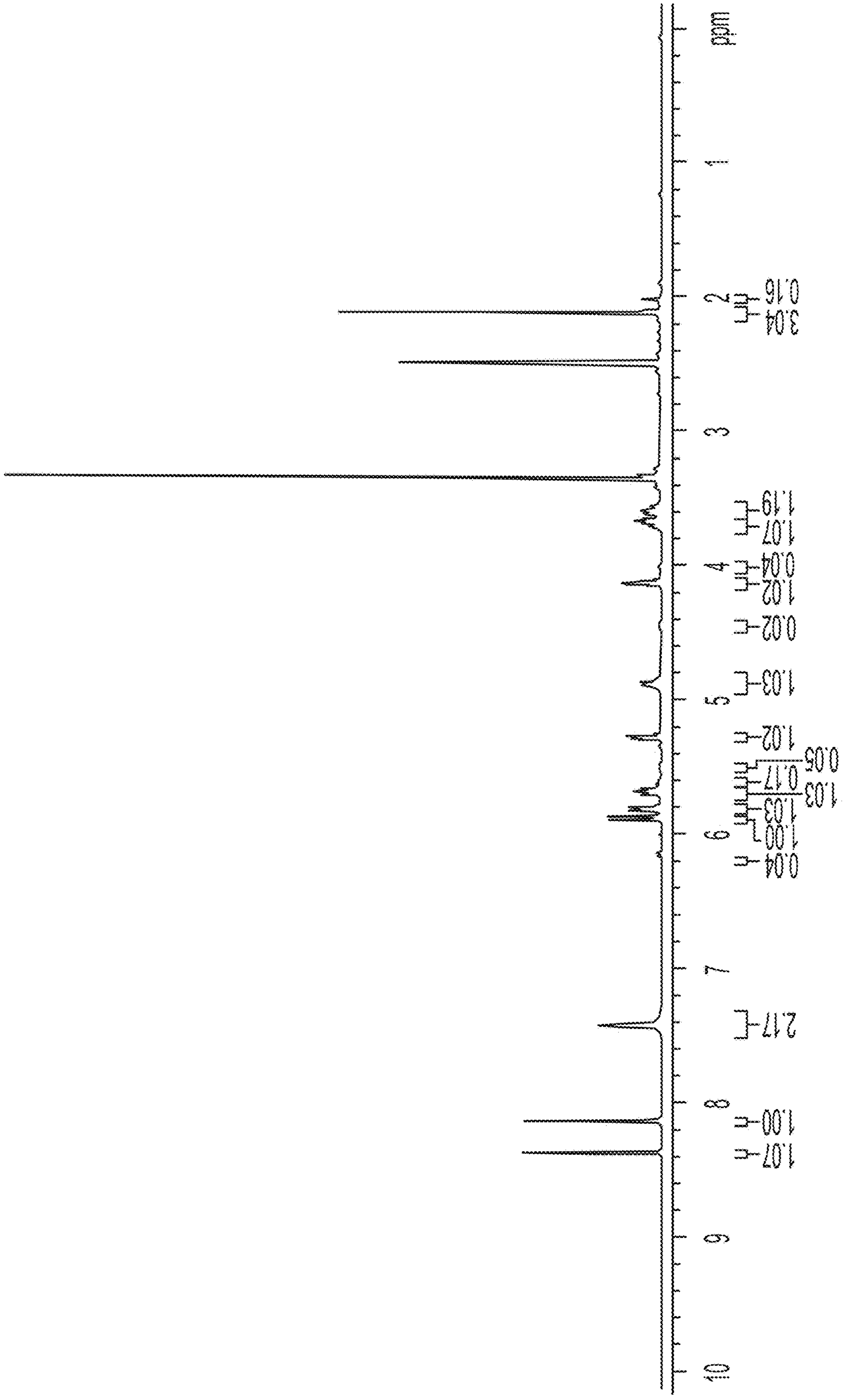
FIG. 45 is a graph depicting $^1H$ NMR (300 MHz, DMSO-$d_6$) of 3'-OAc Adenosine 22 (major).
Figure 46:
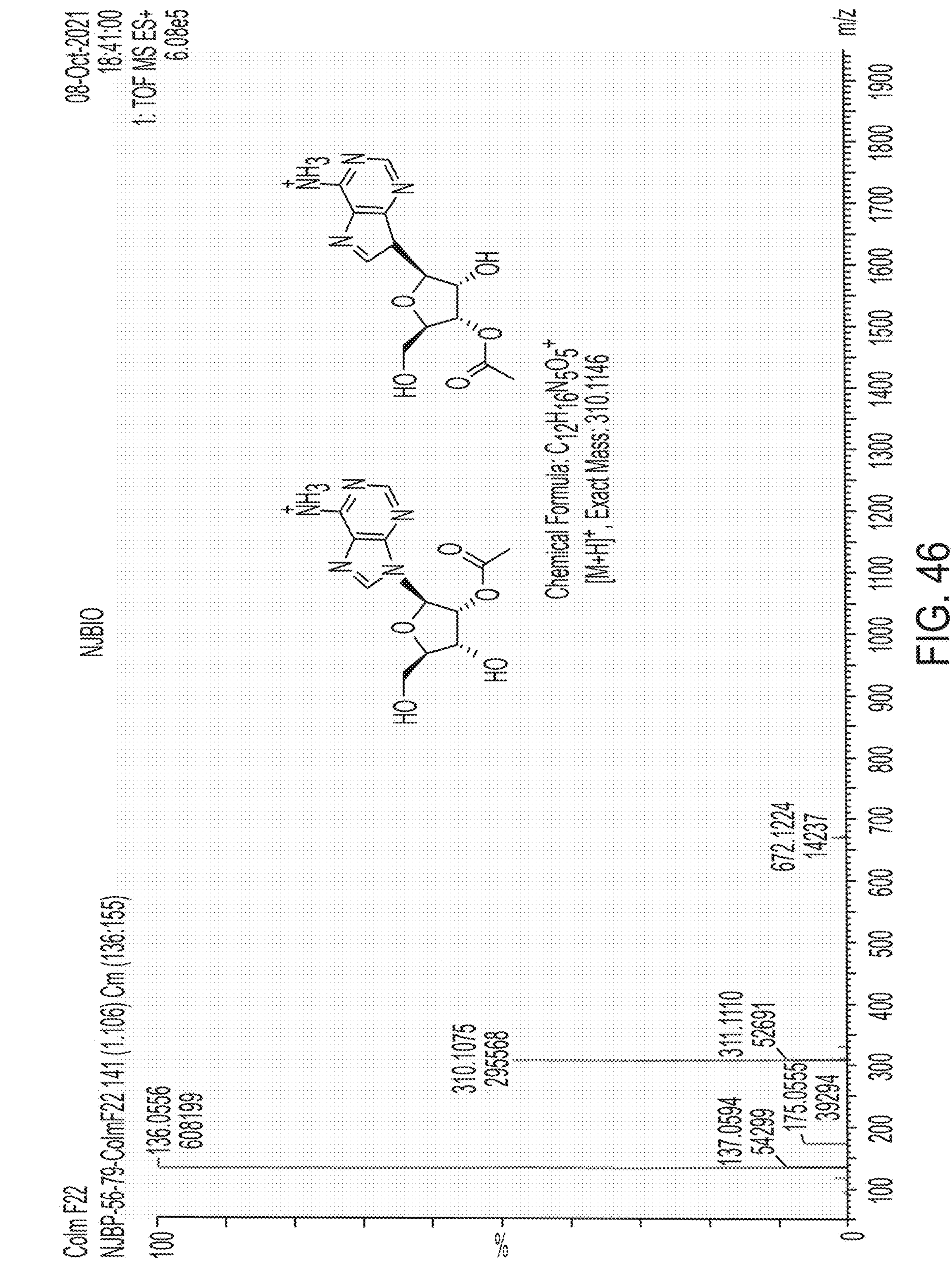
FIG. 46 is a mass spectrum ($ESI^+$, 100% $CH_3OH$, TOF) of 3'-OAc Adenosine 22 (major).
Figure 47:
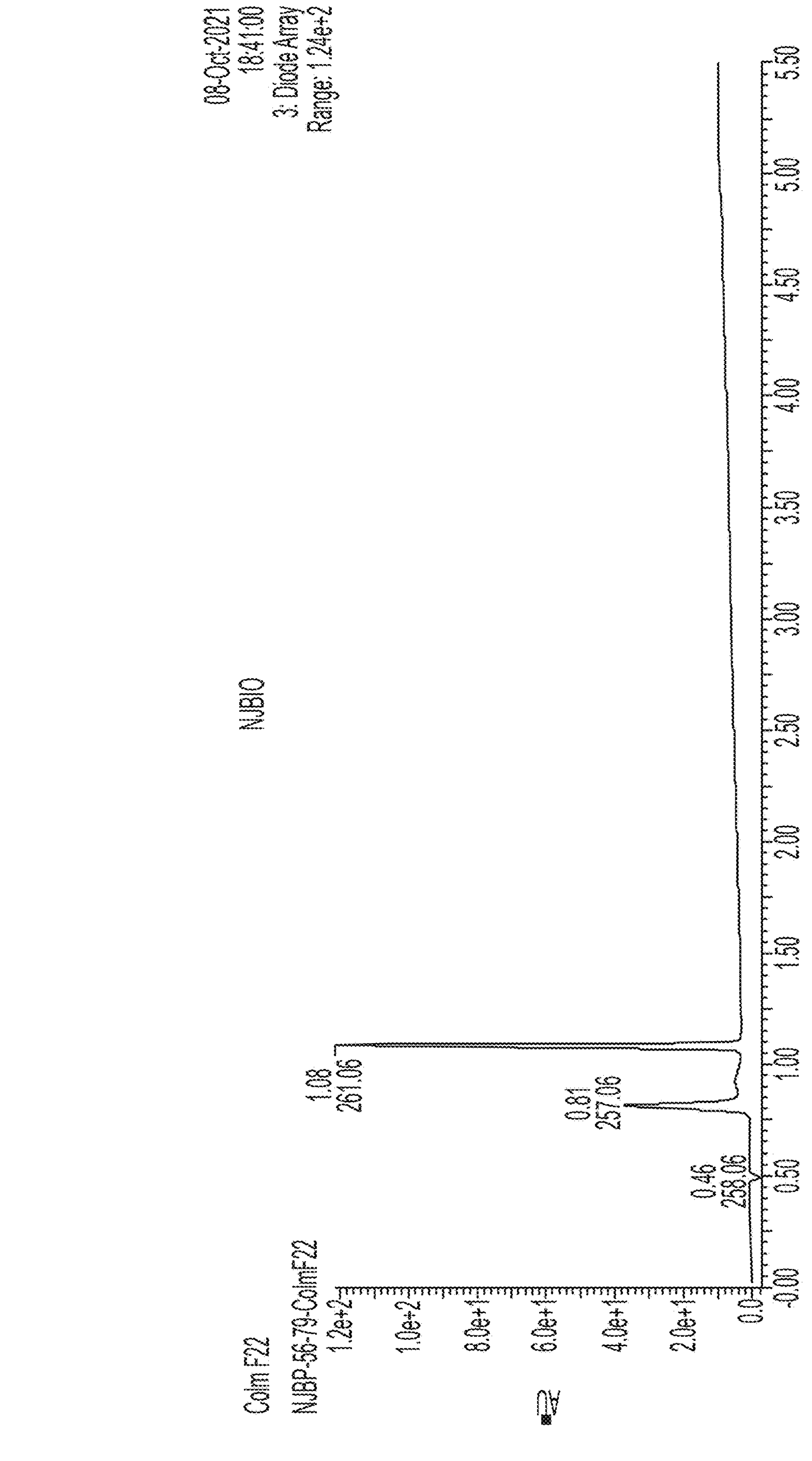
FIG. 47 is a HPLC chromatogram ($CH_3OH$) of 3'-OAc Adenosine 22 (major).
Figure 48:
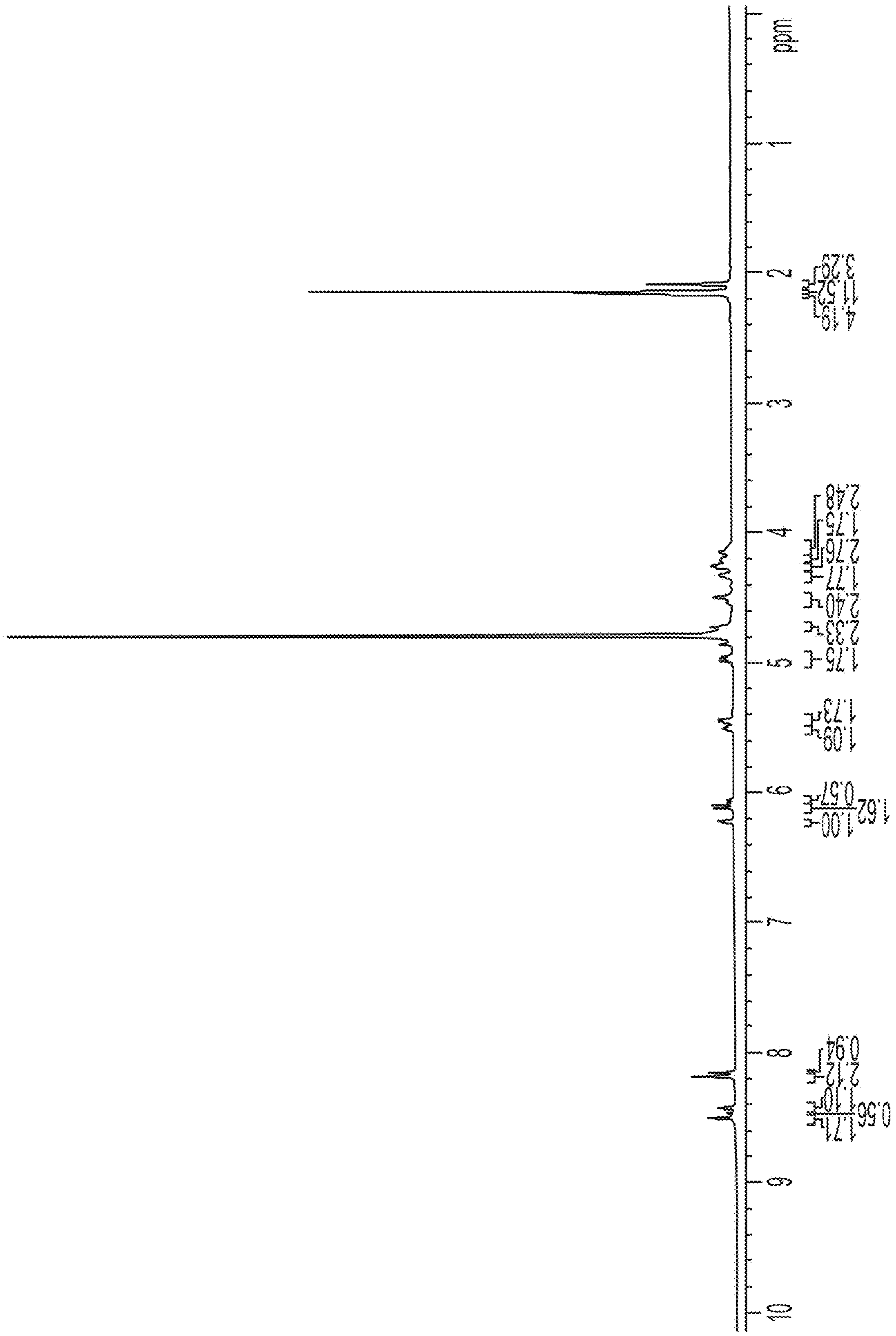
FIG. 48 is a graph depicting $^1H$ NMR (300 MHZ, $D_2O$) of 2'-O-Acetyl Adenosine triphosphate sodium salt 24.
Figure 49:
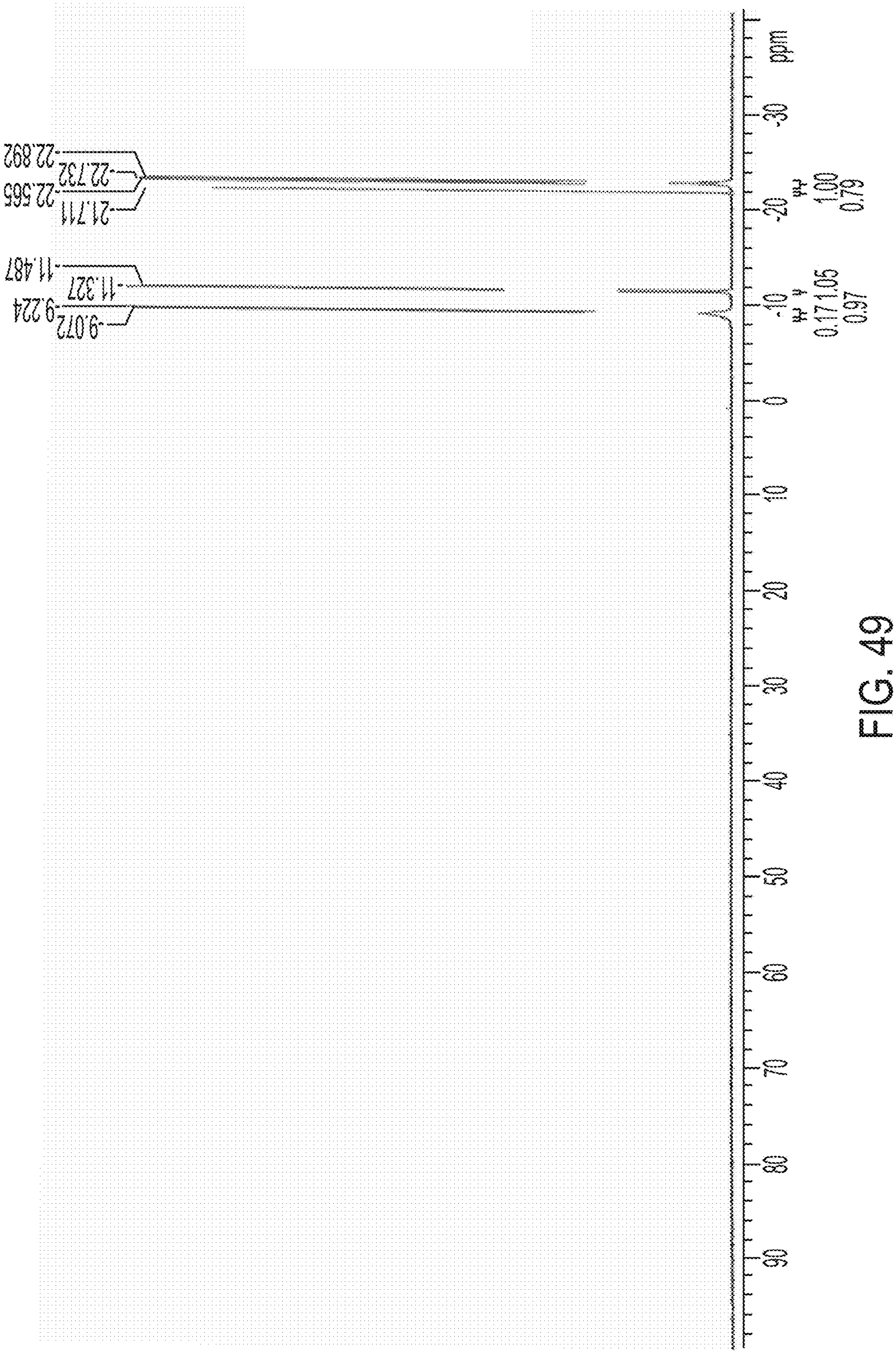
FIG. 49 is a graph depicting $^{31}P$ NMR (121 MHZ, $D_2O$) of 2'-O-Acetyl Adenosine triphosphate sodium salt 24.
Figure 50:
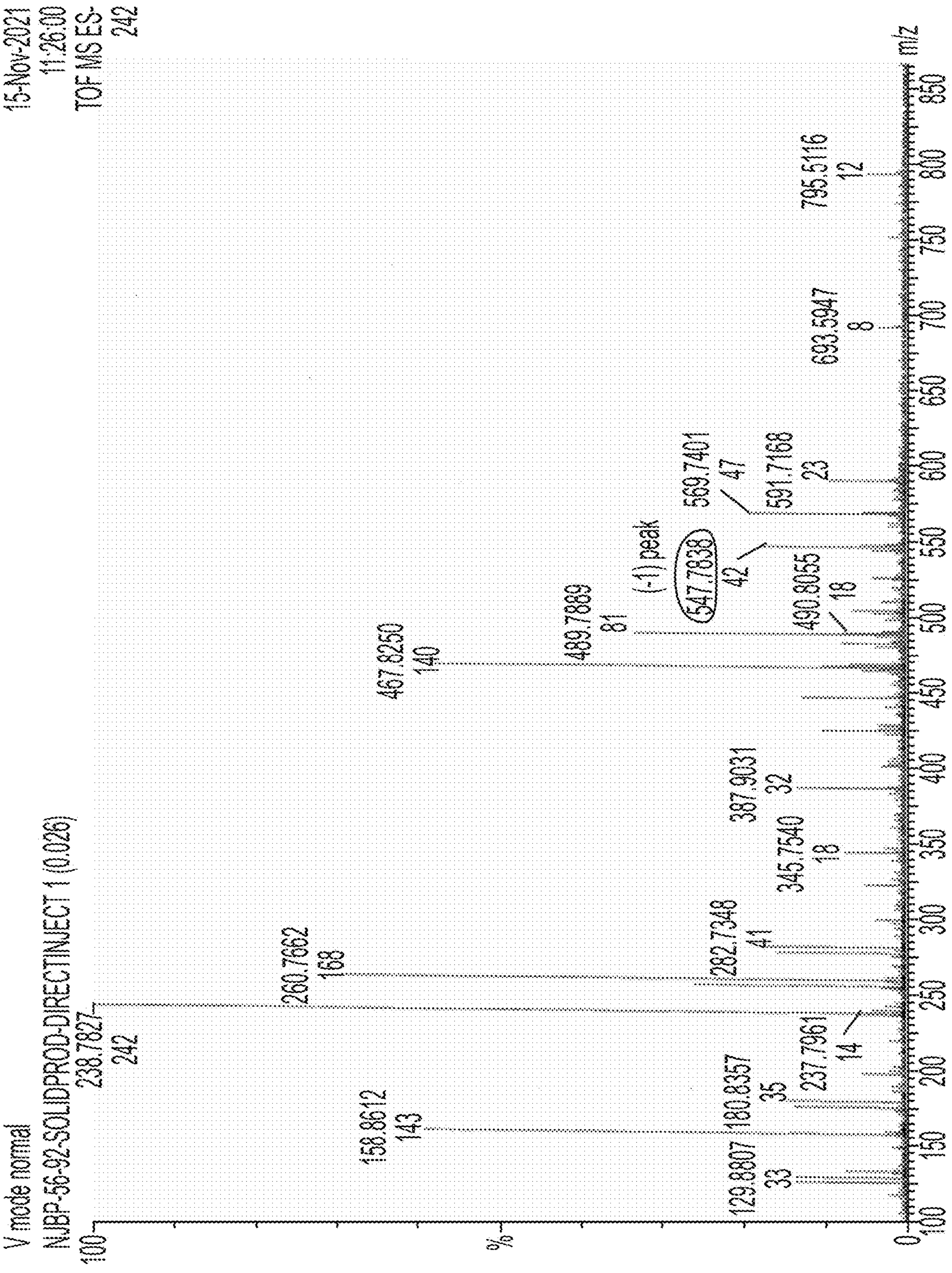
FIG. 50 is a mass spectrum ($ESI^-$, 100% $CH_3OH$, TOF) of 2'-O-Acetyl Adenosine triphosphate sodium salt 24.
Figure 51:
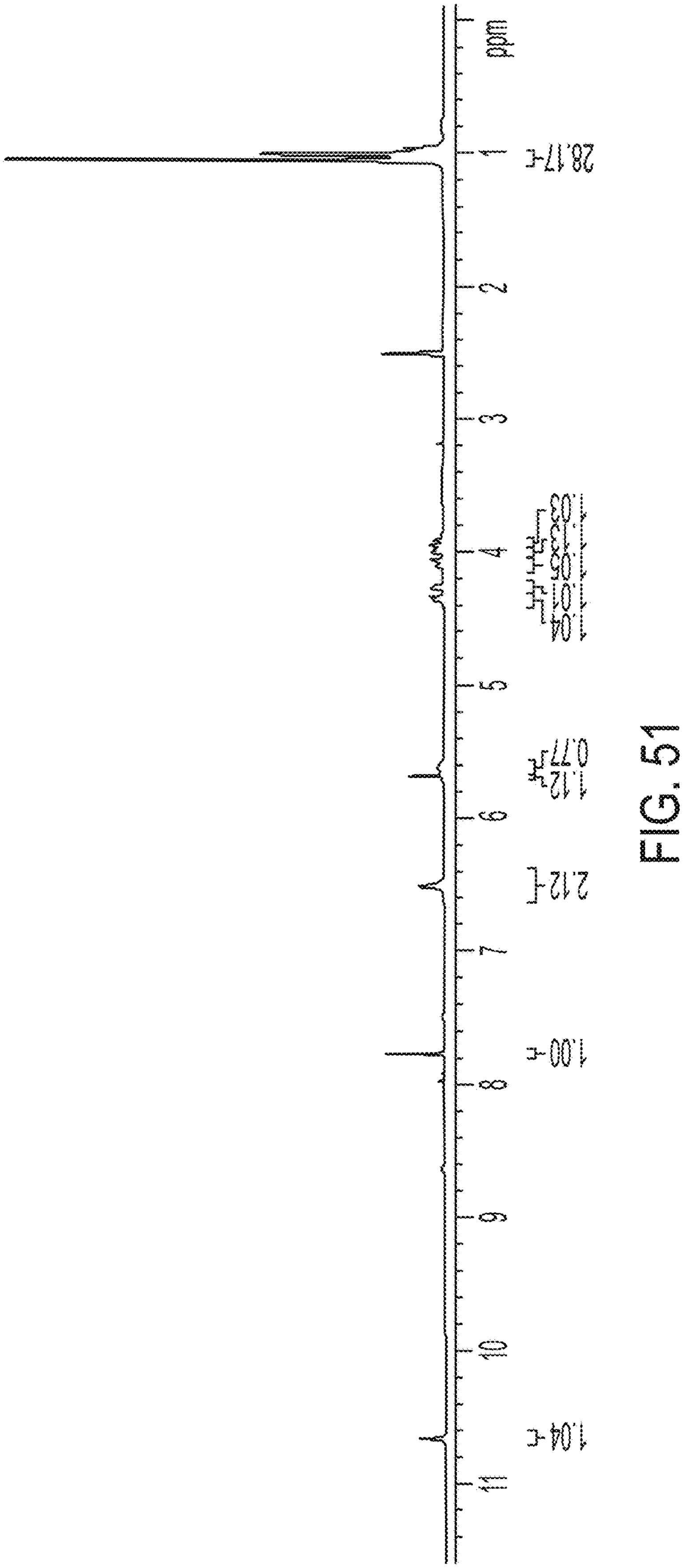
FIG. 51 is a graph depicting $^1H$ NMR (300 MHz, DMSO-$d_6$) of Silyl-protected Guanosine 26.
Figure 52:
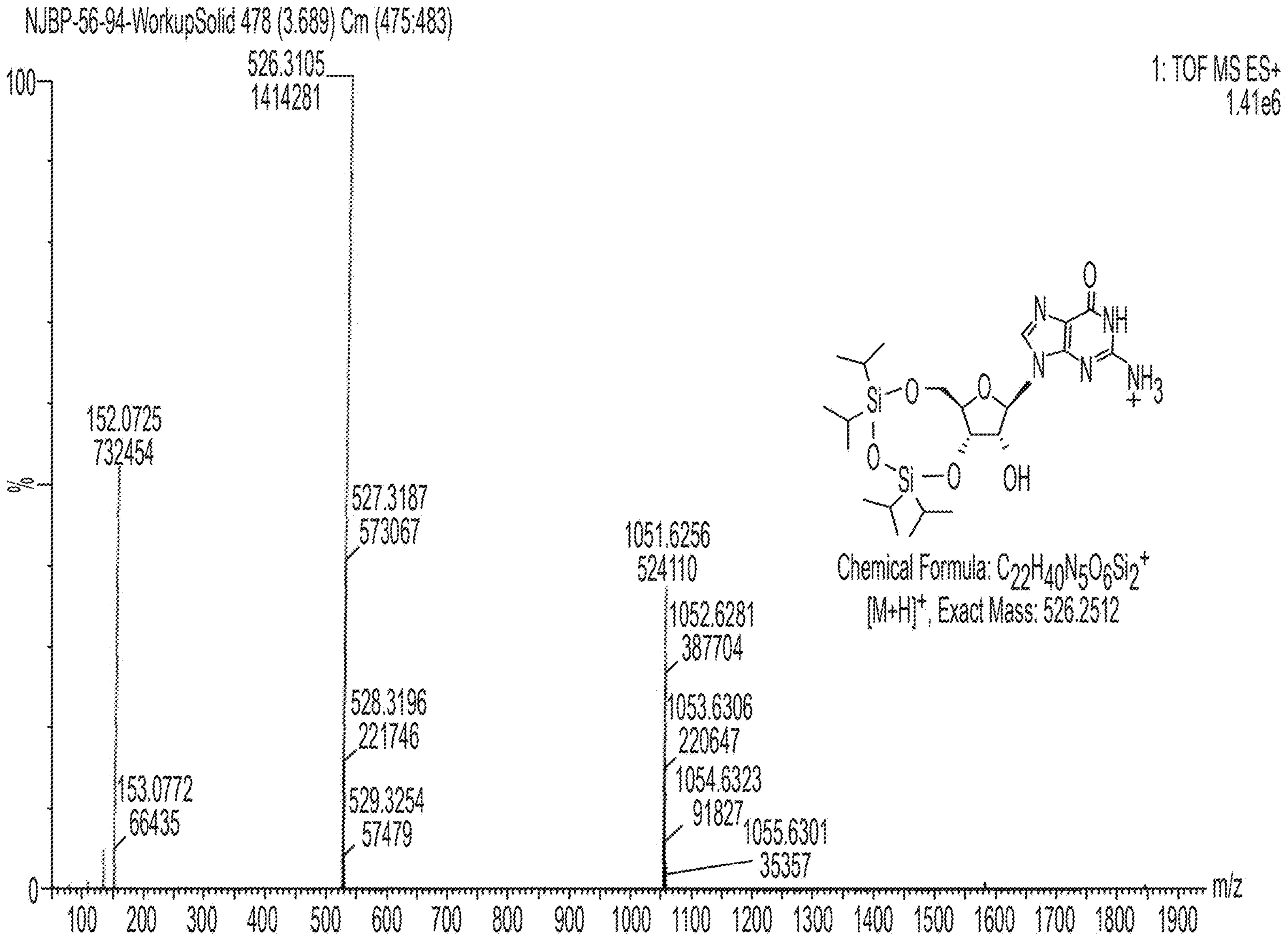
FIG. 52 is a mass spectrum ($ESI^+$, 100% $CH_3OH$, TOF) of Silyl-protected Guanosine 26.
Figure 53:
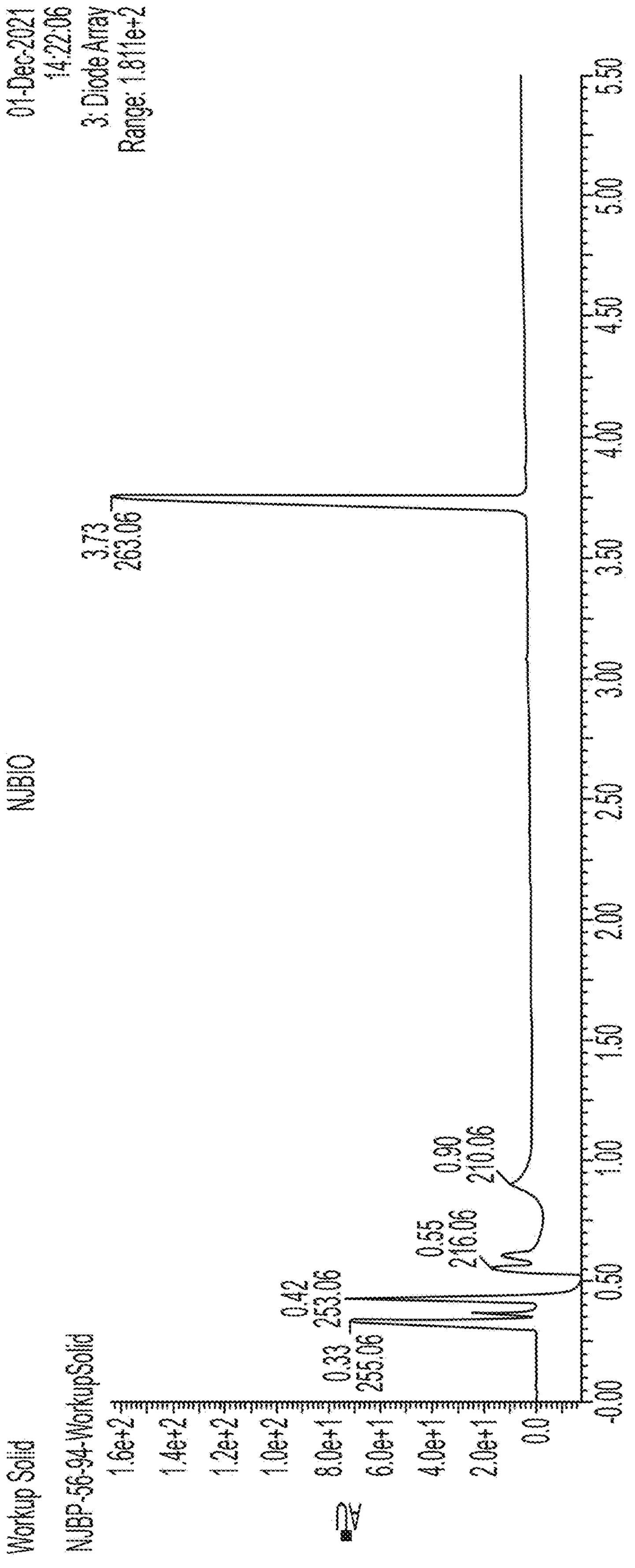
FIG. 53 is a HPLC chromatogram ($CH_3OH$) of Silyl-protected Guanosine 26.
Figure 54:
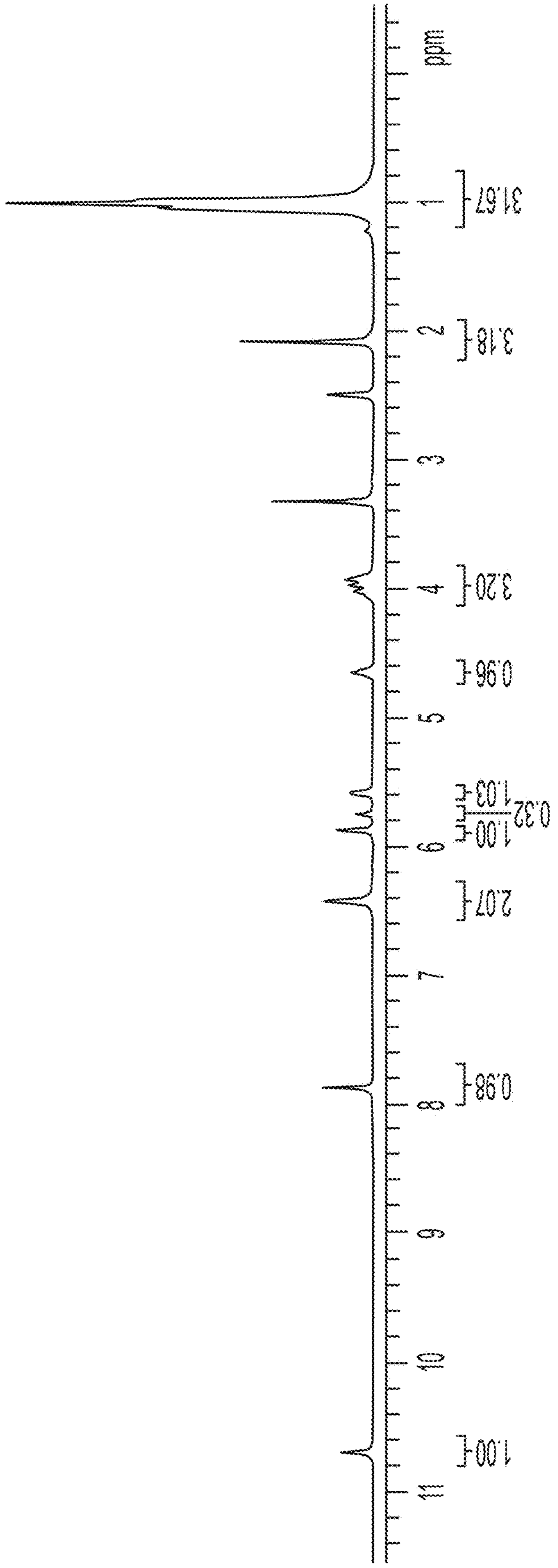
FIG. 54 is a graph depicting $^1H$ NMR (300 MHz, DMSO-$d_6$) of 2'-O-Acetyl-silyl-protected guanosine 27.
Figure 55:
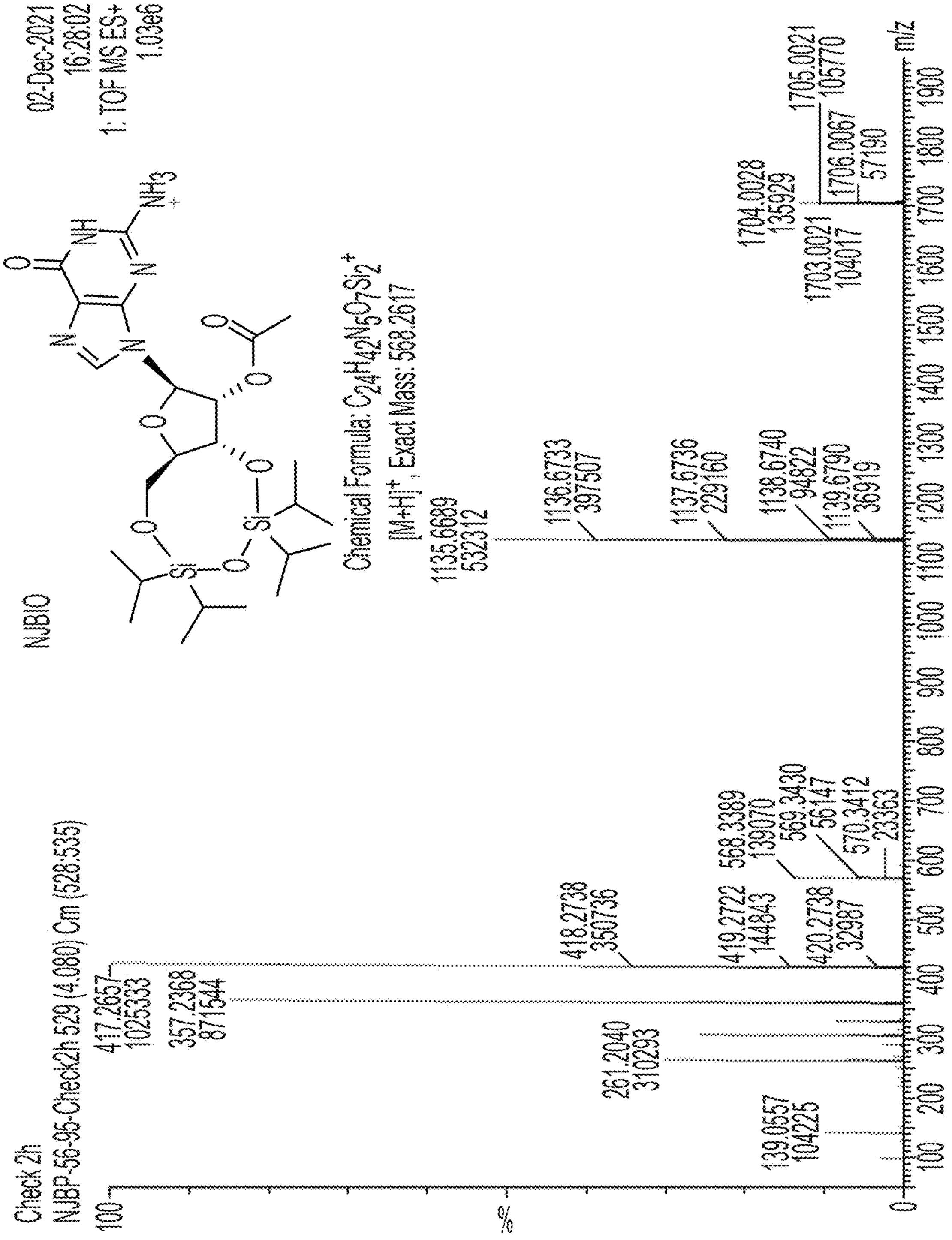
FIG. 55 is a mass spectrum ($ESI^+$, 100% $CH_3OH$, TOF) of 2'-O-Acetyl-silyl-protected guanosine 27.
Figure 56:
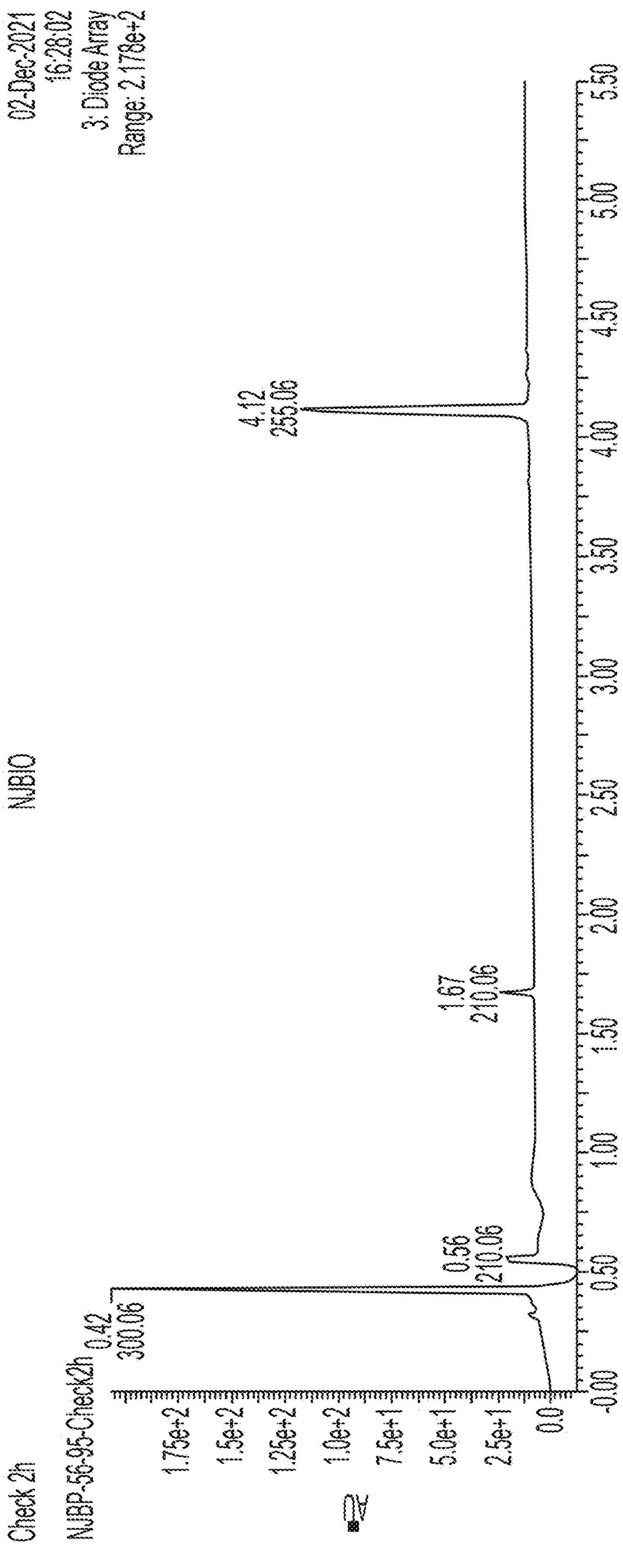
FIG. 56 is a HPLC chromatogram ($CH_3OH$) of 2'-O-Acetyl-silyl-protected guanosine 27.
Figure 57:
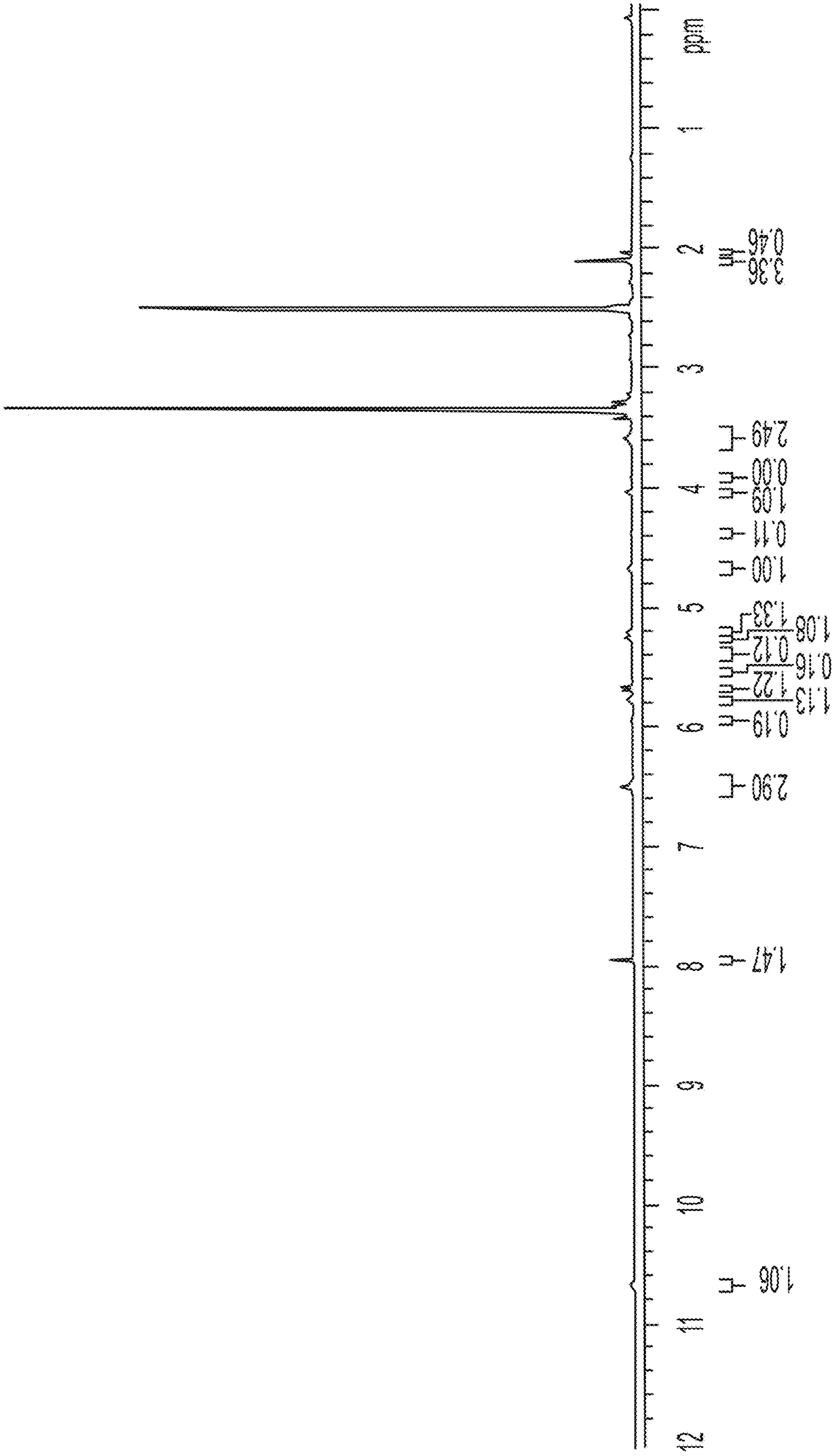
FIG. 57 is a graph depicting $^1H$ NMR (300 MHz, DMSO-$d_6$) of 2'-O-Acetyl guanosine 28.
Figure 58:
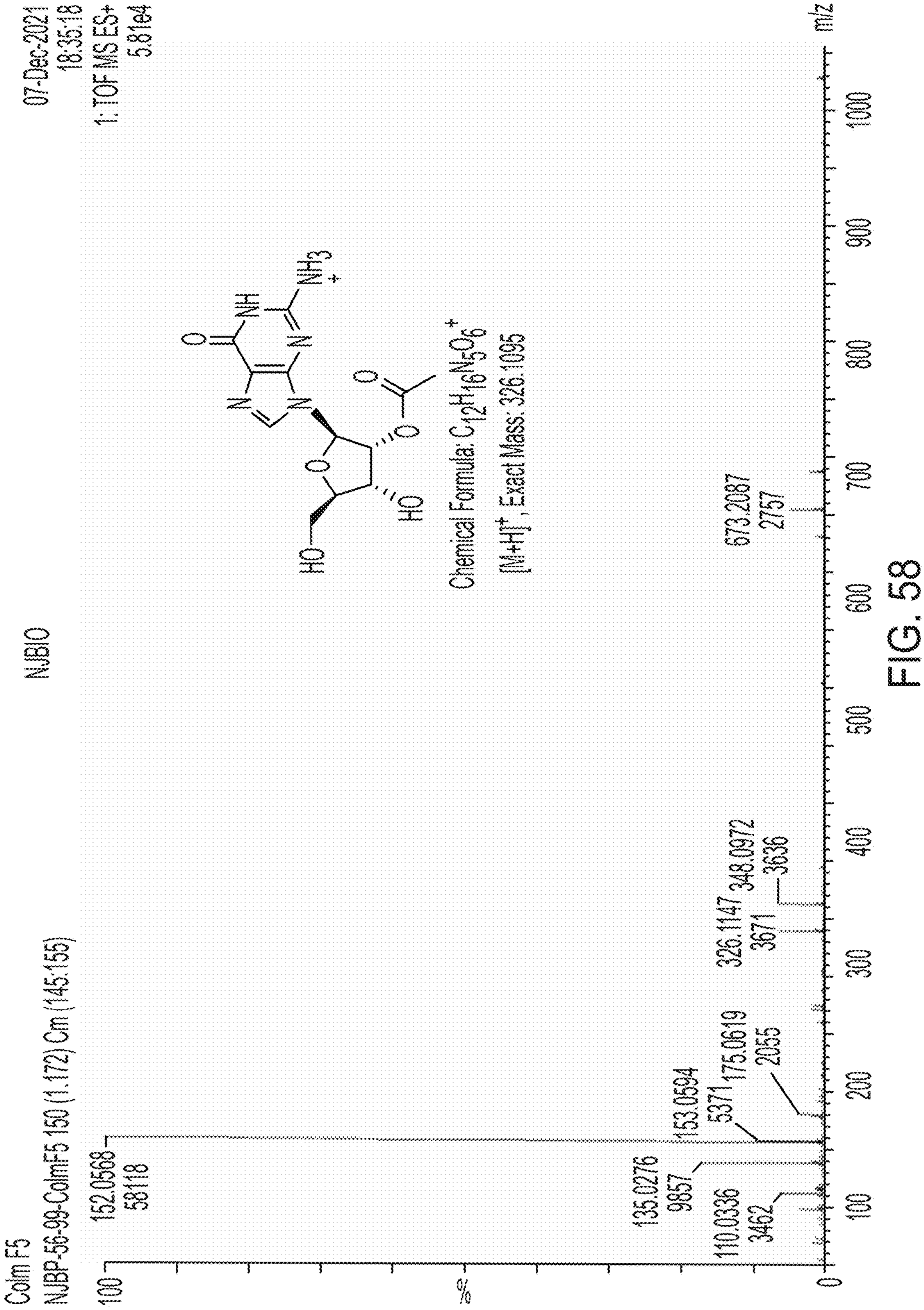
FIG. 58 is a mass spectrum (ESI, 100% $CH_3OH$, TOF) of 2'-O-Acetyl guanosine 28.
Figure 59:
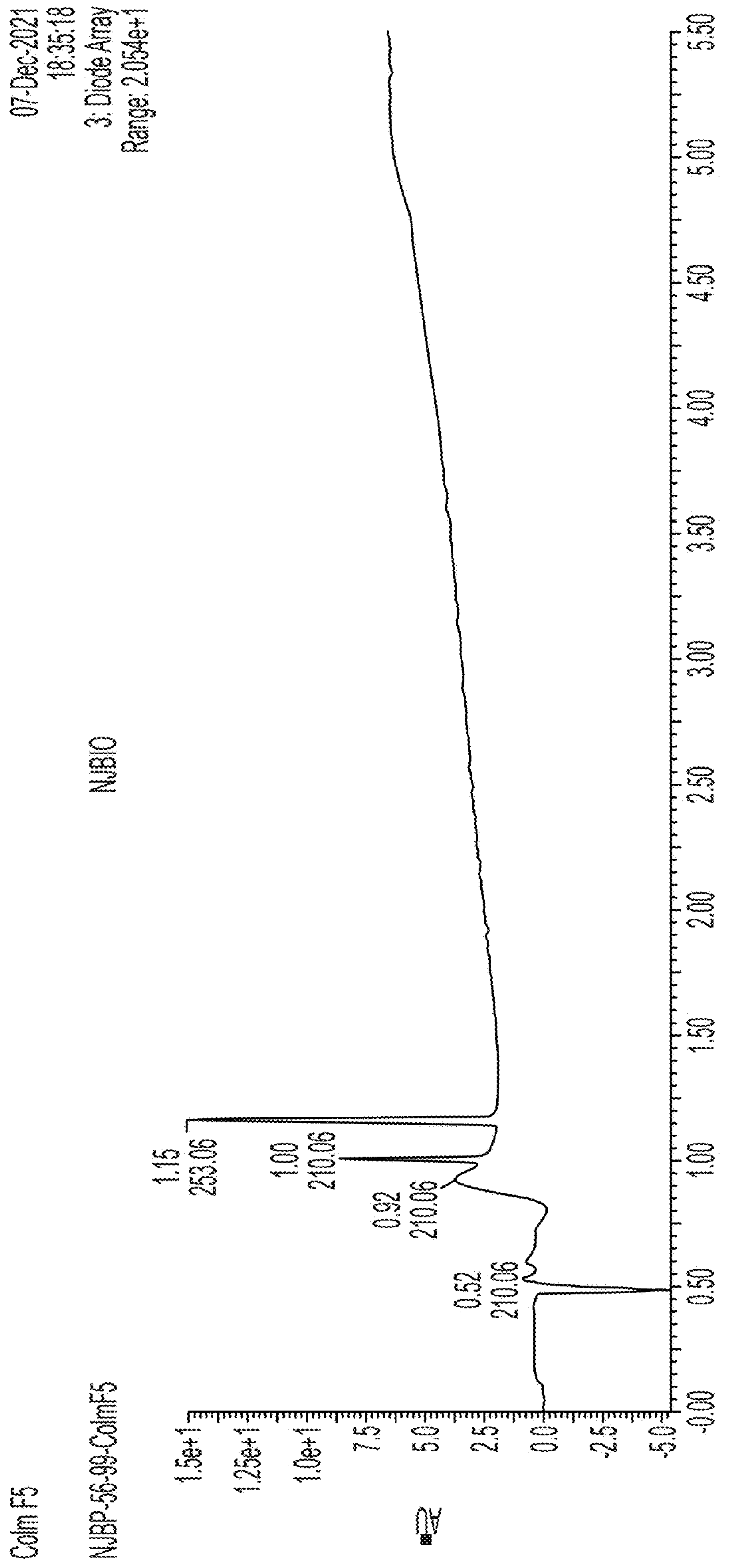
FIG. 59 is a HPLC chromatogram ($CH_3OH$) of 2'-O-Acetyl guanosine 28.
Figure 60:
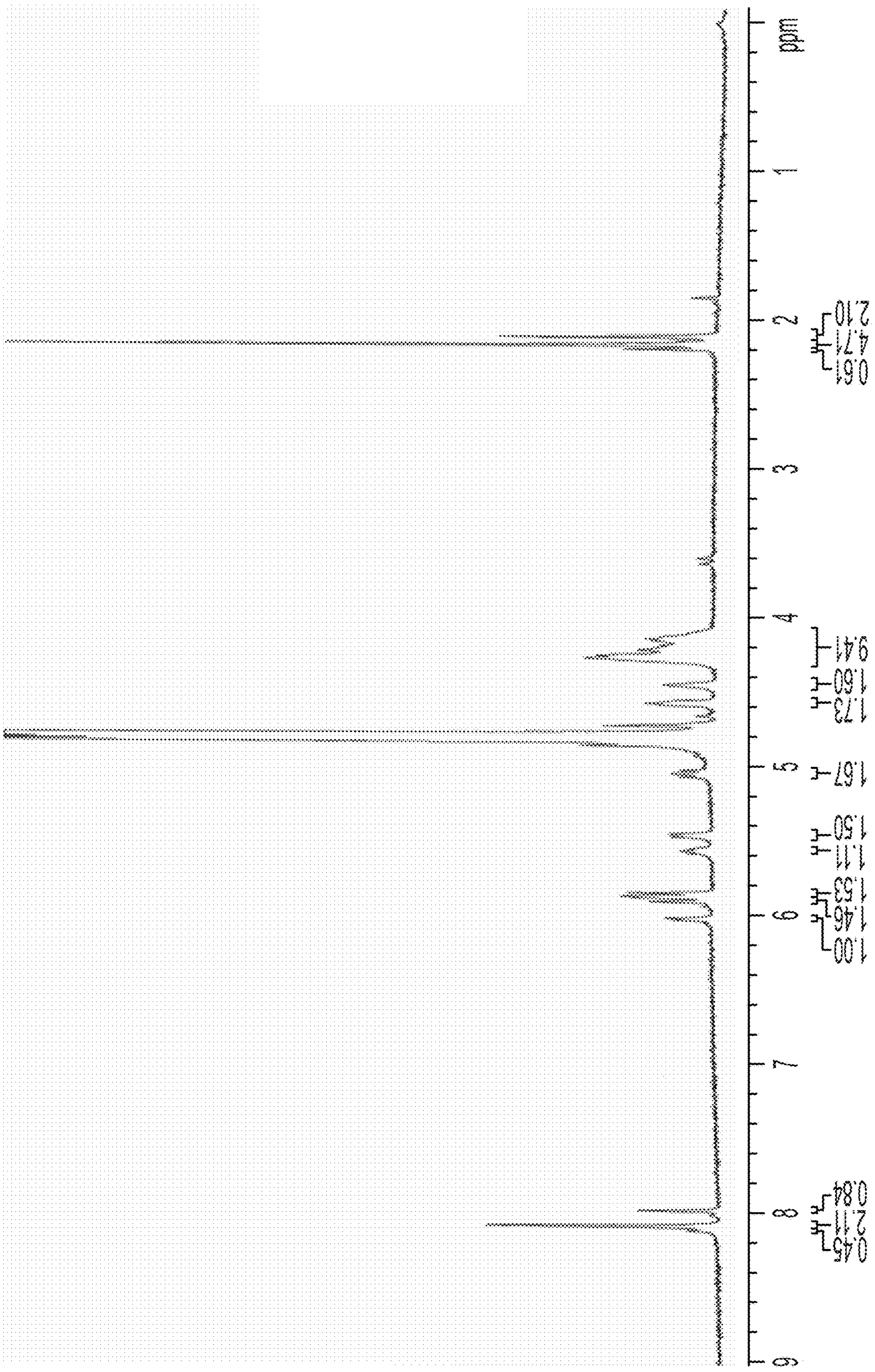
FIG. 60 is a graph depicting 1H NMR (300 MHz, $D_2O$) of 2'-O acetyl-Guanosine Triphosphate 30.
Figure 61:
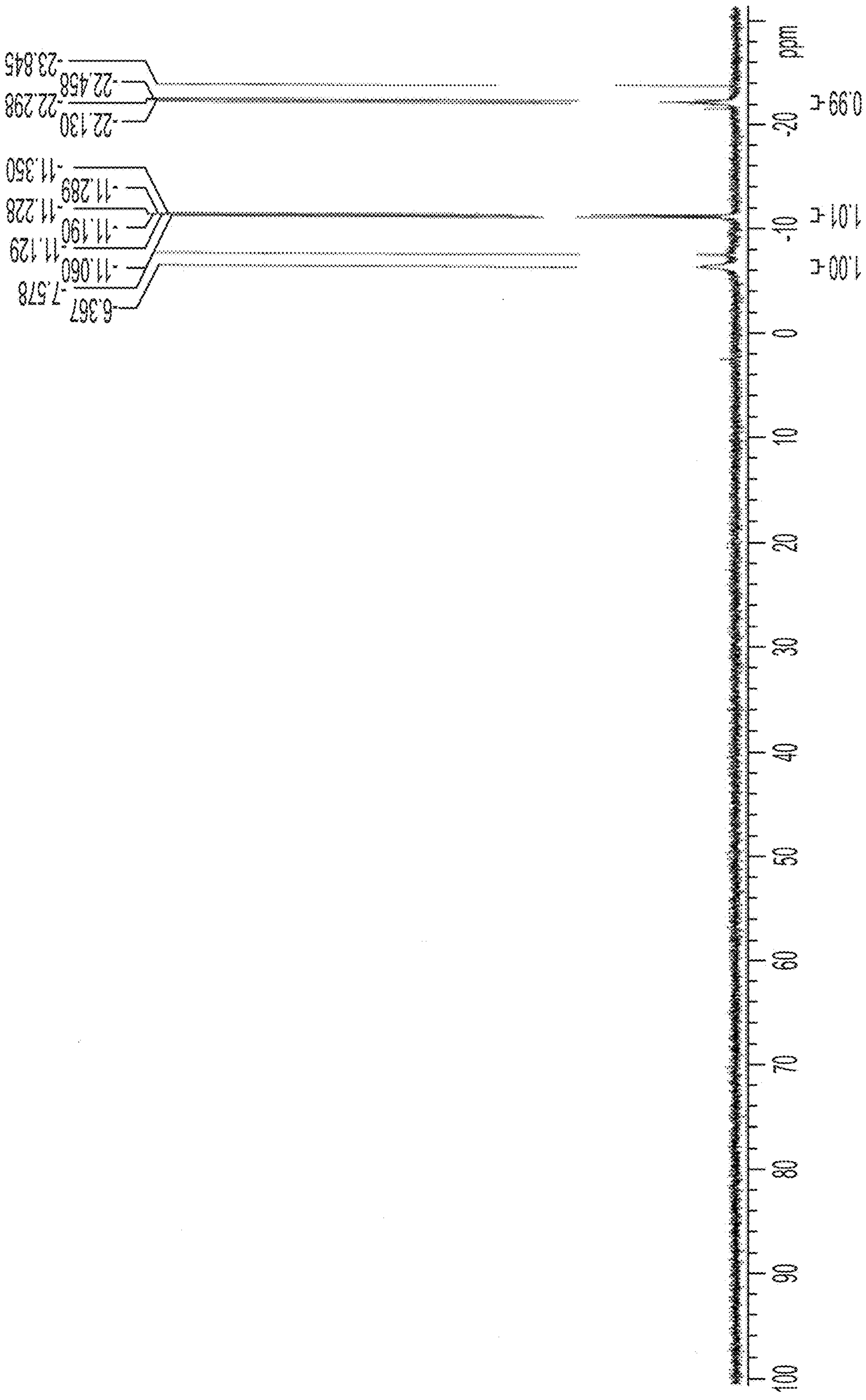
FIG. 61 is a graph depicting $^{31}P$ NMR (121 MHZ, $D_2O$) of 2'-O-acetyl-Guanosine Triphosphate 30.

This Example describes exemplary synthesis methods of 2'-O-acetylated NTPs used in Examples 1 and 2, and as disclosed herein. FIGS. 6-61 provide exemplary structures produced using the synthesis methods disclosed below.

Solvents and reagents were purchased from Sigma-Aldrich, VWR, or Fisher Scientific, and used without further purification. Substrates were purchased from Combi-blocks and used without further purification. Reactions were monitored either by thin-layer chromatography (TLC) or by analytical liquid chromatography-mass spectrometry (LC-MS) employing a Waters Acquity Ultra Performance LC system and a Synapt high-definition mass spectrometer. 1H NMR and $^{31}$P NMR spectra were recorded on a Varian Unity INOVA spectrometer (300 MHz). All chemical shifts are reported in ppm and coupling constants, J, are reported in hertz (Hz). NMR solvent peaks were referenced as follows: (1H NMR) CDCl3: 7.27 ppm, DMSO-d6: 2.50 ppm, D2O: 4.65 ppm. Compounds were purified by flash column chromatography on a Teledyne ISCO Combi-Flash system using normal phase silica gel (SiliCycle Inc.) or reverse phase (Teledyne Gold-C18 or C18Aq) pre-packed columns and AKTA avant chromatography system on HiTrap™ DEAE FF pre-packed columns. The purity of compounds was determined by analytical HPLC (Waters Acquity Ultra Performance) using an Acquity UPLC CSH C18 1.7 μm (50 mm×2.1 mm) column and flow rate of 0.3 mL/min. Gradient conditions: solvent A (0.05% formic acid in water) and solvent B (0.05% formic acid in acetonitrile): 0-0.1 min 95% A, 0.1-4.0 min 5-95% B (linear gradient), 4.0-5.0 min 95% B, UV detection at 254 nm and 220 nm and Waters Spherisorb, SAX column 80 Å, 5 μm 4.6 mm×250 mm.

Synthesis of TIPDSilyl-Protected Cytidine (2)

Scheme 1. Synthesis of Silyl-protected Cytidine 2

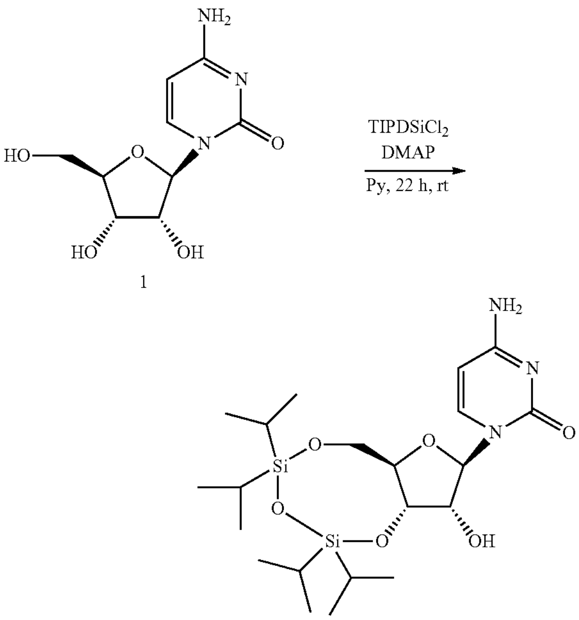

1

2

Cytidine 1 (3.0 g, 12.34 mmol) was dissolved in pyridine and co-evaporated (3×30 mL) to a white suspension. The co-evaporated substrate 1 was dissolved in pyridine (40 mL) and 1,3-Dichloro-1,1,3,3-tetraisopropyldisiloxane (TIPDSC12) (4.3428 mL, 13.575 mmol) and 4-Dimethylaminopyridine (DMAP) (0.7539 g, 6.171 mmol) were added. The reaction was stirred at room temperature for ~24 h and monitored by TLC. Once no starting material was detected, the mixture was diluted with CH2C12 (25 mL). The resulting solution was transferred to a separatory funnel and washed with water (1×25 mL). The aqueous layer was then extracted with additional CH2C12 (2×25 mL). The organic layers were combined and washed with brine and dried over MgSO4 provide crude silyl-protected 2 as a white solid and purified by silica gel flash chromatography (CH2C12/CH3OH, 5% modified with Et3N) to yield 2 (3.91 g, 65%). TLC (CH2C12: CH3OH=95/5, v/v): Rf=0.75. 1H NMR (300 MHz, DMSO-d6, δ): 7.69 (d, 3J=7.4 Hz, 1H), 7.15 (d, $^{3}$J=13.0 Hz, 2H), 5.63 (t, 3J=5.9 Hz, 2H), 5.52 (s, 1H), 4.16-3.85 (m, 5H), 1.04-0.94 (m, 28H). MS (ESI+, 100% CH3OH, TOF): m/z calc'd for [C21H40N3O6Si2]+ [M+H]+ 486.2450; found 486.2000.

Synthesis of Diacetylated Silyl-Protected Cytidine 3

Scheme 2. Synthesis of Diacetylated Silyl-protected Cytidine 3

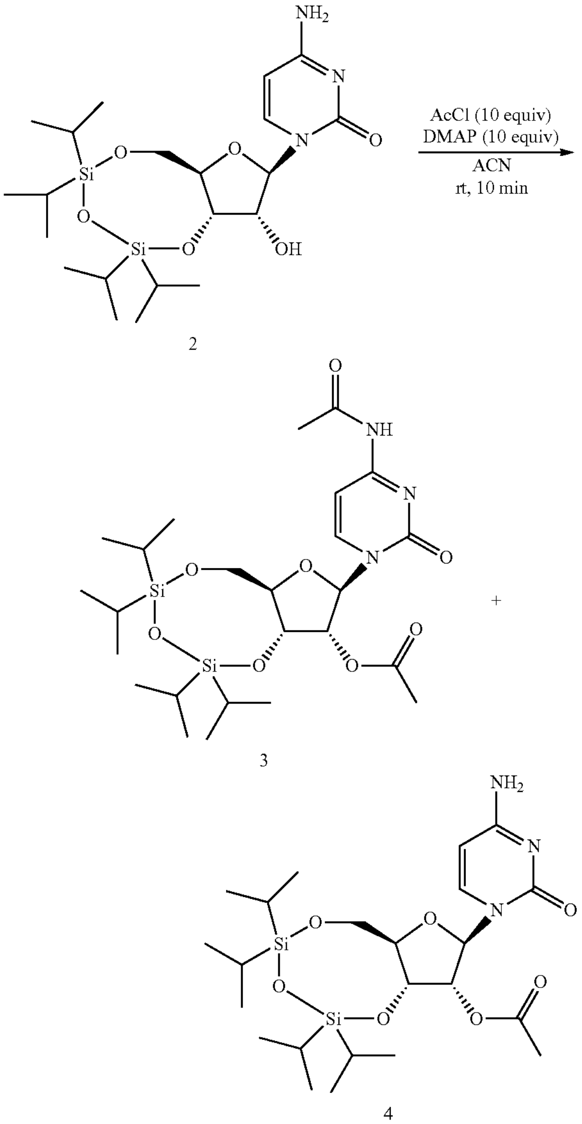

2

3

4

To an oven-dried RBF (25 mL), cytidine 2 (0.2 g, 0.412 mmol) was dissolved in anhyd. CH3CN (10 mL) to form a white emulsion. 4-Dimethylaminopyridine (DMAP) (0.2518 g, 2.061 mmol) was added followed by acetyl chloride (AcCl) (29.3 μl, 4.122 mmol). The solution dissolved and reaction was stirred under argon for 10 min at room temperature. Once the reaction was complete, reaction mixture was concentrated, and crude material was dissolved in dichloromethane CH2C12 (25 mL). The resulting solution was transferred to a separatory funnel and washed with water (1x25 mL). The aqueous layer was then extracted with additional CH2C12 (2x25 mL). The organic layers were combined and washed with brine and dried over magnesium sulfate MgSO4 provide crude silyl-protected 3 as a white solid. The residue was purified by flash column chromatography (ethyl acetate/methanol 9:1) to yield as a major fraction compound 3 yield 82% and a minor compound 4 yield 18%. TLC (Ethyl acetate: CH3OH=9/1, v/v): Rf=0.90; 1H NMR (300 MHz, DMSO-d6, δ): 10.94 (s, 1H), 8.01 (d, 3J=7.6 Hz, 1H), 7.18 (d, 3J=7.5 Hz, 1H), 5.68 (s, 1H), 5.44 (d, 3J=5.1 Hz, 1H), 4.41-4.37 (m, 1H), 4.16-4.10 (m, 1H), 3.94-3.89 (m, 2H), 2.06 (s, 6H), 0.93 (m, 27H). MS (ESI+, 100% CH3OH, TOF): m/z calc'd for [C25H44N3O8Si2]+ [M+H]+570.2661; found 570.2802.

Synthesis of Mono-2'O-Acetylated Silyl-Protected Cytidine 4

Scheme 3. Synthesis of Mono-2′ O-acetylated Silyl-protected Cytidine 4

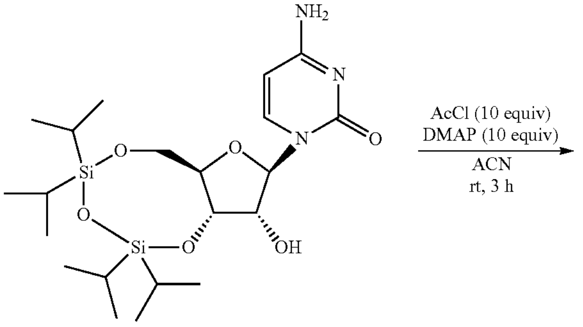

2

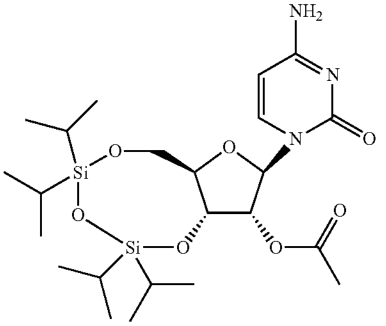

+

4

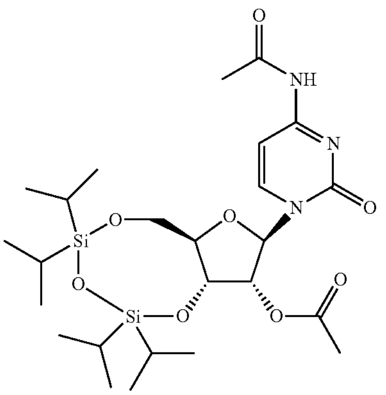

+

3

-continued

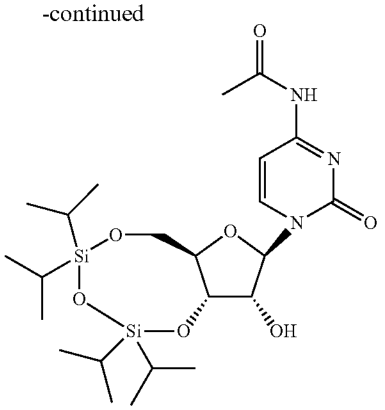

5

Alternatively, compound 4 is synthesized as follows. Cytidine 2 (0.2 g, 0.412 mmol) was dissolved in anhyd. $CH_3CN$ (10 mL) and forms a white emulsion. 4-Dimethylaminopyridine (DMAP) (0.2518 g, 2.061 mmol) was added followed by acetyl chloride (AcCl) (29.3 μl, 4.122 mmol). The solution dissolved and reaction was stirred under argon for 3 h at room temperature. Once no starting material is observed, reaction mixture was concentrated, and crude material was dissolved in dichloromethane $CH_2Cl_2$ (25 mL) The resulting solution was transferred to a separatory funnel and washed with water (1x25 mL). the aqueous layer was then extracted with additional $CH_2Cl_2$ (2x25 mL). The organic layers were combined and washed with brine and dried over $MgSO_4$ provide crude silyl protected as a white solid. The residue was purified by flash column chromatography (ethyl acetate/methanol 9:1) to yield as a major fraction compound 4 (yield 63%) and a minor compound 3 (yield 13%) and 5 (yield 18%). TLC (Ethyl acetate: $CH_3OH$=9/1, v/v): Rf=0.54; $^1H$ NMR (300 MHZ, DMSO-$d_6$, δ): 10.86 (s, 1H), 8.09 (d, $^3J$=7.3 Hz, 1H), 7.16 (d, $^3J$=7.3 Hz, 1H), 5.74-5.71 (m, 1H), 5.55-5.53 (m, 1H), 4.20-4.13 (m, 1H), 4.02-3.94 (m, 3H), 3.94-3.86 (m, 1H), 2.05 (s, 3H), 1.02-0.91 (m, 31H). MS ($ESI^+$, 100% $CH_3OH$, TOF): m/z calc'd for $[C_{23}H_{42}N_3O_7Si_2]^+$ $[M+H]^+$ 528.2556; found 528.2685.

Synthesis of N-Ac,2'-OAc Cytidine 6

Scheme 4. Synthesis of N, O-Diacetylated Cytidine 6 (forms mixture of 2′-OAc and 3′-OAc Regioisomers)

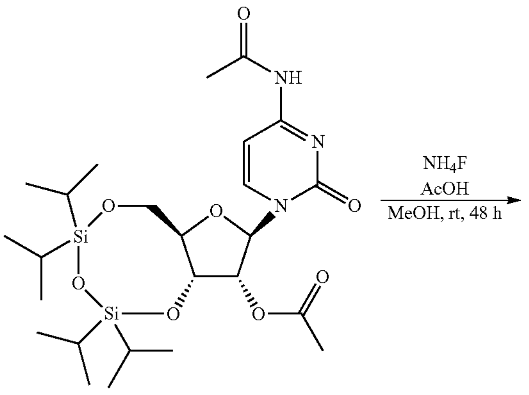

3

-continued

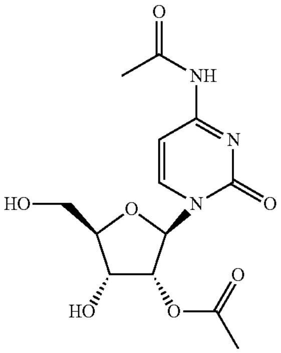

6
(mixture of 2'/3' isomers)

To an oven-dried RBF (25 mL), cytidine 3 (1.2 g, 2.11 mmol) was dissolved in anhyd. methanol (21 mL). Acetic acid (0.277 mL, 4.85 mmol) and ammonium fluoride $NH_4F$ (0.172 g, 4.64 mmol) were added to the solution. The reaction mixture was stirred for 48 h at room temperature. Once no starting material is observed, reaction mixture was concentrated, and crude material was dry loaded on silica. The compound was purified on flash column chromatography (ethyl acetate/methanol 9:1) to yield compound 6 as a white solid (0.352 g, 51%) 1H NMR (300 MHz, DMSO-$d_6$, δ): (mixture of 2'-OAc and 3'-OAc Regioisomers) 10.91 (s, 1.2H), 8.41-8.32 (m, 1.4H), 7.20-7.14 (m, 1.4H), 5.91 (d, $^3J$=3.8 Hz, 0.4H), 5.82 (d, $^3J$=4.8 Hz, 1H), 5.13 (t, $^3J$=4.5 Hz, 0.4H), 4.98 (t, $^3J$=5.0 Hz, 1H), 4.26 (t, $^3J$=4.9 Hz, 1H), 4.18 (t, $^3J$=5.6 Hz, 0.4H), 4.09 (dt, $^3J$=4.8, $^4J$=2.5 Hz, 1H), 3.89-3.87 (m, 0.5H), 3.69 (m, 1.4H), 3.59-3.51 (m, 1.4H), 2.06 (m, 8.4H). MS ($ESI^+$, 100% $CH_3OH$, TOF): m/z calc'd for $[C_{13}H_{18}N_3O_7]^+$ $[M+H]^+$ 328.1139; found 328.2317.

Synthesis of Monoacetyl Cytidine 7

Scheme 5. Synthesis of Monoacetyl Cytidine 7

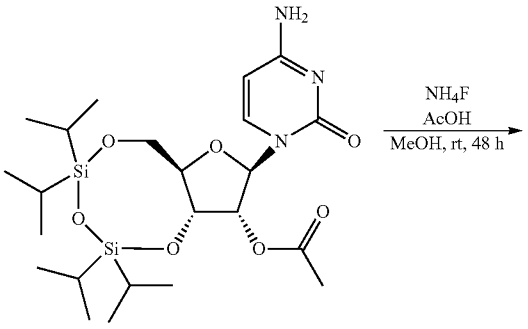

4

-continued

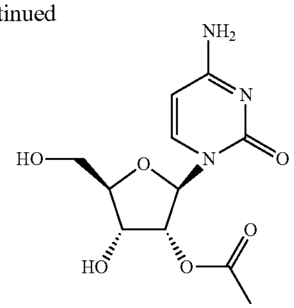

7
(mixture of 2'/3' isomers)

To an oven-dried RBF (25 mL), cytidine analog 4 (0.61 g, 1.16 mmol) was dissolved in anhyd. methanol (12 mL). Acetic acid (0.153 mL, 2.68 mmol) and ammonium fluoride $NH_4F$ (0.095 g, 2.56 mmol) were added to the solution. The reaction was stirred for 48 h at room temperature. Once no starting material was observed, reaction mixture was concentrated, and crude material was dry loaded on silica. The compound was purified on flash column chromatography (ethyl acetate/methanol 9:1) to yield as compound 7 as a white solid (0.216 g, 46%) 1H NMR (300 MHz, DMSO-$d_6$, δ): (Mixture of 2'-OAc and 3'-OAc regioisomers) 7.81 (t, $^3J$=8.0 Hz, 1.8H (signal overlap)), 7.26-7.11 (m, 4H), 5.95 (d, $^3J$=5.1 Hz, 0.3H), 5.81 (d, $^3J$=5.9 Hz, 1H), 5.72 (m, 2.3H), 5.61 (d, $^3J$=5.7 Hz, 1H), 5.05-4.98 (m, 2H), 4.21 (m, 1.3H), 4.04-3.97 (m, 2H), 3.91 (d, $^3J$=3.1 Hz, 1H), 3.84-3.79 (m, 1H), 3.65-3.50 (m, 4H), 2.06 (s, 3H), 2.03 (s, 1H). MS ($ESI^+$, 100% $CH_3OH$, TOF): m/z calc'd for $[C_{11}H_{16}N_3O_6]^+$ $[M+H]^+$ 286.1034; found 286.1571.

Thiophosphorylation Reaction of the Cytidine Derivative

Scheme 6. Triphosphorylation and salt exchange to form Diacetylated cytidine triphosphate sodium salt 9.

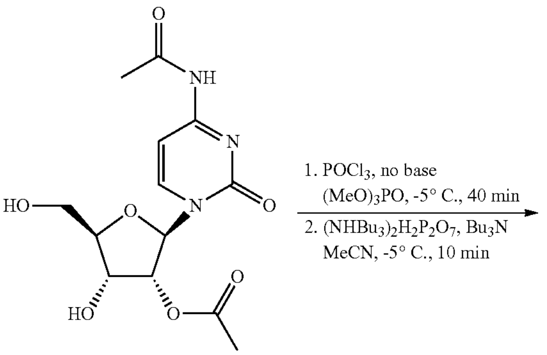

6

-continued

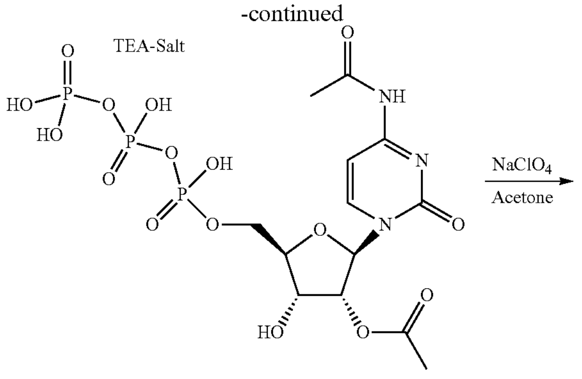

8

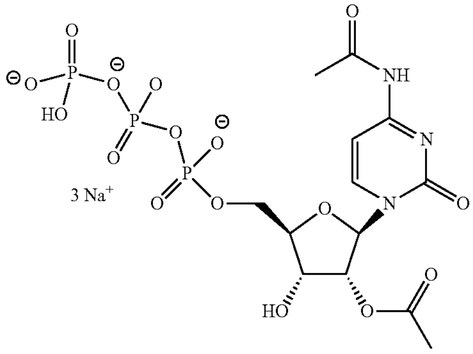

9

Method adapted from literature (See Kore, A. R.; et. al. Curr. Protoc. Nucleic Acid Chem. 2012, Unit 13.10). In an oven-dried vial, tributylammonium pyrophosphate (0.143 g, 0.26 mmol) was dissolved in anhyd. acetonitrile (1.1 mL). tributylamine (0.44 mL, 1.83 mmol) was added and the mixture was kept at −20° C. To a separate oven-dried, argon-filled round-bottom flask equipped with a stir bar, cytidine derivative 6 (0.10 g, 0.31 mmol) was added and dissolved in trimethyl phosphate (1.4 mL). The reaction mixture was evacuated, refilled three times with Argon and stirred for 10 min at room temperature. The RBF/vial was cooled in an ice bath (5° C. to 0° C.) and stirred for 30 min. The first portion of phosphorous oxychloride (20 μl, 0.21 mmol) was added and stirred for 10 min. The second portion of phosphorus oxychloride (20 μl, 0.21 mmol) was added and reaction stirred for 35 min. The pyrophosphate solution was then added dropwise to the mixture, the flask cooled with ice/NaCl bath (−5° C. to −10° C.) and stirred for 15 min. The septum was removed, and water (7.3 mL) was added dropwise to the mixture. The solution was transferred to a separatory funnel and the aqueous layer was extracted with $CH_2Cl_2$ (3×2 mL) and the organic layer was discarded. The pH of the aqueous layer was adjusted to 6.5 using ammonium hydroxide and stored at 4° C. overnight. The pH of the solution was rechecked and readjusted if needed. Compound is purified on the AKTA purification system. The column was connected to the AKTA purifier equipped with a programmable gradient pump system and a UV detector and washed with water, 2.0 M NaCl followed by water. The product solution was loaded onto the column at a flow rate of 75 ml/min with UV detection at 254 nm. The column was eluted with linear gradient of 0 to 1M triethylammonium bicarbonate (TEAB) buffer. The appropriate fractions were analyzed by analytical HPLC using mobile phase A and mobile phase B. 10 μl of the fraction was injected through the 5 μM Hypersil SAX column (4.6 mm×25 cm) at a flow rate of 1.0 mL/min using gradient conditions:

0% to 50% mobile phase B over 5 min
50% to 75% mobile phase B over 5 min
75% to 100% mobile phase B over 2 min
100% mobile phase B for 2 min
100% to 0% mobile phase B over 2 min.

The appropriate fractions containing the phosphate were combined and concentrated it down (35° C. to 38° C. water bath and vacuum 1 to 10 mm). The resulting residue was coevaporated with water (3×2 ml). and dried under vacuum overnight. The resulting triethylamine salt of cytidine triphosphate was dissolved in water (2.6 mL)

Sodium perchlorate (0.422 g, 3.46 mmol) was dissolved in acetone (7.6 mL) in centrifuge vial and the CTP solution was added dropwise into to the sodium perchlorate/acetone solution over a period of 5 min. The resulting mixture was centrifuged for 10 min at 704×g, 4° C. and the supernatant liquid discarded. The resultant pellet was dried under vacuum for 1 h and dissolved in water (2.6 mL) the dissolution into sodium perchlorate/acetone solution and centrifuge process repeated. The resulting solid was dried at ambient temperature under high vacuum overnight and weighed to yield the sodium salt of CTP 9 as a white solid (0.027 g, 14%) $^1$H NMR (300 MHZ, $D_2O$, δ): (mixture of regioisomers) 8.23 (d, $^3$J=7.4 Hz, 1H), 7.77 (d, $^3$J=7.6 Hz, 1H), 7.20 (d, $^3$J=7.7 Hz, 1H), 5.97-5.94 (m, 1H), 5.83-5.80 (m, 2H), 4.23-4.10 (m, 11H), 2.07-2.03 (m, 6H). $^{31}$P NMR (121 MHZ, $D_2O$, δ): −5.49 (d, $^3$J=16.1 Hz, 1P), −10.68 (dd, $^3$J=15.7, $^4$J=7.4 Hz, 1P), −19.13-−19.62 (m, 1P).

Thiophosphorylation of 2'-O-acetyl-Cytidine

Scheme 7. Triphosphorylation and Salt exchange to form 2′-O-Acetyl Cytidine triphosphate sodium salt 11(Mixture of 2′-OAc and 3′-OAc Regioisomers)

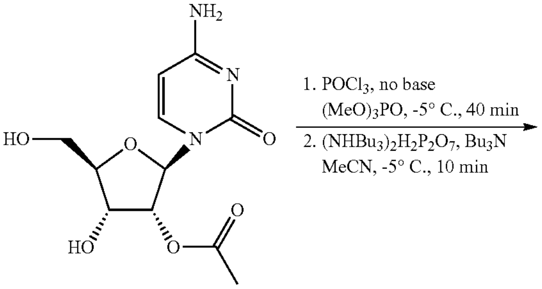

7

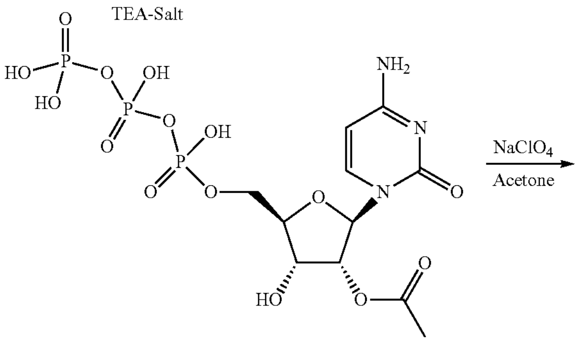

10

-continued

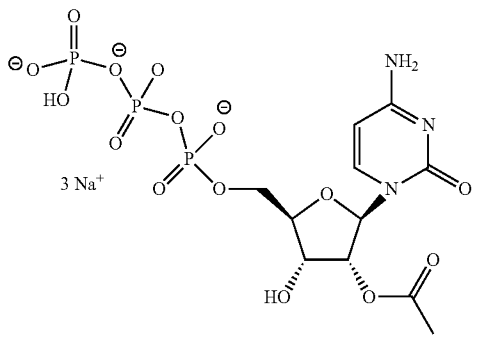

11

-continued

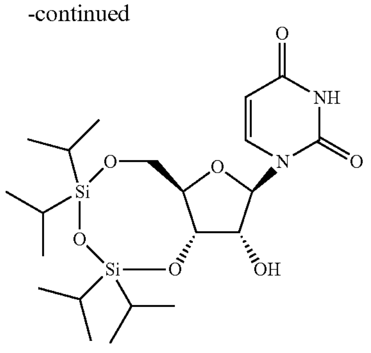

13

General procedure for triphosphorylation followed as described above on the described scale. In an oven-dried vial, dissolve tributylammonium pyrophosphate (0.164 g, 0.30 mmol) in anhyd. acetonitrile (1.3 mL) and tributylamine (0.50 mL, 2.10 mmol) and mixture stored in −20° C. To an oven-dried, argon-filled round-bottom flask or vial equipped with a stir bar, cytidine derivative (0.10 g, 0.35 mmol) is added and dissolved in trimethyl phosphate (1.60 mL). The reaction mixture is evacuated and refilled three times with Argon. The reaction mixture is stirred for 10 min at room temperature. Cool the RBF/vial in an ice bath (5° C. to 0° C.) and stir for 30 min. Add the first portion of phosphorous oxychloride (22.9 μl, 0.25 mmol) and stir for 10 min. Add the second portion of phosphorus oxychloride (22.9 μl, 0.25 mmol) to the vial and stir 35 min. Add the pyrophosphate solution to the mixture. Cool the flask with ice/NaCl bath (−5° C. to −10° C.) and stir for 15 min. The septum is removed, and water (7.3 mL) was added dropwise to the mixture. The solution was transferred to a separatory funnel and the aqueous layer was extracted with $CH_2Cl_2$ (3×2 mL) and the organic layer is discarded. Adjust the pH of the aqueous layer to 6.5 using ammonium hydroxide. Purification and Salt exchange performed as described in the procedure above to yield 11 as a white solid (0.025 g, 14%). $^1$H NMR (300 MHZ, $D_2O$, δ): 7.82 (d, $^3$J=7.56 Hz, 1H), 5.97 (d, $^3$J=7.7 Hz, 1H), 5.84 (d, $^3$J=4.4 Hz, 1H), 4.28-4.24 (m, 1H), 4.16 (t, $^3$J=4.75 Hz, 1H), 4.11-4.05 (m, 4H), 2.06-2.02 (m, 3H). $^{31}$P NMR (121 MHz; $D_2O$, δ): −7.55--7.86 (m, 1P), −11.30 (d, $^3$J=19.1 Hz, 1P), −22.36 (m, 1P).

TIPDSi-Protection of Uridine

Scheme 8. Synthesis of Silyl-protected uridine 13

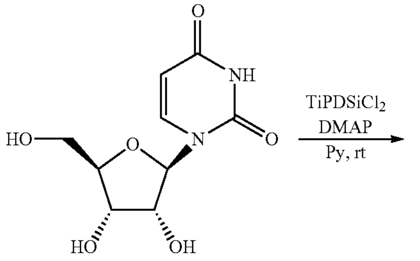

12

Uridine 12 (3.0 g, 12.30 mmol) was dissolved in pyridine and co-evaporated (3×30 mL) to a white suspension. The co-evaporated substrate 12 was dissolved in pyridine (40 mL) and $TIPDSCl_2$ (4.260 mL, 13.52 mmol) and DMAP (0.7508 g, 6.14 mmol) were added. The reaction was stirred at room temperature for ~24 h and monitored by TLC. Once no starting material was detected, mixture was diluted with $CH_2Cl_2$ (25 mL). The resulting solution was transferred to a separatory funnel and washed with water (1×25 mL). The aqueous layer was then extracted with additional $CH_2Cl_2$ (2×25 mL). The organic layers were combined and washed with brine and dried over $MgSO_4$ provide crude silyl-protected 13 as a white solid which was purified by silica gel flash chromatography ($CH_2Cl_2/CH_3OH$, modified with 5% $Et_3N$) Yield (3.67 g, 61%). Compound 13 was stored at −20° C. until it was used. TLC ($CH_2Cl_2$: $CH_3OH$=95/5, v/v): Rf=0.75; 1H NMR (300 MHz, DMSO-$d_6$, δ): 11.36 (s, 1H), 8.54 (dd, $^3$J=5.8, $^4$J=1.7 Hz, 1H), 7.66 (d, $^3$J=8.1 Hz, 1H), 5.60 (d, $^3$J=4.4 Hz, 1H), 4.12-4.07 (m, 4H), 3.96-3.85 (m, 3H), 1.01 (d, $^3$J=3.9 Hz, 36H). MS (ESI$^+$, 100% $CH_3OH$, TOF): m/z calc'd for $[C_{21}H_{39}N_2O_7Si_2]^+$ [M+H]$^+$ 487.2290; found 487.3135.

Acetylation of Silyl-Protected Uridine

Scheme 9. Synthesis of 2′-O-Acetyl Silyl Protected Uridine 14

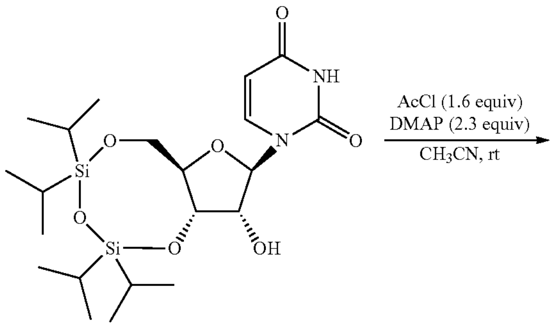

13

-continued

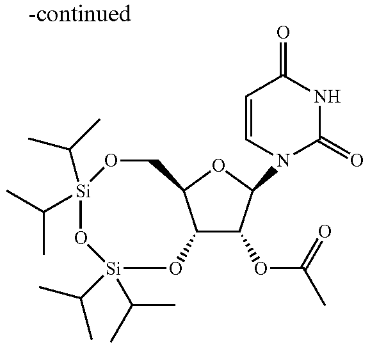

14

To an oven-dried RBF (25 mL), uridine 13 (2.0 g, 4.11 mmol) was dissolved in anhyd. $CH_3CN$ (40 mL) and forms a white emulsion. DMAP (1.16 g, 9.46 mmol) was added followed by acetyl chloride AcCl (0.67 mL, 9.46 mmol). The solution dissolved and reaction was stirred under argon for 35 min at room temperature. Once the reaction was complete (no starting material detected), reaction mixture was concentrated, and crude material was dissolved in dichloromethane $CH_2Cl_2$ (25 mL). The resulting solution was transferred to a separatory funnel and washed with water (1×25 mL). The aqueous layer was then extracted with additional $CH_2Cl_2$ (2×25 mL). The organic layers were combined and washed with brine and dried over magnesium sulfate $MgSO_4$ provide crude silyl-protected 14 as a white solid. The residue was purified by flash column chromatography (ethyl acetate/methanol 9:1) to yield as a major compound 14 yield (1.88 g, 87%) TLC (ethyl acetate: $CH_2Cl_2$=1/1, v/v): Rf=0.75; 1H NMR (300 MHz, DMSO-$d_6$, δ): 11.40 (s, 1H), 7.64 (d, $^3J$=8.1 Hz, 1H), 5.63 (d, $^3J$=1.4 Hz, 1H), 5.56 (dd, $^3J$=8.0, $^4J$=2.0 Hz, 1H), 5.49 (dd, $^3J$=5.7, $^4J$=1.3 Hz, 1H), 4.53 (dd, $^3J$=8.4, $^4J$=5.8 Hz, 1H), 4.04 (m, 1H), 3.91 (m, 1H), 3.81 (dt, $^3J$=7.8, $^4J$=3.7 Hz, 1H), 2.05 (s, 3H), 1.02-0.93 (m, 28H). MS ($ESI^+$, 100% $CH_3OH$, TOF): m/z calc'd for $[C_{23}H_{40}N_2NaO_8Si_2]^+$ $[M+Na]^+$ 551.2215; found 551.2078.

Silyl-Deprotection of Acetylated Uridine

-continued

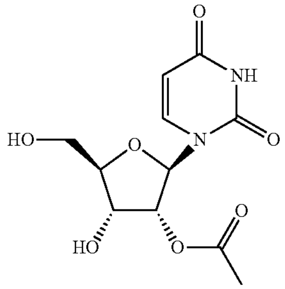

15

To an oven-dried RBF (25 mL), compound 14 (1.2 g, 2.27 mmol) was dissolved in anhyd. methanol (22 mL). Acetic acid (0.299 mL, 5.22 mmol) followed by $NH_4F$ (0.185 g, 5.00 mmol) were added to the solution. The reaction mixture was stirred for 48 h at room temperature. Once no starting material was observed, reaction mixture was concentrated, and crude material was dry loaded on silica. The compound was purified on flash column chromatography (ethyl acetate/methanol 9:1) to yield as compound 15 as a white solid (0.222 g, 34%) (mixture of 2'-OAc and 3'-OAc regioisomers). $^1H$ NMR (300 MHz, DMSO-$d_6$, δ): 11.37 (s, 1.4H), 7.87 (d, $^3J$=12.2, d, $^3J$=8.1 Hz, (two overlapping doublets) 1.6H), 5.96 (d, $^3J$=5.9 Hz, 0.6H), 5.79 (d, $^3J$=6.8 Hz, 1H), 5.74-5.64 (m, 2.6H), 5.51 (d, $^3J$=5.4 Hz, 0.6H), 5.27 (t, $^3J$=5.0 Hz, 1H), 5.20 (t, $^3J$=4.8 Hz, 0.6H), 5.11-5.06 (m, 1.6H), 4.22 (dq, $^3J$=11.5, $^4J$=5.7 Hz, 1.6H), 4.04-3.97 (m, 1.6H), 3.87 (m, 0.6H), 3.66-3.51 (m, 3H), 2.07 (s, 3H), 2.03 (s, 1.7H). MS ($ESI^+$, 100% $CH_3OH$, TOF): m/z calc'd for $[C_{11}H_{14}N_2NaO_7]^+$ $[M+Na]^+$ 309.0693; found 309.2410.

Thiophosphorylation Reaction of the Uridine Derivative

Scheme 10. Synthesis of 2' O-acetyl uridine 15

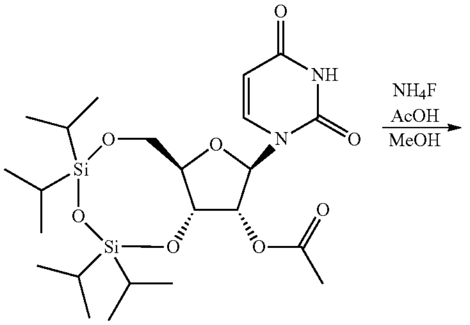

14

Scheme 11. Triphosphorylation and Salt exchange, synthesis of 2'-O-Acetyl Uridine Triphosphate sodium salt 17

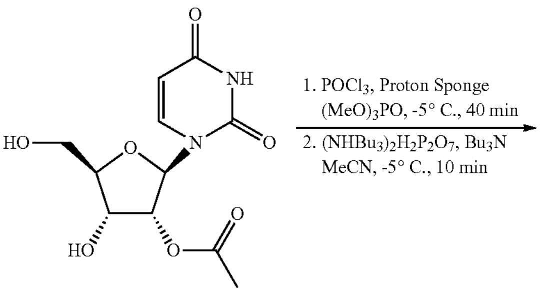

15

-continued

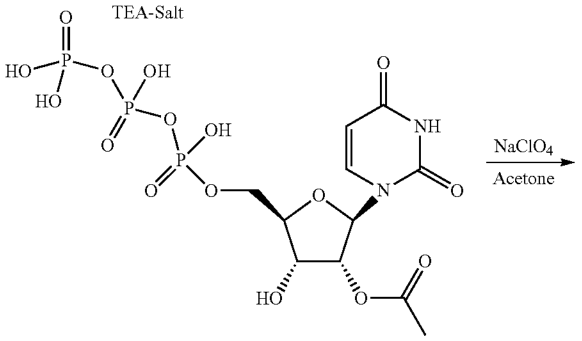

16

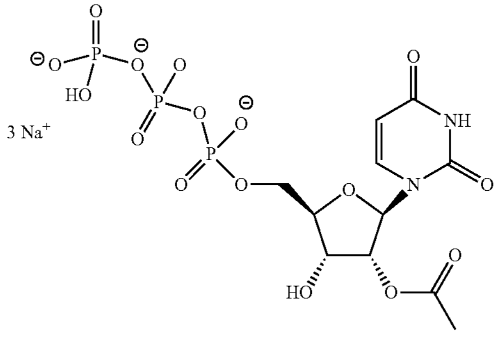

17

Method adapted from literature. In an oven-dried vial, tributylammonium pyrophosphate (0.114 g, 0.21 mmol) was dissolved in anhyd. $CH_3CN$ (0.90 mL). Tributylamine (0.35 mL, 1.47 mmol) was added and mixture stored in −20° C. To a separate oven-dried, argon-filled round-bottom flask or vial equipped with a stir bar, uridine derivative 15 (0.07 g, 0.25 mmol) and proton sponge (0.052 g, 0.25 mmol) is added and dissolved in trimethyl phosphate (0.84 mL). The reaction mixture is evacuated and refilled three times with Argon. The reaction mixture was stirred for 10 min at room temperature, then cooled the RBF/vial in an ice/NaCl bath (−5° C. to −10° C.) and stir for 30 min. The first portion of phosphorous oxychloride (13.5 μl, 0.14 mmol) was added and stir for 5 min. The second portion of phosphorus oxychloride (9.3 μl, 0.10 mmol) was added and stir 10 min. The cold pyrophosphate solution was added and stir for 10 min. The septum was removed, and water (7.3 mL) was added dropwise to the mixture. The solution was transferred to a separatory funnel and the aqueous layer was extracted with $CH_2Cl_2$ (3×2 mL) and the organic layer is discarded. Adjust the pH of the aqueous layer to 6.5 using ammonium hydroxide. Purification and Salt exchange performed as described in the general procedure above to yield 17 as a white solid (4.2 mg, 3%). 1H NMR (300 MHZ, $D_2O$, δ): 7.81 (d, $^3J$=8.4 Hz, 2H), 5.83-5.78 (m, 3H), 4.30-4.21 (m, 3H), 4.08 (m, 4H), 3.50 (d, $^3J$=11.4 Hz, 1H), 2.05 (s, 3H). $^{31}P$ NMR (121 MHZ, $D_2O$, δ): −6.18 (m, 1P), −11.17 (m, 1P), −21.68 (s, 1P).

TIPDSi-Protection of Adenosine

Scheme 12. Synthesis of Silyl-protected Adenosine 19

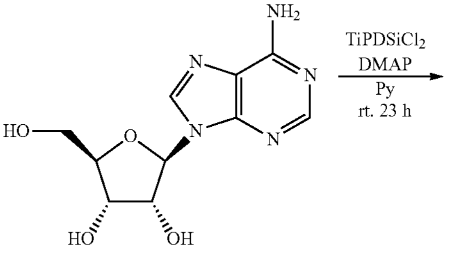

28

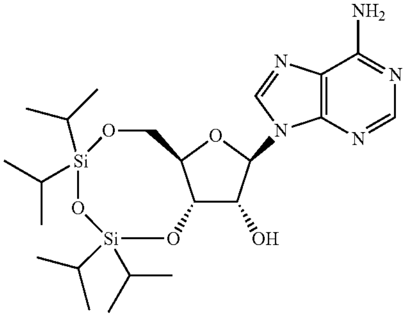

19

To a 100 mL round bottom flask, adenosine 18 (0.3 g, 1.12 mmol) was dissolved in pyridine and coevaporated (3×5 mL) to a white suspension. The co-evaporated substrate 18 was dissolved in pyridine (4 mL) and $TIPDSCl_2$ (0.40 mL, 1.25 mmol) and DMAP (0.0686 g, 0.561 mmol) were added. The reaction was stirred at room temperature for ~23 h and monitored by TLC. Once no starting material was detected, mixture was diluted with $CH_2Cl_2$ (25 mL). The resulting solution was transferred to a separatory funnel and washed with water (1×25 mL). The aqueous layer was then extracted with additional $CH_2Cl_2$ (2×15 mL). The organic layers were combined and washed with brine and dried over $MgSO_4$ provide crude silyl-protected 19 as a white solid which was purified by silica gel flash chromatography ($CH_2Cl_2$/$CH_3OH$, 5%; 0.05% $Et_3N$) Yield (0.885 g, 76%). Compound 19 was stored at −20° C. until it was used. 1H NMR (300 MHz, DMSO-$d_6$, δ): 8.19 (s, 1H), 8.05 (s, 1H), 5.85 (s, 1H), 5.63 (d, $^3J$=4.6 Hz, 1H), 4.79-4.75 (m, 1H), 4.49 (t, $^3J$=4.7 Hz, 1H), 4.06-3.88 (m, 3H), 1.02 (s, 28H). MS ($ESI^+$, 100% $CH_3OH$, TOF): m/z calc'd for $[C_{22}H_{40}N_5O_5Si_2]^+$ $[M+H]^+$ 510.2563; found 510.3010.

Acetylation of Silyl-Protected Adenosine

Scheme 13. Synthesis of 2'-OAc-Adenosine 20

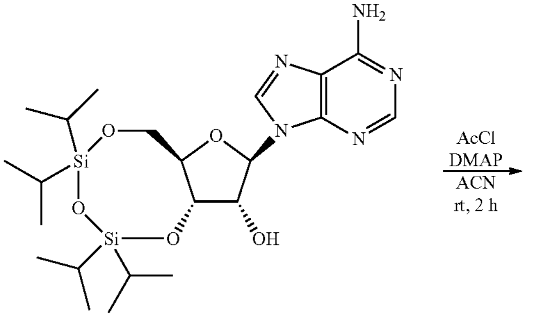

19

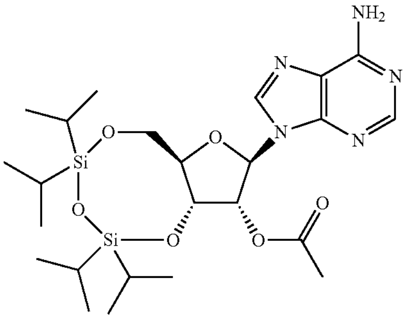

20

To an oven-dried RBF (25 mL), adenosine 19 (5.83 g, 11.44 mmol) was dissolved in anhyd. $CH_3CN$ (100 mL) and forms a white emulsion. 4-Dimethylaminopyridine DMAP (3.214 g, 26.31 mmol) was added followed by acetyl chloride AcCl (1.3 mL, 18.30 mmol). The solution dissolved and reaction was stirred under argon for 1.5 h at room temperature. Once the reaction was complete, reaction mixture was concentrated, and crude material was dissolved in dichloromethane $CH_2Cl_2$ (25 mL). The resulting solution was transferred to a separatory funnel and washed with water (1×25 mL). The aqueous layer was then extracted with additional $CH_2Cl_2$ (2×25 mL). The organic layers were combined and washed with brine (1×25 mL) and dried over magnesium sulfate $MgSO_4$ provide crude silyl-protected 20 as a white solid. The residue was purified by flash column chromatography ($CH_2Cl_2/CH_3OH$, modified with 5% $Et_3N$) to yield as a major fraction compound 20 yield (5.567 g, 88%) TLC ($CH_2Cl_2/CH_3OH$, modified with 5% $Et_3N$, v/v): 1H NMR (300 MHz, DMSO-$d_6$, δ): 8.23 (s, 1H), 8.02 (s, 1H), 7.39 (s, 2H), 6.07 (s, 1H), 5.86 (dd, $^3J$=5.8, $^4J$=1.0 Hz, 1H), 5.24 (dd, $^3J$=8.4, $^4J$=5.8 Hz, 1H), 4.01-3.87 (m, 3H), 2.08 (s, 3H), 1.04-0.93 (m, 36H). MS ($ESI^+$, 100% $CH_3OH$, TOF): m/z calc'd for $[C_{24}H_{42}N_5O_6Si_2]^+$ $[M+H]^+$ 552.2668; found 552.2981.

Silyl-Deprotection of Acetylated Adenosine

Scheme 14. Synthesis of 2'-OAc Adenosine 21

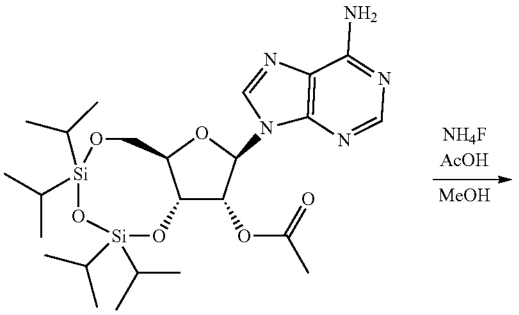

20

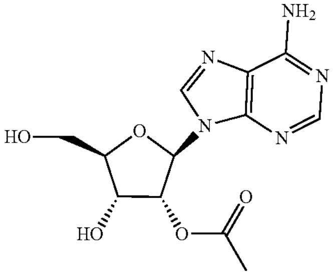

21

+

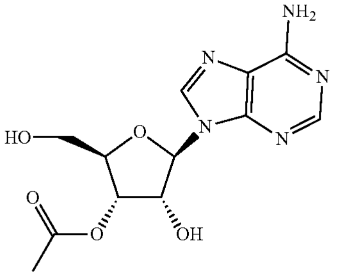

22

To an oven-dried RBF (50 mL), adenosine derivative 20 (0.50 g, 0.906 mmol) was dissolved in anhyd. methanol (10 mL). Acetic acid (1.2 mL, 2.08 mmol) followed by ammonium fluoride $NH_4F$ (0.074 g, 1.99 mmol) were added to the solution. The reaction was stirred for 6 h at 70° C. Once no starting material is observed, reaction mixture was concentrated, and crude material was concentrated and redissolved in water (1×15 mL) and filtered through a celite plug and plug rinsed with water (3×15 mL). The compound was purified on an aqueous reverse flash chromatography ($H_2O$/$CH_3CN$ 7:3) to yield 21 (minor) as a white solid (0.0258 g, 9% mixture of 2'-OAc and 3'-OAc isomers) and 22 (major) as a white solid (0.064 g, 23%, mixture of 2'-OAc and 3'-OAc isomers).

(Minor Peak on the reverse-phase chromatogram): 1H NMR (300 MHz, DMSO-$d_6$, δ): (mixture of 2'-OAc and 3'-OAc regioisomers); 8.36 (s, 1H), 8.12 (s, 1H), 7.39 (s, 2H), 6.13 (d, $^3J$=6.4 Hz, 1H), 5.61 (m, 2H), 5.48 (dd, $^3J$=7.0, $^4J$=4.5 Hz, 1H), 4.95 (m, 0.04H, corresponding to 3'-OAc regioisomer) 4.44-4.41 (m, 1H), 3.98 (m, 1H), 3.70-3.65 (m, 1H), 3.58-3.52 (m, 1H), 2.10 (s, 0.1H), 2.00 (s, 3H). MS ($ESI^+$, 100% $CH_3OH$, TOF): m/z calc'd for $[C_{12}H_{16}N_5O_5]^+$ $[M+H]^+$ 310.1146; found 310.1014.

(Major Peak on the reverse-phase chromatogram): 1H NMR (300 MHz, DMSO-$d_6$, δ): (mixture of 2'-OAc and 3'-OAc isomers): 8.36 (s, 1H), 8.12 (s, 1H), 7.41 (s, 2H), 6.145 (d, $^3J$=6.47, 0.04H corresponding to the 2'-OAc isomer), 5.87 (d, $^3J$=7.2 Hz, 1H), 5.80 (d, $^3J$=5.7 Hz, 1H), 5.67 (dd, $^3J$=7.5, $^4J$=4.5 Hz, 1H), 5.26 (dd, $^3J$=5.2, $^4J$=1.9 Hz, 1H), 4.86 (q, $^3J$=5.9 Hz, 1H), 4.12 (d, $^3J$=2.1 Hz, 1H), 3.67 (dt, $^3J$=12.2, $^4J$=4.0 Hz, 1H), 3.57 (ddd, $^3J$=11.8, $^4J$=7.9, $^4J$=3.6 Hz, 1H), 2.10 (s, 3H). MS ($ESI^+$, 100% $CH_3OH$, TOF): m/z calc'd for $[C_{12}H_{16}N_5O_5]^+$ $[M+H]^+$ 310.1146; found 310.1075.

Thiophosphorylation Reaction of the Adenosine Derivative

Scheme 15. Synthesis of 2'-O-Acetyl Adenosine triphosphate sodium salt 24 via a triphosphorylation and Salt exchange protocol

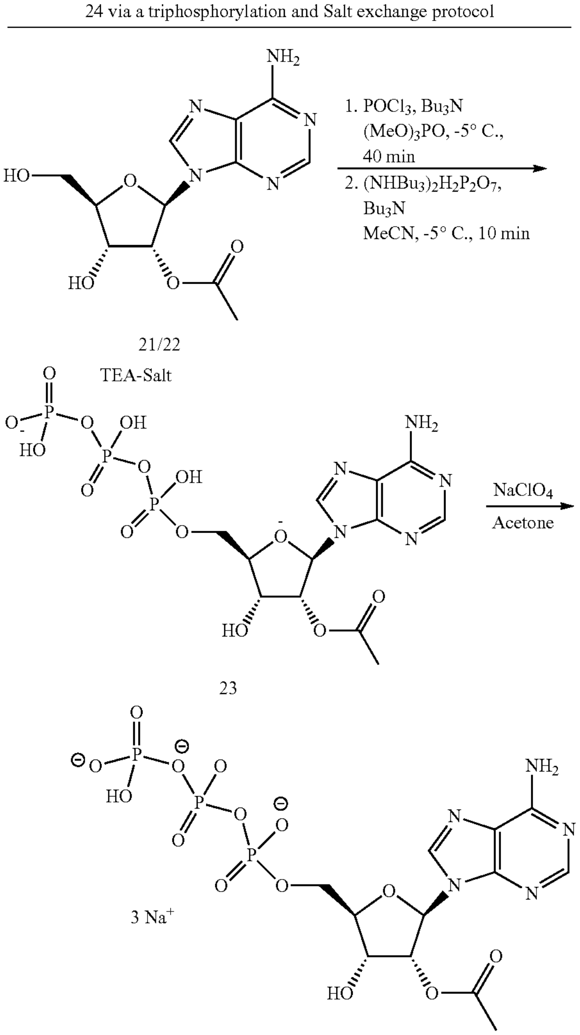

21/22

23

24

Method adapted from literature. In an oven-dried, argon-filled vial, dissolve tributylammonium pyrophosphate (0.109 g, 0.199 mmol) in anhyd. acetonitrile (0.85 mL) and tributylamine (0.33 mL, 1.391 mmol) and mixture stored in −20° C. To an oven-dried, argon-filled round-bottom flask or vial equipped with a stir bar, adenosine derivative mixture 21/22 (2'-OAc/3'-OAc isomers) (0.0725 g, 0.234 mmol) and tributyl amine (0.11 ml, 0.467 mmol) is added and dissolved in trimethyl phosphate (1 mL). The reaction mixture is evacuated and refilled three times with Argon. The reaction mixture is stirred for 10 min at room temperature. Cool the RBF/vial in an ice/NaCl bath (−5° C. to −10° C.) and stir for 30 min. Add the first portion of phosphorous oxychloride (26 μl, 0.278 mmol) and stir for 3 min. Add the second portion of phosphorus oxychloride (13 μl, 0.139 mmol) to the vial and stir 5 min. Add pyrophosphate solution and stir for 10 min. The reaction was monitored on the HPLC-SAX column. The septum is removed, and water (5 mL) was added dropwise to the mixture. The solution was transferred to a separatory funnel and the aqueous layer was extracted with $CH_2Cl_2$ (3×2 mL) and the organic layer is discarded. Adjust the pH of the aqueous layer to 6.5 using ammonium. Purification was done on the AKTA column and the appropriate fractions containing the phosphate combined and concentrated down in a water bath (35° to 38° C. and vacuum 1 to 10 mm). The resulting residue was co-evaporated with water (3×2 ml). and dry it under vacuum overnight. Dissolve the resulting triethylamine salt of cytidine triphosphate in water (2.6 mL).

Sodium perchlorate (0.062 g, 0.508 mmol) was dissolved in acetone (2.5 mL) in a 15 mL centrifuge vial and the ATP solution was added dropwise into to the sodium perchlorate/acetone solution over a period of 5 min. The resulting mixture was centrifuged for 10 min at 704×g, 4° C. and the supernatant liquid discarded. The resultant pellet was dried under vacuum for 1 h and dissolved in water (2.6 mL) the dissolution into sodium perchlorate/acetone solution and centrifuge process repeated. The resulting solid was dried at ambient temperature under high vacuum overnight and weighed to yield the sodium salt of ATP 24 as a white solid (30.8 mg, 21%). 1H NMR (300 MHZ, $D_2O$, δ): 8.34 (d, $^3J$=10.3 Hz, 2H), 8.27 (s, 1H), 8.03 (d, $^3J$=2.3 Hz, 2H), 8.00 (s, 1H), 6.07 (dd, $^3J$=4.1, $^4J$=1.8 Hz, 1H), 5.96 (d, $^3J$=7.6 Hz, 1H), 5.92-5.90 (m, 1H), 5.37-5.33 (m, 1H), 5.30 (dd, $^3J$=5.4, $^4J$=1.7 Hz, 2H), 4.84-4.79 (m, 2H), 4.58 (dd, $^3J$=3.5, $^4J$=1.6 Hz, 2H), 4.38-4.33 (m, 2H), 4.18-4.16 (m, 2H), 4.12-4.08 (m, 3H), 4.08-4.03 (m, 2H), 4.01-3.95 (m, 2H), 2.00 (d, $^3J$=5.3 Hz, 15H), 1.94 (s, 3H). $^{31}P$ NMR (121 MHz, $D_2O$, δ): -8.68--9.23 (m, 1P), −11.41 (d, $^3J$=19.5 Hz, 1P), −22.73 (t, $^3J$=19.6 Hz, 1P). MS (ESI, 100% $CH_3OH$, TOF): m/z calc'd for $[C_{12}H_{17}N_5O_{14}P_3]^-$ $[M-H]^-$ 547.9990; found 547.7838.

TIPDSi-Protection of Guanosine

Scheme 16. Synthesis of Silyl-protected Guanosine 26

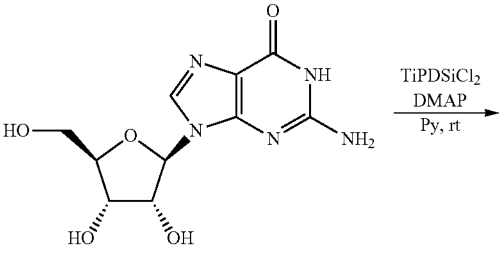

25

-continued

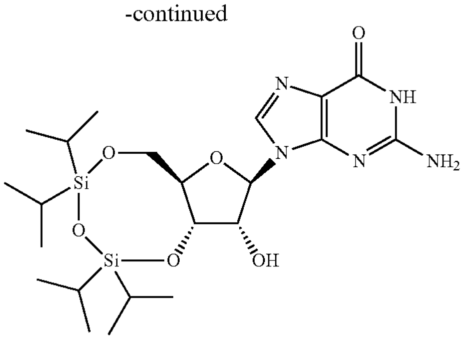

26

To a 100 mL round bottom flask, guanosine 25 (1.5 g, 5.30 mmol) was dissolved in pyridine and coevaporated (3x15 mL) to a white suspension. The co-evaporated substrate 25 was dissolved in pyridine (19 mL) and TIPDSCl$_2$ (1.86 mL, 5.83 mmol) and DMAP (0.323 g, 2.65 mmol) were added. The reaction was stirred at room temperature for ~23 h and monitored by TLC. Once no starting material was detected, mixture was diluted with $CH_2Cl_2$ (25 mL). Water was added and precipitation occurs. The mixture was filtered on a short plug of celite to provide crude silyl-protected 26 as a white solid Yield (1.3916 g, 50%). Compound 26 was stored at −20° C. until it was used. $^1$H NMR (300 MHz, DMSO-d$_6$, δ) 10.64 (s, 1H), 7.75 (s, 1H), 6.49 (s, 2H), 5.65 (s, 1H), 5.59 (s, 1H), 4.33 (dd, $^3$J=8.0, $^3$J=5.1 Hz, 1H), 4.24-4.23 (m, 1H), 4.06 (dd, $^3$J=12.6, $^3$J=2.9 Hz, 1H), 3.97 (dt, $^3$J=7.9, $^4$J=2.8 Hz, 1H), 3.90 (m, 1H), 1.02-0.98 (m, 28H). MS (ESI$^+$, 100% $CH_3OH$, TOF): m/z calc'd for $[C_{22}H_{40}N_5O_6Si_2]^+$ [M+H]$^+$ 526.2512; found 526.3105.

Acetylation of Silyl-Protected Guanosine

Scheme 17. Synthesis of 2′-O-Acetyl-silyl-protected guanosine 27

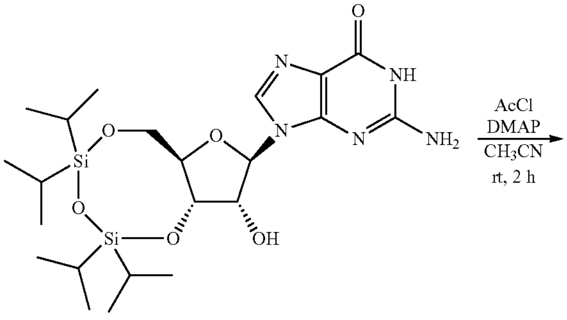

26

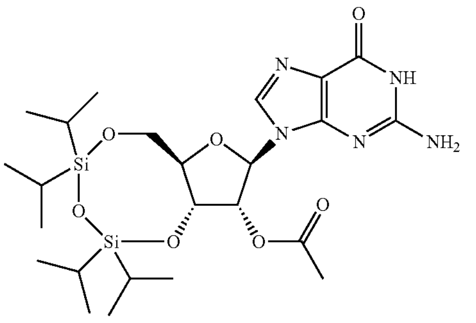

27

To an oven-dried RBF (25 mL), guanosine 26 (1.084 g, 2.062 mmol) was dissolved in anhyd. $CH_3CN$ (20 mL) and forms a white emulsion. 4-Dimethylaminopyridine DMAP (0.58 g, 4.742 mmol) was added followed by acetyl chloride (AcCl) (0.23 mL, 3.299 mmol). The solution dissolved and reaction was stirred under argon for 30 min at room temperature. Once the reaction was complete (monitored by TLC, reaction mixture was concentrated, and crude material was dissolved in $CH_2Cl_2$ (25 mL). The resulting solution was transferred to a separatory funnel and washed with water (2x25 mL). The aqueous layer was then extracted with additional $CH_2Cl_2$ (2x25 mL). The organic layers were combined and washed with brine and dried over $MgSO_4$ provide crude silyl-protected 27 as a white solid. The residue was purified by flash column chromatography ($CH_2Cl_2$/$CH_3OH$, modified with 5% $Et_3N$) to yield white solid (0.9295 g, 79%) $^1$H NMR (300 MHz, DMSO-d$_6$, δ): 10.68 (s, 1H), 7.86 (s, 1H), 6.41 (s, 2H), 5.85 (s, 1H), 5.73 (s, 0.3H), 5.57 (d, $^3$J=2.3 Hz, 1H), 4.63 (s, 1H), 4.01-3.91 (m, 3H), 2.07 (s, 3H), 1.00 (m, 32H). MS (ESI$^+$, 100% $CH_3OH$, TOF): m/z calc'd for $[C_{24}H_{42}N_5O_7Si_2]^+$ [M+H]$^+$ 568.2617; found 568.3389

Silyl-Deprotection of Acetylated Guanosine

Scheme 18. Synthesis of 2′-OAc-Guanosine 28

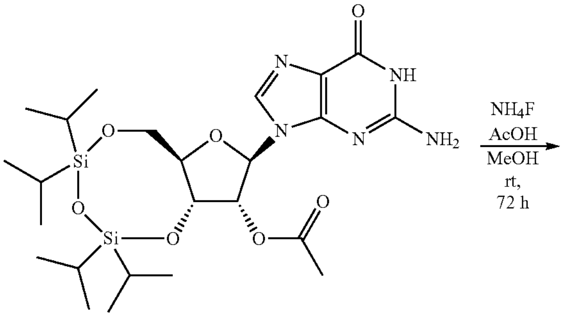

27

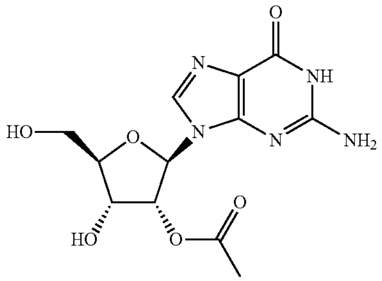

28

To an oven-dried RBF (50 mL), guanosine analog 27 (0.7239 g, 1.275 mmol) was dissolved in anhyd. methanol (13 mL). Acetic acid (170 μL, 2.932 mmol) followed by ammonium fluoride $NH_4F$ (0.1039 g, 2.805 mmol) were added to the solution. The reaction was stirred for 72 h at room temperature. Once no starting material is observed on TLC, reaction mixture was concentrated, and crude material was concentrated and redissolved in water (1x25 mL) and filtered through a celite plug and plug rinsed with water (3x25 mL). The compound was purified on an aqueous reverse flash chromatography ($H_2O$/$CH_3CN$ 7:3) to yield major compound 28 as a white solid (0.011 g, 23%) and minor compound 28 as a white solid (0.0047 g, 4%) 1H NMR (300 MHz, DMSO-$d_6$, δ): 10.66 (s, 1H), 7.94 (s, 1H), 6.49-6.45 (m, 3H), 5.77-5.75 (m, 1H), 5.66 (d, $^3J$=7.2 Hz, 1H), 5.26-5.21 (m, 1H), 5.20 (dt, $^3J$=5.4, $^4J$=2.7 Hz, 1H), 4.69-4.62 (m, 1H), 4.36 (dt, $^3J$=3.2, $^4J$=1.5 Hz,), 4.03-4.00 (m, 1H), 3.62-3.51 (m, 3H), 2.08 (s, 3H), 2.01 (s, 0.05H). MS ($ESI^+$, 100% $CH_3OH$, TOF): m/z calc'd for $[C_{12}H_{16}N_5O_5]^+$ $[M+H]^+$ 326.1095; found 326.1147

Thiophosphorylation Reaction of the Guanosine Derivative

Scheme 19. Triphosphorylation and salt exchange, synthesis of 2'-OAc guanosine triphosphate sodium salt 30

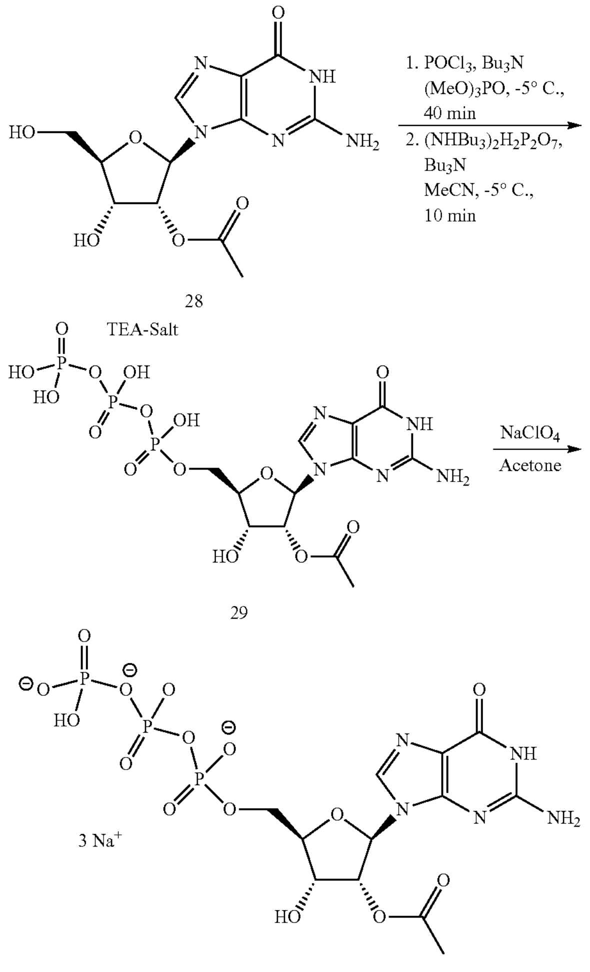

28

29

30

Method adapted from literature. In an oven-dried vial, dissolve tributylammonium pyrophosphate (0.136 g, 0.249 mmol) in anhyd. acetonitrile (1.3 mL) and tributylamine (0.41 mL, 1.740 mmol) and mixture stored in −20° C. To an oven-dried, argon-filled round-bottom flask or vial equipped with a stir bar, guanosine derivative (0.0954 g, 0.293 mmol) and tributyl amine (0.21 ml, 0.87 mmol) is added and dissolved in trimethyl phosphate (1 mL). The reaction mixture is evacuated and refilled three times with Argon. The reaction mixture is stirred for 10 min at room temperature. Cool the RBF/vial in an ice/NaCl bath (−5° C. to −10° C.) and stir for 30 min. Add the first portion of phosphorous oxychloride (35 μl, 0.373 mmol) and stir for 3 min. Add the second portion of phosphorus oxychloride (23 μl, 0.249 mmol) to the vial and stir 5 min. Add pyrophosphate solution and stir for 10 min. The reaction was monitored on the HPLC-SAX column. The septum was removed and water (5 mL) was added dropwise to the mixture. The solution was transferred to a separatory funnel and the aqueous layer was extracted with $CH_2Cl_2$ (3×2 mL) and the organic layer is discarded. Adjust the pH of the aqueous layer to 6.5 using ammonium hydroxide. Purification was done on the AKTA column and the appropriate fractions containing the phosphate combined and concentrated down in a water bath (35° to 38° C. and vacuum 1 to 10 mm). The resulting residue was coevaporated with water (3×2 ml). and dry it under vacuum overnight. The resulting triethylamine salt of Guanosine triphosphate was dissolved in water (2.6 mL)

Sodium perchlorate (0.0954 g, 0.781 mmol) was dissolved in acetone (3 mL) in a 15 mL centrifuge vial and the GTP solution was added dropwise into to the sodium perchlorate/acetone solution over a period of 5 min. The resulting mixture was centrifuged for 10 min at 704× g, 4° C. and the supernatant liquid discarded. The resultant pellet was dried under vacuum for 1 h and dissolved in water (2.6 mL) the dissolution into sodium perchlorate/acetone solution and centrifuge process repeated. The resulting solid was dried at ambient temperature under high vacuum overnight and weighed to yield the sodium salt of GTP 30 as a white solid (6.4 mg, 4%). 1H NMR (300 MHZ, $D_2O$, δ): 8.11 (s, 0.3H), 8.08 (s, 2H), 7.98 (s, 1H), 6.02 (d, $^3J$=3.6 Hz, 1H), 5.87 (dd, $^3J$=10.2, $^3J$=7.2 Hz, 2H), 5.57 (d, $^3J$=4.7 Hz, 1H), 5.46 (dd, $^3J$=5.3, $^3J$=0.6 Hz, 1H), 5.04 (t, $^3J$=6.6 Hz, 1H), 4.59-4.56 (m, 1H), 4.45 (s, 1H), 4.27-4.12 (m, 7H), 2.19 (s, 1H), 2.16 (s, 3H), 2.11 (s, 1H). $^{31}P$ NMR (121 MHZ, $D_2O$, δ): −6.27--6.62 (m, 1P), −11.21 (dt, $^3J$=19.7, $^3J$=7.7 Hz, 1P), −22.25 (m, 1P).

EXEMPLARY EMBODIMENTS

Embodiment 1. A modified ribonucleotide comprising a nucleoside, wherein the nucleoside comprises a ribose moiety comprising an acetyl group, wherein the ribose is 2'-O-acetylated and the modified ribonucleotide has a structure of:

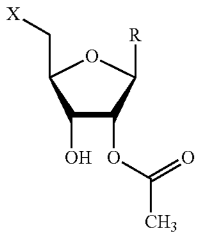

(a) wherein X is a 5' monophosphate, a 5' diphosphate, or a 5' triphosphate; and (b) wherein R is a nucleobase chosen from: adenine or a modified version thereof, a guanine or a modified version thereof, a cytosine or a modified version thereof, or a uracil or a modified version thereof.

Embodiment 2. The modified ribonucleotide of embodiment 1, wherein the nucleobase is adenine.

Embodiment 3. The modified ribonucleotide of embodiment 2, wherein the modified ribonucleotide has a 5' triphosphate and a structure of:

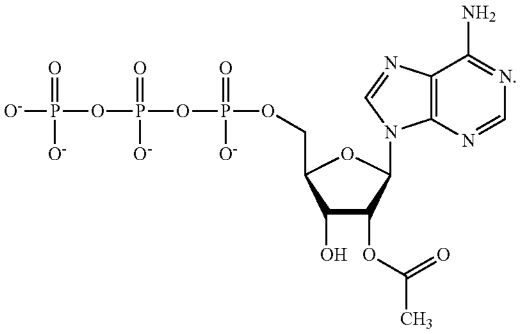

Embodiment 4. The modified ribonucleotide of embodiment 1, wherein the nucleobase is guanine.

Embodiment 5. The modified ribonucleotide of embodiment 4, wherein the modified ribonucleotide has a 5' triphosphate and a structure of:

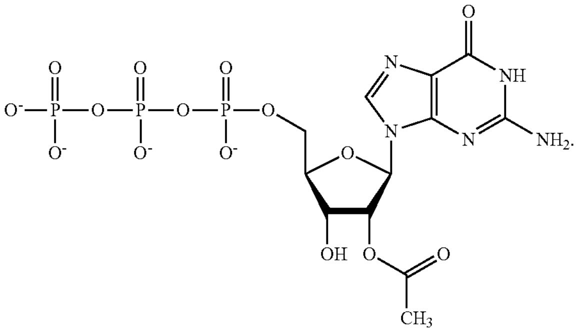

Embodiment 6. The modified ribonucleotide of embodiment 1, wherein the nucleobase is cytosine.

Embodiment 7. The modified ribonucleotide of embodiment 6, wherein the modified ribonucleotide has a 5' triphosphate and a structure of:

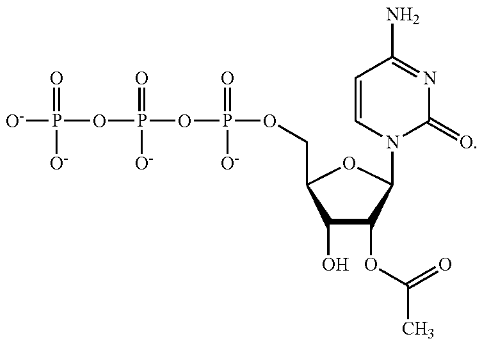

Embodiment 8. The modified ribonucleotide of embodiment 1, wherein the nucleobase is N4-acetylcytidine.

Embodiment 9. The modified ribonucleotide of embodiment 8, wherein the modified ribonucleotide has a 5' triphosphate and a structure of:

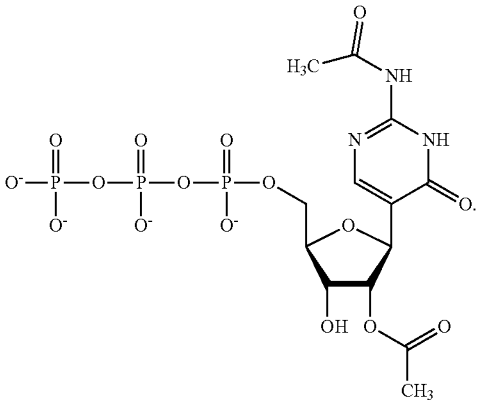

Embodiment 10. The modified ribonucleotide of embodiment 1, wherein the nucleobase is uracil.

Embodiment 11. The modified ribonucleotide of embodiment 10, wherein the modified ribonucleotide has a 5' triphosphate and a structure of and has a structure of:

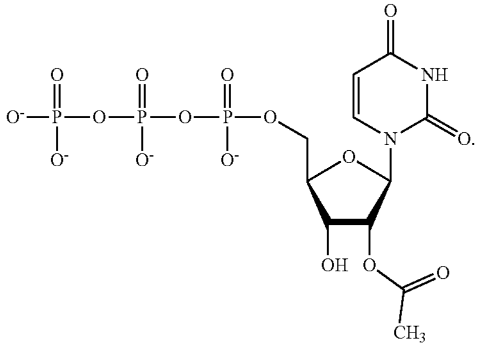

Embodiment 12. The modified ribonucleotide of embodiment 1, wherein the nucleobase is 5-hydroxymethyluridine.

Embodiment 13. The modified ribonucleotide of embodiment 12, wherein the modified ribonucleotide has a 5' triphosphate and a structure of and has a structure of:

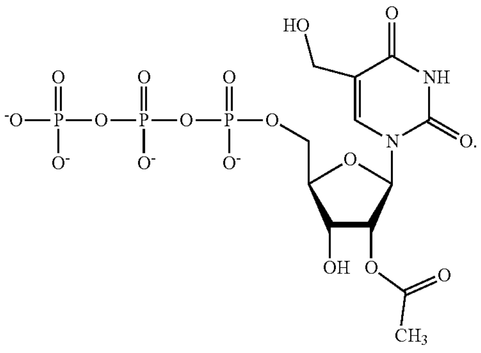

Embodiment 14. The modified ribonucleotide of embodiment 1, wherein the nucleobase is N1-methylpseudouridine.

Embodiment 15. The modified ribonucleotide of embodiment 14, wherein the modified ribonucleotide has a 5' triphosphate and a structure of and has a structure of:

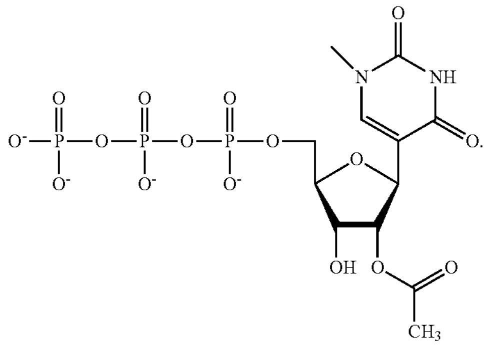

Embodiment 16. A polyribonucleotide comprising one or more modified ribonucleotides according to any one of the preceding embodiments.

Embodiment 17. The polyribonucleotide of embodiment 16, wherein at least 5%, at least 10%, at least 15%, at least 20%, at least 25%, at least 30%, at least 35%, at least about 40%, at least 45%, at least 50%, at least 55%, at least 60%, at least 65%, at least 70%, at least 75%, at least 80%, at least 85%, at least 90%, at least 95%, or at least 99% of the ribose moieties are acetylated (2'-O-acetylated).

Embodiment 18. The polyribonucleotide of embodiment 16, wherein at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, of the ribose moieties are acetylated (2'-O-acetylated).

Embodiment 19. The polyribonucleotide of any one of embodiments 16-18, wherein 100% of the ribose moieties are acetylated (2'-O-acetylated).

Embodiment 20. The polyribonucleotide of embodiment 16, wherein about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of the ribose moieties are acetylated (2'-O-acetylated).

Embodiment 21. The polyribonucleotide of embodiment 20, wherein at least 95% of the ribose moieties are 2'-O-acetylated.

Embodiment 22. The polyribonucleotide of any one of embodiments 16-21, wherein the polyribonucleotide comprises a cap structure and the cap structure does not comprise a 2'-O-acetylated ribose.

Embodiment 23. The polyribonucleotide of any one of embodiments 16-21, wherein the polyribonucleotide comprises a cap structure and the cap structure comprises a 2'-O-acetylated ribose.

Embodiment 24. The polyribonucleotide of any one of embodiments 16-22, wherein the polyribonucleotide further comprises a modification comprising: a modified backbone, a modified nucleobase, or any combination thereof.

Embodiment 25. The polyribonucleotide of embodiment 24, wherein the polyribonucleotide comprises a modified nucleobase.

Embodiment 26. The polyribonucleotide of embodiment 25, wherein the nucleobase comprising a modification is chosen from adenine, guanine, cytosine, or uracil. Embodiment 27. The polyribonucleotide of embodiment 26, wherein the nucleobase is adenine.

Embodiment 28. The polyribonucleotide of embodiment 26, wherein the nucleobase is guanine.

Embodiment 29. The polyribonucleotide of embodiment 26, wherein the nucleobase is cytosine.

Embodiment 30. The polyribonucleotide of embodiment 26, wherein the nucleobase is uracil.

Embodiment 31. The polyribonucleotide of any one of embodiments 14-16, wherein the modification comprises N4-acetyl-cytidine (ac4C), 5-hydroxymethyluridine, N1-pseudomethyluridine, pseudouridine, pyridin-4-one ribonucleoside, 5-aza-uridine, 6-aza-uridine, 2-thio-5-aza-uridine, 2-thio-uridine (s2U), 5-methyl cytidine (m5C), 5-aza-cytidine, 6-aza-cytidine, pseudoisocytidine, 3-methyl-cytidine (m3C), 5-formyl-cytidine (f5C), N4-methyl-cytidine (m4C), 2-amino-purine, 2, 6-diaminopurine, 2-amino-6-halo-purine, 6-halo-purine, inosine (I), 1-methyl-inosine (m1 I), wyosine (imG), methylwyosine (mimG), or a combination thereof.

Embodiment 32. The polyribonucleotide of any one of embodiments 16-31, wherein the ribonucleotide comprises a nucleoside comprising an acetyl group, wherein the nucleoside is N4-acetylcytidine.

Embodiment 33. The polyribonucleotide of any one of embodiments 16-31, wherein the ribonucleotide comprises a nucleoside comprising an acetyl group, wherein the nucleoside is N4-acetylcytidine and the modified ribonucleotide has a structure of:

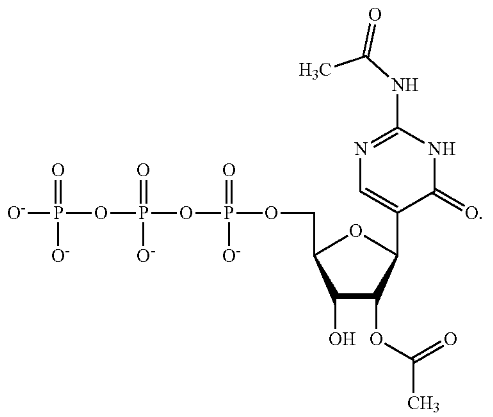

Embodiment 34. The polyribonucleotide of embodiment 32 or 33, wherein the polyribonucleotide comprises cytidine residues and wherein about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of cytidine residues in the polyribonucleotide comprise N4-acetylcytidine.

Embodiment 35. The polyribonucleotide of embodiment 32 or 33, wherein the polyribonucleotide comprises cytidine residues and wherein at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of cytidine residues in the polyribonucleotide comprise N4-acetylcytidine.

Embodiment 36. The polyribonucleotide of any one of embodiments 33-35, wherein at least 1% of N4-acetylcytidine residues comprise a 2'-O-acetylated ribose.

Embodiment 37. The polyribonucleotide of embodiment 33 or 34, wherein no more than 90% of N4-acetylcytidine residues comprise a 2'-O-acetylated ribose.

Embodiment 38. The polyribonucleotide of any one of embodiments 33-35, wherein the polyribonucleotide further comprises one or more additional ribonucleotide, e.g., modified ribonucleotides, in addition to N-acetylcytidine.

Embodiment 39. The polyribonucleotide of embodiment 38, wherein the one or more ribonucleotides (e.g., modified ribonucleotides) comprises a nucleoside chosen from: an adenosine, a guanosine, a cytidine or a uridine, or a combination thereof.

Embodiment 40. The polyribonucleotide of any one of embodiments 16-39, wherein the ribonucleotide comprises a nucleoside comprising a hydroxymethyl group, wherein the nucleoside is 5-hydroxymethyluridine.

Embodiment 41. The polyribonucleotide of any one of embodiments 16-39, wherein the ribonucleotide comprises a nucleoside comprising a hydroxymethyl group, wherein the nucleoside is 5-hydroxymethyluridine, and the modified ribonucleotide has the structure of:

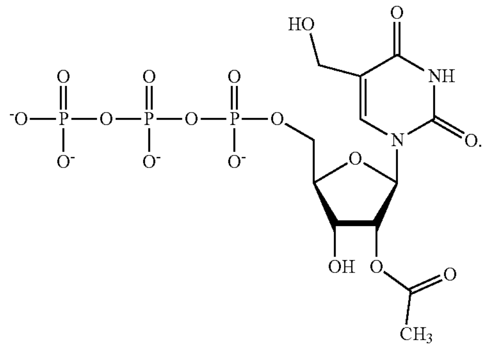

Embodiment 42. The polyribonucleotide of embodiment 40 or 41, wherein the polyribonucleotide comprises uridine residues and wherein about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of uridine residues in the polyribonucleotide comprise 5-hydroxymethyluridine.

Embodiment 43. The polyribonucleotide of embodiment 40 or 41, wherein the polyribonucleotide comprises uridine residues and wherein at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of uridine residues in the polyribonucleotide comprise 5-hydroxymethyluridine.

Embodiment 44. The polyribonucleotide of any one of embodiments 41-43, wherein at least 1% of 5-hydroxymethyluridine residues comprises a 2'-O-acetylated ribose.

Embodiment 45. The polyribonucleotide of any one of embodiments 41-43, wherein no more than 90% of 5-hydroxymethyluridine residues comprises a 2-O acetylated ribose.

Embodiment 46. The polyribonucleotide of any one of embodiments 39-44, wherein the polyribonucleotide further comprises one or more additional ribonucleotides, e.g., modified ribonucleotides, in addition to 5-hydroxymethyluridine.

Embodiment 47. The polyribonucleotide of embodiment 46, wherein the one or more ribonucleotides (e.g., modified ribonucleotides) comprises a nucleoside chosen from: an adenosine, a guanosine, a cytidine or a uridine, or a combination thereof.

Embodiment 48. The polyribonucleotide of any one of embodiments 16-46, wherein the ribonucleotide comprises a nucleoside comprising a N1-methylpseudouridine.

Embodiment 49. The polyribonucleotide of any one of embodiments 16-46, wherein the ribonucleotide comprises a nucleoside comprising a N1-methylpseudouridine and the modified ribonucleotide has the structure of:

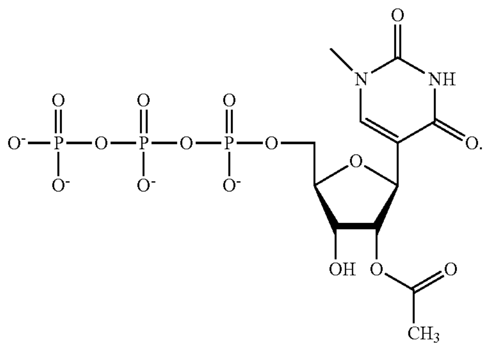

Embodiment 50. The polyribonucleotide of embodiment 48 or 49, wherein the polyribonucleotide comprises uridine residues and wherein about 5% to 99%, about 5% to 95%, about 5% to 90%, about 5% to 85%, about 5% to 80%, about 5% to 75%, about 5% to 70%, about 5% to 65%, about 5% to 60%, about 5% to 55%, about 5% to 50%, about 5% to 45%, about 5% to 40%, about 5% to 35%, about 5% to 30%, about 5% to 25%, about 5% to 20%, about 5% to 15%, about 5% to 10%, about 10% to 99%, about 15% to 99%, about 20% to 99%, about 25% to 99%, about 30% to 99%, about 35% to 99%, about 40% to 99%, about 45% to 99%, about 50% to 99%, about 55% to 99%, about 60% to 99%, about 65% to 99%, about 70% to 99%, about 80% to 99%, about 85% to 99%, about 90% to 99%, or about 95% to 99% of uridine residues in the polyribonucleotide comprise N1-methylpseudouridine.

Embodiment 51. The polyribonucleotide of embodiment 48 or 49, wherein the polyribonucleotide comprises uridine residues and wherein at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of uridine residues in the polyribonucleotide comprise N1-methylpseudouridine.

Embodiment 52. The polyribonucleotide of any one of embodiments 48-51, wherein at least 1% of N1-methylpseudouridine residues comprises a 2'-O-acetylated ribose.

Embodiment 53. The polyribonucleotide of any one of embodiments 48-51, wherein no more than 90% of N1-methylpseudouridine residues comprises a 2'-O-acetylated ribose.

Embodiment 54. The polyribonucleotide of any one of embodiments 48-53, wherein the polyribonucleotide further comprises one or more additional ribonucleotides, e.g., modified ribonucleotides, in addition to N1-methylpseudouridine.

Embodiment 55. The polyribonucleotide of embodiment 54, wherein the one or more ribonucleotides (e.g., modified ribonucleotides) comprises a nucleoside chosen from: an adenosine, a guanosine, a cytidine or a uridine, or a combination thereof.

Embodiment 56. The polyribonucleotide of any one of embodiments 16-55, wherein when the polyribonucleotide comprises one or more modified ribonucleotides of a particular type comprising a 2'-O-acetylated ribose, at least 1% of modified ribonucleotides of the particular type have a 2-O acetylate ribose.

Embodiment 57. The polyribonucleotide of any one of embodiments 16-55, wherein when the polyribonucleotide comprises one or more modified ribonucleotides of a particular type comprising a 2'-O-acetylated ribose, no more than 90% of modified ribonucleotides of the particular type have a 2'-O-acetylated ribose.

Embodiment 58. The polyribonucleotide of embodiment 56 or 57, wherein the polyribonucleotide further comprises: (i) one or more ribonucleotides; and/or (ii) one or more modified ribonucleotides.

Embodiment 59. The polyribonucleotide of any one of embodiments 16-58, characterized in that when assessed in a cell, tissue or an organism that has been administered the polyribonucleotide, reduced immunogenicity is observed relative to an appropriate reference comparator.

Embodiment 60. The polyribonucleotide of embodiment 59, wherein a reference comparator comprises an otherwise similar cell, tissue or organism that has been administered a comparable polyribonucleotide that includes fewer 2'-O-acetylated ribose (e.g., does not include any 2'-O-acetylated ribose) than a polyribonucleotide in a composition.

Embodiment 61. The polyribonucleotide of embodiment 59, wherein reduced immunogenicity comprises reduced activation of an innate immune response induced toxicity.

Embodiment 62. The polyribonucleotide of embodiment 61, wherein reduced activation of an immune response comprises reduced activation of pathways of NFkb, IRF, and/or other cytokines resulting from inflammation in the cell, tissue or organism.

Embodiment 63. The polyribonucleotide of any one of embodiments 60-62, wherein reduced immunogenicity allows for repeated dosing of the polyribonucleotide.

Embodiment 64. The polyribonucleotide of any one of embodiments 60-63, wherein reduced immunogenicity allows for administration of a higher dose of the polyribonucleotide related to an appropriate reference comparator.

Embodiment 65. The polyribonucleotide of embodiment 64, wherein a reference comparator comprises a comparable polyribonucleotide that includes fewer 2'-O-acetylated ribose (e.g., does not include any 2'-O-acetylated ribose) than a polyribonucleotide in a composition.

Embodiment 66. The polyribonucleotide of any one of the preceding embodiments, characterized in that when assessed in a cell, tissue or an organism that has been administered the polyribonucleotide, increased cell viability is observed relative to an appropriate reference comparator.

Embodiment 67. The polyribonucleotide of embodiment 66, wherein a reference comparator is the cell viability of a cell, tissue or organism that has been administered a comparable polyribonucleotide that includes fewer 2'-O-acetylated ribose (e.g., does not include any 2'-O-acetylated ribose).

Embodiment 68. The polyribonucleotide of embodiment 66 or 67, wherein cell viability is a measure of the length of time one or more cells of the cell, tissue or subject live.

Embodiment 69. The polyribonucleotide of embodiment 66 or 67, wherein cell viability is a measure of a number of cells of the cell, tissue or subject alive at one or more time points.

Embodiment 70. The polyribonucleotide of any one of the preceding embodiments, characterized in that when assessed in a cell, tissue or an organism that has been administered the polyribonucleotide, increased persistence of polyribonucleotide is observed relative to an appropriate reference comparator.

Embodiment 71. The polyribonucleotide of embodiment 70, wherein a reference comparator is the persistence of a comparable polyribonucleotide that includes fewer 2'-O-acetylated ribose (e.g., does not include any 2'-O-acetylated ribose).

Embodiment 72. The polyribonucleotide of embodiment 70 or 71, wherein persistence of the polyribonucleotide is increased by at least 15%, at least 20%, at least 30%, at least 40%, at least 50%, at least 60%, at least 70%, at least 80%, at least 90%, or at least 95%.

Embodiment 73. The polyribonucleotide of any one of embodiments 70-72, wherein increased persistence is a result of increased resistance to one or more nucleases.

Embodiment 74. The polyribonucleotide of embodiment 73, wherein one or more nucleases comprises an endonuclease.

Embodiment 75. The polyribonucleotide of embodiment 73, wherein one or more nucleases comprises an exonuclease.

Embodiment 76. The polyribonucleotide of any one of embodiments 70-75, wherein increased persistence allows for a polyribonucleotide to be dosed at a lesser amount and/or frequency as compared to an otherwise similar polyribonucleotide that includes fewer 2'-O-acetylated ribose (e.g., does not include any 2'-O-acetylated ribose).

Embodiment 77. The polyribonucleotide of any one of the preceding embodiments, characterized in that when assessed in a cell, tissue or an organism that has been administered the polyribonucleotide, increased expression and/or activity of a gene product encoded by a polyribonucleotide is observed relative to an appropriate reference comparator.

Embodiment 78. The polyribonucleotide of embodiment 77, wherein a reference comparator is the expression and/or activity of a gene product in a cell, tissue or organism that has been administered a comparable polyribonucleotide that includes fewer 2'-O-acetylated ribose (e.g., does not include any 2'-O-acetylated ribose).

Embodiment 79. The polyribonucleotide of embodiment 78, wherein expression and/or activity of a gene product is increased by at least 15%, at least 20%, at least 30%, at least 40%, at least 50%, at least 60%, at least 70%, at least 80%, at least 90%, or at least 95%.

Embodiment 80. The polyribonucleotide of any one of embodiments 16-79, wherein the polyribonucleotide comprises a coding region.

Embodiment 81. The polyribonucleotide of embodiment 79, wherein the coding region encodes a gene product, e.g., a payload.

Embodiment 82: The polyribonucleotide of embodiment 81, wherein the gene product is or comprises a polypeptide.

Embodiment 83: The polyribonucleotide of embodiment 81, wherein the gene product is or comprises a transcript.

Embodiment 84. The polyribonucleotide of any one of embodiments 16-79, wherein the polyribonucleotide is a messenger RNA (mRNA).

Embodiment 85. The polyribonucleotide of any one of embodiments 16-79, wherein the polyribonucleotide is a circRNA.

Embodiment 86. The polyribonucleotide of any one of embodiments 16-79, wherein the polyribonucleotide is a gRNA.

Embodiment 87. The polyribonucleotide of any one of embodiments 16-79, wherein the polyribonucleotide is an inhibitory RNA.

Embodiment 88. The polyribonucleotide of any one of embodiments 16-79, wherein the polyribonucleotide is an miRNA or siRNA.

Embodiment 89. The polyribonucleotide of any one of embodiments 16-79, wherein the polyribonucleotide is an antisense oligonucleotide.

Embodiment 90. The polyribonucleotide of any one of embodiments 16-79, wherein the polyribonucleotide is a long non-coding RNA.

Embodiment 91. A method of manufacturing an RNA composition comprising introducing one or more modified ribonucleotides according to any one of embodiments 1-15 into a polyribonucleotide.

Embodiment 92. The method of embodiment 91, wherein the method does not comprise removing double-stranded RNA from the RNA composition.

Embodiment 93. The method of embodiments 91 or 92, wherein the method is an in vitro transcription reaction method.

Embodiment 94. The method of any one of embodiments 91-94, wherein the method further comprises introducing one or more unmodified ribonucleotides.

Embodiment 95. A method of producing a polyribonucleotide comprising a step of incubating an in vitro transcription mixture, wherein the in vitro transcription mixture comprises: a DNA template; at least one RNA polymerase or a variant or a fragment thereof; and a plurality of ribonucleotides comprising at least one modified ribonucleotide comprising a 2'-O-acetylated ribose; thereby producing a polyribonucleotide comprising a 2'-O-acetylated ribose.

Embodiment 96. The method of embodiment 95, wherein the method produces a plurality of polyribonucleotides.

Embodiment 97. An in vitro transcription mixture comprising: (i) a DNA template; (ii) at least one RNA polymerase or a variant or a fragment thereof; and (iii) a plurality of ribonucleotides comprising at least one modified ribonucleotide comprising a 2'-O-acetylated ribose.

Embodiment 98. The in vitro transcription mixture of embodiment 97, wherein the mixture produces a polyribonucleotide comprising a 2'-O-acetylated ribose.

Embodiment 99. The in vitro transcription mixture of embodiment 49, wherein the mixture produces a plurality of polyribonucleotides.

Embodiment 100. The method of embodiment 96, or the mixture of embodiment 97-99, wherein each polyribonucleotide in the plurality of polyribonucleotides comprises a 2'-O-acetylated ribose.

Embodiment 101. The method or mixture of embodiment 100, wherein each polyribonucleotide in the plurality has at least 5% 2'-O-acetylated ribose.

Embodiment 102. The method or mixture of embodiment 100, wherein each polyribonucleotide in the plurality has no more than 90% 2'-O-acetylated ribose.

Embodiment 103. The method or mixture of embodiment 100, wherein each polyribonucleotide in the plurality has 100% 2'-O-acetylated ribose.

Embodiment 104. The method of embodiment 95 or the mixture of embodiment 97, wherein the RNA polymerase is chosen from: a bacteriophage RNA polymerase, a mitochondrial RNA polymerase, a eukaryotic RNA polymerase, a bacterial RNA polymerase, or a combination thereof.

Embodiment 105. The method of embodiment 104 or the mixture of embodiment 104, wherein the RNA polymerase comprises a T7 RNA polymerase, a T3 RNA polymerase, a SP6 RNA polymerase, a N4 virion RNA polymerase, a viral RNA polymerase, or a variant of any of the foregoing.

Embodiment 106. The method of embodiment 95 or the mixture of embodiment 97, wherein the polyribonucleotide comprises a coding region.

Embodiment 107. The method of embodiment 95 or the mixture of embodiment 97, wherein the polyribonucleotide comprises a guide RNA, a short hairpin RNA, an siRNA, a microRNA, a long non-coding RNA, a circular RNA, or a messenger RNA (mRNA), or a combination thereof.

Embodiment 108. The method of embodiment 106 or 107, or the mixture of embodiment 106 or 107, wherein the polyribonucleotide encodes one or more target polypeptides.

Embodiment 109. A composition comprising one or more polyribonucleotides of any one of embodiments 16-90.

Embodiment 110. A composition comprising one or more polyribonucleotides made according to the method of any one of embodiments 91-96 or 100-108.

Embodiment 111. A composition comprising one or more polyribonucleotide made using the in vitro transcription reaction mixture of any one of embodiments 97-108.

Embodiment 112. The composition of any one of embodiments 109-111, wherein the composition is a pharmaceutical composition.

Embodiment 113. The composition of embodiment 112, wherein the pharmaceutical composition is or comprises an immunogenic composition.

Embodiment 114. The composition of embodiment 112, wherein the pharmaceutical composition is or comprises a vaccine.

Embodiment 115. The composition of embodiment 112, wherein the pharmaceutical composition is or comprises a gene therapy.

Embodiment 116. The composition of embodiment 112, wherein the pharmaceutical composition is or comprises a chemotherapy.

Embodiment 117. The composition of embodiment 112, wherein the pharmaceutical composition is or comprises a protein replacement therapy.

Embodiment 118. The composition of embodiment 112, wherein the pharmaceutical composition is or comprises an immunotherapy.

Embodiment 119. The composition of embodiment 112, wherein the pharmaceutical composition is or comprises a cell engineering therapy.

Embodiment 120. The composition of embodiment 112, wherein the composition comprises double stranded RNA.

Embodiment 121. A method comprising administering one or more polyribonucleotides according to any one of embodiments 16-90, or a composition according to any one of embodiments 109-120 to a cell, tissue or subject.

Embodiment 122. The method of embodiment 121, further comprising determining cell viability of the cell, tissue or subject.

Embodiment 123. The method of embodiment 122, wherein cell viability is a measure of the length of time one or more cells of the cell, tissue or subject live.

Embodiment 124. The method of embodiment 122, wherein cell viability is a measure of a number of cells of the cell, tissue or subject alive at one or more time points.

Embodiment 125. The method of any one of embodiments 121-124, wherein the cell, tissue or subject to which the polyribonucleotide or a composition comprising the same has been administered exhibits improved cell viability as compared to a reference cell viability.

Embodiment 126. The method of embodiment 125, wherein the reference cell viability is the cell viability of a cell, tissue or subject that has been administered a comparable polyribonucleotide or a composition comprising the same that includes fewer 2'-O-acetylated ribose (e.g., does not include any 2'-O-acetylated ribose).

Embodiment 127. The method of any one of embodiments 121-126, further comprising determining an immune system response of the cell, tissue or subject to which the polyribonucleotide or a composition comprising the same has been administered.

Embodiment 128. The method of embodiment 127, wherein the immune response comprises an innate immune system response comprising innate immune system induced toxicity.

Embodiment 129. The method of embodiment 128, wherein determining an innate immune system response comprises determining a level of NF-κB, IRF, and/or other inflammatory cytokines in the cell, tissue or subject.

Embodiment 130. The method of any one of embodiments 127-129, wherein the cell, tissue or subject to which the polyribonucleotide or a composition comprising the same has been administered exhibits a reduced innate immune system response as compared to a reference.

Embodiment 131. The method of embodiment 130, wherein the reference is an innate immune system response of a cell, tissue or subject that has been administered a comparable polyribonucleotide or a composition comprising the same that includes fewer 2'-O-acetylated ribose (e.g., does not include any 2'-O-acetylated ribose).

Embodiment 132. The method of any one of embodiments 121-131, further comprising determining efficacy of the polyribonucleotide or a composition comprising the same in the cell, tissue or subject to which the polyribonucleotide or a composition comprising the same has been administered.

Embodiment 133. The method of embodiment 132, wherein determining efficacy comprises determining an antibody response or cellular response in the cell, tissue or subject.

Embodiment 134. The method of embodiment 132 or 133, wherein the cell, tissue or subject to which the polyribonucleotide or a composition comprising the same has been administered exhibits an increased antibody response or cellular response as compared to a reference.

Embodiment 135. The method of embodiment 134, wherein the reference is an antibody response or cellular response of a cell, tissue or subject that has been administered a comparable polyribonucleotide or a composition comprising the same that includes fewer 2'-O-acetylated ribose (e.g., does not include any 2'-O-acetylated ribose).

Embodiment 136. The method of any one of embodiments 121-135, further comprising determining persistence of a polyribonucleotide in the cell, tissue or subject as compared to a reference.

Embodiment 137. The method of embodiment 136, wherein the reference is persistence of a comparable polyribonucleotide or a composition comprising the same that includes fewer 2'-O-acetylated ribose (e.g., does not include any 2'-O-acetylated ribose) which has been administered to a cell tissue or subject.

Embodiment 138. The method of embodiment 136 or 137, wherein administration of the polyribonucleotide results in increase persistence of the polyribonucleotide as compared to a reference.

Embodiment 139. The method of embodiment 138, wherein persistence of the polyribonucleotide is increased by at least 15%, at least 20%, at least 30%, at least 40%, at least 50%, at least 60%, at least 70%, at least 80%, at least 90%, or at least 95%.

Embodiment 140. The method of any one of embodiments 121-139, further comprising determining expression and/or activity of a gene product encoded by a polyribonucleotide in the cell, tissue or subject as compared to a reference.

Embodiment 141. The method of embodiment 140, wherein the reference is expression and/or activity of a comparable polyribonucleotide or a composition comprising the same that includes fewer 2'-O-acetylated ribose (e.g., does not include any 2'-O-acetylated ribose) which has been administered to a cell tissue or subject.

Embodiment 142. The method of embodiment 141 or 142, wherein administration of the polyribonucleotide results in increased expression and/or activity of the polyribonucleotide as compared to a reference.

Embodiment 143. The method of embodiment 142, wherein expression and/or activity of a gene product is increased by at least 15%, at least 20%, at least 30%, at least 40%, at least 50%, at least 60%, at least 70%, at least 80%, at least 90%, or at least 95%.

Embodiment 144. The method of any one of embodiments 121-143, wherein the method comprises administering the polyribonucleotide or a composition comprising the same to the cell, tissue or subject at least two times.

Embodiment 145. The method of any one of embodiments 121-144, wherein the method comprises administering the polyribonucleotide or a composition comprising the same to the cell, tissue or subject at least 2 times, at least 3 times, at least 4 times, at least 5 times, at least 6 times, at least 7 times, at least 8 times, at least 9 times or at least 10 times.

Embodiment 146. The method of embodiment 144 or 145, wherein at least two administrations of the polyribonucleotide or a composition comprising the same to the cell, tissue or subject does not result in reduced efficacy of the polyribonucleotide or a composition comprising the same compared to administration of one dose of the polyribonucleotide or a composition comprising the same.

Embodiment 147. The method of any one of embodiments 121-146, wherein the method comprises administering the polyribonucleotide or a composition comprising the same to the cell, tissue or subject at a higher dose compared to an appropriate reference comparator.

Embodiment 148. The method of embodiment 147, wherein the reference comparator comprises a comparable polyribonucleotide that includes fewer 2'-O-acetylated ribose (e.g., does not include any 2'-O-acetylated ribose).

Embodiment 149. The method of any one of embodiments 121-148, wherein the cell is a mammalian cell, the tissue is a mammalian tissue, or the subject is a mammal.

Embodiment 150. The method of embodiment 149, wherein the mammal is a human.

Embodiment 151. The method of any one of embodiments 121-150, wherein the method is a method to stimulate an immune response.

Embodiment 152. The method of any one of embodiments 121-150, wherein the method is a vaccination method.

Embodiment 153. The method of any one of embodiments 121-150, wherein the method is a gene therapy method.

Embodiment 154. The method of embodiment 153, wherein the gene therapy method comprises delivery of one or more components of a gene therapy such as a gRNA.

Embodiment 155. The method of any one of embodiments 121-150, wherein the method is a cell therapy engineering method.

Embodiment 156. The method of any one of embodiments 121-150, wherein the method is an immunotherapy method.

Embodiment 157. The method of embodiment 156, wherein the immunotherapy method comprises delivery of an antibody therapy and/or an immune checkpoint therapy.

Embodiment 158. The method of any one of embodiments 121-150, wherein the method is a protein replacement therapy method.

Embodiment 159. The method of embodiment 158, wherein the protein replacement therapy method comprises delivery of an enzyme replacement therapy.

Embodiment 160. The method of any one of embodiments 121-150, wherein the method is a chemotherapeutic method.

Embodiment 161. A method of vaccination comprising administering one or more polyribonucleotides according to any one of embodiments 16-90, or a composition according to any one of embodiments 109-120 to a cell, tissue or subject.

Embodiment 162. A method of immunotherapy comprising administering one or more polyribonucleotides according to any one of embodiments 16-90, or a composition according to any one of embodiments 109-120 to a cell, tissue or subject.

Embodiment 163. A method of gene therapy comprising administering one or more polyribonucleotides according to any one of embodiments 16-90, or a composition according to any one of embodiments 109-120 to a cell, tissue or subject.

Embodiment 164. A method of protein replacement therapy, comprising administering one or more polyribonucleotides according to any one of embodiments 16-90, or a composition according to any one of embodiments 109-120 to a cell, tissue or subject.

Embodiment 165. A method of cell engineering therapy, comprising administering one or more polyribonucleotides according to any one of embodiments 16-90, or a composition according to any one of embodiments 109-120 to a cell, tissue or subject.

Embodiment 166. A method of increasing persistence of a polyribonucleotide in a cell, tissue or subject, comprising administering one or more polyribonucleotides according to any one of embodiments 16-90, or a composition according to any one of embodiments 109-120 to a cell, tissue or subject.

Embodiment 167. A method of increasing expression and/or activity of a gene product encoded by a polyribonucleotide in a cell, tissue or subject, comprising administering one or more polyribonucleotides according to any one of embodiments 16-90, or a composition according to any one of embodiments 109-120 to a cell, tissue or subject.

Embodiment 168. A cell comprising a polyribonucleotide according to any one of embodiments 116-90, or a composition according to any one of embodiments 109-120.

Embodiment 169. Use of a modified ribonucleotide according to embodiment 1 in the production of a polyribonucleotide.

Embodiment 170. Use of a polyribonucleotide according to any one of embodiments 16-90, or a composition according to any one of embodiments 109-120 to stimulate an immune response.

Embodiment 171. Use of a polyribonucleotide according to any one of embodiments 16-90, or a composition according to any one of embodiments 109-120 as a vaccine.

Embodiment 172. Use of a polyribonucleotide according to any one of embodiments 16-90, or a composition according to any one of embodiments 109-120 as an immunotherapy.

Embodiment 173. Use of a polyribonucleotide according to any one of embodiments 16-90, or a composition according to any one of embodiments 109-120 as a gene therapy.

Embodiment 174. Use of a polyribonucleotide according to any one of embodiments 16-90, or a composition according to any one of embodiments 109-120 as a protein replacement therapy.

Embodiment 175. Use of a polyribonucleotide according to any one of embodiments 116-90, or a composition according to any one of embodiments 109-120, as a cell engineering therapy.

Embodiment 176. Use of a polyribonucleotide according to any one of embodiments 16-90, or a composition according to any one of embodiments 109-120 as a chemotherapy.

Embodiment 177. The use of any one of embodiments 169-176, wherein the polyribonucleotide or a composition comprising the same is administered to a cell, tissue or subject.

Embodiment 178. The use of embodiment 177, wherein the cell is a mammalian cell, the tissue is a mammalian tissue, or the subject is a mammal.

Embodiment 179. The use of embodiment 178, wherein the mammal is a human.

EQUIVALENTS

Those skilled in the art will recognize, or be able to ascertain using no more than routine experimentation, many equivalents to the specific embodiments of the invention described herein. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Further, it should also be understood that any embodiment or aspect of the invention can be explicitly excluded from the claims, regardless of whether the specific exclusion is recited in the specification. The scope of the present invention is not intended to be limited to the above Description, but rather is as set forth in the claims that follow.

What is claimed is:

1. An in vitro transcription mixture comprising:
(a) a DNA template,
(b) at least one RNA polymerase, and
(c) a plurality of ribonucleotides comprising one or more modified ribonucleotides, wherein the one or more modified ribonucleotides comprises:
(i) a 5'-triphosphate, and
(ii) a nucleoside comprising a 2'-O-acetylated ribose and a nucleobase, wherein the nucleobase is an adenine or a modified version thereof, a guanine or a modified version thereof, a cytosine or a modified version thereof, or a uracil or a modified version thereof.

2. The in vitro transcription mixture of claim 1, wherein the mixture further comprises one or more polyribonucleotides, whereby the one or more polyribonucleotides were produced by incubating components (a), (b) and (c) in the mixture.

3. The in vitro transcription mixture of claim 2, wherein the one or more polyribonucleotides comprises ribose moieties that are 2'-O-acetylated.

4. The in vitro transcription mixture of claim 3, wherein the one or more polyribonucleotides has at least 5% ribose moieties that are 2'-O-acetylated.

5. The in vitro transcription mixture of claim 3, wherein all of the ribose moieties in the one or more polyribonucleotides are 2'-O-acetylated.

6. The in vitro transcription mixture of claim 2, wherein the one or more polyribonucleotides comprises one or more ribonucleotides that do not comprise a 2'-O-acetylated ribose.

7. The in vitro transcription mixture of claim 1, wherein the RNA polymerase is or comprises: a bacteriophage RNA polymerase, a mitochondrial RNA polymerase, a eukaryotic RNA polymerase, a bacterial RNA polymerase, or any combination thereof.

8. The in vitro transcription mixture of claim 1, wherein the RNA polymerase is or comprises: a T7 RNA polymerase, a T3 RNA polymerase, a SP6 RNA polymerase, a N4 virion RNA polymerase, a viral RNA polymerase, or a variant of any of the foregoing.

9. The in vitro transcription mixture of claim 2, wherein the one or more polyribonucleotides comprises a coding region.

10. The in vitro transcription mixture of claim 9, wherein the one or more polyribonucleotides encodes one or more target polypeptides.

11. The in vitro transcription mixture of claim 2, wherein the one or more polyribonucleotides comprises a guide RNA, a short hairpin RNA, an siRNA, a microRNA, a long non-coding RNA, a circular RNA, or any combination thereof.

12. The in vitro transcription mixture of claim 1, wherein the one or more modified ribonucleotides comprise one or more subsets of modified ribonucleotides, wherein each subset of modified ribonucleotides comprises a nucleobase that is N4-acetyl-cytidine (ac4C), 5-hydroxymethyluridine, N1-methylpseudouridine, pyridin-4-one ribonucleoside, 5-aza-uridine, 6-aza-uridine, 2-thio-5-aza-uridine, 2-thio-uridine (s2U), 5-methyl cytidine (m5C), 5-aza-cytidine, 6-aza-cytidine, pseudoisocytidine, 3-methyl-cytidine (m3C), 5-formyl-cytidine (f5C), N4-methyl-cytidine (m4C), 2-amino-purine, 2, 6-diaminopurine, 2-amino-6-halo-purine, 6-halo-purine, inosine (I), 1-methyl-inosine (m1 I), wyosine (imG), or methylwyosine (mimG).

13. The in vitro transcription mixture of claim 12, wherein the one or more subsets of modified ribonucleotides comprise:

(i) a subset of modified ribonucleotides comprising a nucleobase that is N4-acetyl-cytidine (ac4C), (ii) a subset of modified ribonucleotides comprising a nucleobase that is 5-hydroxymethyluridine, (iii) a subset of modified ribonucleotides comprising a nucleobase that is N1-methylpseudouridine, or (iv) any combination thereof.

14. The in vitro transcription mixture of claim 2, further comprising a 5' cap.

15. The in vitro transcription mixture of claim 2, wherein the one or more polyribonucleotides further comprise a 5' cap.

16. The in vitro transcription mixture of claim 14, wherein the 5' cap does not comprise a 2'-O-acetylated ribose.

17. The in vitro transcription mixture of claim 14, wherein the 5' cap comprises a 2'-O-acetylated ribose.

18. An in vitro transcription mixture comprising:

(a) a DNA template, (b) at least one RNA polymerase, and (c) a plurality of ribonucleotides comprising one or more modified ribonucleotides, wherein the one or more modified ribonucleotides comprises:

(i) a 5'-triphosphate, and (ii) a nucleoside comprising a 2'-O-acetylated ribose and a nucleobase, wherein the nucleobase is N4-acetylcytosine.

19. The in vitro transcription mixture of claim 18, wherein the mixture further comprises one or more polyribonucleotides, wherein the one or more polyribonucleotides were produced by incubating components (a), (b) and (c) in the mixture, wherein the one or more polyribonucleotides comprise ribonucleotides comprising cytidine, and wherein at least about 5% of the ribonucleotides comprising cytidine nucleosides comprise an N4-acetylcytosine nucleobase.

20. The in vitro transcription mixture of claim 18, wherein the one or more modified ribonucleotides further comprises:

(i) a 5'-triphosphate, and (ii) a nucleoside comprising a 2'-O-acetylated ribose and a nucleobase, wherein the nucleobase is 5-hydroxymethyluracil.

21. The in vitro transcription mixture of claim 18, further comprising a 5' cap.

22. The in vitro transcription mixture of claim 19, wherein the one or more polyribonucleotides further comprise a 5' cap.

23. An in vitro transcription mixture comprising:

(a) a DNA template, (b) at least one RNA polymerase, and (c) a plurality of ribonucleotides comprising one or more modified ribonucleotides, wherein the one or more modified ribonucleotides comprises:

(i) a 5'-triphosphate, and (ii) a nucleoside comprising a 2'-O-acetylated ribose and a nucleobase, wherein the nucleobase is 5-hydroxymethyluracil.

24. The in vitro transcription mixture of claim 23, wherein the mixture further comprises one or more polyribonucleotides, wherein the one or more polyribonucleotides were produced by incubating components (a), (b) and (c) in the mixture, wherein the one or more polyribonucleotides comprise ribonucleotides comprising uridine, and wherein at least about 5% of the ribonucleotides comprising uridine nucleosides comprise a 5-hydroxymethyluracil nucleobase.

25. The in vitro transcription mixture of claim 23, further comprising a 5' cap.

26. The in vitro transcription mixture of claim 24, wherein the one or more polyribonucleotides further comprise a 5' cap.

27. The in vitro transcription mixture of claim 23, wherein the one or more modified ribonucleotides further comprises:

(i) a 5'-triphosphate, and (ii) a nucleoside comprising a 2'-O-acetylated ribose and a nucleobase, wherein the nucleobase is N4-acetylcytosine.

* * * * *

SEQUENCE LISTING

```
Sequence total quantity: 4
SEQ ID NO: 1            moltype = DNA  length = 78
FEATURE                 Location/Qualifiers
source                  1..78
                        mol_type = other DNA
                        organism = synthetic construct
SEQUENCE: 1
cttgttcttt ttgcagaagc tcagaataaa cgctcaactt tggccaccat ggaagatgcc  60
aaaaacatta agaagggc                                                78

SEQ ID NO: 2            moltype = DNA  length = 157
FEATURE                 Location/Qualifiers
source                  1..157
                        mol_type = other DNA
                        organism = synthetic construct
SEQUENCE: 2
agaatgtgaa gaaactttct ttttattagg agcagatacg aatggctaca ttttggggga  60
caacattttg taaagtgtaa gttggtatta tgtagcttag agactccatt cgggtgttct  120
tgaggctggt ctatcattac acggcgatct tgccgcc                           157

SEQ ID NO: 3            moltype = DNA  length = 45
FEATURE                 Location/Qualifiers
source                  1..45
                        mol_type = other DNA
                        organism = synthetic construct
SEQUENCE: 3
gaatttaata cgactcacta taaggcttgt tctttttgca gaagc                  45

SEQ ID NO: 4            moltype = DNA  length = 149
FEATURE                 Location/Qualifiers
source                  1..149
                        mol_type = other DNA
                        organism = synthetic construct
SEQUENCE: 4
tttttttttt tttttttttt tttttttttt tttttttttt tttttttttt tttttttttt  60
tttttttttt tttttttttt tttttttttt tttttttttt tttttttttt tttttttttt  120
agaatgtgaa gaaactttct ttttattag                                    149
```